(12) United States Patent
Robertson et al.

(10) Patent No.: US 9,235,683 B2
(45) Date of Patent: Jan. 12, 2016

(54) APPARATUS, SYSTEM, AND METHOD FOR MANAGING ADHERENCE TO A REGIMEN

(75) Inventors: Timothy Robertson, Belmont, CA (US); Gregory Moon, Palo Alto, CA (US); Arna Ionescu, San Francisco, CA (US); Yashar Behzadi, San Francisco, CA (US); David O'Reilly, Palo Alto, CA (US); Aaron Filner, San Francisco, CA (US); Erika Karplus, Silverthorne, CO (US); Danielle Cojuangco, San Francisco, CA (US); Sara Burgess, Mill Valley, CA (US)

(73) Assignee: Proteus Digital Health, Inc., Redwood, CA (US)

( * ) Notice: Subject to any disclaimer, the term of this patent is extended or adjusted under 35 U.S.C. 154(b) by 0 days.

(21) Appl. No.: 13/292,440

(22) Filed: Nov. 9, 2011

(65) Prior Publication Data

US 2013/0117696 A1    May 9, 2013

(51) Int. Cl.
G06F 3/048    (2013.01)
G06F 19/00    (2011.01)

(52) U.S. Cl.
CPC ........ *G06F 19/3418* (2013.01); *G06F 19/3456* (2013.01); *G06F 19/3487* (2013.01)

(58) Field of Classification Search
CPC ....................................................... G06F 3/048
USPC ......................................................... 715/763
See application file for complete search history.

(56) References Cited

U.S. PATENT DOCUMENTS

| 3,589,943 A | 6/1971 | Grubb et al. |
| 3,607,788 A | 9/1971 | Adolph |
| 3,628,669 A | 12/1971 | McKinnis et al. |

(Continued)

FOREIGN PATENT DOCUMENTS

| CN | 1991868 | 7/2007 |
| CN | 101005470 | 7/2007 |

(Continued)

OTHER PUBLICATIONS

Kit Yee Au-Yeung et al. "A Networked System for Self-Management of Drug Therapy and Wellness" (Proceeding WH '10 Wireless Health 2010, Oct. 2010, pp. 1-9, ACM, ISBN: 978-1-60558-989-3).*

(Continued)

*Primary Examiner* — Jennifer To
*Assistant Examiner* — Xuyang Xia

(57) ABSTRACT

A method of managing adherence to a regimen in a subscription based computer implemented healthcare information environment. The method includes receiving at a mobile device information from a receiver that a dose was ingested by a living subject. The mobile device comprises a processor, a memory and a display coupled to the processor. The method provides wirelessly communicating the information over a wireless network to a backend computer processing system and receiving from the computer at the backend processing system a personal information stream characterizing behavior of the living subject based on the received information over a predetermined period. An apparatus includes an adherence package including a foldable sheet, at least one of blister pack coupled to the foldable sheet, at least one ingestible device associated with a dose, and a perforation provided on the foldable sheet to enable removal of the at the least one blister pack.

28 Claims, 52 Drawing Sheets
(48 of 52 Drawing Sheet(s) Filed in Color)

(56) References Cited

U.S. PATENT DOCUMENTS

| | | |
|---|---|---|
| 3,642,008 A | 2/1972 | Bolduc |
| 3,679,480 A | 7/1972 | Brown et al. |
| 3,682,160 A | 8/1972 | Murata |
| 3,719,183 A | 3/1973 | Schwartz |
| 3,799,802 A | 3/1974 | Schneble, Jr. et al. |
| 3,828,766 A | 8/1974 | Krasnow |
| 3,837,339 A | 9/1974 | Aisenberg et al. |
| 3,893,111 A | 7/1975 | Cotter |
| 3,944,064 A | 3/1976 | Bashaw et al. |
| 3,967,202 A | 6/1976 | Batz |
| 3,989,050 A | 11/1976 | Buchalter |
| 4,017,856 A | 4/1977 | Wiegand |
| 4,055,178 A | 10/1977 | Harrigan |
| 4,062,750 A | 12/1977 | Butler |
| 4,077,397 A | 3/1978 | Ellis |
| 4,077,398 A | 3/1978 | Ellis |
| 4,082,087 A | 4/1978 | Howson |
| 4,090,752 A | 5/1978 | Long |
| 4,106,348 A | 8/1978 | Auphan |
| 4,129,125 A | 12/1978 | Lester |
| 4,166,453 A | 9/1979 | McClelland |
| 4,239,046 A | 12/1980 | Ong |
| 4,251,795 A | 2/1981 | Shibasaki et al. |
| 4,269,189 A | 5/1981 | Abraham |
| 4,331,654 A | 5/1982 | Morris |
| 4,345,588 A | 8/1982 | Widder et al. |
| 4,418,697 A | 12/1983 | Tama |
| 4,425,117 A | 1/1984 | Hugemann |
| 4,439,196 A | 3/1984 | Higuchi |
| 4,494,950 A | 1/1985 | Fischell |
| 4,559,950 A | 12/1985 | Vaughan |
| 4,564,363 A | 1/1986 | Bagnall et al. |
| 4,578,061 A | 3/1986 | Lemelson |
| 4,635,641 A | 1/1987 | Hoffman |
| 4,654,165 A | 3/1987 | Eisenber |
| 4,663,250 A | 5/1987 | Ong et al. |
| 4,669,479 A | 6/1987 | Dunseath |
| 4,681,111 A | 7/1987 | Silvian |
| 4,687,660 A | 8/1987 | Baker et al. |
| 4,725,997 A | 2/1988 | Urquhart et al. |
| 4,763,659 A | 8/1988 | Dunseath |
| 4,767,627 A | 8/1988 | Caldwell et al. |
| 4,784,162 A | 11/1988 | Ricks |
| 4,793,825 A | 12/1988 | Benjamin et al. |
| 4,809,705 A | 3/1989 | Ascher |
| 4,844,076 A | 7/1989 | Lesho |
| 4,876,093 A | 10/1989 | Theeuwes et al. |
| 4,896,261 A | 1/1990 | Nolan |
| 4,975,230 A | 12/1990 | Pinkhasov |
| 4,987,897 A | 1/1991 | Funke |
| 5,000,957 A | 3/1991 | Eckenhoff et al. |
| 5,016,634 A | 5/1991 | Vock et al. |
| 5,079,006 A | 1/1992 | Urquhart |
| 5,167,626 A | 12/1992 | Casper et al. |
| 5,176,626 A | 1/1993 | Soehendra |
| 5,245,332 A | 9/1993 | Katzenstein |
| 5,261,402 A | 11/1993 | DiSabito |
| 5,263,481 A | 11/1993 | Axelgaard et al. |
| 5,279,607 A | 1/1994 | Schentag et al. |
| 5,281,287 A | 1/1994 | Lloyd |
| 5,283,136 A | 2/1994 | Peled et al. |
| 5,305,745 A | 4/1994 | Zacouto |
| 5,318,557 A | 6/1994 | Gross |
| 5,394,882 A | 3/1995 | Mawhinney |
| 5,395,366 A | 3/1995 | D'Andrea et al. |
| 5,436,091 A | 7/1995 | Shackle et al. |
| 5,443,461 A | 8/1995 | Atkinson et al. |
| 5,443,843 A | 8/1995 | Curatolo et al. |
| 5,458,141 A | 10/1995 | Neil et al. |
| 5,485,841 A | 1/1996 | Watkin et al. |
| 5,511,548 A | 4/1996 | Riazzi et al. |
| 5,567,210 A | 10/1996 | Bates et al. |
| 5,596,302 A | 1/1997 | Mastrocola et al. |
| D377,983 S | 2/1997 | Sabri et al. |
| 5,600,548 A | 2/1997 | Nguyen et al. |
| 5,634,466 A | 6/1997 | Gruner |
| 5,634,468 A | 6/1997 | Platt |
| 5,645,063 A | 7/1997 | Straka et al. |
| 5,705,189 A | 1/1998 | Lehmann et al. |
| 5,720,771 A | 2/1998 | Snell |
| 5,738,708 A | 4/1998 | Peachey et al. |
| 5,740,811 A | 4/1998 | Hedberg |
| 5,757,326 A | 5/1998 | Koyama et al. |
| 5,792,048 A | 8/1998 | Schaefer |
| 5,802,467 A | 9/1998 | Salazar |
| 5,833,716 A | 11/1998 | Bar-Or |
| 5,845,265 A | 12/1998 | Woolston |
| 5,862,803 A | 1/1999 | Besson |
| 5,862,808 A | 1/1999 | Albarello |
| 5,868,136 A | 2/1999 | Fox |
| 5,921,925 A | 7/1999 | Cartmell et al. |
| 5,925,030 A | 7/1999 | Gross et al. |
| 5,925,066 A | 7/1999 | Kroll et al. |
| 5,957,854 A | 9/1999 | Besson et al. |
| 5,963,132 A | 10/1999 | Yoakum |
| 5,974,124 A | 10/1999 | Schlueter, Jr. et al. |
| 5,981,166 A | 11/1999 | Mandecki |
| 5,999,846 A | 12/1999 | Pardey et al. |
| 6,023,631 A | 2/2000 | Cartmell et al. |
| 6,038,464 A | 3/2000 | Axelgaard et al. |
| 6,042,710 A | 3/2000 | Dubrow |
| 6,047,203 A | 4/2000 | Sackner |
| 6,076,016 A | 6/2000 | Feierbach et al. |
| 6,081,734 A | 6/2000 | Batz |
| 6,083,248 A | 7/2000 | Thompson |
| 6,090,489 A | 7/2000 | Hayakawa et al. |
| 6,091,975 A | 7/2000 | Daddona et al. |
| 6,095,985 A | 8/2000 | Raymond et al. |
| 6,115,636 A | 9/2000 | Ryan |
| 6,117,077 A | 9/2000 | Del Mar et al. |
| 6,122,351 A | 9/2000 | Schlueter, Jr. et al. |
| 6,141,592 A | 10/2000 | Pauly |
| 6,149,940 A | 11/2000 | Maggi et al. |
| 6,200,265 B1 | 3/2001 | Walsh et al. |
| 6,204,764 B1 | 3/2001 | Maloney |
| 6,206,702 B1 | 3/2001 | Hayden et al. |
| 6,217,744 B1 | 4/2001 | Crosby |
| 6,231,593 B1 | 5/2001 | Meserol |
| 6,245,057 B1 | 6/2001 | Sieben et al. |
| 6,269,058 B1 | 7/2001 | Yamanoi et al. |
| 6,275,476 B1 | 8/2001 | Wood |
| 6,285,897 B1 | 9/2001 | Kilcoyne et al. |
| 6,287,252 B1 | 9/2001 | Lugo |
| 6,288,629 B1 | 9/2001 | Cofino et al. |
| 6,289,238 B1 | 9/2001 | Besson et al. |
| 6,315,719 B1 | 11/2001 | Rode et al. |
| 6,342,774 B1 | 1/2002 | Kreisinger et al. |
| 6,344,824 B1 | 2/2002 | Takasugi et al. |
| 6,358,202 B1 | 3/2002 | Arent |
| 6,364,834 B1 | 4/2002 | Reuss |
| 6,366,206 B1 | 4/2002 | Ishikawa et al. |
| 6,368,190 B1 | 4/2002 | Easter et al. |
| 6,371,927 B1 | 4/2002 | Brune |
| 6,374,670 B1 | 4/2002 | Spelman |
| 6,380,858 B1 | 4/2002 | Yarin et al. |
| 6,390,088 B1 | 5/2002 | Nohl et al. |
| 6,394,953 B1 | 5/2002 | Devlin et al. |
| 6,394,997 B1 | 5/2002 | Lemelson |
| 6,409,674 B1 | 6/2002 | Brockway et al. |
| 6,426,863 B1 | 7/2002 | Munshi |
| 6,432,292 B1 | 8/2002 | Pinto et al. |
| 6,440,069 B1 | 8/2002 | Raymond et al. |
| 6,441,747 B1 | 8/2002 | Khair |
| 6,453,199 B1 | 9/2002 | Kobozev |
| 6,477,424 B1 | 11/2002 | Thompson et al. |
| 6,482,156 B2 | 11/2002 | Iliff |
| 6,494,829 B1 | 12/2002 | New et al. |
| 6,496,705 B1 | 12/2002 | Ng et al. |
| 6,526,315 B1 | 2/2003 | Inagawa |
| 6,531,026 B1 | 3/2003 | Takeichi et al. |
| 6,544,174 B2 | 4/2003 | West |
| 6,564,079 B1 | 5/2003 | Cory |
| 6,572,636 B1 | 6/2003 | Hagen et al. |
| 6,577,893 B1 | 6/2003 | Besson et al. |

(56) References Cited

U.S. PATENT DOCUMENTS

| | | |
|---|---|---|
| 6,579,231 B1 | 6/2003 | Phipps |
| 6,595,929 B2 | 7/2003 | Stivoric |
| 6,599,284 B2 | 7/2003 | Faour et al. |
| 6,605,038 B1 | 8/2003 | Teller |
| 6,605,046 B1 | 8/2003 | Del Mar |
| 6,609,018 B2 | 8/2003 | Cory |
| 6,612,984 B1 | 9/2003 | Kerr |
| 6,632,175 B1 | 10/2003 | Marshall |
| 6,632,216 B2 | 10/2003 | Houzego et al. |
| 6,635,279 B2 | 10/2003 | Kolter et al. |
| 6,643,541 B2 | 11/2003 | Mok et al. |
| 6,654,638 B1 | 11/2003 | Sweeney |
| 6,663,846 B1 | 12/2003 | McCombs |
| 6,673,474 B2 | 1/2004 | Yamamoto |
| 6,680,923 B1 | 1/2004 | Leon |
| 6,689,117 B2 | 2/2004 | Sweeney et al. |
| 6,694,161 B2 | 2/2004 | Mehrotra |
| 6,704,602 B2 | 3/2004 | Berg et al. |
| 6,720,923 B1 | 4/2004 | Hayward et al. |
| 6,738,671 B2 | 5/2004 | Christophersom et al. |
| 6,740,033 B1 | 5/2004 | Olejniczak et al. |
| 6,745,082 B2 | 6/2004 | Axelgaard et al. |
| 6,755,783 B2 | 6/2004 | Cosentino |
| 6,757,523 B2 | 6/2004 | Fry |
| 6,759,968 B2 | 7/2004 | Zierolf |
| 6,773,429 B2 | 8/2004 | Sheppard et al. |
| 6,800,060 B2 | 10/2004 | Marshall |
| 6,801,137 B2 | 10/2004 | Eggers et al. |
| 6,814,706 B2 | 11/2004 | Barton et al. |
| 6,822,554 B2 | 11/2004 | Vrijens et al. |
| 6,836,862 B1 | 12/2004 | Erekson et al. |
| 6,839,659 B2 | 1/2005 | Tarassenko et al. |
| 6,840,904 B2 | 1/2005 | Goldberg |
| 6,842,636 B2 | 1/2005 | Perrault |
| 6,845,272 B1 | 1/2005 | Thomsen |
| 6,864,780 B2 | 3/2005 | Doi |
| 6,879,810 B2 | 4/2005 | Bouet |
| 6,882,881 B1 | 4/2005 | Lesser et al. |
| 6,897,788 B2 | 5/2005 | Khair et al. |
| 6,909,878 B2 | 6/2005 | Haller |
| 6,922,592 B2 | 7/2005 | Thompson et al. |
| 6,928,370 B2 | 8/2005 | Anuzis et al. |
| 6,929,636 B1 | 8/2005 | Von Alten |
| 6,937,150 B2 | 8/2005 | Medema |
| 6,942,616 B2 | 9/2005 | Kerr |
| 6,951,536 B2 | 10/2005 | Yokoi |
| 6,957,107 B2 | 10/2005 | Rogers et al. |
| 6,959,929 B2 | 11/2005 | Pugnet et al. |
| 6,968,153 B1 | 11/2005 | Heinonen |
| 6,987,965 B2 | 1/2006 | Ng et al. |
| 6,990,082 B1 | 1/2006 | Zehavi et al. |
| 7,002,476 B2 | 2/2006 | Rapchak |
| 7,004,395 B2 | 2/2006 | Koenck |
| 7,009,634 B2 | 3/2006 | Iddan et al. |
| 7,009,946 B1 | 3/2006 | Kardach |
| 7,013,162 B2 | 3/2006 | Gorsuch |
| 7,016,648 B2 | 3/2006 | Haller |
| 7,020,508 B2 | 3/2006 | Stivoric |
| 7,024,248 B2 | 4/2006 | Penner et al. |
| 7,031,745 B2 | 4/2006 | Shen |
| 7,031,857 B2 | 4/2006 | Tarassenko et al. |
| 7,039,453 B2 | 5/2006 | Mullick |
| 7,044,911 B2 | 5/2006 | Drinan et al. |
| 7,046,649 B2 | 5/2006 | Awater et al. |
| 7,076,437 B1 | 7/2006 | Levy |
| 7,118,531 B2 | 10/2006 | Krill |
| 7,127,300 B2 | 10/2006 | Mazar et al. |
| 7,146,228 B2 | 12/2006 | Nielsen |
| 7,146,449 B2 | 12/2006 | Do et al. |
| 7,149,581 B2 | 12/2006 | Goedeke et al. |
| 7,154,071 B2 | 12/2006 | Sattler et al. |
| 7,155,232 B2 | 12/2006 | Godfrey et al. |
| 7,160,258 B2 | 1/2007 | Imran |
| 7,161,484 B2 | 1/2007 | Tsoukalis |
| 7,164,942 B2 | 1/2007 | Avrahami |
| 7,171,166 B2 | 1/2007 | Ng et al. |
| 7,171,177 B2 | 1/2007 | Park et al. |
| 7,171,259 B2 | 1/2007 | Rytky |
| 7,176,784 B2 | 2/2007 | Gilbert et al. |
| 7,187,960 B2 | 3/2007 | Abreu |
| 7,188,767 B2 | 3/2007 | Penuela |
| 7,194,038 B1 | 3/2007 | Inkinen |
| 7,206,630 B1 | 4/2007 | Tarler |
| 7,209,790 B2 | 4/2007 | Thompson et al. |
| 7,215,660 B2 | 5/2007 | Perlman |
| 7,215,991 B2 | 5/2007 | Besson |
| 7,218,967 B2 | 5/2007 | Bergelson |
| 7,231,451 B2 | 6/2007 | Law |
| 7,243,118 B2 | 7/2007 | Lou |
| 7,246,521 B2 | 7/2007 | Kim |
| 7,249,212 B2 | 7/2007 | Do |
| 7,252,792 B2 | 8/2007 | Perrault |
| 7,253,716 B2 | 8/2007 | Lovoi et al. |
| 7,261,690 B2 | 8/2007 | Teller |
| 7,270,633 B1 | 9/2007 | Goscha |
| 7,273,454 B2 | 9/2007 | Raymond et al. |
| 7,285,090 B2 | 10/2007 | Stivoric et al. |
| 7,289,855 B2 | 10/2007 | Nghiem |
| 7,291,497 B2 | 11/2007 | Holmes |
| 7,292,139 B2 | 11/2007 | Mazar et al. |
| 7,294,105 B1 | 11/2007 | Islam |
| 7,313,163 B2 | 12/2007 | Liu |
| 7,317,378 B2 | 1/2008 | Jarvis et al. |
| 7,318,808 B2 | 1/2008 | Tarassenko et al. |
| 7,336,929 B2 | 2/2008 | Yasuda |
| 7,342,895 B2 | 3/2008 | Serpa |
| 7,346,380 B2 | 3/2008 | Axelgaard et al. |
| 7,349,722 B2 | 3/2008 | Witkowski et al. |
| 7,352,998 B2 | 4/2008 | Palin |
| 7,353,258 B2 | 4/2008 | Washburn |
| 7,357,891 B2 | 4/2008 | Yang et al. |
| 7,359,674 B2 | 4/2008 | Markki |
| 7,366,558 B2 | 4/2008 | Virtanen et al. |
| 7,368,190 B2 | 5/2008 | Heller et al. |
| 7,368,191 B2 | 5/2008 | Andelman et al. |
| 7,373,196 B2 | 5/2008 | Ryu et al. |
| 7,375,739 B2 | 5/2008 | Robbins |
| 7,376,435 B2 | 5/2008 | McGowan |
| 7,382,263 B2 | 6/2008 | Danowski et al. |
| 7,387,607 B2 | 6/2008 | Holt |
| 7,388,903 B2 | 6/2008 | Godfrey et al. |
| 7,389,088 B2 | 6/2008 | Kim |
| 7,392,015 B1 | 6/2008 | Farlow |
| 7,395,106 B2 | 7/2008 | Ryu et al. |
| 7,396,330 B2 | 7/2008 | Banet |
| 7,404,968 B2 | 7/2008 | Abrams et al. |
| 7,413,544 B2 | 8/2008 | Kerr |
| 7,414,534 B1 | 8/2008 | Kroll et al. |
| 7,414,543 B2 | 8/2008 | Rye et al. |
| 7,415,242 B1 | 8/2008 | Ngan |
| 7,424,268 B2 | 9/2008 | Diener |
| 7,424,319 B2 | 9/2008 | Muehlsteff |
| 7,427,266 B2 | 9/2008 | Ayer et al. |
| 7,471,665 B2 | 12/2008 | Perlman |
| 7,499,674 B2 | 3/2009 | Salokannel |
| 7,502,643 B2 | 3/2009 | Farringdon et al. |
| 7,505,795 B1 | 3/2009 | Lim et al. |
| 7,510,121 B2 | 3/2009 | Koenck |
| 7,512,448 B2 | 3/2009 | Malick |
| 7,515,043 B2 | 4/2009 | Welch |
| 7,519,416 B2 | 4/2009 | Sula et al. |
| 7,523,756 B2 | 4/2009 | Minai |
| 7,525,426 B2 | 4/2009 | Edelstein |
| 7,539,533 B2 | 5/2009 | Tran |
| 7,542,878 B2 | 6/2009 | Nanikashvili |
| 7,551,590 B2 | 6/2009 | Haller |
| 7,554,452 B2 | 6/2009 | Cole |
| 7,558,620 B2 | 7/2009 | Ishibashi |
| 7,575,005 B2 | 8/2009 | Mumford |
| 7,616,111 B2 | 11/2009 | Covannon |
| 7,616,710 B2 | 11/2009 | Kim et al. |
| 7,617,001 B2 | 11/2009 | Penner et al. |
| 7,639,473 B2 | 12/2009 | Hsu et al. |
| 7,640,802 B2 | 1/2010 | King et al. |

(56) References Cited

U.S. PATENT DOCUMENTS

| | | |
|---|---|---|
| 7,647,112 B2 | 1/2010 | Tracey |
| 7,647,185 B2 | 1/2010 | Tarassenko et al. |
| 7,653,031 B2 | 1/2010 | Godfrey et al. |
| 7,668,437 B1 | 2/2010 | Yamada et al. |
| 7,672,703 B2 | 3/2010 | Yeo et al. |
| 7,672,714 B2 | 3/2010 | Kuo |
| 7,673,679 B2 | 3/2010 | Harrison et al. |
| 7,678,043 B2 | 3/2010 | Gilad |
| 7,689,437 B1 | 3/2010 | Teller et al. |
| 7,697,994 B2 | 4/2010 | VanDanacker et al. |
| 7,720,036 B2 | 5/2010 | Sadri et al. |
| 7,729,776 B2 | 6/2010 | Von Arx et al. |
| 7,733,224 B2 | 6/2010 | Tran |
| 7,736,318 B2 | 6/2010 | Cosentino |
| 7,756,587 B2 | 7/2010 | Penner et al. |
| 7,779,614 B1 | 8/2010 | McGonagle et al. |
| 7,796,043 B2 | 9/2010 | Euliano et al. |
| 7,797,033 B2 | 9/2010 | D'Andrea et al. |
| 7,806,852 B1 | 10/2010 | Jurson |
| 7,809,399 B2 | 10/2010 | Lu |
| 7,844,341 B2 | 11/2010 | Von Arx et al. |
| 7,904,133 B2 | 3/2011 | Gehman et al. |
| D639,437 S | 6/2011 | Bishay et al. |
| 8,025,149 B2 | 9/2011 | Sterry et al. |
| 8,036,731 B2 | 10/2011 | Kimchy et al. |
| 8,073,707 B2 | 12/2011 | Teller et al. |
| 8,083,128 B2 | 12/2011 | Dembo et al. |
| 8,123,576 B2 | 2/2012 | Kim |
| 8,180,425 B2 | 5/2012 | Selvitelli et al. |
| 8,200,320 B2 | 6/2012 | Kovacs |
| 8,214,007 B2 | 7/2012 | Baker et al. |
| 8,224,667 B1 * | 7/2012 | Miller et al. ............ 705/2 |
| 8,238,998 B2 | 8/2012 | Park |
| 8,249,686 B2 | 8/2012 | Libbus et al. |
| 8,258,962 B2 | 9/2012 | Robertson et al. |
| 8,285,356 B2 | 10/2012 | Bly et al. |
| 8,290,574 B2 | 10/2012 | Felid et al. |
| 8,301,232 B2 | 10/2012 | Albert et al. |
| 8,308,640 B2 | 11/2012 | Baldus et al. |
| 8,315,687 B2 | 11/2012 | Cross et al. |
| 8,369,936 B2 | 2/2013 | Farringdon et al. |
| 8,386,009 B2 | 2/2013 | Lindberg et al. |
| 8,389,003 B2 | 3/2013 | Mintchev et al. |
| 8,440,274 B2 | 5/2013 | Wang |
| 8,597,186 B2 | 12/2013 | Hafezi et al. |
| 9,047,746 B1 * | 6/2015 | Euliano, II ............ G08B 23/00 |
| 2001/0027331 A1 | 10/2001 | Thompson |
| 2001/0031071 A1 | 10/2001 | Nichols et al. |
| 2001/0044588 A1 | 11/2001 | Mault |
| 2001/0051766 A1 | 12/2001 | Gazdzinski |
| 2001/0056262 A1 | 12/2001 | Cabiri et al. |
| 2002/0002326 A1 | 1/2002 | Causey et al. |
| 2002/0026111 A1 | 2/2002 | Ackerman |
| 2002/0032384 A1 | 3/2002 | Raymond et al. |
| 2002/0032385 A1 | 3/2002 | Raymond et al. |
| 2002/0040278 A1 | 4/2002 | Anuzis et al. |
| 2002/0077620 A1 | 6/2002 | Sweeney et al. |
| 2002/0132226 A1 | 9/2002 | Nair |
| 2002/0138009 A1 | 9/2002 | Brockway et al. |
| 2002/0192159 A1 | 12/2002 | Reitberg |
| 2002/0193669 A1 | 12/2002 | Glukhovsky |
| 2002/0193846 A1 | 12/2002 | Pool et al. |
| 2002/0198470 A1 | 12/2002 | Imran et al. |
| 2003/0017826 A1 | 1/2003 | Fishman |
| 2003/0023150 A1 | 1/2003 | Yokoi et al. |
| 2003/0028226 A1 | 2/2003 | Thompson |
| 2003/0063522 A1 | 4/2003 | Sagar |
| 2003/0065536 A1 | 4/2003 | Hansen |
| 2003/0076179 A1 | 4/2003 | Branch et al. |
| 2003/0083559 A1 | 5/2003 | Thompson |
| 2003/0126593 A1 | 7/2003 | Mault |
| 2003/0130714 A1 | 7/2003 | Nielsen et al. |
| 2003/0135128 A1 | 7/2003 | Suffin et al. |
| 2003/0135392 A1 | 7/2003 | Vrijens et al. |
| 2003/0152622 A1 | 8/2003 | Louie-Helm et al. |
| 2003/0158466 A1 | 8/2003 | Lynn et al. |
| 2003/0158756 A1 | 8/2003 | Abramson |
| 2003/0162556 A1 | 8/2003 | Libes |
| 2003/0164401 A1 | 9/2003 | Andreasson et al. |
| 2003/0167000 A1 | 9/2003 | Mullick et al. |
| 2003/0171791 A1 | 9/2003 | KenKnight |
| 2003/0171898 A1 | 9/2003 | Tarassenko et al. |
| 2003/0181788 A1 | 9/2003 | Yokoi et al. |
| 2003/0181815 A1 | 9/2003 | Ebner et al. |
| 2003/0185286 A1 | 10/2003 | Yuen |
| 2003/0187337 A1 | 10/2003 | Tarassenko et al. |
| 2003/0187338 A1 | 10/2003 | Say et al. |
| 2003/0195403 A1 | 10/2003 | Berner et al. |
| 2003/0213495 A1 | 11/2003 | Fujita et al. |
| 2003/0214579 A1 | 11/2003 | Iddan |
| 2003/0216622 A1 | 11/2003 | Meron et al. |
| 2003/0216625 A1 | 11/2003 | Phipps |
| 2003/0216666 A1 | 11/2003 | Ericson et al. |
| 2003/0216729 A1 | 11/2003 | Marchitto |
| 2003/0229382 A1 | 12/2003 | Sun et al. |
| 2003/0232895 A1 | 12/2003 | Omidian et al. |
| 2004/0008123 A1 | 1/2004 | Carrender et al. |
| 2004/0018476 A1 | 1/2004 | LaDue |
| 2004/0019172 A1 | 1/2004 | Yang et al. |
| 2004/0034295 A1 | 2/2004 | Salganicoff |
| 2004/0049245 A1 | 3/2004 | Gass |
| 2004/0073095 A1 | 4/2004 | Causey et al. |
| 2004/0073454 A1 | 4/2004 | Urquhart et al. |
| 2004/0077995 A1 | 4/2004 | Ferek-Petric |
| 2004/0082982 A1 | 4/2004 | Gord et al. |
| 2004/0087839 A1 | 5/2004 | Raymond et al. |
| 2004/0092801 A1 | 5/2004 | Drakulic |
| 2004/0106859 A1 | 6/2004 | Say et al. |
| 2004/0111011 A1 | 6/2004 | Uchiyama et al. |
| 2004/0115517 A1 | 6/2004 | Fukuda et al. |
| 2004/0121015 A1 | 6/2004 | Chidlaw et al. |
| 2004/0122297 A1 | 6/2004 | Stahmann et al. |
| 2004/0148140 A1 | 7/2004 | Tarassenko et al. |
| 2004/0153007 A1 | 8/2004 | Harris |
| 2004/0167226 A1 | 8/2004 | Serafini |
| 2004/0167801 A1 | 8/2004 | Say et al. |
| 2004/0171914 A1 | 9/2004 | Avni |
| 2004/0193020 A1 | 9/2004 | Chiba |
| 2004/0193029 A1 | 9/2004 | Gluhovsky |
| 2004/0193446 A1 | 9/2004 | Mayer et al. |
| 2004/0199222 A1 | 10/2004 | Sun et al. |
| 2004/0215084 A1 | 10/2004 | Shimizu et al. |
| 2004/0218683 A1 | 11/2004 | Batra |
| 2004/0220643 A1 | 11/2004 | Schmidt |
| 2004/0224644 A1 | 11/2004 | Wu |
| 2004/0225199 A1 | 11/2004 | Evanyk |
| 2004/0253304 A1 | 12/2004 | Gross et al. |
| 2004/0258571 A1 | 12/2004 | Lee et al. |
| 2004/0260154 A1 | 12/2004 | Sidelnik |
| 2004/0267240 A1 | 12/2004 | Gross et al. |
| 2005/0017841 A1 | 1/2005 | Doi |
| 2005/0020887 A1 | 1/2005 | Goldberg |
| 2005/0021103 A1 | 1/2005 | DiLorenzo |
| 2005/0021370 A1 | 1/2005 | Riff |
| 2005/0024198 A1 | 2/2005 | Ward |
| 2005/0027205 A1 | 2/2005 | Tarassenko et al. |
| 2005/0038321 A1 | 2/2005 | Fujita et al. |
| 2005/0043634 A1 | 2/2005 | Yokoi et al. |
| 2005/0043894 A1 | 2/2005 | Fernandez |
| 2005/0054897 A1 | 3/2005 | Hashimoto et al. |
| 2005/0055014 A1 | 3/2005 | Coppeta et al. |
| 2005/0062644 A1 | 3/2005 | Leci |
| 2005/0065407 A1 | 3/2005 | Nakamura et al. |
| 2005/0070778 A1 | 3/2005 | Lackey |
| 2005/0075145 A1 | 4/2005 | Dvorak et al. |
| 2005/0090753 A1 | 4/2005 | Goor et al. |
| 2005/0092108 A1 | 5/2005 | Andermo |
| 2005/0096514 A1 | 5/2005 | Starkebaum |
| 2005/0096562 A1 | 5/2005 | Delalic et al. |
| 2005/0101843 A1 | 5/2005 | Quinn |
| 2005/0101872 A1 | 5/2005 | Sattler |
| 2005/0115561 A1 | 6/2005 | Stahmann et al. |
| 2005/0116820 A1 | 6/2005 | Goldreich |
| 2005/0117389 A1 | 6/2005 | Worledge |

(56) References Cited

U.S. PATENT DOCUMENTS

| | | |
|---|---|---|
| 2005/0121322 A1 | 6/2005 | Say et al. |
| 2005/0131281 A1 | 6/2005 | Ayer et al. |
| 2005/0137480 A1 | 6/2005 | Alt et al. |
| 2005/0143623 A1 | 6/2005 | Kojima |
| 2005/0148883 A1 | 7/2005 | Boesen |
| 2005/0151625 A1 | 7/2005 | Lai |
| 2005/0154428 A1 | 7/2005 | Bruinsma |
| 2005/0156709 A1 | 7/2005 | Gilbert et al. |
| 2005/0165323 A1 | 7/2005 | Montgomery |
| 2005/0177069 A1 | 8/2005 | Takizawa |
| 2005/0182389 A1 | 8/2005 | LaPorte |
| 2005/0187789 A1 | 8/2005 | Hatlestad et al. |
| 2005/0192489 A1 | 9/2005 | Marshall |
| 2005/0197680 A1 | 9/2005 | DelMain et al. |
| 2005/0228268 A1 | 10/2005 | Cole |
| 2005/0234307 A1 | 10/2005 | Heinonen |
| 2005/0240305 A1 | 10/2005 | Bogash et al. |
| 2005/0245794 A1 | 11/2005 | Dinsmoor |
| 2005/0245839 A1 | 11/2005 | Stivoric et al. |
| 2005/0259768 A1 | 11/2005 | Yang et al. |
| 2005/0261559 A1 | 11/2005 | Mumford |
| 2005/0267556 A1 | 12/2005 | Shuros et al. |
| 2005/0267756 A1 | 12/2005 | Schultz et al. |
| 2005/0277912 A1 | 12/2005 | John |
| 2005/0277999 A1 | 12/2005 | Strother et al. |
| 2005/0280539 A1 | 12/2005 | Pettus |
| 2005/0285746 A1 | 12/2005 | Sengupta |
| 2005/0288594 A1 | 12/2005 | Lewkowicz et al. |
| 2006/0001496 A1 | 1/2006 | Abrosimov et al. |
| 2006/0028727 A1 | 2/2006 | Moon et al. |
| 2006/0036134 A1 | 2/2006 | Tarassenko et al. |
| 2006/0058602 A1 | 3/2006 | Kwiatkowski et al. |
| 2006/0061472 A1 | 3/2006 | Lovoi et al. |
| 2006/0065713 A1 | 3/2006 | Kingery |
| 2006/0068006 A1 | 3/2006 | Begleiter |
| 2006/0074283 A1 | 4/2006 | Henderson |
| 2006/0074319 A1 | 4/2006 | Barnes et al. |
| 2006/0078765 A1 | 4/2006 | Yang et al. |
| 2006/0095091 A1 | 5/2006 | Drew |
| 2006/0095093 A1 | 5/2006 | Bettesh et al. |
| 2006/0100533 A1 | 5/2006 | Han |
| 2006/0109058 A1 | 5/2006 | Keating |
| 2006/0110962 A1 | 5/2006 | Powell |
| 2006/0122474 A1 | 6/2006 | Teller et al. |
| 2006/0122667 A1 | 6/2006 | Chavan et al. |
| 2006/0136266 A1 | 6/2006 | Tarassenko et al. |
| 2006/0142648 A1 | 6/2006 | Banet |
| 2006/0145876 A1 | 7/2006 | Kimura |
| 2006/0148254 A1 | 7/2006 | McLean |
| 2006/0149339 A1 | 7/2006 | Burnes |
| 2006/0155174 A1 | 7/2006 | Glukhovsky et al. |
| 2006/0155183 A1 | 7/2006 | Kroecker |
| 2006/0158820 A1 | 7/2006 | Takiguchi |
| 2006/0161225 A1 | 7/2006 | Sormann et al. |
| 2006/0179949 A1 | 8/2006 | Kim |
| 2006/0183992 A1 | 8/2006 | Kawashima |
| 2006/0183993 A1 | 8/2006 | Horn |
| 2006/0184092 A1 | 8/2006 | Atanasoska et al. |
| 2006/0204738 A1 | 9/2006 | Dubrow et al. |
| 2006/0210626 A1 | 9/2006 | Spaeder |
| 2006/0216603 A1 | 9/2006 | Choi |
| 2006/0218011 A1 | 9/2006 | Walker |
| 2006/0229053 A1 | 10/2006 | Sivard |
| 2006/0235489 A1 | 10/2006 | Drew |
| 2006/0243288 A1 | 11/2006 | Kim et al. |
| 2006/0247505 A1 | 11/2006 | Siddiqui |
| 2006/0253005 A1 | 11/2006 | Drinan |
| 2006/0255064 A1 | 11/2006 | Donaldson |
| 2006/0265246 A1 | 11/2006 | Hoag |
| 2006/0267774 A1 | 11/2006 | Feinberg et al. |
| 2006/0270346 A1 | 11/2006 | Ibrahim |
| 2006/0273882 A1 | 12/2006 | Posamentier |
| 2006/0276702 A1 | 12/2006 | McGinnis |
| 2006/0280227 A1 | 12/2006 | Pinkney |
| 2006/0282001 A1 | 12/2006 | Noel |
| 2006/0289640 A1 | 12/2006 | Mercure |
| 2006/0293607 A1 | 12/2006 | Alt |
| 2007/0000776 A1 | 1/2007 | Karube et al. |
| 2007/0002038 A1 | 1/2007 | Suzuki |
| 2007/0006636 A1 | 1/2007 | King et al. |
| 2007/0008113 A1 | 1/2007 | Spoonhower et al. |
| 2007/0016089 A1 | 1/2007 | Fischell et al. |
| 2007/0027386 A1 | 2/2007 | Such |
| 2007/0027388 A1 | 2/2007 | Chou |
| 2007/0038054 A1 | 2/2007 | Zhou |
| 2007/0049339 A1 | 3/2007 | Barak et al. |
| 2007/0055098 A1 | 3/2007 | Shimizu et al. |
| 2007/0060797 A1 | 3/2007 | Ball |
| 2007/0060800 A1 | 3/2007 | Drinan et al. |
| 2007/0066929 A1 | 3/2007 | Ferren et al. |
| 2007/0073353 A1 | 3/2007 | Rooney et al. |
| 2007/0096765 A1 | 5/2007 | Kagan |
| 2007/0106346 A1 | 5/2007 | Bergelson |
| 2007/0123772 A1 | 5/2007 | Euliano |
| 2007/0129622 A1 | 6/2007 | Bourget |
| 2007/0130287 A1 | 6/2007 | Kumar |
| 2007/0135691 A1 | 6/2007 | Zingelewicz et al. |
| 2007/0135803 A1 | 6/2007 | Belson |
| 2007/0142721 A1 | 6/2007 | Berner et al. |
| 2007/0156016 A1 | 7/2007 | Betesh |
| 2007/0160789 A1 | 7/2007 | Merical |
| 2007/0162089 A1 | 7/2007 | Mosesov |
| 2007/0162090 A1 | 7/2007 | Penner |
| 2007/0167495 A1 | 7/2007 | Brown et al. |
| 2007/0167848 A1 | 7/2007 | Kuo et al. |
| 2007/0173701 A1 | 7/2007 | Al-Ali |
| 2007/0179347 A1 | 8/2007 | Tarassenko et al. |
| 2007/0179371 A1 | 8/2007 | Peyser et al. |
| 2007/0180047 A1 | 8/2007 | Dong et al. |
| 2007/0185393 A1 | 8/2007 | Zhou |
| 2007/0191002 A1 | 8/2007 | Ge |
| 2007/0196456 A1 | 8/2007 | Stevens |
| 2007/0207793 A1 | 9/2007 | Myer |
| 2007/0207858 A1 | 9/2007 | Breving |
| 2007/0208233 A1 | 9/2007 | Kovacs |
| 2007/0213659 A1 | 9/2007 | Trovato et al. |
| 2007/0237719 A1 | 10/2007 | Jones |
| 2007/0244370 A1 | 10/2007 | Kuo et al. |
| 2007/0249946 A1 | 10/2007 | Kumar et al. |
| 2007/0255198 A1 | 11/2007 | Leong et al. |
| 2007/0255330 A1 | 11/2007 | Lee |
| 2007/0270672 A1* | 11/2007 | Hayter ................. 600/309 |
| 2007/0279217 A1 | 12/2007 | Venkatraman |
| 2007/0282174 A1 | 12/2007 | Sabatino |
| 2007/0282177 A1 | 12/2007 | Pilz |
| 2007/0291715 A1 | 12/2007 | Laroia et al. |
| 2007/0299480 A1 | 12/2007 | Hill |
| 2008/0014866 A1 | 1/2008 | Lipowski |
| 2008/0015421 A1 | 1/2008 | Penner |
| 2008/0015494 A1 | 1/2008 | Santini et al. |
| 2008/0020037 A1 | 1/2008 | Robertson et al. |
| 2008/0021519 A1 | 1/2008 | DeGeest |
| 2008/0021521 A1 | 1/2008 | Shah |
| 2008/0027679 A1 | 1/2008 | Shklarski |
| 2008/0033273 A1 | 2/2008 | Zhou |
| 2008/0033301 A1 | 2/2008 | Dellavecchia et al. |
| 2008/0038588 A1 | 2/2008 | Lee |
| 2008/0039700 A1 | 2/2008 | Drinan et al. |
| 2008/0045843 A1 | 2/2008 | Tsuji et al. |
| 2008/0046038 A1 | 2/2008 | Hill |
| 2008/0051647 A1 | 2/2008 | Wu et al. |
| 2008/0051667 A1 | 2/2008 | Goldreich |
| 2008/0051767 A1 | 2/2008 | Rossing et al. |
| 2008/0058614 A1 | 3/2008 | Banet |
| 2008/0062856 A1 | 3/2008 | Feher |
| 2008/0065168 A1 | 3/2008 | Bitton et al. |
| 2008/0074307 A1 | 3/2008 | Boric-Lubecke |
| 2008/0077015 A1 | 3/2008 | Boric-Lubecke |
| 2008/0077028 A1 | 3/2008 | Schaldach et al. |
| 2008/0077188 A1 | 3/2008 | Denker et al. |
| 2008/0091089 A1 | 4/2008 | Guillory et al. |
| 2008/0091114 A1 | 4/2008 | Min |
| 2008/0097549 A1 | 4/2008 | Colbaugh |
| 2008/0097917 A1 | 4/2008 | Dicks |

(56) References Cited

U.S. PATENT DOCUMENTS

| | | |
|---|---|---|
| 2008/0099366 A1 | 5/2008 | Niemic et al. |
| 2008/0103440 A1 | 5/2008 | Ferren et al. |
| 2008/0114224 A1 | 5/2008 | Bandy et al. |
| 2008/0119705 A1 | 5/2008 | Patel |
| 2008/0119716 A1 | 5/2008 | Boric-Lubecke |
| 2008/0121825 A1 | 5/2008 | Trovato et al. |
| 2008/0137566 A1 | 6/2008 | Marholev |
| 2008/0139907 A1 | 6/2008 | Rao et al. |
| 2008/0140403 A1 | 6/2008 | Hughes et al. |
| 2008/0146871 A1 | 6/2008 | Arneson et al. |
| 2008/0146889 A1 | 6/2008 | Young |
| 2008/0146892 A1 | 6/2008 | LeBoeuf |
| 2008/0154104 A1 | 6/2008 | Lamego |
| 2008/0166992 A1 | 7/2008 | Ricordi |
| 2008/0175898 A1 | 7/2008 | Jones et al. |
| 2008/0183245 A1 | 7/2008 | Van Oort |
| 2008/0188837 A1 | 8/2008 | Belsky et al. |
| 2008/0194912 A1 | 8/2008 | Trovato et al. |
| 2008/0208009 A1 | 8/2008 | Shklarski |
| 2008/0214901 A1 | 9/2008 | Gehman |
| 2008/0214985 A1 | 9/2008 | Yanaki |
| 2008/0223936 A1 | 9/2008 | Mickle et al. |
| 2008/0243020 A1 | 10/2008 | Chou |
| 2008/0249360 A1 | 10/2008 | Li |
| 2008/0262320 A1 | 10/2008 | Schaefer et al. |
| 2008/0262336 A1 | 10/2008 | Ryu |
| 2008/0269664 A1 | 10/2008 | Trovato et al. |
| 2008/0275312 A1 | 11/2008 | Mosesov |
| 2008/0281636 A1* | 11/2008 | Jung et al. ................ 705/3 |
| 2008/0284599 A1 | 11/2008 | Zdeblick et al. |
| 2008/0288026 A1 | 11/2008 | Cross et al. |
| 2008/0288027 A1 | 11/2008 | Kroll |
| 2008/0294020 A1 | 11/2008 | Sapounas |
| 2008/0299197 A1 | 12/2008 | Toneguzzo et al. |
| 2008/0300572 A1 | 12/2008 | Rankers |
| 2008/0303638 A1 | 12/2008 | Nguyen |
| 2008/0306357 A1 | 12/2008 | Korman |
| 2008/0306359 A1 | 12/2008 | Zdeblick et al. |
| 2008/0306360 A1 | 12/2008 | Robertson et al. |
| 2008/0306362 A1 | 12/2008 | Davis |
| 2008/0311852 A1 | 12/2008 | Hansen |
| 2008/0312522 A1 | 12/2008 | Rowlandson |
| 2008/0316020 A1 | 12/2008 | Robertson |
| 2009/0009330 A1 | 1/2009 | Sakama et al. |
| 2009/0009332 A1 | 1/2009 | Nunez et al. |
| 2009/0024045 A1 | 1/2009 | Prakash |
| 2009/0024112 A1 | 1/2009 | Edwards et al. |
| 2009/0030293 A1 | 1/2009 | Cooper et al. |
| 2009/0030297 A1 | 1/2009 | Miller |
| 2009/0034209 A1 | 2/2009 | Joo |
| 2009/0043171 A1 | 2/2009 | Rule |
| 2009/0048498 A1 | 2/2009 | Riskey |
| 2009/0062634 A1 | 3/2009 | Say et al. |
| 2009/0062670 A1 | 3/2009 | Sterling |
| 2009/0069642 A1 | 3/2009 | Gao |
| 2009/0069655 A1 | 3/2009 | Say et al. |
| 2009/0069656 A1 | 3/2009 | Say et al. |
| 2009/0069657 A1 | 3/2009 | Say et al. |
| 2009/0069658 A1 | 3/2009 | Say et al. |
| 2009/0076340 A1 | 3/2009 | Libbus et al. |
| 2009/0076343 A1 | 3/2009 | James |
| 2009/0076397 A1 | 3/2009 | Libbus et al. |
| 2009/0082645 A1 | 3/2009 | Hafezi et al. |
| 2009/0087483 A1 | 4/2009 | Sison |
| 2009/0088618 A1 | 4/2009 | Arneson |
| 2009/0099435 A1 | 4/2009 | Say et al. |
| 2009/0105561 A1 | 4/2009 | Boyden et al. |
| 2009/0110148 A1 | 4/2009 | Zhang |
| 2009/0112626 A1 | 4/2009 | Talbot |
| 2009/0124871 A1 | 5/2009 | Arshak |
| 2009/0131774 A1 | 5/2009 | Sweitzer |
| 2009/0135886 A1 | 5/2009 | Robertson et al. |
| 2009/0142853 A1 | 6/2009 | Warrington et al. |
| 2009/0149839 A1 | 6/2009 | Hyde et al. |
| 2009/0157113 A1 | 6/2009 | Marcotte |
| 2009/0157358 A1 | 6/2009 | Kim |
| 2009/0161602 A1 | 6/2009 | Matsumoto |
| 2009/0163789 A1 | 6/2009 | Say et al. |
| 2009/0171180 A1 | 7/2009 | Pering |
| 2009/0173628 A1 | 7/2009 | Say et al. |
| 2009/0177055 A1 | 7/2009 | Say et al. |
| 2009/0177056 A1 | 7/2009 | Say et al. |
| 2009/0177057 A1 | 7/2009 | Say et al. |
| 2009/0177058 A1 | 7/2009 | Say et al. |
| 2009/0177059 A1 | 7/2009 | Say et al. |
| 2009/0177060 A1 | 7/2009 | Say et al. |
| 2009/0177061 A1 | 7/2009 | Say et al. |
| 2009/0177062 A1 | 7/2009 | Say et al. |
| 2009/0177063 A1 | 7/2009 | Say et al. |
| 2009/0177064 A1 | 7/2009 | Say et al. |
| 2009/0177065 A1 | 7/2009 | Say et al. |
| 2009/0177066 A1 | 7/2009 | Say et al. |
| 2009/0182206 A1 | 7/2009 | Najafi |
| 2009/0182207 A1 | 7/2009 | Riskey et al. |
| 2009/0182212 A1 | 7/2009 | Say et al. |
| 2009/0182213 A1 | 7/2009 | Say et al. |
| 2009/0182214 A1 | 7/2009 | Say et al. |
| 2009/0182215 A1 | 7/2009 | Say et al. |
| 2009/0182388 A1 | 7/2009 | Von Arx |
| 2009/0187088 A1 | 7/2009 | Say et al. |
| 2009/0187089 A1 | 7/2009 | Say et al. |
| 2009/0187090 A1 | 7/2009 | Say et al. |
| 2009/0187091 A1 | 7/2009 | Say et al. |
| 2009/0187092 A1 | 7/2009 | Say et al. |
| 2009/0187093 A1 | 7/2009 | Say et al. |
| 2009/0187094 A1 | 7/2009 | Say et al. |
| 2009/0187095 A1 | 7/2009 | Say et al. |
| 2009/0187381 A1 | 7/2009 | King et al. |
| 2009/0192351 A1 | 7/2009 | Nishino |
| 2009/0192368 A1 | 7/2009 | Say et al. |
| 2009/0192369 A1 | 7/2009 | Say et al. |
| 2009/0192370 A1 | 7/2009 | Say et al. |
| 2009/0192371 A1 | 7/2009 | Say et al. |
| 2009/0192372 A1 | 7/2009 | Say et al. |
| 2009/0192373 A1 | 7/2009 | Say et al. |
| 2009/0192374 A1 | 7/2009 | Say et al. |
| 2009/0192375 A1 | 7/2009 | Say et al. |
| 2009/0192376 A1 | 7/2009 | Say et al. |
| 2009/0192377 A1 | 7/2009 | Say et al. |
| 2009/0192378 A1 | 7/2009 | Say et al. |
| 2009/0192379 A1 | 7/2009 | Say et al. |
| 2009/0198115 A1 | 8/2009 | Say et al. |
| 2009/0198116 A1 | 8/2009 | Say et al. |
| 2009/0198175 A1 | 8/2009 | Say et al. |
| 2009/0203964 A1 | 8/2009 | Shimizu et al. |
| 2009/0203971 A1 | 8/2009 | Sciarappa |
| 2009/0203972 A1 | 8/2009 | Heneghan |
| 2009/0203978 A1 | 8/2009 | Say et al. |
| 2009/0204265 A1 | 8/2009 | Hackett |
| 2009/0210164 A1 | 8/2009 | Say et al. |
| 2009/0216101 A1 | 8/2009 | Say et al. |
| 2009/0216102 A1 | 8/2009 | Say et al. |
| 2009/0227204 A1 | 9/2009 | Robertson et al. |
| 2009/0227876 A1 | 9/2009 | Tran |
| 2009/0227940 A1 | 9/2009 | Say et al. |
| 2009/0227941 A1 | 9/2009 | Say et al. |
| 2009/0227988 A1 | 9/2009 | Wood et al. |
| 2009/0228214 A1 | 9/2009 | Say et al. |
| 2009/0231125 A1 | 9/2009 | Baldus |
| 2009/0234200 A1 | 9/2009 | Husheer |
| 2009/0243833 A1 | 10/2009 | Huang |
| 2009/0253960 A1 | 10/2009 | Takenaka et al. |
| 2009/0256702 A1 | 10/2009 | Robertson |
| 2009/0264714 A1 | 10/2009 | Chou |
| 2009/0264964 A1 | 10/2009 | Abrahamson |
| 2009/0265186 A1 | 10/2009 | Tarassenko et al. |
| 2009/0273467 A1 | 11/2009 | Elixmann |
| 2009/0277815 A1 | 11/2009 | Kohl |
| 2009/0281539 A1 | 11/2009 | Selig |
| 2009/0292194 A1 | 11/2009 | Libbus et al. |
| 2009/0295548 A1 | 12/2009 | Ronkka |
| 2009/0296677 A1 | 12/2009 | Mahany |
| 2009/0301925 A1 | 12/2009 | Alloro et al. |
| 2009/0303920 A1 | 12/2009 | Mahany |

(56) References Cited

U.S. PATENT DOCUMENTS

| | | |
|---|---|---|
| 2009/0306633 A1 | 12/2009 | Trovato et al. |
| 2009/0312619 A1 | 12/2009 | Say et al. |
| 2009/0318303 A1 | 12/2009 | Delamarche et al. |
| 2009/0318761 A1 | 12/2009 | Rabinovitz |
| 2009/0318779 A1 | 12/2009 | Tran |
| 2009/0318783 A1 | 12/2009 | Rohde |
| 2009/0318793 A1 | 12/2009 | Datta |
| 2010/0001841 A1 | 1/2010 | Cardullo |
| 2010/0006585 A1 | 1/2010 | Flowers et al. |
| 2010/0010330 A1 | 1/2010 | Rankers |
| 2010/0033324 A1 | 2/2010 | Shimizu et al. |
| 2010/0049004 A1 | 2/2010 | Edman et al. |
| 2010/0049006 A1 | 2/2010 | Magar |
| 2010/0049012 A1 | 2/2010 | Dijksman et al. |
| 2010/0049069 A1 | 2/2010 | Tarassenko et al. |
| 2010/0056878 A1 | 3/2010 | Partin |
| 2010/0056891 A1 | 3/2010 | Say et al. |
| 2010/0056939 A1 | 3/2010 | Tarassenko et al. |
| 2010/0057041 A1 | 3/2010 | Hayter |
| 2010/0062709 A1 | 3/2010 | Kato |
| 2010/0063438 A1 | 3/2010 | Bengtsson |
| 2010/0063841 A1 | 3/2010 | D'Ambrosia et al. |
| 2010/0069002 A1 | 3/2010 | Rong |
| 2010/0069717 A1 | 3/2010 | Hafezi et al. |
| 2010/0081894 A1 | 4/2010 | Zdeblick et al. |
| 2010/0099967 A1 | 4/2010 | Say et al. |
| 2010/0099968 A1 | 4/2010 | Say et al. |
| 2010/0099969 A1 | 4/2010 | Say et al. |
| 2010/0100077 A1 | 4/2010 | Rush et al. |
| 2010/0100078 A1 | 4/2010 | Say et al. |
| 2010/0106001 A1 | 4/2010 | Say et al. |
| 2010/0118853 A1 | 5/2010 | Godfrey |
| 2010/0139672 A1 | 6/2010 | Kroll et al. |
| 2010/0160742 A1 | 6/2010 | Seidl et al. |
| 2010/0168659 A1 | 7/2010 | Say et al. |
| 2010/0179398 A1 | 7/2010 | Say et al. |
| 2010/0185055 A1* | 7/2010 | Robertson et al. ............ 600/117 |
| 2010/0191073 A1 | 7/2010 | Tarassenko et al. |
| 2010/0210299 A1 | 8/2010 | Gorbachov |
| 2010/0222652 A1 | 9/2010 | Cho |
| 2010/0228113 A1 | 9/2010 | Solosko |
| 2010/0233026 A1 | 9/2010 | Ismagliov et al. |
| 2010/0234706 A1 | 9/2010 | Gilland |
| 2010/0234715 A1 | 9/2010 | Shin |
| 2010/0234914 A1 | 9/2010 | Shen |
| 2010/0245091 A1 | 9/2010 | Singh |
| 2010/0249881 A1 | 9/2010 | Corndorf |
| 2010/0256461 A1 | 10/2010 | Mohamedali |
| 2010/0259543 A1 | 10/2010 | Tarassenko et al. |
| 2010/0268048 A1 | 10/2010 | Say et al. |
| 2010/0268049 A1 | 10/2010 | Say et al. |
| 2010/0268050 A1 | 10/2010 | Say et al. |
| 2010/0274111 A1 | 10/2010 | Say et al. |
| 2010/0280345 A1 | 11/2010 | Say et al. |
| 2010/0280346 A1 | 11/2010 | Say et al. |
| 2010/0295694 A1 | 11/2010 | Kauffman et al. |
| 2010/0298668 A1 | 11/2010 | Hafezi et al. |
| 2010/0298730 A1 | 11/2010 | Tarassenko et al. |
| 2010/0299155 A1* | 11/2010 | Findlay et al. ................. 705/3 |
| 2010/0312188 A1 | 12/2010 | Robertson et al. |
| 2010/0312577 A1* | 12/2010 | Goodnow et al. .............. 705/2 |
| 2010/0312580 A1 | 12/2010 | Tarassenko et al. |
| 2010/0332443 A1 | 12/2010 | Gartenberg |
| 2011/0004079 A1 | 1/2011 | Al-Ali et al. |
| 2011/0009715 A1 | 1/2011 | O'Reilly et al. |
| 2011/0040203 A1 | 2/2011 | Savage et al. |
| 2011/0050431 A1 | 3/2011 | Hood et al. |
| 2011/0054265 A1 | 3/2011 | Hafezi et al. |
| 2011/0065983 A1 | 3/2011 | Hafezi et al. |
| 2011/0077660 A1 | 3/2011 | Janik et al. |
| 2011/0081860 A1 | 4/2011 | Brown et al. |
| 2011/0105864 A1 | 5/2011 | Robertson et al. |
| 2011/0124983 A1 | 5/2011 | Kroll et al. |
| 2011/0144470 A1 | 6/2011 | Mazar et al. |
| 2011/0193704 A1* | 8/2011 | Harper et al. ............. 340/573.1 |
| 2011/0224912 A1 | 9/2011 | Bhavaraju et al. |
| 2011/0230732 A1 | 9/2011 | Edman et al. |
| 2011/0237924 A1 | 9/2011 | McGusty et al. |
| 2011/0279963 A1 | 11/2011 | Kumar et al. |
| 2012/0024889 A1 | 2/2012 | Robertson et al. |
| 2012/0029309 A1 | 2/2012 | Paquet et al. |
| 2012/0062371 A1 | 3/2012 | Radivojevic et al. |
| 2012/0083715 A1* | 4/2012 | Yuen et al. ................. 600/595 |
| 2012/0089000 A1 | 4/2012 | Bishay et al. |
| 2012/0101396 A1 | 4/2012 | Solosko et al. |
| 2012/0197144 A1 | 8/2012 | Christ et al. |
| 2012/0214140 A1 | 8/2012 | Brynelsen et al. |
| 2012/0265544 A1* | 10/2012 | Hwang et al. .................. 705/1.1 |
| 2012/0299723 A1 | 11/2012 | Hafezi et al. |
| 2012/0310070 A1 | 12/2012 | Kumar et al. |
| 2012/0316413 A1 | 12/2012 | Liu et al. |
| 2013/0030259 A1 | 1/2013 | Thomsen et al. |
| 2013/0057385 A1 | 3/2013 | Murakami et al. |
| 2013/0060115 A1 | 3/2013 | Gehman et al. |

FOREIGN PATENT DOCUMENTS

| | | |
|---|---|---|
| CN | 201076456 | 6/2008 |
| EP | 0344939 | 12/1989 |
| EP | 1246356 | 10/2002 |
| EP | 1534054 | 5/2005 |
| EP | 1702553 | 9/2006 |
| EP | 1789128 | 5/2007 |
| EP | 2143369 | 1/2010 |
| GB | 2432862 | 6/2007 |
| IL | 172917 | 6/2010 |
| JP | 61017949 | 1/1986 |
| JP | 61072712 | 4/1986 |
| JP | 05-228128 | 9/1993 |
| JP | 09-330159 | 12/1997 |
| JP | 10-14898 | 1/1998 |
| JP | 2000-506410 | 5/2000 |
| JP | 2002-224053 | 8/2002 |
| JP | 2002263185 | 9/2002 |
| JP | 2002291684 | 10/2002 |
| JP | 2004-7187 | 1/2004 |
| JP | 2004134384 | 4/2004 |
| JP | 2004-313242 | 11/2004 |
| JP | 2005-073886 | 3/2005 |
| JP | 2005-087552 | 4/2005 |
| JP | 2005-304880 | 4/2005 |
| JP | 2005124708 | 5/2005 |
| JP | 2005-532841 | 11/2005 |
| JP | 2005-532849 | 11/2005 |
| JP | 2006006377 | 1/2006 |
| JP | 2006509574 | 3/2006 |
| JP | 2006-177699 | 7/2006 |
| JP | 2006-187611 | 7/2006 |
| JP | 2006278091 | 10/2006 |
| JP | 2006346000 | 12/2006 |
| JP | 2007159631 | 6/2007 |
| JP | 2007-313340 | 12/2007 |
| JP | 2008011865 | 1/2008 |
| JP | 2008501415 | 1/2008 |
| JP | 2009-061236 | 3/2009 |
| KR | 20020015907 | 3/2002 |
| KR | 20020061744 | 7/2002 |
| KR | 200609977523 | 7/2006 |
| KR | 927471 | 11/2009 |
| KR | 10-2012-09995 | 9/2012 |
| TW | 553735 | 9/2003 |
| TW | 200724094 | 7/2007 |
| WO | WO8802237 | 4/1988 |
| WO | WO9221307 | 12/1992 |
| WO | WO9308734 | 5/1993 |
| WO | WO9319667 | 10/1993 |
| WO | WO9401165 | 1/1994 |
| WO | WO9714112 | 4/1997 |
| WO | WO9739963 | 10/1997 |
| WO | WO9843537 | 10/1998 |
| WO | WO9937290 | 7/1999 |
| WO | WO9959465 | 11/1999 |
| WO | WO0033246 | 6/2000 |
| WO | WO0100085 | 1/2001 |

(56) References Cited

FOREIGN PATENT DOCUMENTS

| | | |
|---|---|---|
| WO | WO0147466 | 7/2001 |
| WO | WO0149364 | 7/2001 |
| WO | WO0174011 | 10/2001 |
| WO | WO0180731 | 11/2001 |
| WO | WO0245489 | 6/2002 |
| WO | WO0258330 | 7/2002 |
| WO | WO0262276 | 8/2002 |
| WO | WO02087681 | 11/2002 |
| WO | WO02095351 | 11/2002 |
| WO | WO03005877 | 1/2003 |
| WO | WO03050643 | 6/2003 |
| WO | WO03068061 | 8/2003 |
| WO | WO2004014225 | 2/2004 |
| WO | WO2004019172 | 3/2004 |
| WO | WO2004039256 | 5/2004 |
| WO | WO2004059551 | 7/2004 |
| WO | WO2004066833 | 8/2004 |
| WO | WO2004066834 | 8/2004 |
| WO | WO2004066903 | 8/2004 |
| WO | WO2004068748 | 8/2004 |
| WO | WO2004068881 | 8/2004 |
| WO | WO2004075751 | 9/2004 |
| WO | WO2004109316 | 12/2004 |
| WO | WO2005011237 | 2/2005 |
| WO | WO2005020023 | 3/2005 |
| WO | WO2005024687 | 3/2005 |
| WO | WO2005041767 | 5/2005 |
| WO | WO2005047837 | 5/2005 |
| WO | WO2005051166 | 6/2005 |
| WO | WO2005053517 | 6/2005 |
| WO | WO2005082436 | 9/2005 |
| WO | WO2005083621 | 9/2005 |
| WO | WO2005110238 | 11/2005 |
| WO | WO2006021932 | 3/2006 |
| WO | WO2006027586 | 3/2006 |
| WO | WO2006028347 | 3/2006 |
| WO | WO2006035351 | 4/2006 |
| WO | WO2006046648 | 5/2006 |
| WO | WO2006055892 | 5/2006 |
| WO | WO2006055956 | 5/2006 |
| WO | WO2006075016 | 7/2006 |
| WO | WO2006100620 | 9/2006 |
| WO | WO2006109072 | 10/2006 |
| WO | WO2006116718 | 11/2006 |
| WO | WO2006119345 | 11/2006 |
| WO | WO2006127355 | 11/2006 |
| WO | WO2007001724 | 1/2007 |
| WO | WO2007001742 | 1/2007 |
| WO | WO2007013952 | 2/2007 |
| WO | WO2007014084 | 2/2007 |
| WO | WO2007014527 | 2/2007 |
| WO | WO2007021496 | 2/2007 |
| WO | WO2007027660 | 3/2007 |
| WO | WO2007028035 | 3/2007 |
| WO | WO2007036687 | 4/2007 |
| WO | WO2007036741 | 4/2007 |
| WO | WO2007036746 | 4/2007 |
| WO | WO2007040878 | 4/2007 |
| WO | WO2007067054 | 6/2007 |
| WO | WO2007071180 | 6/2007 |
| WO | WO2007096810 | 8/2007 |
| WO | WO2007101141 | 9/2007 |
| WO | WO2007115087 | 10/2007 |
| WO | WO2007120946 | 10/2007 |
| WO | WO2007127316 | 11/2007 |
| WO | WO2007127879 | 11/2007 |
| WO | WO2007127945 | 11/2007 |
| WO | WO2007128165 | 11/2007 |
| WO | WO2007130491 | 11/2007 |
| WO | WO2007133526 | 11/2007 |
| WO | WO2007143535 | 12/2007 |
| WO | WO2007149546 | 12/2007 |
| WO | WO2006104843 | 1/2008 |
| WO | WO2008008281 | 1/2008 |
| WO | WO2008012700 | 1/2008 |
| WO | WO2008030482 | 3/2008 |
| WO | WO2008052136 | 5/2008 |
| WO | WO2008061138 | 5/2008 |
| WO | WO2008063626 | 5/2008 |
| WO | WO2008066617 | 6/2008 |
| WO | WO2008076464 | 6/2008 |
| WO | WO2008089232 | 7/2008 |
| WO | WO2008091683 | 7/2008 |
| WO | WO2008095183 | 8/2008 |
| WO | WO2008097652 | 8/2008 |
| WO | WO2008101107 | 8/2008 |
| WO | WO2008112577 | 9/2008 |
| WO | WO2008112578 | 9/2008 |
| WO | WO2008120156 | 10/2008 |
| WO | WO2008133394 | 11/2008 |
| WO | WO2008134185 | 11/2008 |
| WO | WO2008150633 | 12/2008 |
| WO | WO2009001108 | 12/2008 |
| WO | WO2009006615 | 1/2009 |
| WO | WO2009029453 | 3/2009 |
| WO | WO2009036334 | 3/2009 |
| WO | WO2009051829 | 4/2009 |
| WO | WO2009051830 | 4/2009 |
| WO | WO2009063377 | 5/2009 |
| WO | WO2009081348 | 7/2009 |
| WO | WO2009111664 | 9/2009 |
| WO | WO2009146082 | 12/2009 |
| WO | WO2010000085 | 1/2010 |
| WO | WO2010009100 | 1/2010 |
| WO | WO2010011833 | 1/2010 |
| WO | WO2010019778 | 2/2010 |
| WO | WO2010057049 | 5/2010 |
| WO | WO2010075115 | 7/2010 |
| WO | WO2010080765 | 7/2010 |
| WO | WO2010080843 | 7/2010 |
| WO | WO2010107563 | 9/2010 |
| WO | WO2010115194 | 10/2010 |
| WO | WO2010132331 | 11/2010 |
| WO | WO2010135516 | 11/2010 |
| WO | WO2011068963 | 6/2011 |
| WO | WO2011133799 | 10/2011 |
| WO | WO2011159336 | 12/2011 |
| WO | WO2011159337 | 12/2011 |
| WO | WO2011159338 | 12/2011 |
| WO | WO2011159339 | 12/2011 |
| WO | WO2012104657 | 8/2012 |
| WO | WO2012158190 | 11/2012 |
| WO | WO2013012869 | 1/2013 |

OTHER PUBLICATIONS

Baskiyar, S. "A Real-time Fault Tolerant Intra-body Network" Dept. of Comp. Sci & Soft Eng; Auburn University; Proceedings of the 27th Annual IEEE Conference; 0742-1303/02 (2002) IEEE; 6 pp.

Lin et al., "Do Physiological Data Relate to Traditional Usability Indexes?" Proceedings of OZCHI 2005, Canberra, Australia (2005) 10 pp.

Mandryk et al., "A physiological approach for continuously modeling user emotion in interactive play environments" Proceedings of Measuring Behavior (2008) (Maastrichtm the Netherlandsm Aug. 26-29) 2 pp.

Mandryk et al., "Objectively Evaluating Entertainment Technology" Simon Fraser University; CHI (2004) ACM 1-58113-703-6/04/0004; 2 pp.

"PALO Bluetooth Baseband" PALO Bluetooth Resource Center (2002) Retrieved from internet Dec. 12, 2012 at URL: http://palowireless.com/bluearticles/baseband.asp; first cited in Office Action dated Jan. 17, 2013 for EP08853901.0.

Trutag, Technologies, Inc., Spectral Microtags for Authentication and Anti-Counterfeiting; "Product Authentication and Brand Protection Solutions"; http://www.trutags.com/; downloaded Feb. 12, 2013; 1 pp.

Jimbo et al., "Gastric-fluid-utilized micro battery for micro medical devices" The Sixth International Workshop on Micro and Nanotechnology for Power Geneartion and Energy Conservation Applications, (2006) pp. 97-100.

(56) References Cited

OTHER PUBLICATIONS

Jung, S. "Dissolvable 'Transient Electronics' Will Be Good for Your Body and the Environment" MedGadget; Oct. 1, 2012; Onlne website: http://medgadget.com/2012/10/dissolvable-transient-electronics-will-be-good-for-your-body-and-the-environment.html; downloaded Oct. 24, 2012; 4 pp.

Owano, N., "Study proposes smart sutures with sensors for wounds" phys.org. Aug. 2012. http://phys.org/news/2012-08-smart-sutures-sensors-wounds.html.

Platt, D., "Modulation and Deviation" AE6EO, Foothills Amateur Radio Society; Oct. 26, 2007; 61 pp.

Aade, "AADE 37th Annual Meeting San Antonio Aug. 4-7, 2010" American Association of Diabetes Educators (2010); http://www.diabeteseducator.org/annualmeeting/2010/index.html; 2 pp.

Arshak et al., A Review and Adaptation of Methods of Object Tracking to Telemetry Capsules IC-Med (2007) vol. 1, No. 1, Issue 1, 12pp.

"ASGE Technology Status Evaluation Report: wireless capsule endoscopy" American Soc. For Gastrointestinal Endoscopy (2006) vol. 63, No. 4; 7 pp.

Aydin et al., "Design and implementation considerations for an advanced wireless interface in miniaturized integrated sensor Microsystems" Sch. of Eng. & Electron., Edinburgh Univ., UK; (2003); abstract.

Barrie, Heidelberg pH capsule gastric analysis. Texbook of Natural Medicine, (1992), Pizzorno, Murray & Barrie.

Bohidar et al., "Dielectric Behavior of Gelatin Solutions and Gels" Colloid Polym Sci (1998) 276:81-86.

Brock, "Smart Medicine: The Application of Auto-ID Technology to Healthcare" Auto-ID Labs (2002) http://www.autoidlabs.org/uploads/media/MIT-AUTOID-WH-010.pdf.

Carlson et al., "Evaluation of a non-invasive respiratory monitoring system for sleeping subjects" Physiological Measurement (1999) 20(1): 53.

Coury, L. "Conductance Measurement Part 1: Theory"; Current Separations, 18:3 (1999) p. 91-96.

Delvaux et al., "Capsule endoscopy: Technique and indications" Clinical Gastoenterology (2008) vol. 22, Issue 5, pp. 813-837.

Dhar et al., "Electroless nickel plated contacts on porous silicon" Appl. Phys. Lett.68 (10) pp. 1392-1393 (1996).

Eldek A., "Design of double dipole antenna with enhanced usable bandwidth for wideband phased array applications" Progress in Electromagnetics Research PIER 59, 1-15 (2006).

Fawaz et al., "Enhanced Telemetry System using CP-QPSK Band-Pass Modulation Technique Suitable for Smart Pill Medical Application" IFIP IEEE Dubai Conference (2008); http://www.asic.fh-offenburg.de/downloads/ePille/IFIP_IEEE_Dubai_Conference.pdf.

Ferguson et al., "Dialectric Constant Studies III Aqueous Gelatin Solutions" J. Chem. Phys. 2, 94 (1934) p. 94-98.

Furse C. M., "Dipole Antennas" J. Webster (ed). Wiley Encyclopedia of Electrical and Electronics Engineering (1999) p. 575-581.

Gaglani S. "Put Your Phone, or Skin, on Vibrate" MedGadget (2012) http://medgadget.com/2012/03/put-your-phone-or-skin-on-vibrate.html 8pp.

Gilson, D.R. "Molecular dynamics simulation of dipole interactions", Department of Physics, Hull University, Dec. 2002, p. 1-43.

Given Imaging, "Agile Patency Brochure" (2006) http://www.inclino.no/documents/AgilePatencyBrochure_Global_GMB-0118-01.pdf;4pp.

Gonzalez-Guillaumin et al., "Ingestible capsule for impedance and pH monitoring in the esophagus" IEEE Trans Biomed Eng. (2007) 54(12): 2231-6; abstract.

Greene, "Edible RFID microchip monitor can tell if you take your medicine" Bloomberg Businessweek (2010) 2 pp.; http://www.businessweek.com/idg/2010-03-31/edible-rfid-microchip-monitor-can-tell-if-you-take-your-medicine.html.

Halthion Medical Technologies "Providing Ambulatory Medical Devices Which Monitor, Measure and Record" webpage. Online website: http://www.halthion.com/;downloaded May 30, 2012.

Heydari et al., "Analysis of the PLL jitter due to power/ground and substrate noise"; IEEE Transactions on Circuits and Systems (2004) 51(12): 2404-16.

Hoover et al., "Rx for health: Engineers design pill that signals it has been swallowed" University of Florida News (2010) 2pp.; http://news.ufl.edu/2010/03/31/antenna-pill-2/.

ISFET—Ion Sensitive Field-Effect Transistor; Microsens S.A. pdf document. Office Action dated Jun. 13, 2011 for U.S. Appl. No. 12/238,345; 4pp.

Intromedic, MicroCam Innovative Capsule Endoscope Pamphlet. (2006) 8 pp (http://www.intromedic.com/en/product/productinfo.asp).

Juvenile Diabetes Research Foundation International (JDRF), "Artificial Pancreas Project" (2010); http://www.artificialpancreasproject.com/; 3 pp.

Kamada K., "Electrophoretic deposition assisted by soluble anode" Materials Letters 57 (2003) 2348-2351.

Li, P-Y, et al. "An electrochemical intraocular drug delivery device", Sensors and Actuators A 143 (2008) p. 41-48.

Lifescan, "OneTouch UltraLink™" http://www.lifescan.com/products/meters/ultralink (2010) 2 pp.

MacKay et al., "Radio Telemetering from within the Body Inside Information is Revealed by Tiny Transmitters that can be Swallowed or Implanted in Man or Animal" Science (1991) 1196-1202; 134; American Association for the Advancement of Science, Washington D.C.

MacKay et al., "Endoradiosonde" Nature, (1957) 1239-1240, 179 Nature Publishing Group.

McKenzie et al., "Validation of a new telemetric core temperature monitor" J. Therm. Biol. (2004) 29(7-8):605-11.

Medtronic, "CareLink Therapy Management Software for Diabetes" (2010); https://carelink.minimed.com/patient/entry.jsp?bhcp=1; 1 pp.

Medtronic, "Carelink™ USB" (2008) http://www.medtronicdiabetes.com/pdf/carelink_usb_factsheet.pdf 2pp.

Medtronic "The New MiniMed Paradigm® REAL-Time Revel™ System" (2010) http://www.medtronicdiabetes.com/products/index.html; 2 pp.

Medtronic, "Mini Med Paradigm® Revel™ Insulin Pump" (2010) http://www.medtronicdiabetes.com/products/insulinpumps/index.html; 2 pp.

Medtronic, Mini Med Paradigm™ Veo™ System: Factsheet (2010). http://www.medtronic-diabetes.com.au/downloads/Paradigm%20Veo%20Factsheet.pdf ; 4 pp.

Melanson, "Walkers swallow RFID pills for science" Engadget (2008); http://www.engadget.com/2008/07/29/walkers-swallow-rfid-pills-for-science/.

Minimitter Co. Inc. "Actiheart" Traditional 510(k) Summary. Sep. 27, 2005.

Minimitter Co. Inc. Noninvasive technology to help your studies succeed. Mini Mitter.com Mar. 31, 2009.

Mini Mitter Co, Inc. 510(k) Premarket Notification Mini-Logger for Diagnostic Spirometer. Sep. 21, 1999.

Mini Mitter Co, Inc. 510(k) Premarket Notification for VitalSense. Apr. 22, 2004.

Minimitter Co. Inc. VitalSense Integrated Physiological Monitoring System Product Description. (2005).

Minimitter Co. Inc. VitalSense Wireless Vital Signs Monitoring. Temperatures.com Mar. 31, 2009.

Mojaverian et al., "Estimation of gastric residence time of the Heidelberg capsule in humans: effect of varying food composition" Gastroenterology (1985) 89:(2): 392-7.

"New 'smart pill' to track adherence" E-Health-Insider (2010) http://www.e-health-insider.com/news/5910/new_'smart_pill'_monitors_medicines.

NPL_AntennaBasics.pdf, Radio Antennae, http://www.erikdeman.de/html/sail018h.htm; (2008) 3pp.

O'Brien et al., "The Production and Characterization of Chemically Reactive Porous Coatings of Zirconium Via Unbalanced Magnetron Sputtering" Surface and Coatings Technology (1996) 86-87; 200-206.

(56) References Cited

OTHER PUBLICATIONS

Park, "Medtronic to Buy MiniMed for $3.7 Billion" (2001) HomeCare; http://homecaremag.com/mag/medical_medtronic_buy_minimed/; 2 pp.

"RFID "pill" monitors marchers" RFID News (2008) http://www.rfidnews.org/2008/07/23/rfid-pill-monitors-marchers/.

Rolison et al., "Electrically conductive oxide aerogels: new materials in electrochemistry" J. Mater. Chem. (2001) 1, 963-980.

Roulstone, et al., "Studies on Polymer Latex Films: I. A study of latex film morphology" Polymer International 24 (1991) pp. 87-94.

Sanduleanu et al., "Octave tunable, highly linear, RC-ring oscillator with differential fine-coarse tuning, quadrature outputs and amplitude control for fiber optic transceivers" (2002) IEEE MTT-S International Microwave Symposium Digest 545-8.

Santini, J.T. et al, "Microchips as controlled drug delivery-devices", Agnew. Chem. Int. Ed. (2000), vol. 39, p. 2396-2407.

"SensiVida minimally invasive clinical systems" Investor Presentation Oct. 2009 28pp; http://www.sensividamedtech.com/SensiVidaGeneralOctober09.pdf.

Shawgo, R.S. et al. "BioMEMS from drug delivery", Current Opinion in Solid State and Material Science 6 (2002), p. 329-334.

Shin et al., "A Simple Route to Metal Nanodots and Nanoporous Metal Films"; Nano Letters, vol. 2, No. 9 (2002) pp. 933-936.

Shrivas et al., "A New Platform for Bioelectronics-Electronic Pill", Cummins College, (2010).; http://www.cumminscollege.org/downloads/electronics_and_telecommunication/Newsletters/Current%20Newsletters.pdf; First cited in third party client search conducted by Patent Eagle Search May 18, 2010.

"Smartlife awarded patent for knitted transducer" Innovation in Textiles News: http://www.innovationintextiles.com/articles/208.php; 2pp. (2009).

"The SmartPill Wireless Motility Capsule" Smartpill, The Measure of GI Health; (2010) http://www.smartpillcorp.com/index.cfm?pagepath=Products/The_SmartPill_Capsule&id=17814.

Solanas et al., "RFID Technology for the Health Care Sector" Recent Patents on Electrical Engineering (2008) 1, 22-31.

Soper, S.A. et al. "Bio-Mems Technologies and Applications", Chapter 12, "MEMS for Drug Delivery", p. 325-346 (2007).

Swedberg, "University Team Sees Ingestible RFID Tag as a Boon to Clinical Trials" RFID Journal Apr. 27, 2010; http://www.rfidjournal.com/article/view/7560/13pp.

Tajalli et al., "Improving the power-delay performance in subthreshold source-coupled logic circuits" Integrated Circuit and System Design. Power and Timing Modeling, Optimization and Simulation, Springer Berlin Heidelberg (2008) 21-30.

Tatbul et al., "Confidence-based data management for personal area sensor networks" ACM International Conference Proceeding Series (2004) 72.

Tierney, M.J. et al "Electroreleasing Composite Membranes for Delivery of Insulin and other Biomacromolecules", J. Electrochem. Soc., vol. 137, No. 6, Jun. 1990, p. 2005-2006.

U.S. Appl. No. 12/238,345, filed Sep. 25, 2008, Hooman et al., Non-Final Office Action mailed Jun. 13, 2011 22pp.

Walkey, "MOSFET Structure and Processing"; 97.398* Physical Electronics Lecture 20; Office Action dated Jun. 13, 2011 for U.S. Appl. No. 12/238,345; 24 pp.

Watson, et al., "Determination of the relationship between the pH and conductivity of gastric juice" Physiol Meas. 17 (1996) pp. 21-27.

Wongmanerod et al., "Determination of pore size distribution and surface area of thin porous silicon layers by spectroscopic ellipsometry" Applied Surface Science 172 (2001) 117-125.

Xiaoming et al., "A telemedicine system for wireless home healthcare based on bluetooth and the internet" Telemedicine Journal and e-health (2004) 10(S2): S110-6.

Yang et al., "Fast-switching frequency synthesizer with a discriminator-aided phase detector" IEEE Journal of Solid-State Circuits (2000) 35(10): 1445-52.

Yao et al., "Low Power Digital Communication in Implantable Devices Using Volume Conduction of Biological Tissues" Proceedings of the 28th IEEE, EMBS Annual International Conference, Aug. 30-Sep. 3, 2006.

Zimmerman, "Personal Area Networks: Near-field intrabody communication" IBM Systems Journal (1996) 35 (3-4):609-17.

Description of ePatch Technology Platform for ECG and EMG, located it http://www.madebydelta.com/imported/images/DELTA_Web/documents/ME/ePatch_ECG_EMG.pdf, Dated Sep. 2, 2010.

Zworkin, "A Radio Pill" Nature, (1957) 898, 179 Nature Publishing Group.

Winter, J. et al. "The material properties of gelatin gels"; USA Ballistic Research Laboratories, Mar. 1975, p. 1-157.

Hotz "The Really Smart Phone" The Wall Street Journal, What They Know (2011); 6 pp.; http://online.wsj.com/article/SB10001424052748704547604576263261679848814.html?mod=djemTECH_t.

Evanczuk, S., "PIC MCU software library uses human body for secure communications link" EDN Network; edn.com; Feb. 26, 2013 Retrieved from Internet Jun. 19, 2013 at http://www.edn.com/electronics-products/other/4407842/PIC-MCU-software-library-uses-human-body-for-secure-communications-link; 5 pp.

Kim et al., "A Semi-Interpenetrating Network System for a Polymer Membrane"; Eur. Polym. J. vol. 33 No. 7; pp. 1009-1014 (1997).

* cited by examiner

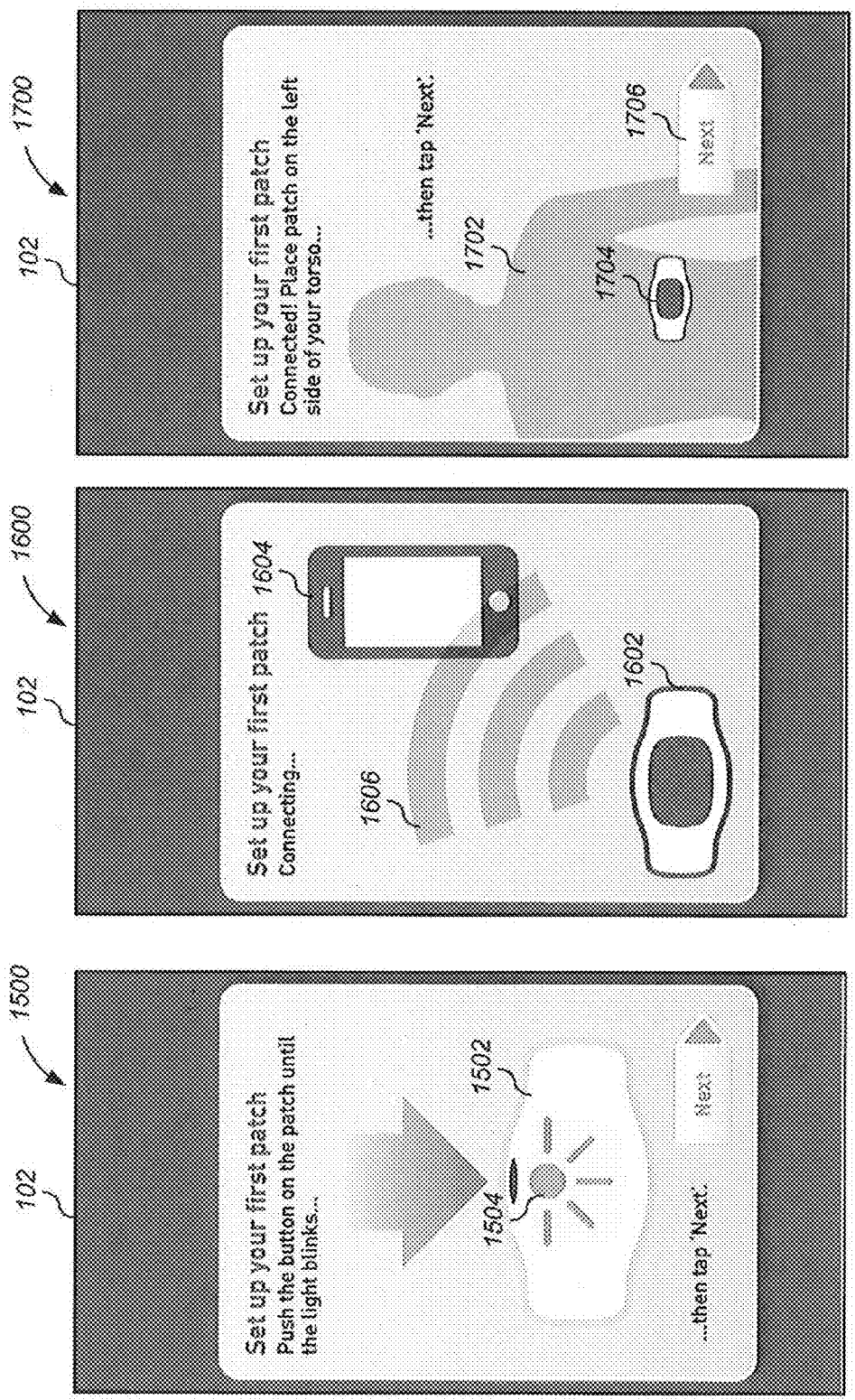

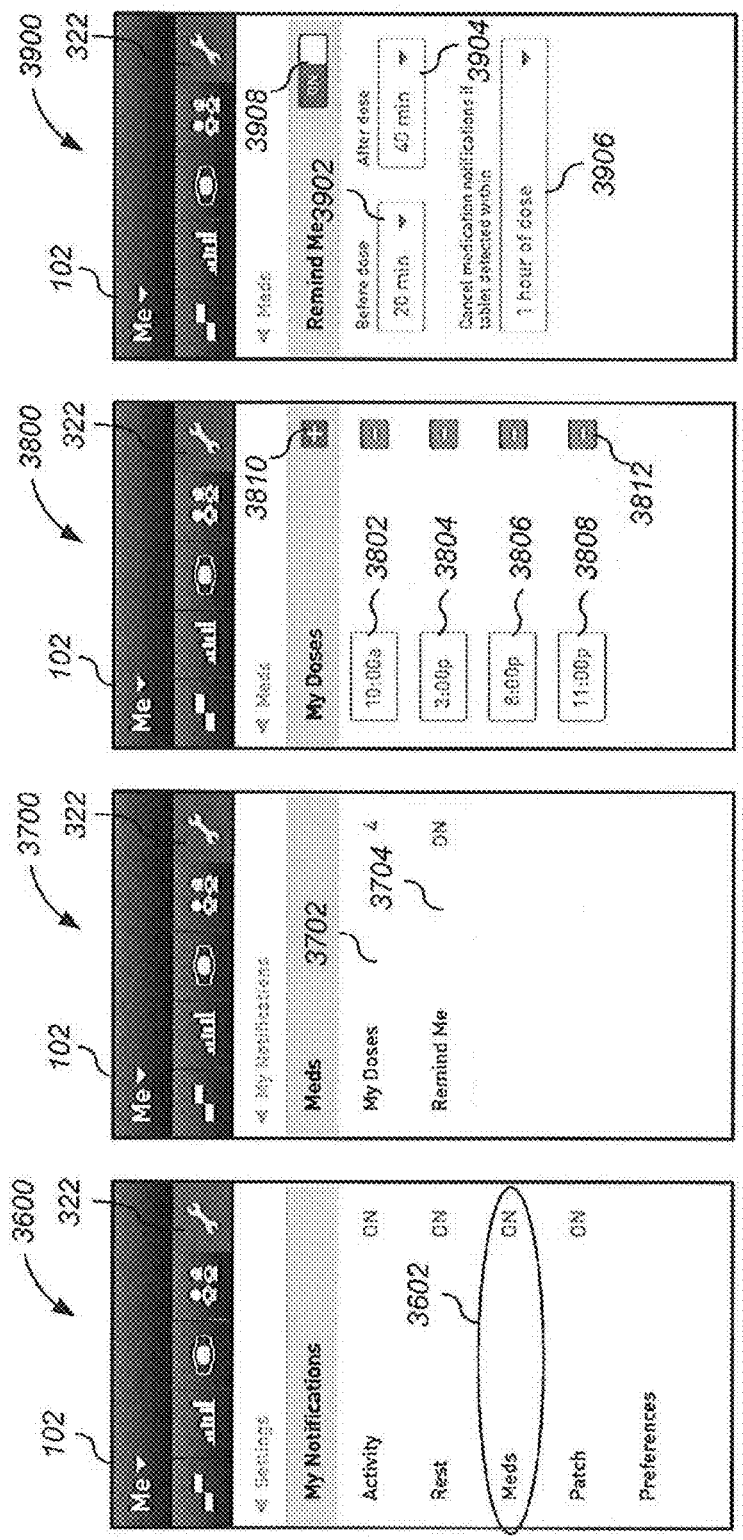

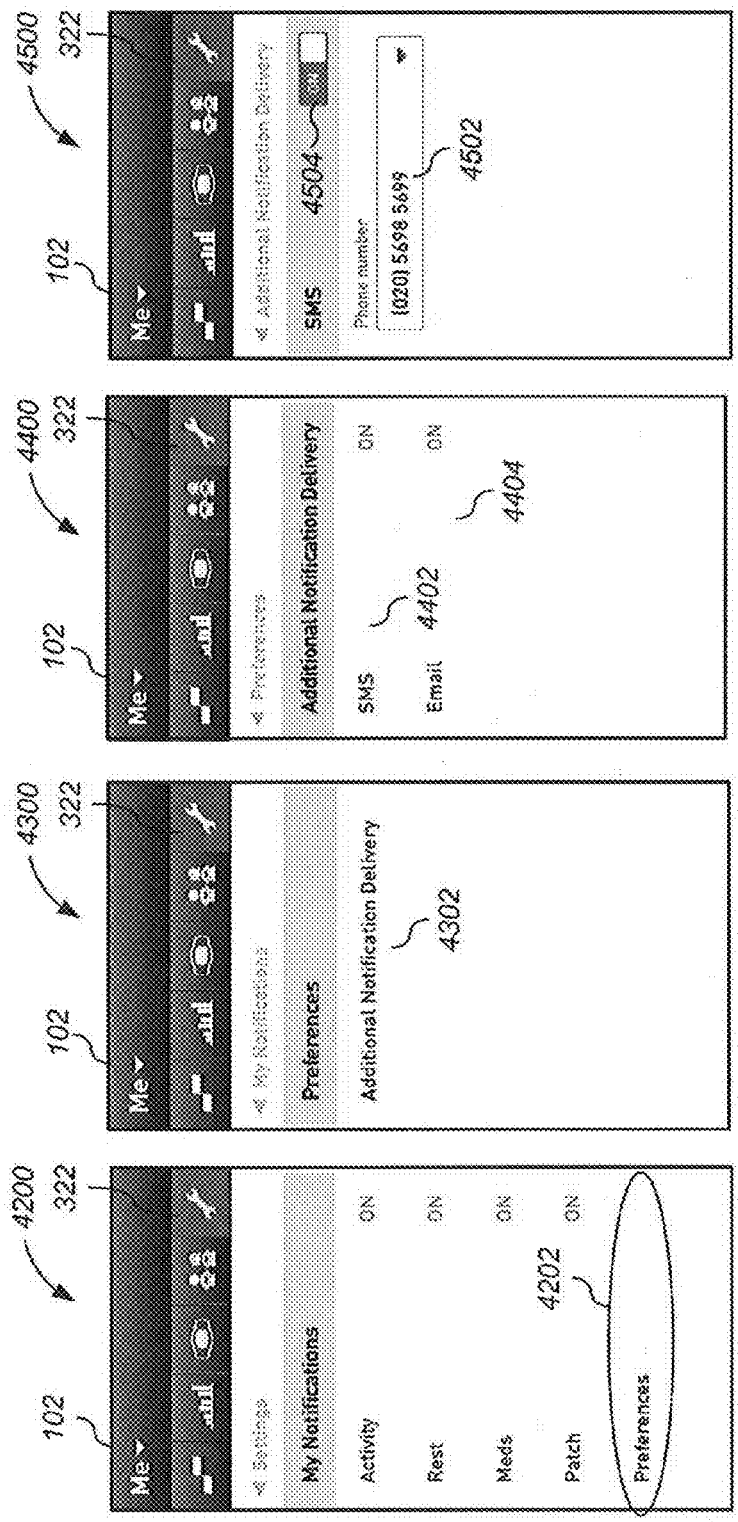

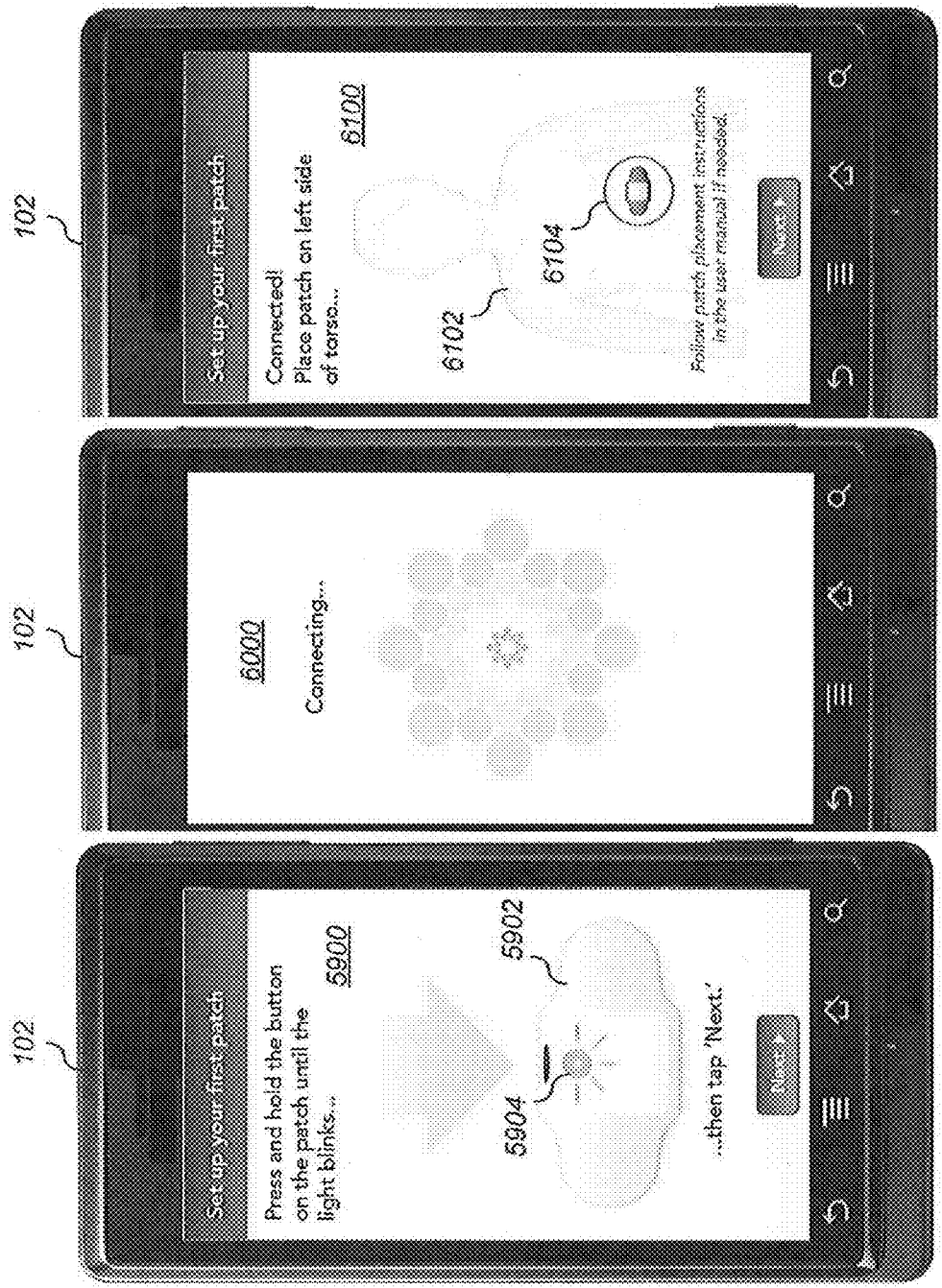

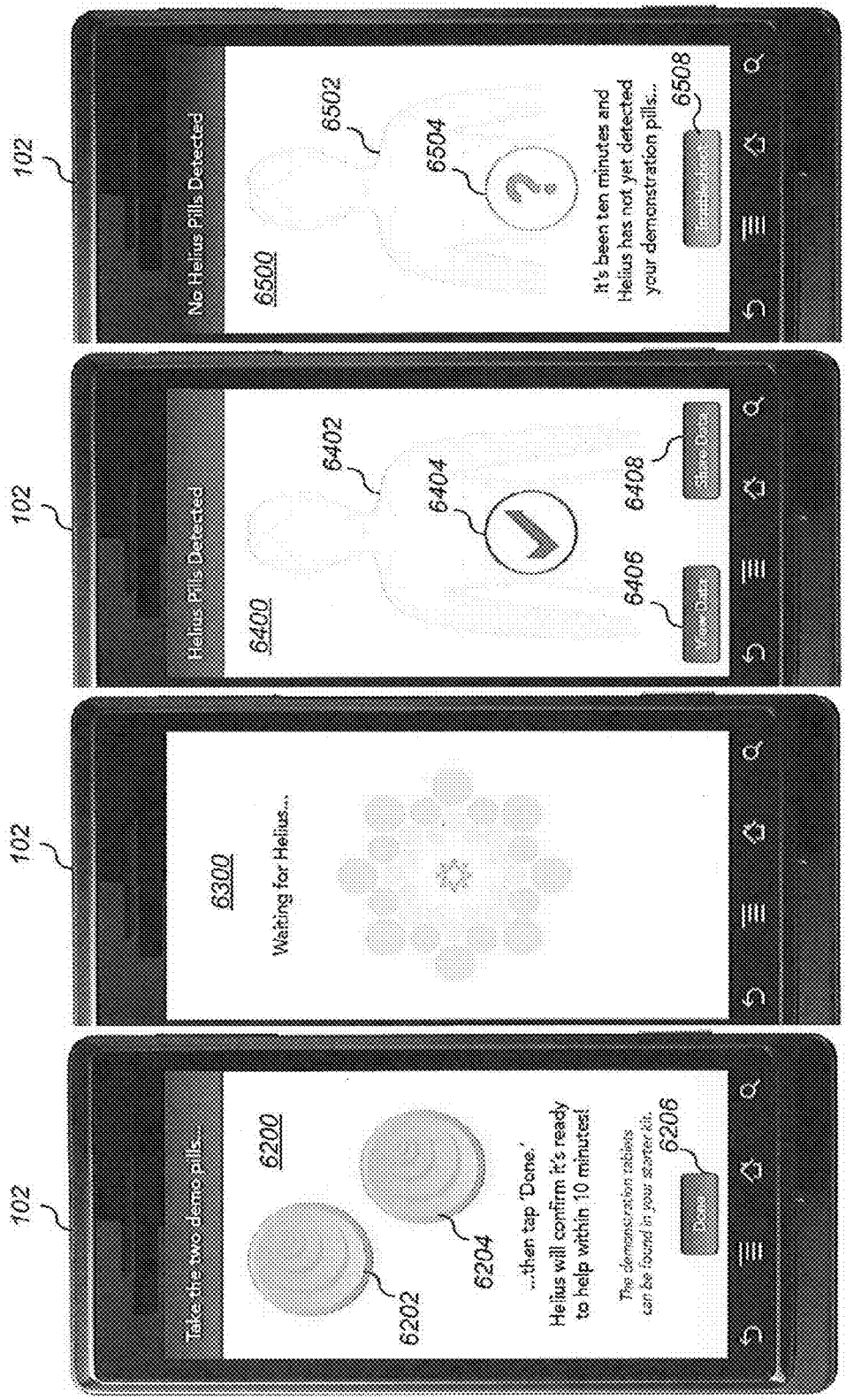

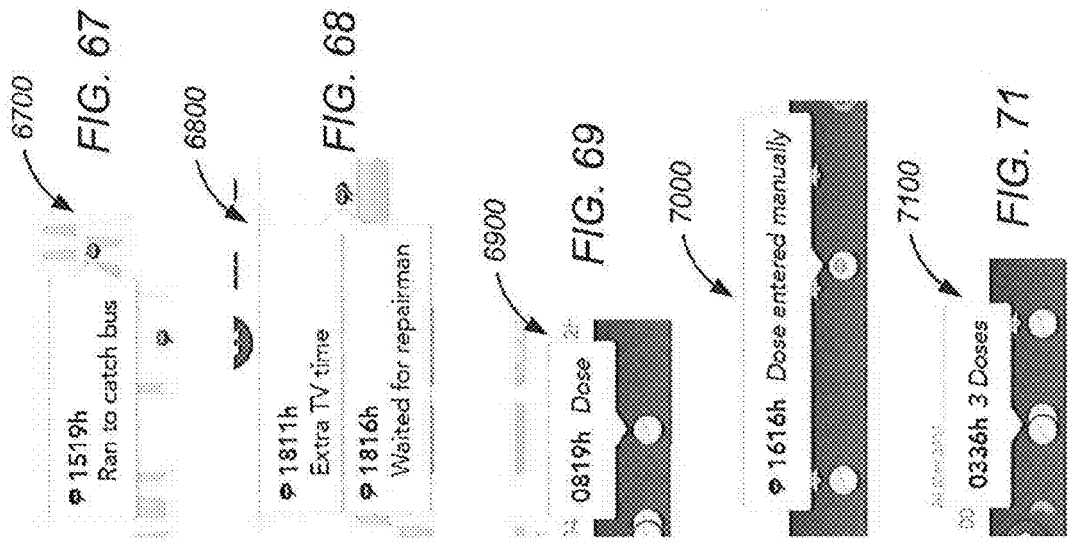
FIG. 67
FIG. 68
FIG. 69
FIG. 70
FIG. 71
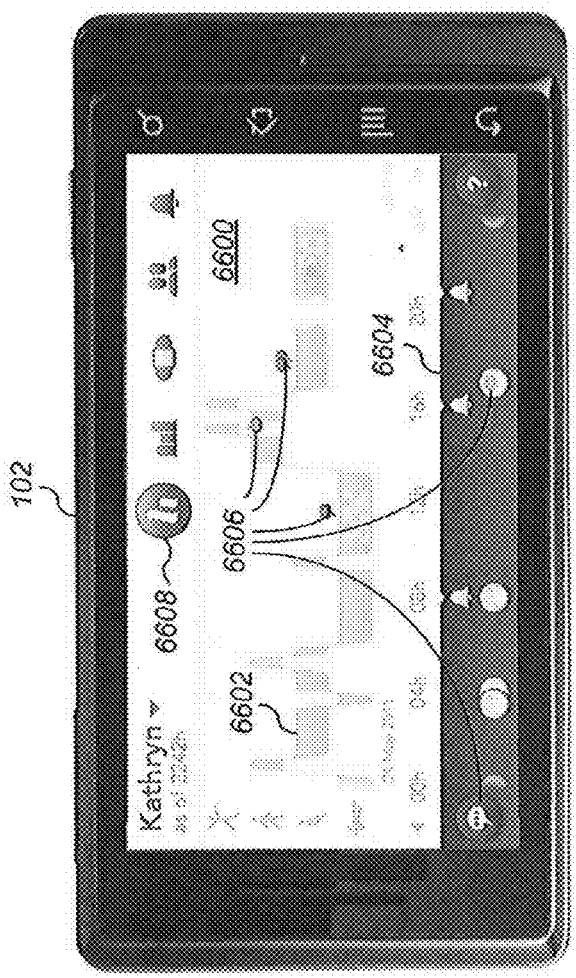
FIG. 66

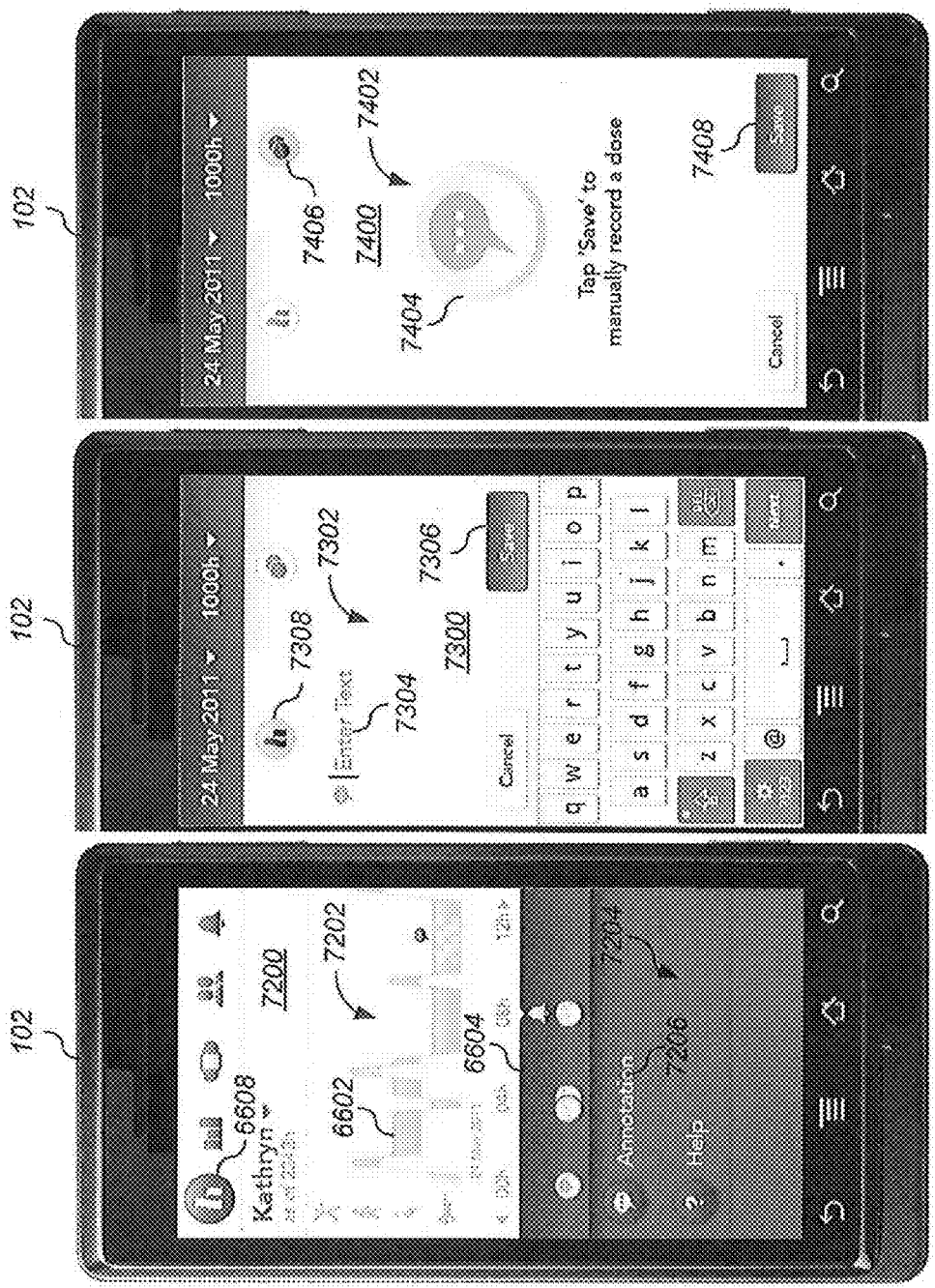

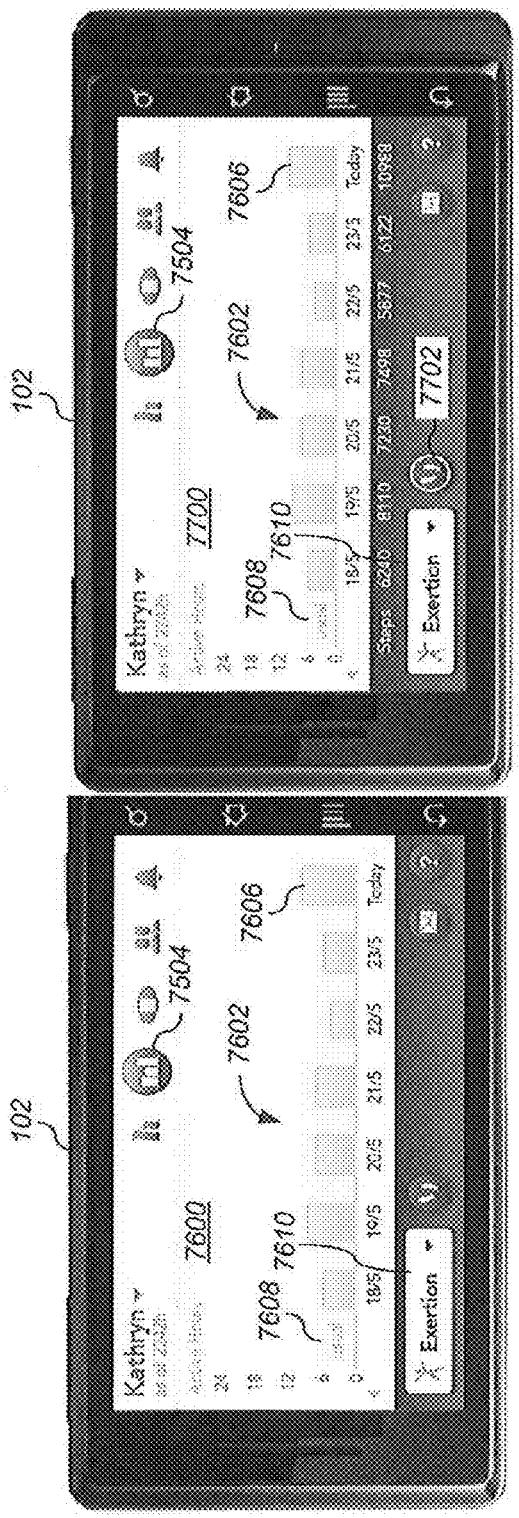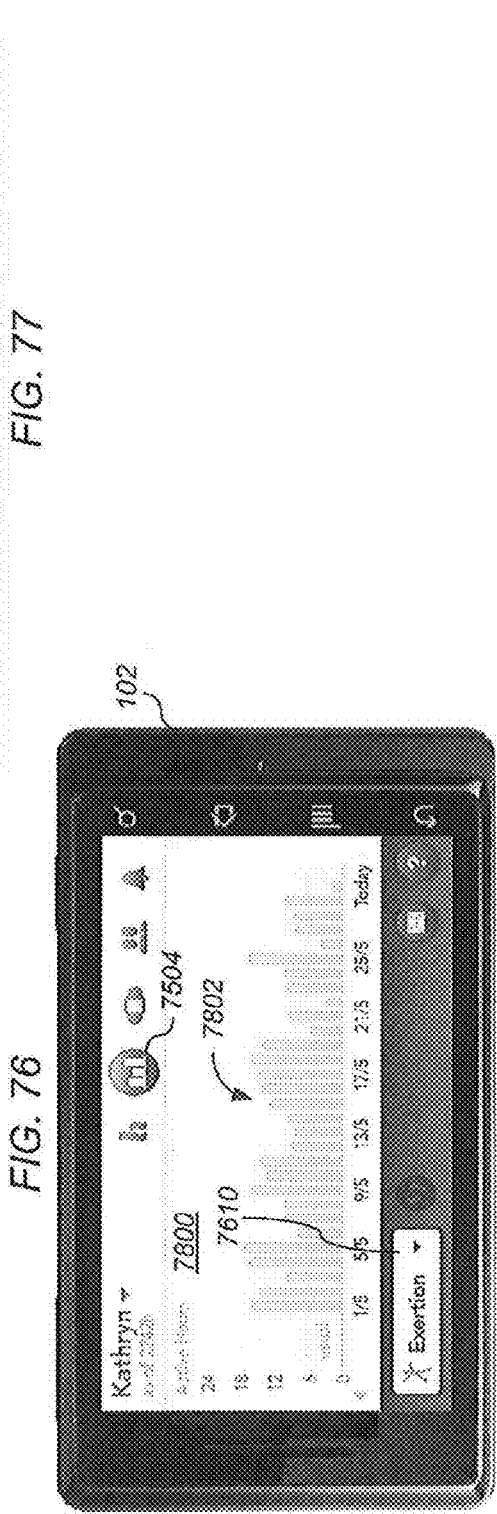

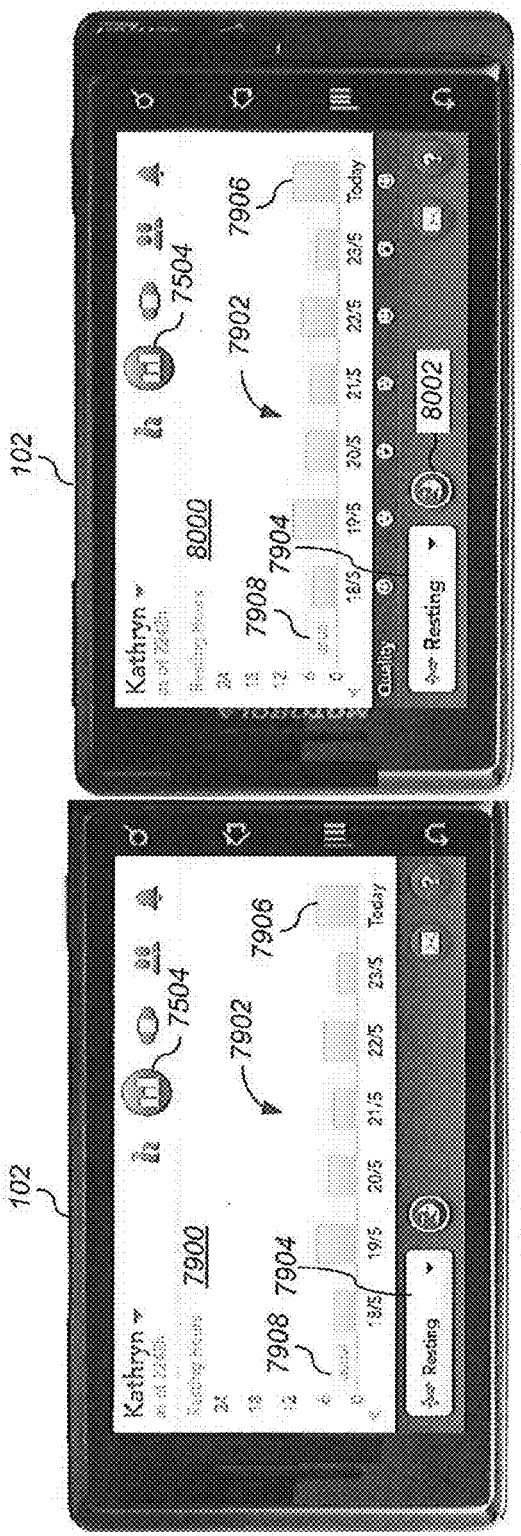
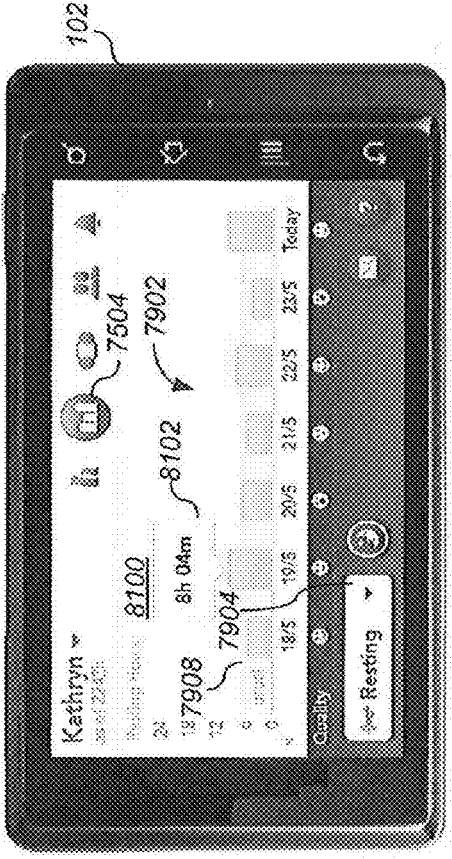
FIG. 79
FIG. 80
FIG. 81

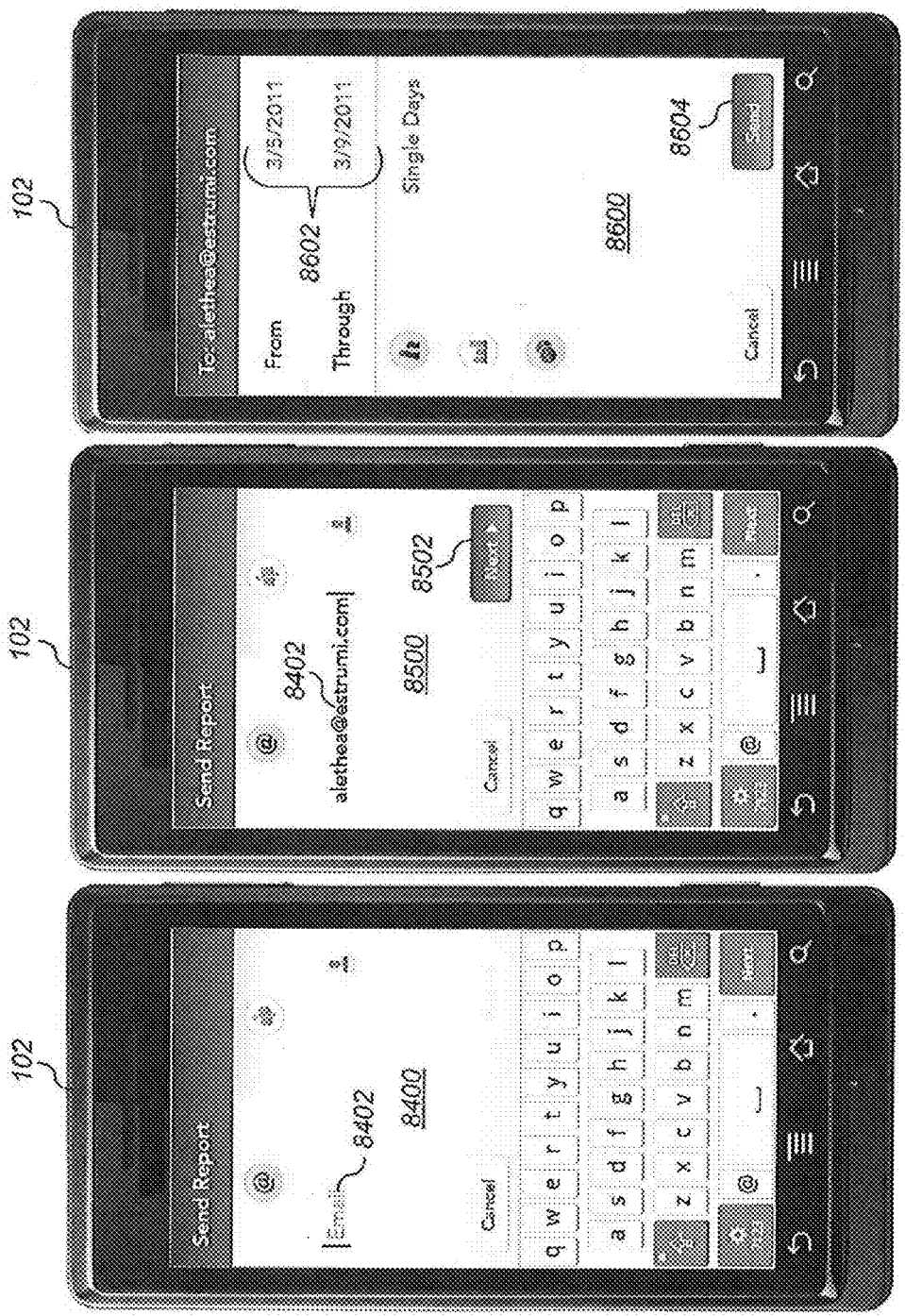

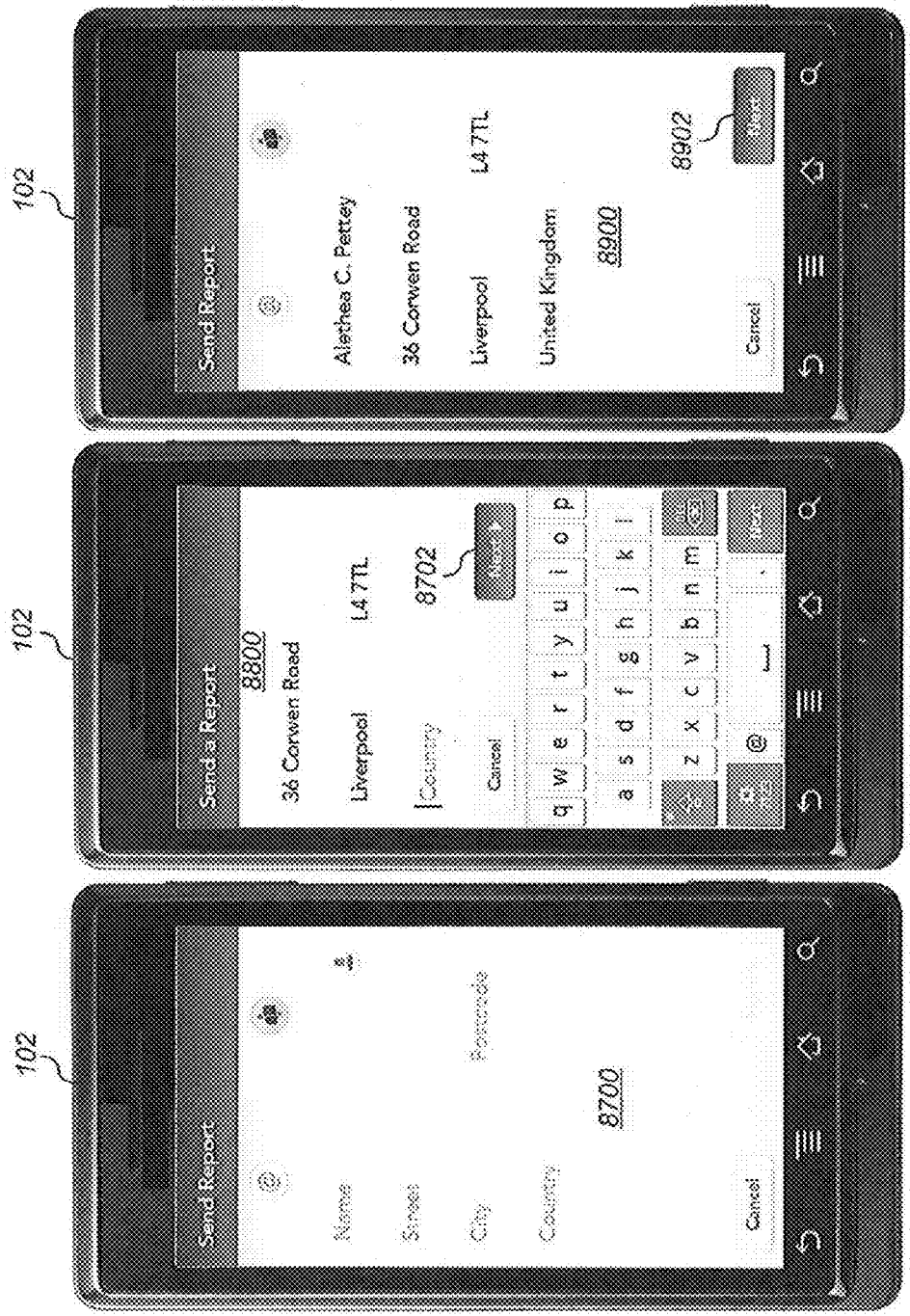

FIG. 90

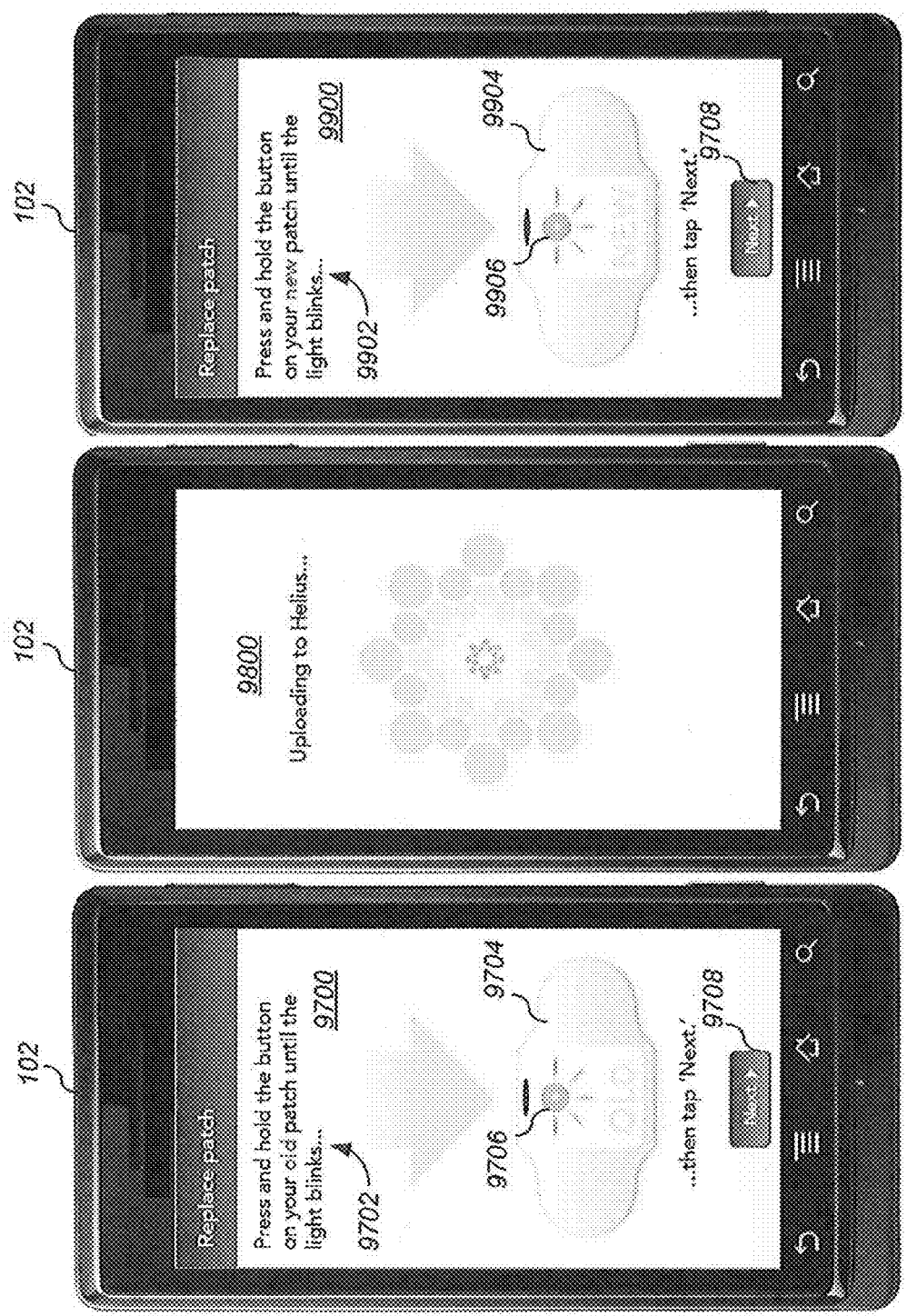

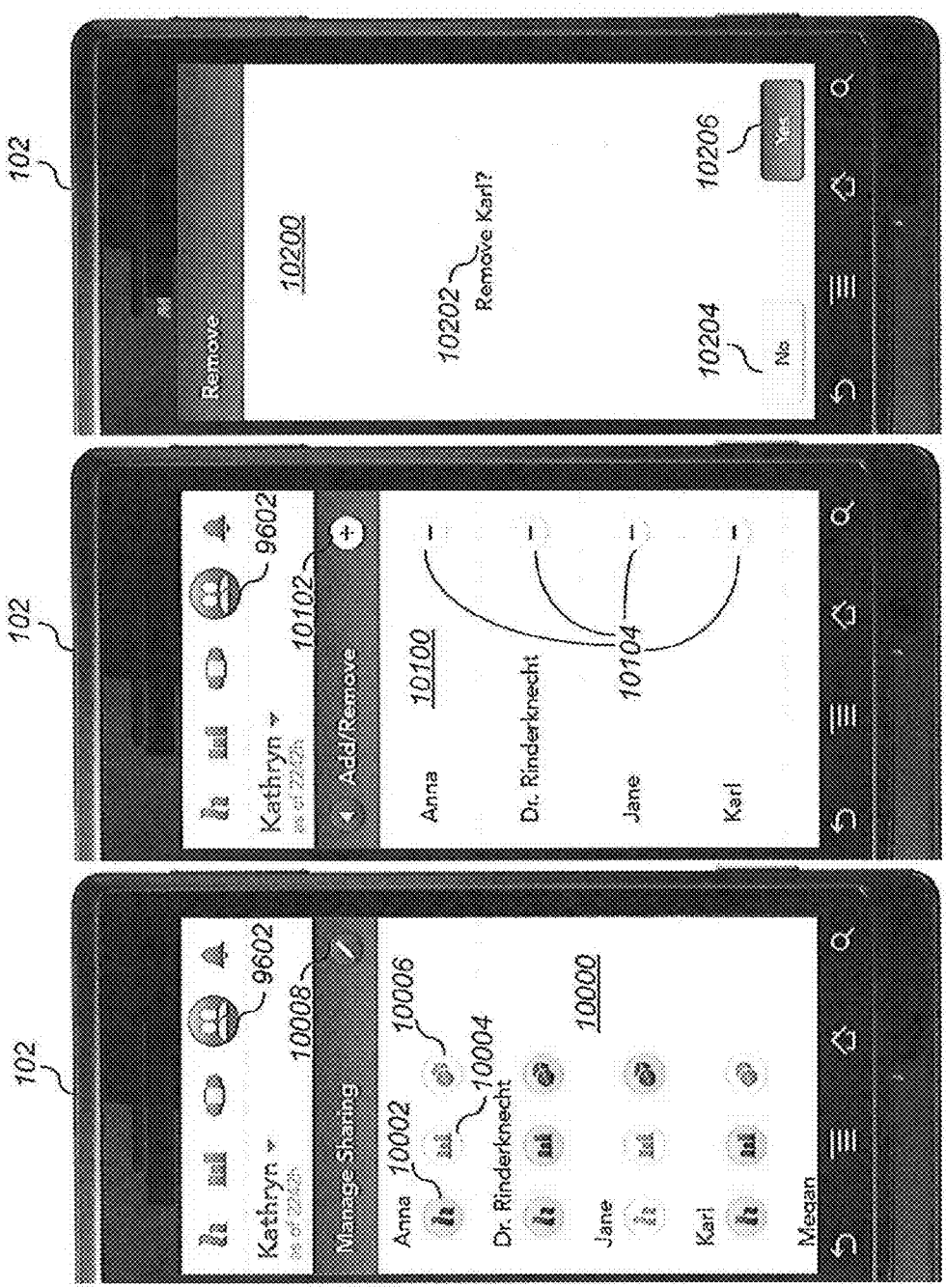

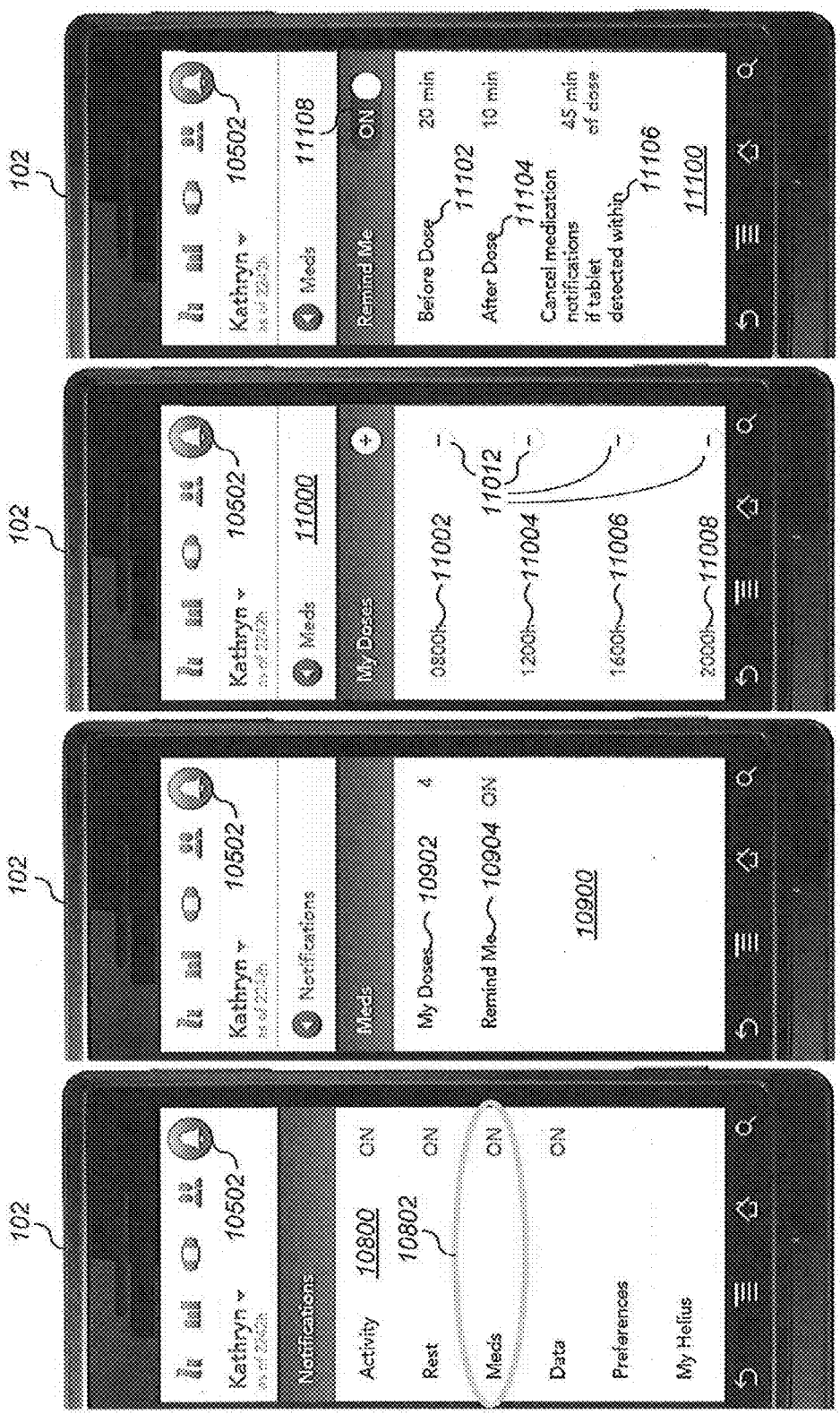

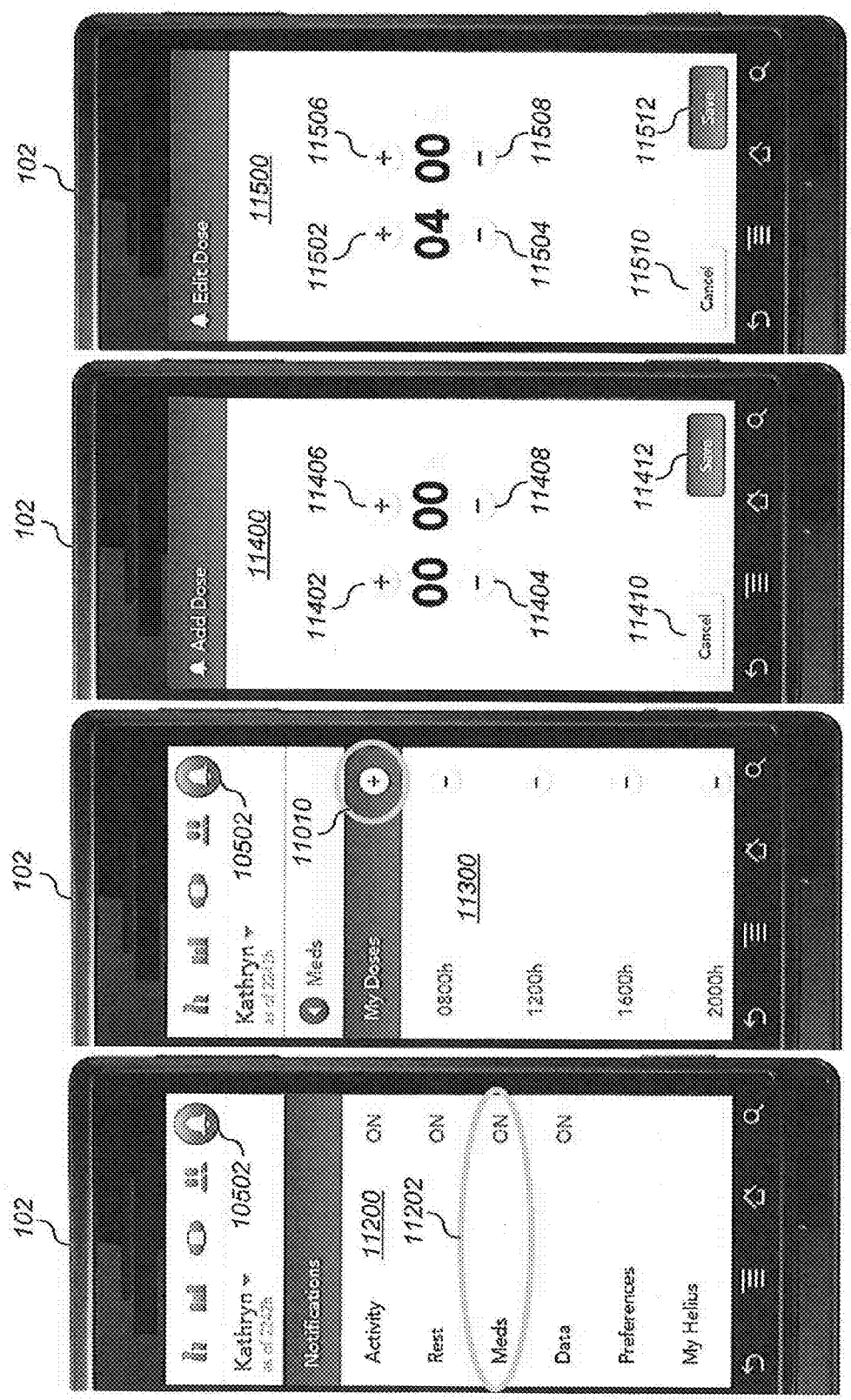

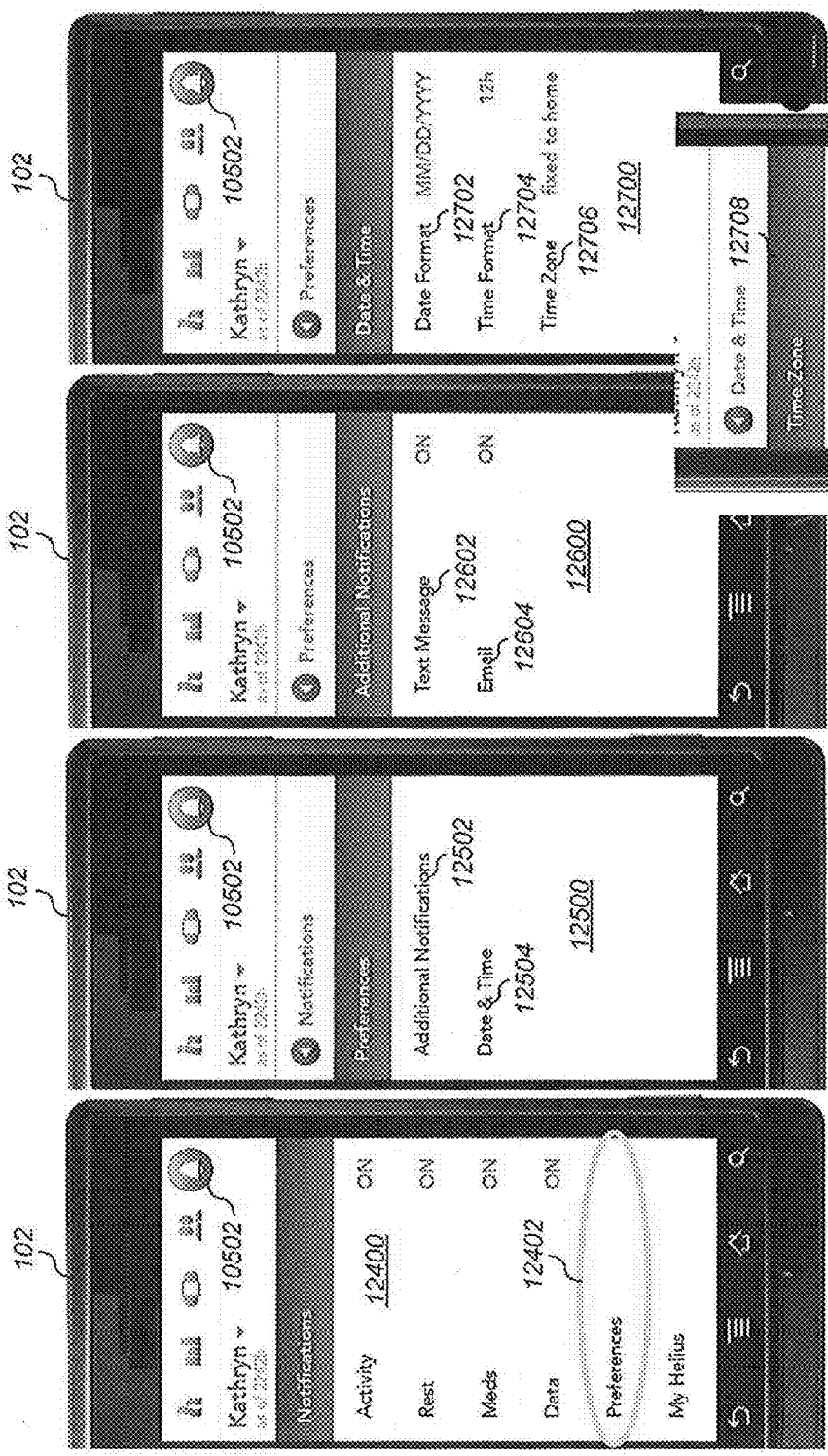
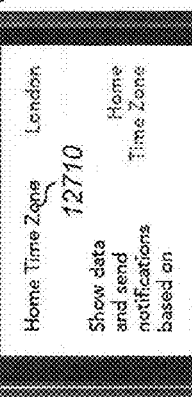
FIG. 124
FIG. 125
FIG. 126
FIG. 127A
FIG. 127B

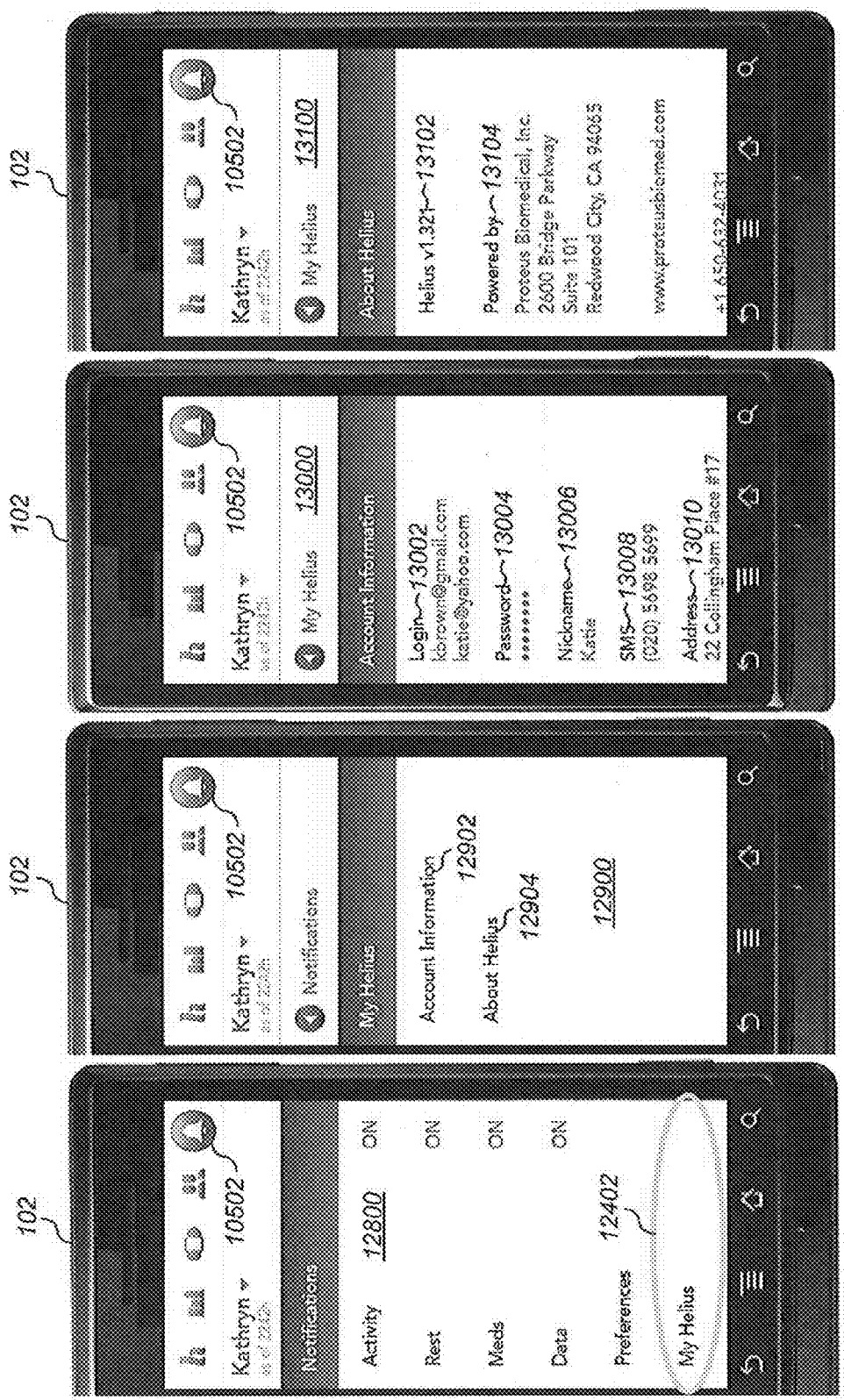

APPARATUS, SYSTEM, AND METHOD FOR MANAGING ADHERENCE TO A REGIMEN

COPYRIGHT AND TRADEMARK NOTICE

A portion of the disclosure of this patent document contains material to which a claim for copyright and trademark is made. The copyright and trademark owner has no objection to the facsimile reproduction by anyone of the patent document or the patent disclosure, as it appears in the Patent and Trademark Office patent file or records, but reserves all other copyright and trademark rights whatsoever.

INTRODUCTION

The present disclosure is related generally to a healthcare subscription information system, apparatus, and method therefor. The subscription information system transforms existing medication adherence packaging into a digital tool for tracking activity, medication, and, trending metrics associated with the patient. The system assists patients in taking medications on schedule and managing activities of daily life by facilitating communication between patients and third parties such as caregivers, loved ones, spouses, family members, friends, physicians, pharmacists, among others, for example. A mobile device apparatus, system, and method may be employed for detecting a communication from a device such as an ingestible device, e.g., an ingestible event marker (IEM) device associated with a medication. In the case of an IEM device associated with a medication event, for example, a receiver, e.g., a wearable patch device worn by the person taking the medication, detects the ingestion of an IEM device embedded in a medicinal dose. The present disclosure is related to a mobile device such as a handheld portable device, computer, mobile telephone, sometimes referred to as a smartphone, tablet personal computer (PC), kiosk, desktop computer, or laptop computer, or any combination thereof, configured to, among other things, detect the ingestion of an ingestible device by a patient; receive communications related to the ingestible device, e.g., from a receiver; communicate the information to a back end processing system' and/or assist the patient in managing ingestion of medication, physical activity, and communications with third parties.

Generally, detecting the ingestion of an IEM device is done by detection electronics provided in the form factor of a receiver, e.g., a wearable receiver (e.g., a patch). The wearable receiver may be worn on an outer surface of the skin; an implantable receiver; a partially implantable receiver; a receiver configured in or to be worn as apparel, (e.g., a wristband receiver). In alternative aspects, the receiver may be embodied as a mobile device, e.g., a mobile phone.

The patch, for example, may include wet or dry electrodes which are made to contact the skin. An adhesive layer may be provided on the patch to affix the entire patch arrangement to the patient. When an IEM device is ingested by the patient and comes into contact with stomach fluids, the IEM device initiates a communication which is detected by the detection circuitry of the patch to indicate that the particular IEM device was ingested by the patient.

To address various issues associated with medication adherence, a subscription information system described herein, layered above conventional adherence packaging products is needed. Currently, pharmacies provide medication adherence packages that are pre-filled by a pharmacist in a set of blister packs containing enough medication for pre-determined period such as, for example, several days, a week, or a month supply of medication at different dosage times.

What is needed is the addition of an ingestible device, e.g., an IEM device, associated with prescribed medication dose into each of the blister packs to identify ingestion and medication-related events and a processing system to track and manage the identified data and the medication process to document adherence and provide feedback, e.g., to the patient, to the caregiver, etc. A subscription information system layered on top of conventional adherence packaging is needed to assist a patient in taking the medication on schedule, managing activities of normal daily life, such as, getting up and moving around, taking medication, ensuring the patient is getting adequate rest. Assistance with these activities is provided by the system by facilitating communication between the patient, third parties, and a back end processing system that records and tracks the patient's medication and physical patterns and stores them in a database. In one aspect, a receiver (e.g., patch with electronic functionality) is worn by the patient to detect the ingestion of an IEM device. The wearable receiver then communicates the event to a mobile device. In another aspect, the IEM device may communicate directly with the mobile device without the need of a wearable receiver. In either aspect, the mobile device communicates the information received from the IEM device in a discreet private manner to a back end processing system. The backend processing system stores the information, analyzes the information, and provides feedback to the patient via the mobile device.

SUMMARY

In one aspect, a method of managing adherence to a regimen in a subscription based computer implemented healthcare information environment is provides. At a mobile device information is received from a receiver that a dose was ingested by a living subject. The mobile device comprises a processor, a memory coupled to the processor, and a display coupled to the processor. The information is wirelessly communicated over a wireless network to a backend computer processing system. A personal information stream is received from the computer at the backend processing system. The personal information stream characterizes behavior of the living subject based on the received information over a predetermined period.

In one aspect, an adherence package is provided. The adherence package comprises a sheet with a plurality of tear-away strips associated with a personalized dose.

In one aspect, a system for managing adherence to a regimen in a subscription based computer implemented healthcare information environment is provided. The system comprises a mobile device configured to receive information from a receiver that a dose was ingested by a living subject. The mobile device comprises a processor, a memory coupled to the processor, and a display coupled to the processor. The information is wirelessly communicated over a wireless network to a backend computer processing system. A personal information stream is received from the computer at the backend processing system. The personal information stream characterizes behavior of the living subject based on the received information over a period.

FIGURES

The patent or application file contains at least one drawing executed in color. Copies of this patent or patent application publication with color drawing(s) will be provided by the Office upon request and payment of the necessary fee.

FIGS. 15-18 illustrate various aspects of GUIs for a display screen of a mobile device for wearing and demonstrating the wearable receiver.

FIGS. 36-39 illustrate various aspects of Utilities GUIs for a display screen of a mobile device for tailoring the subscription information system based on personal needs and requirements of the patient.

FIGS. 42-45 illustrate various aspects of GUIs for a display screen of a mobile device for tailoring the subscription information system based on personal needs of a patient.

FIGS. 56-135 illustrate ornamental designs for various aspects of GUIs for a display screen of a mobile device, where:

FIGS. 56-58 illustrate the ornamental design for various GUIs for a display screen of a mobile device for creating an account.

FIGS. 59-61 illustrate ornamental designs for several additional "Onboarding" GUIs for a display screen of a mobile device for setting up a wearable receiver.

FIGS. 62-65 illustrate ornamental designs for several additional "Onboarding" GUIs for a display screen of a mobile device for demonstrating the healthcare subscription information system according to the present disclosure.

FIGS. 66-71 illustrate ornamental designs for several additional "Ribbon" GUIs for a display screen of a mobile device for viewing annotations.

FIGS. 72-74 illustrate ornamental designs for several additional "Ribbon" GUIs for a display screen of a mobile device for making annotations.

FIGS. 76-78 illustrate ornamental designs for several additional "Charts" GUIs for a display screen of a mobile device for displaying charts associated with patient exertion periods.

FIGS. 79-81 illustrate ornamental designs for several additional "Charts" GUIs for a display screen of a mobile device for displaying charts associated with patient rest periods.

FIGS. 84-86 illustrate ornamental designs for several additional "Charts" GUIs for a display screen of a mobile device for sending reports associated with patient via email.

FIGS. 87-89 illustrate ornamental designs for several additional "Charts" GUIs for a display screen of a mobile device for sending reports associated with patient via the post.

FIG. 90 illustrates the "Send Report" GUI shown in FIG. 87, with a series of address book GUI screens for a display screen of a mobile device for populating the "Send Report" GUI using a local address book.

FIGS. 97-99 illustrate ornamental designs for several additional "Patch" GUIs for a display screen of a mobile device for replacing the wearable receiver.

FIGS. 100-104 illustrate ornamental designs for several "Share" GUIs for a display screen of a mobile device for managing permissions and adding/removing caregivers.

FIGS. 108-111 illustrate ornamental designs for several additional "Notifications" GUIs for a display screen of a mobile device for notifying patients of medication dosing times and reminders.

FIGS. 112-115 illustrate ornamental designs for several additional "Notifications" GUIs for a display screen of a mobile device for adding daily medications dose times.

FIGS. 120-123 illustrate ornamental designs for several additional "Notifications" GUIs for a display screen of a mobile device for providing data alerts.

FIGS. 124-127 illustrate ornamental designs for several additional "Notifications" GUIs for a display screen of a mobile device for setting notification preferences.

FIGS. 128-131 illustrate ornamental designs for several additional "Notifications" GUIs for a display screen of a mobile device for displaying information about the account and about the system.

FIGS. 132-135 illustrate ornamental designs for several additional "Notifications" GUIs for a display screen of a mobile device for editing account.

DESCRIPTION

Figure 1:
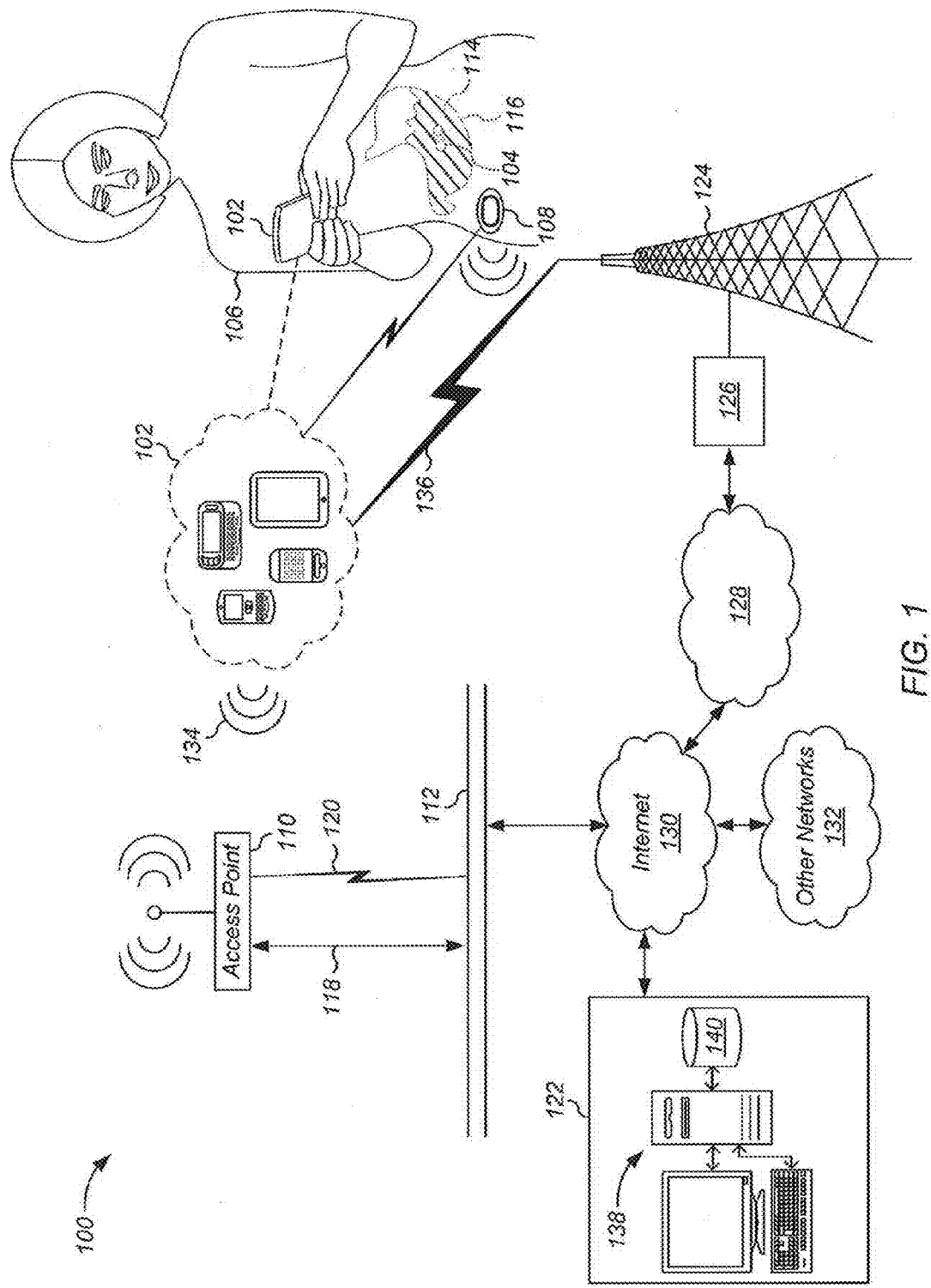
FIG. 1 illustrates one aspect of a system comprising a mobile device for detecting an electrical signal generated by an ingestible event marker (IEM) device and/or communicating data related thereto.

In various aspects, the present disclosure is directed generally to an apparatus, system, and method for managing adherence to a regimen in a subscription based computer implemented healthcare information environment. For example, the regimen may be a medication regimen, an exercise regimen, a combination of medication and exercise regimen, etc. In accordance with the present disclosure, medication adherence packaging is transformed into a digital tool that assists in taking medications on schedule and managing activities of daily life by facilitating communication between users (e.g., patients) and third parties, such as, for example, personal caregivers (e.g., carers), loved ones, spouses, family members, friends, physicians, pharmacists, among others. In one aspect, a wearable receiver (e.g., electronic patch) is worn by a person taking medications. As used herein, the term "medication" includes ingestible preparations such as pharmaceuticals, such as prescribed or over-the-counter preparations; vitamins; placebos, etc. Medications may be provided in one or more form factors, e.g., pills, tablets, capsules, gel capsules, soft gel capsules, etc. The wearable receiver detects a communication from an ingestible device such as an implantable device, an implantable pulse generator such as a pacemaker, for example, a stent; an implantable transceiver; an ingestible device, such as an ingestible event marker (IEM) device, an ingestible RFID device, an ingestible coil or antenna device; among other devices. In the case of an IEM device, a microelectronic circuit is associated with a medication, e.g., a medicinal dose, to indicate the occurrence of a medication event, for example. The wearable patch device is worn by the person taking the medication to detect the ingestion of the medicinal dose comprising an IEM device embedded therein. The wearable receiver communicates the information to a mobile device. In one aspect, the present disclosure provides a system where the mobile device communicates over one or more than one wireless network to communicate information associated with medication dosing events to a back-end processing system that manages the administration of medication and facilitates communication between the person taking the medication and third parties such as their caregivers, physicians, and/or pharmacists, for example. In one aspect, an adherence package according to the present disclosure comprises, in addition to the medication, a wearable receiver and an IEM device.

The subscription information system according to the present disclosure enables focus on care management of and communication with the patient. Various aspects of the system may be configured to convey trends in activities of daily life, including activity, rest, and medication taking. Also, in other aspects, the system may be configured to assist managing activities of daily life, including taking the appropriate medications on schedule and managing amount and timing of activity and rest. In various aspects, the system also may be configured to facilitate communication between patients and designated third parties. In various aspects, the system may be configured for patients who are primarily responsible for their own care, taking multiple medications, and who are candidates for adherence support. In other aspects, the system may be configured for patients with personal caregivers who assist with or oversee their care. In other aspects, the system may be configured for patients who are capable of using, or have a caregiver capable of using smartphone technology.

In one aspect, the subscription information system according to the present disclosure may be based on adherence packaging products already available on the market. Pharmacies may provide these adherence packages where the pharmacist pre-fills a set of blister packs with a person's medications at different dosage times for a predetermined period such as a day, a week, a month, and so forth. The present disclosure adds one more component, an ingestible device, into at least one blister. For example, a medicinal dose (e.g., a tablet) is added into each of the existing blisters, where the medicinal dose includes an event marker or other ingestible device such as an IEM device, RFID device, etc. In another example, a placebo is added to at least one of the blisters, where the placebo includes an ingestible device such as an IEM device, RFID device, etc.

In one aspect, the subscription information system according to the present disclosure is based on a predetermined adherence packaging form factor and assists a person in taking medication on schedule and managing their activities of daily life. Activities of daily life, among other things, include getting up and moving around, taking medications, ensuring they get adequate rest. One way of assisting with these activities is by facilitating communication between the patient and their caregivers. It will be appreciated, that the subscription information system according to the present disclosure is not intended to replace other forms of communication between the patient and third parties. It is meant, however, to facilitate communication and to provide a layer of information that a patient, carer, etc., would not otherwise have and to focus on interpersonal communication with people on things that are not tactical, generally speaking. Thus, for example, when a relative calls an ill person, the conversation can focus on some normal daily activity such as the book she is reading rather than focusing on whether the person took their medications or whether they exercised for ten minutes on that day.

Once the information is communicated to a mobile device, the subscription information system according to the present disclosure provides a graphical user interface (GUI). In one aspect, the GUI is associated with the mobile device and provides a personal information stream which is effectively a timeline for any given day in the form of an activity indicator, e.g., displayed as an "activity ribbon," that shows in a simple and concise manner how the person is spending each moment of the day. For example, generally, people will spend a lot of time sleeping, then get up to run some errands, and maybe rest in their chair and watch television when they are done. Later they may get up and go for a walk that elevates their heart rate, get a little exercise, and then return home to sit, rest, and eventually go to sleep. In one aspect, an activity ribbon is provided to show how a person transitions between different states throughout a predetermined period such as day or night. Accordingly, at a glance, the person can readily tell if, in a given night, they have been really disruptive and getting up to go to the bathroom multiple times, or if they tossed and turned all night with really sleeping restfully. This information can be obtained just by looking at the state of an activity ribbon as displayed on a mobile device display GUIs. In addition, in one aspect, the medication events timeline associated with the person can be shown below the activity ribbon along a running time line. Accordingly, the subscription information system according to the present disclosure presents the scheduled medication times as one set of icons and the actual detected medication ingestion times by another set of icons. A person can visually correlate the scheduled versus actual medication times without judgment as presented by the GUI. In this manner, the absence of judgment may enhance usability of the system which, in turn, optimizes adherence to various regimens.

The subscription information system according to the present disclosure provides certain value propositions across the stakeholders, e.g., for the patient, the caregiver, the physician, and the pharmacy. For the patient, the subscription information system according to the present disclosure provides personalized data-driven feedback notifications to help the patient manage his or her daily life. The system further provides earlier detection of negative trends, easier communication with personal physicians, and decreased isolation via an enhanced sense of connectedness. Overall, the system may provide the patient with better quality relationships with caregivers and with less focus on tactical care needs. In addition, use of the system may result in significant cost savings as a result of adherence to medication regimens, e.g., costs otherwise incurred due to non-adherence such as the cost of treating escalated illnesses, etc.

For the caregiver, the subscription information system according to the present disclosure provides reassurance that a loved one is doing okay. Personalized data-driven notifications are set as per personal thresholds. This also leads to better quality relationships with patients with less focus on tactical care needs.

For the pharmacist, the subscription information system according to the present disclosure provides improved adherence to medication by the patient and to increased prescriptions. The system also provides consumer pay, subscription-based mobile phone applications, premium priced adherence packaging services, and increased share of care-at-home services. In addition, the system provides increased consumer loyalty, store traffic and retail cross-selling and new ways to partner with local trusts and health authorities, among other things.

For clarity of disclosure, these and other aspects of the present disclosure will now be described in conjunction with the associated figures. Also, prior to describing the subscription information system, the disclosure first turns to a description of an overall system in which the subscription information system may be practiced. Accordingly, turning now to FIG. 1, where one aspect of a system 100 is illustrated. The system 100 comprises a mobile device 102 (e.g., a first node), such as a mobile communication device, for detecting a communication associated with the ingestible event marker 104 (IEM), e.g., an electrical signal generated by the IEM 104; data associated with the electrical signal and communicated from a receiver to the mobile device 102, etc. As shown, a living subject such as a patient 106 has recently ingested an IEM device 104 and is holding a mobile device 102 in her hands. In one aspect, the patient 106 puts on a wearable receiver 108 (e.g., electronic patch) that senses a communication from the IEM device 104 via one or more electrodes and then communicates with the mobile device 102. The mobile device 102 is configured to communicate to a backend processing system such as a remote processing system 122 using a variety of techniques over a variety of wired or wireless communication networks as described in more detail hereinbelow.

Various aspects of an IEM device are disclosed in commonly assigned U.S. Patent Application Publication No. 2008-0284599 A1 entitled, "Pharma-Informatics System" filed on Apr. 28, 2006, which is herein entirely incorporated by reference.

The architecture and operation of a typical wearable receiver 108 and various related aspects are disclosed in commonly assigned U.S. Patent Application Publication No 2010-0312188 A1 entitled "Body-Associated Receiver and Method" filed on Dec. 15, 2009, and is further explained in more detail below in connection with FIG. 54 whereas the architecture and operation of a typical IEM device 104 is explained in more detail below in connection with FIG. 55.

In one aspect, shortly after the patient 106 ingests an IEM device 104, the digestive fluids 114 in the stomach 116 activate the IEM device 104 to begin conducting a unique electrical current signature, which corresponds to various data. The data, for example, may include data identifying the IEM device 104, data identifying the medication, etc. In various aspects, for example, an IEM device 104 or components thereof may pass through the patient's system. In various aspects, the IEM device 104 may be partially or fully digestible. In various aspects, IEM devices 104 may be configured to communicate continuously or intermittently with the wearable receiver 108 after ingestion. In other aspects, an IEM device 104 may be configured to be selectively activated, deactivated, and/or reactivated.

The electrical current signature generated by the IEM device 104 while disintegrating in the digestive fluids 114 is detectable by a detection arrangement portion of the wearable receiver 108 coupled to the patient 106.

In use, after the patient 106 ingests the IEM device 104, the electrodes portion of the wearable receiver 108 contacting the skin of the patient 106 pick up the current signal generated by the activated IEM device 104. Once the detection arrangement is in place, an application is launched on the mobile device 102 and the patient 106 takes their medication from the blister pack, which includes the IEM device 104. The application may be launched automatically upon detection of a transmission from the wearable receiver 108 or may be launched by user selection using conventional techniques such as a mouse over and click, pushbutton switch activation, virtual pushbutton switch activation, voice recognition, vibration, tapping a GUI element, orientation of the device, for example.

With reference still to FIG. 1, the wearable receiver 108 acts as a first node for the detection of the unique current signature generated by the IEM 104 and the mobile device 102 acts as a second node for the detection of a communication from the wearable receiver 108. In response to a detection of the unique current signature generated by the IEM device 104 via the wearable receiver 108, the mobile device 102 may perform a number of functions. In one aspect, the mobile device 102 may store the time and date when the communication was detected, which corresponds approximately to the time and date of ingestion of the IEM device 104 by the patient 106. In addition, the mobile device 102 may store the information encoded in local memory. For example, the identity of the IEM device 104, the type of medication associated with the IEM device 104, the manufacturer of the medication and/or IEM device 104, among other information, may be encoded by the unique electrical current signature, without limitation.

Generally, however, the mobile device 102 transmits the detected information associated with the IEM device 104 either to a wireless node 110 (e.g., a third node or local node) or to a cellular tower 124 in order to transmit the information to a remote processing system 122, also known as a backend processing system. The wireless node 110 may comprise, for example, a mobile station or fixed station having wireless capabilities. Examples for the wireless node 110 may include any of the examples given for the mobile device 102, and further may include a wireless access point, base station or node, base station radio/transceiver, router, switch, hub, gateway, and so forth. In one aspect, for example, the wireless node 110 may comprise a base station for a cellular radiotelephone communications system. Although some aspects may be described with the wireless node 110 implemented as a base station by way of example, it may be appreciated that other aspects may be implemented using other wireless devices as well. The wireless node 110 may be a communication hub, access point, another mobile device, and so on. Accordingly, the wireless node 110 may act as a local access point to wide area networks such as the Internet to communicate the information received from the IEM device 104 to a node 122, which is remotely located from the first and second nodes, e.g., the mobile device 102 and the wireless node 110, respectively. The remote node 122 may be a healthcare facility (physician's office, hospital, pharmacy), drug manufacturer, nutrition center, back end patient healthcare data processing facility, backend processing system, and the like.

In one aspect, the mobile device 102 communicates with the wireless node 110 over a wireless medium 134. In various aspects, the mobile device 102 and the wireless node 110 may comprise or be implemented by a wireless device. The wireless device generally may comprise various physical or logical elements implemented as hardware, software, or any combination thereof, as desired for a given set of design parameters or performance constraints. In various aspects, the physical or logical elements may be connected by one or more communications media. For example, communication media may comprise wired communication media, wireless communication media, or a combination of both, as desired for a given implementation. In various implementations, the described aspects of the mobile device 102 and/or the wireless node 110 may comprise part of a cellular communication system to communicate with a cellular network 128 via cellular tower 124 over wireless medium 136.

As shown in FIG. 1, the wireless node 110 is in communication with a remote node 122, e.g., a backend processing system. The remote node 122 comprises a processing system 138 communicatively coupled to a database 140. Information associated with patients, including identity and medication types and doses, may be stored in the database 140. In one aspect, the processing system 138 receives information from the mobile device 102 via the wireless node 110 and accesses the information in the database 140 to provide information to the care provider through the wireless node 110 and/or the mobile device 102. The remote node 122 can communicate various information; for example, identification information such as a photo of the patient for identification, a photo of the IEM device 104 before it is ingested, the type of medication combined with the IEM device 104, as well as confirmation of the type and dose of medication that the patient ingested. The wireless node 110 can communicate with the remote node 122 using any mode and frequency of communication that is available at the site, such as wireless, G2, G3, G4, real-time, periodically based on predetermined time delays, as well as store and forward at later time.

Vehicles of communication between the wireless node 110 and the remote node 122 include a network. In various aspects, the network may comprise a LAN as well as a WAN including without limitation Internet, wired channels, wireless channels, communication devices including telephones, computers, wire, radio, optical or other electromagnetic channels, and combinations thereof, including other devices and/or components capable of/associated with communicating data. For example, the communication environments include in-body communications, various devices, various modes of communications such as wireless communications, wired communications, and combinations of the same.

The processing system 138 at the remote node 122 may comprise servers configured as desired, e.g., to provide for subject directed permissions. For example, the servers may be configured to allow a family caregiver to participate in the subject's therapeutic regimen, e.g., via an interface (such as a web interface) that allows the family caregiver to monitor alerts and trends generated by the server, and provide support back to the patient. The servers also may be configured to provide responses directly to the subject, e.g., in the form of subject alerts, subject incentives, which are relayed to the subject via the communication device. The servers also may interact with a health care professional, e.g., RN, physician, which can use data processing algorithms to obtain measures of health and compliance of the subject, e.g., wellness index summaries, alerts, cross-patient benchmarks, and provide informed clinical communication and support back to the patient. The servers also may interact with pharmacies, nutrition centers, and drug manufactures.

In one aspect, the remote node 122 may store information received from the mobile device 102 in the database 140. Such information may comprise the approximate time and date stamp when the IEM device 104 was ingested by the patient 106. In addition, an identification number such as a serial number, for example, associated with the IEM device 104, the individual patient identification, the source of the medication, and the expiration date or shelf life of the medication combined with the IEM device 104 may be stored in the database 140.

Still with reference to FIG. 1, in one aspect, shortly after the IEM device 104 is ingested by the patient 106, the IEM device 104 communicates information to the wearable receiver 108 via the detection arrangement, e.g., the electrodes. The wearable receiver 108, in turn, communicates the information to the mobile device 102, which may communicate the information either to the wireless local node 110 (e.g., via a Wi-Fi connection) or may communicate with a cellular tower 124 and base station 126 and can access the Internet 130 via a cellular network 128. Accordingly, information received by the mobile device 102 from the IEM device 104 can be communicated to the remote node 122 via the Internet 130 through the cellular network 128. The processing system 138 at the remote node 122 receives the information from the mobile device 102 and may store it in the database 140.

In another aspect, the mobile device 102 communicates with a local wireless access point 110 (e.g., Wi-Fi), which is coupled to a LAN 112. The LAN 112 is coupled to a WAN such as the Internet 130, which is coupled to the remotely located remote node 122. Upon detecting the unique electrical current signature generated by the IEM device 104, (e.g., by way of receiving data/information associated with the electrical current signature from the wearable receiver 108), the mobile device 102 can communicate the information to the processing system 138 at the remote node 122 via the access point 110, LAN 112, and Internet 130. The processing system 138 stores the information in the database 140. The remote node 122 can access other networks 132 for additional processing of the information associated with the IEM device 104 stored in the database 140.

In another aspect, the mobile device 102 may transmit information associated with the IEM device 104 to another mobile device. The other mobile device then communicates with the cellular tower 124, base station 126, cellular network 128, and the Internet 130 to the remote node 122. In another aspect, the other mobile device communicates with the access point 110, LAN 112, and the Internet 130 to the remote node 122. Once communication is established with the remote node 112, the information associated with the IEM device 104 can be processed by the processing system and/or stored in the database 140. Additional details associated with the system 100 are described hereinbelow.

Figure 2:
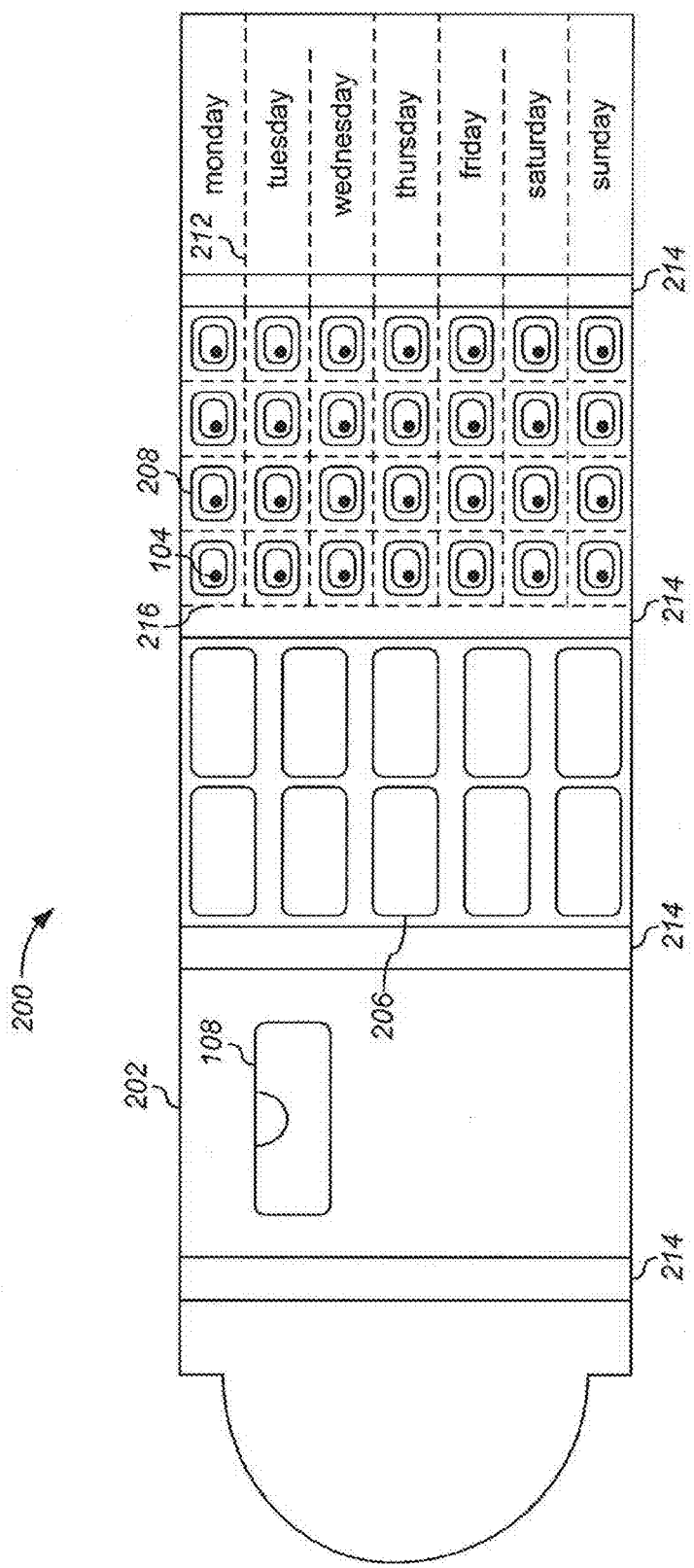
FIG. 2 illustrates one aspect of a weekly medication adherence package received by the patient.

In connection with the description of FIGS. 2-51, for conciseness and clarity reference will also be made to the system 100 and elements thereof shown in FIG. 1. Having described a basic system, in which the subscription information system according to the present disclosure may be implemented, the description now turns to FIG. 2, which illustrates one aspect of a weekly adherence package 200 received by the patient 106. The adherence package 200 comprises, for example, a foldable sheet 202 that can be creased at various sections 214 and folded into a discreet and convenient package for the patient 106 to use. The contents of the adherence package 200 generally include a wearable receiver 108 (e.g., an electronic patch), a plurality of identification labels 206, and a plurality of blisters 208 containing a predetermined supply of medications located therein. Each blister 208 may be filled by the pharmacist and may include an IEM device 104 for tracking the medication events and generating a medication timeline as described in detail hereinbelow. It will be appreciated that each daily dosing section of the adherence package 200 may include any number of blisters 208 based on the medication needs and requirements of the patient 106. As shown, the adherence package 200 includes a weekly supply of medication where each day includes four dosing events, and therefore, there are twenty-eight separate blisters 208. The weekly blister pack supply of medications also includes a perforation 212 along a horizontal direction so that the patient 106 can remove one or more than one day's personalized supply of medication and take with him by simply tearing along the perforation 212. It will be appreciated that although the perforations are shown along a horizontal direction for tearing off a daily supply of medications, the perforations also can be provided along a vertical direction 216. In other aspects, the medication blister packs associated with various predetermined time periods, e.g., individual days of the week, may be configured in a vertical direction rather than a horizontal direction as shown in FIG. 2. In that aspect, the daily perforations would be provided along a vertical rather than horizontal direction.

In a general sense, the adherence package 200 comprises a sheet 202 with a plurality of tear-away strips associated with a personalized dose. At least one blister pack 208 may be coupled to the sheet for containing the personalized dose and a perforation 212 provided on the sheet 202 to enable removal of the at the least one blister pack 208 from the sheet 202 by tearing along the perforation 212. In one aspect of the adherence package 200, at least one of the plurality of tear-away strips comprises an indicia thereon to correlate a time period with the at least one tear-away strip. As illustrated such indicia corresponds to days of the week, although the indicia also may correspond to times of the day, and so on. In another aspect of the adherence package 200, at least one of the plurality of tear-away strips comprises an indicia 206 thereon to correlate a personalized dose with the at least one tear-away strip. In one aspect, the adherence package 200 further comprises at least one receiver 108 configured to be associated with a living subject 106 and to receive a communication from an ingestible device 104. The receiver 108 comprises communication circuits to wirelessly communicate with a mobile device 102. In one aspect, the adherence package 200 further comprises a mobile device 102 configured to communicate with the at least one receiver. In one aspect, the adherence package 200 further comprises at least one ingestible device 104.

In various aspects, in order to receive the weekly medication adherence package 200, the patient 106 must enroll, subscribe, register, etc., to the subscription information system according to the present disclosure. Although initially, the patient 106 will receive a start-up kit, the patient 106 will eventually receive weekly medication adherence packages 200 on a weekly or monthly basis, for example. It will be appreciated, however, that a medication adherence package may be implemented in various forms based on whether it is part of an initial purchase, an ongoing weekly, monthly, or other subscription, or an alternative do-it-yourself configuration, which may simply include refill blister packs and wearable receivers, as described hereinbelow. For example, in one aspect, as part of the initial purchase, the patient 106 receives a start-up kit which includes a personal code, a wearable receiver 108 (e.g., electronic patch), several demonstration tablets, and instructions on how to get started using the kit. If the patient 106 does not own a mobile device 102, one may be provided with the initial purchase. Thus, in one aspect, the start-up kit also may comprise a pre-installed smartphone (e.g., Android) along with use instructions. As part of ongoing monthly subscription, for example, the patient 106 would receive a package similar to the weekly medication adherence package 200 shown in FIG. 2. A month's supply would include, for example, four weekly medication adherence packages 200. Each weekly adherence package 200 may include a box of six wearable receivers 108 and wipes and twenty-eight blisters 208 for storing a weekly supply of medication at four daily doses. Each daily dose would also comprise an IEM device 104. A do-it-yourself supply, may include a box of wearable receivers 108 (e.g., one or two or more and preferably six wearable receivers 108) and a multi-count blister pack, one box per daily dosing event.

Within minutes of receiving the initial start-up adherence package and opening it up, the patient 106 is able to install the appropriate applications on the mobile device 102 in order to start collecting data from the wearable receiver 108. The wearable receiver 108 starts collecting activity data after the patient ingests demonstration tablets. Eventually, the patient 106 will receive the actual weekly medication adherence package 200 which contains actual medications and a corresponding IEM device 104 for each medication blister 208 to track the medication events. Once the system is operational, a GUI application launched on the mobile device 102 can be configured to display a variety of personal information such activity and medication streams, personal notifications, insights into activity and medication trends, among others, which are described in detail hereinbelow in connection with FIGS. 3-51, for example.

Figure 3:
FIG. 3 illustrates one aspect of a personal information stream graphical user interface (GUI) for a display screen of a mobile device.

FIG. 3 illustrates one aspect of a personal information stream graphical user interface 300 (GUI) for a display screen of a mobile device 102. The left top portion of the personal information stream GUI 300 shows the patient's name "Kathryn" along with several GUI elements or icons displayed along the top horizontal portion of the GUI 300. These GUI elements, for example, may include a first GUI element 316 which corresponds to the display of an activity timeline, generally in the form of an activity ribbon 306 and a medication timeline. One skilled in the art will recognize that the display of an activity timeline may be embodied in various formats and, as such, is not limited to any particular expression thereof. A second GUI element 318 corresponds to the display of activity and/or medication trends. A third GUI element 320 corresponds to the display of configurations, initial set-up, management, and replacement of the wearable receiver 108. A fourth GUI element 322 corresponds to managing and control of data sharing functions such as invitations and control which data is being shared with the invitee. A fifth GUI element 324 corresponds to system utility tools to personalize and tailor the system to the needs and requirements of the patient 106.

To activate the GUI 300 the user selects the first GUI element 316 and the display screen of the mobile device 102 shows the activity timeline 302 and a medication timeline 304. In FIG. 3, the personal information stream comprising the activity timeline 302 and the medication timeline 304 corresponds to a single 24-hour day. The personal information stream however, may be customized to cover periods of one week, one month, or any suitable custom tailored period. The activity timeline 302 comprises an activity ribbon 306 that shows how the patient 106 is spending each moment of the day being tracked. The activity timeline 302 is shown along the bottom horizontal axis and the level of activity is shown along the vertical axis on the left side of the GUI 300. In the aspect shown in FIG. 3, the level of patient activity is displayed as four discrete increments, namely, sleep 308, rest 310, moderate physical activity 312, and elevated physical activity 314. The activity ribbon 306 scrolls over the timeline and tracks the patient's activities throughout the day. A comment bubble 326 is provided for the patient 106 to enter personal notes to clarify any particular recorded level of activity. Also shown along the bottom horizontal portion of the GUI 300 is the medication timeline 304, which is marked by an icon of a tablet 328 to indicate the time when a particular medication event occurred. The system displays the times when medications are scheduled to be taken as one set of icons and the actual ingestions corresponding to the detection of the IEM device 104, as detected by the wearable device 108, as another set of icons 328. Accordingly, the system 100 provides no judgment and allows the patient 106, or third party, to visually correlate daily physical activity levels and medication events by simply presenting the information on the personal information stream GUI 300.

Accordingly, generally, patients will spend a lot of time sleeping and then they will get up and run some errands and then maybe rest in their chair and watch television at mid-day. Later they may get up and go for a walk that elevates their heart rate, get a little exercise and then come back and sit and rest until they go to sleep. The activity ribbon 306 shows the patient how the patient 106 flows between all those different states throughout a day. Therefore, at a glance, the user can tell if the patient 106, in a given night, for example, has been really disruptive and has been getting up multiple times to go to the bathroom or if they were tossing and turning and not really sleeping restfully. This can be seen by looking at the state of the activity ribbon 306. For example a sub-activity portion 330 of the activity ribbon 306 shows that the patient was restless during a period of time when they should have been sleeping.

Figure 4:
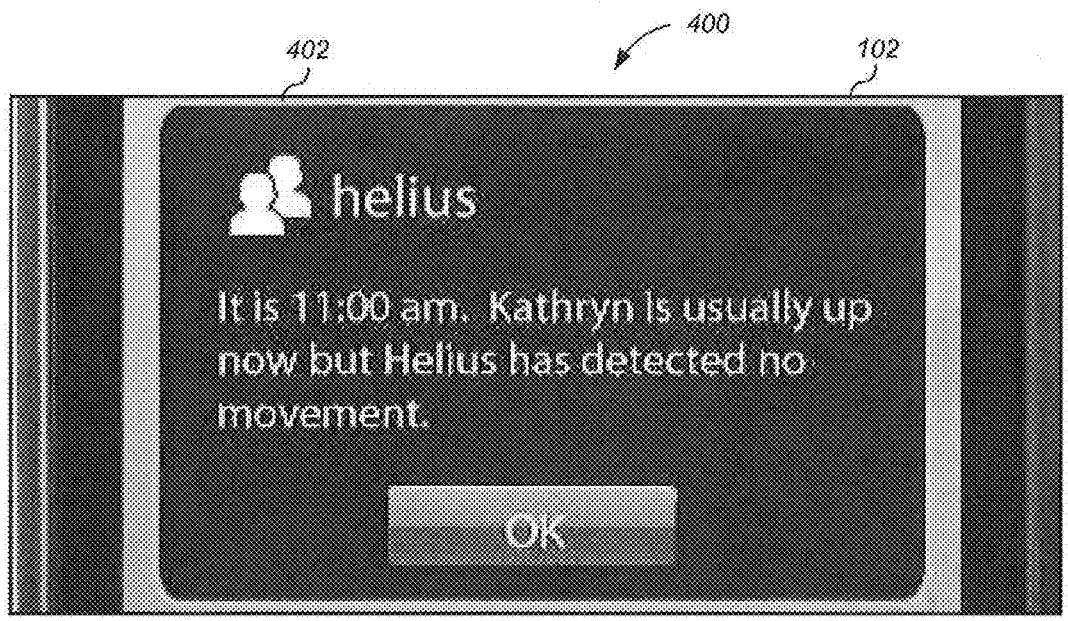
FIG. 4 illustrates one aspect of a personal notification GUI for a display screen of a mobile device.

FIG. 4 illustrates one aspect of a personal notification GUI 400 for a display screen of a mobile device 102. The personal notification GUI 400 is provided to the mobile device 102 of a third party that has been selected by the patient 106, such as the patient's caregiver, to notify the caregiver of the occurrence or lack of occurrence of a particular event. The personal notification GUI 400 also may be used to invite the third party to view the patient's data. This is referred to as the sharing function. The patient 106 has complete control over what data the third party can view. The illustrated personal notification GUI 400 provides a notification 402 that the system 100 has not detected any movement by the patient 106 even though at the stated time the patient 106 is usually up and about. The caregiver can then follow up with a suitable action. Other aspects of the personal notification functions are described hereinbelow.

Figure 5:
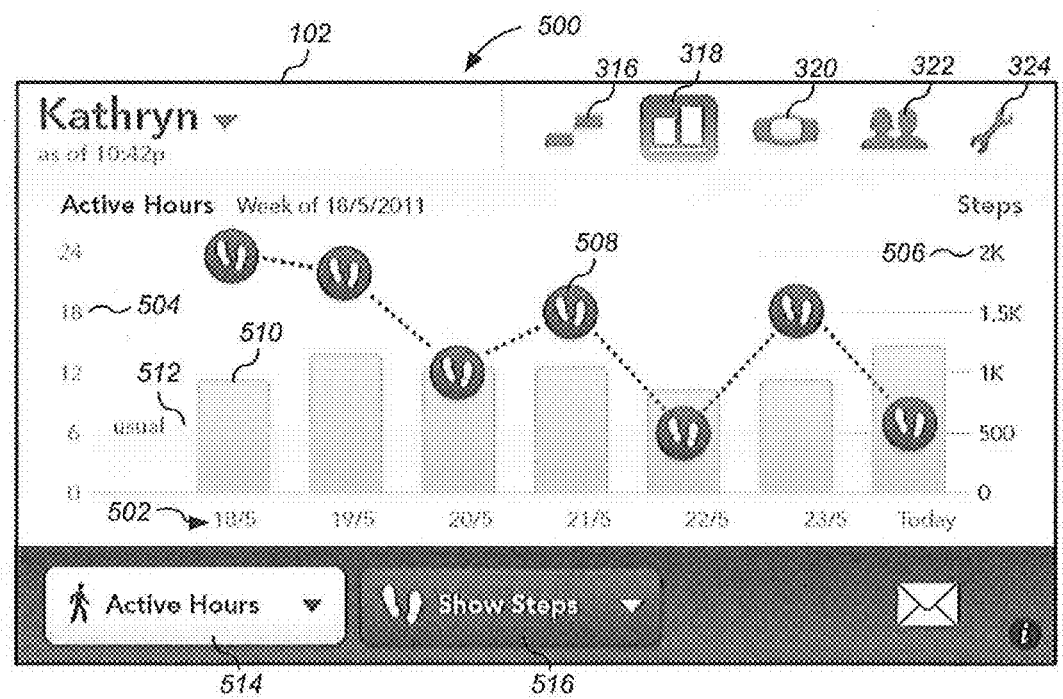
FIG. 5 illustrates one aspect of an activity trend GUI for a display screen of a mobile device.

FIG. 5 illustrates one aspect of an activity trend GUI 500 for a display screen of a mobile device 102. To activate the activity trends GUI 500 the second GUI element 318 is selected. As shown, the activity trends GUI 500 provides the patient's physical activity trend for a given week. The corresponding days of the week 502 are shown along the bottom horizontal portion of the GUI 500. A first button 514 shows the number of active hours 504 when selected. The corresponding number of hours 504 that the patient 106 is physically active during the course of a day is shown along the left vertical portion of the GUI 500 axis. The active hours 504 are graphed using a bar graph 510. A horizontal line 512 represents the usual number of hours 504 that the patient is active during the course of a day. A second button 516 shows the number of steps 506 taken by the patient when selected by the user. The number of steps 506 taken by the patient during the course of a day is provided along the right vertical axis. The number of steps 506 taken by a patient is graphed using icons 508 that look like a pair of footprints positioned within a circle. The number of steps 506 taken by the patient 106 is shown along the left vertical portion of the GUI 500.

Having described the subscription information system according to the present disclosure in general terms, one use aspect of the subscription information system is now described with reference to the foregoing FIGS. 1-5 and subsequent FIGS. 6-11. Accordingly, once a patient 106 decides to participate in a medication adherence program, they can purchase an adherence start-up kit from the pharmacist.

Figure 6:
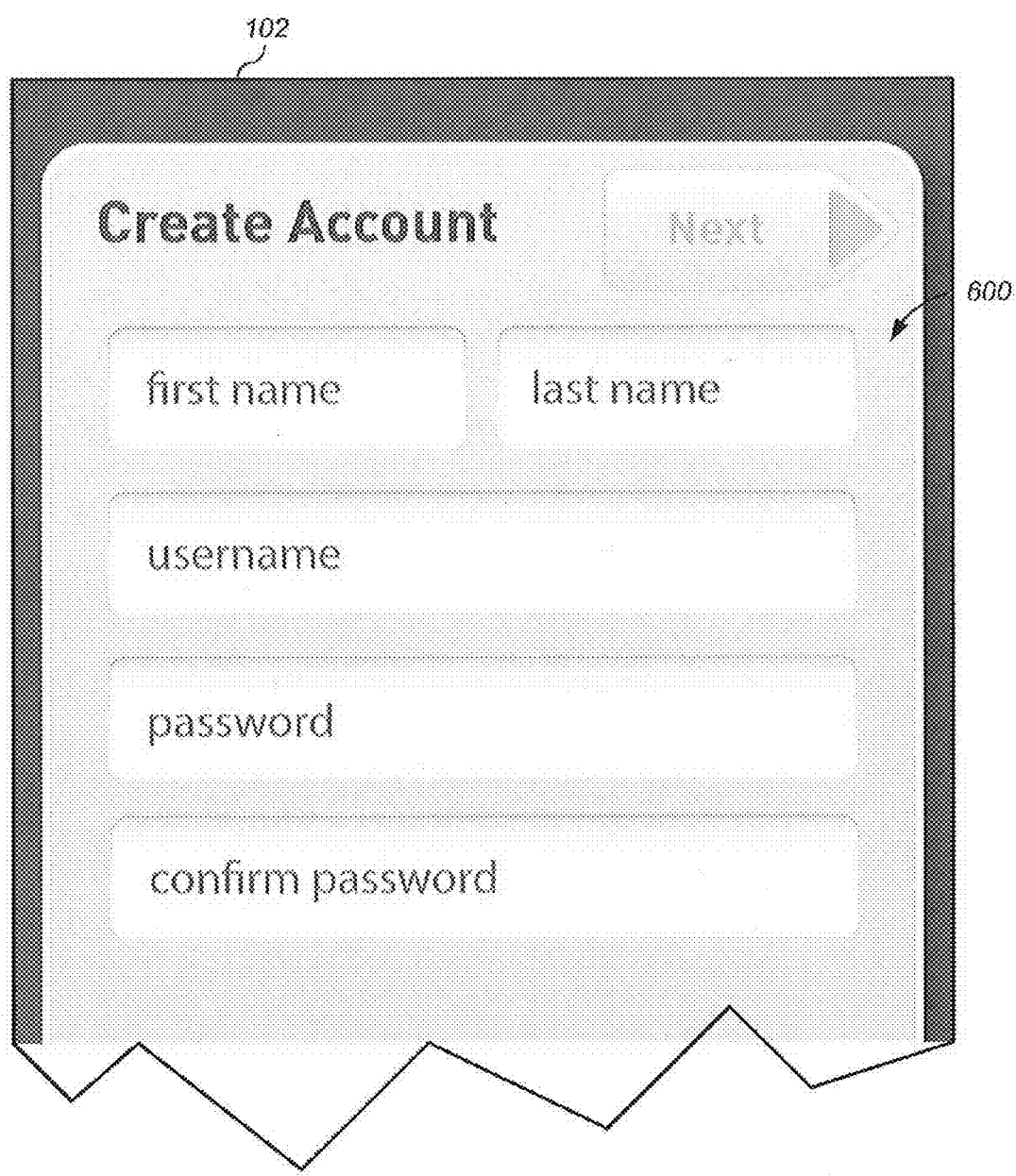
FIG. 6 illustrates one aspect of an account creation GUI for a display screen of a mobile device.

FIG. 6 illustrates one aspect of an account creation GUI 600 for a display screen of a mobile device 102. The subscription information system 100 is set up by first creating an account, pairing the wearable receiver 108 with a mobile device 102, ingesting some demonstration tablets provided in the start-up kit, launching an application, and then viewing the data shown on the display of the mobile device 102. The system 100 starts providing data to the mobile device 102 with activity capture as soon as the patient 106 sets up the start-up kit. The actual adherence package 200 is generally provided a few days after the start-up kit is set up. As shown in FIG. 6, after the patient 106 pairs the wearable receiver 108 with the mobile device 102, an application is launched by the mobile device 102 to create an account. In response, the account creation GUI 600 is shown by the mobile device 102 display. The patient 106 enters the required information in the appropriate text box, such as, "first name," "last name," "username," "password," and "confirm password."

Figure 7:
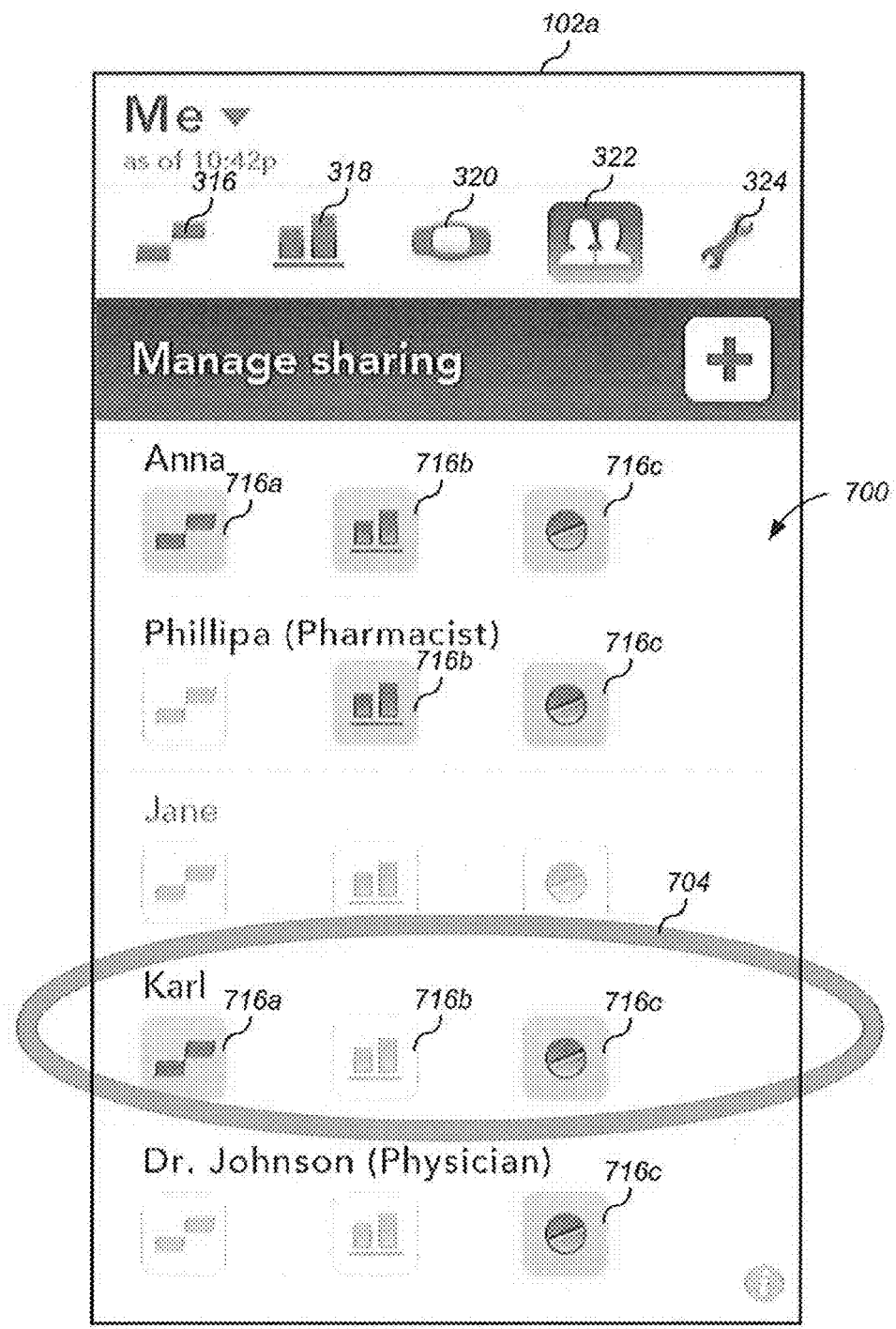
FIG. 7 illustrates one aspect of a "Manage sharing" GUI for a display screen of a mobile device enabling a patient to select with whom to share data and what data to share.
Figure 8:
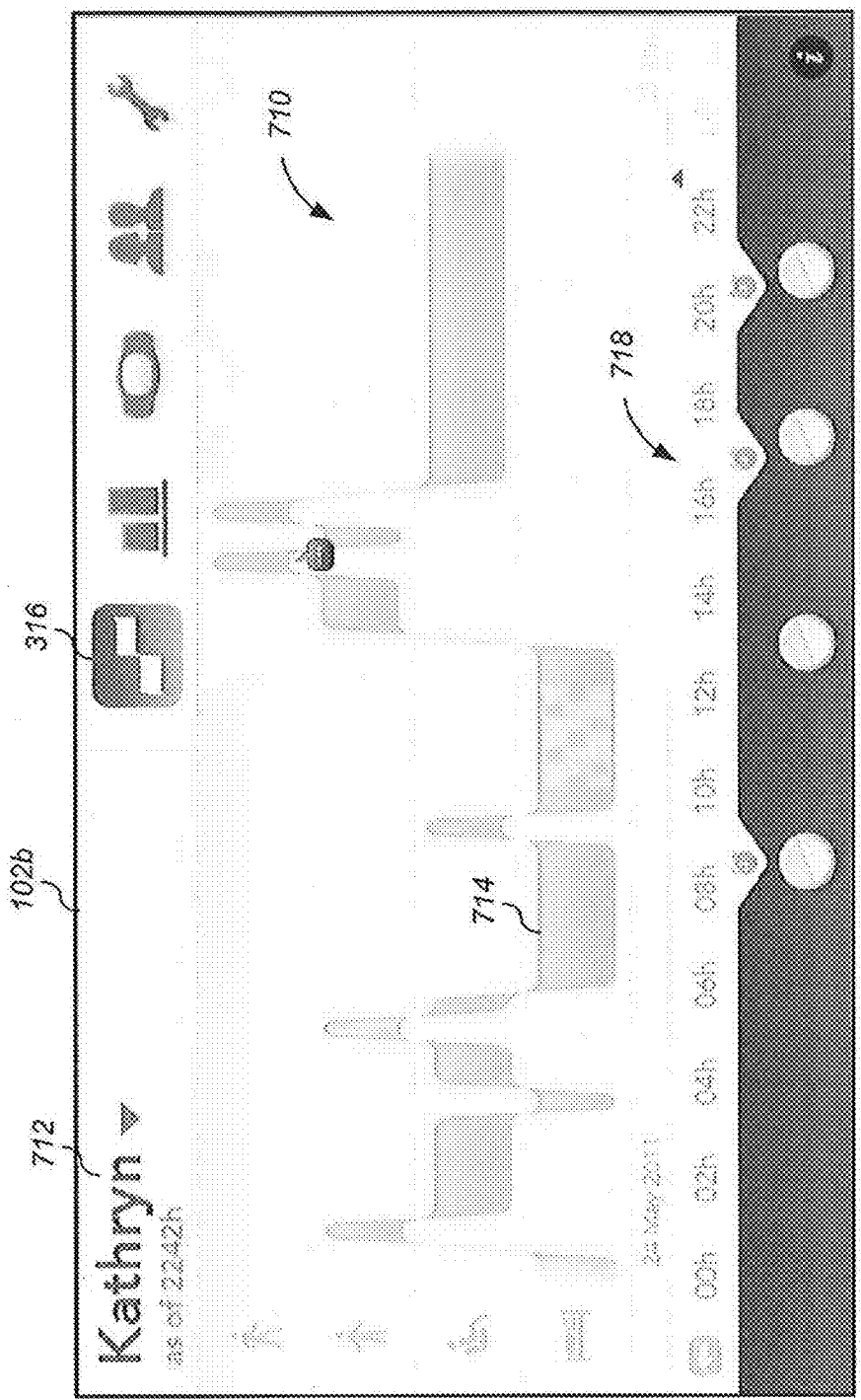
FIG. 8 illustrates one aspect of a third party caregiver GUI for a display screen of a mobile device for sharing information with a patient.

FIG. 7 illustrates one aspect of a "Manage sharing" GUI 700 for a display screen of a mobile device 102a enabling a patient to select with whom to share data and what data to share. FIG. 8 illustrates one aspect of a third party caregiver GUI 710 for a display screen of a mobile device 102b for sharing information with a patient. FIGS. 7 and 8 illustrate a patient's mobile device 102a and a third party mobile device 102b, respectively. The third party has been invited and approved for sharing information with the patient 106 as described hereinbelow. FIG. 7 illustrates a patient (Kathryn) mobile device 102a display showing a "Manage sharing" GUI 700 to enable the patient 106 to select with whom to share data and what data to share. As shown in FIG. 7, the "Manage sharing" GUI 700 shows several elements including the group of GUI elements 316, 318, 320, 322, 324 described in connection with FIG. 3 icons 702 displayed along the top horizontal portion of the GUI 700. Each GUI element corresponds to a different action including, for example, the first GUI element 316 corresponds to the display of activity and medication timelines, the second GUI element 318 corresponds to the display of activity and/or medication trends, the third GUI element 320 corresponds to the display of configurations, initial set-up, management, and replacement of the wearable receiver 108, the fourth GUI element 322 corresponds to managing and control of data sharing functions such as invitations and control which data is being shared with the invitee, and the fifth GUI element 324 corresponds to system utility tools to personalize and tailor the system to the needs and requirements of the patient 106.

In particular, as shown in FIG. 7, the fourth GUI element 322 has been selected to open and display the "Manage sharing" GUI 700. Using the "Manage sharing" GUI 700 the patient 106 can control who can share data and what data can be shared with an invitee. As shown, the "Manage sharing" GUI 700 displays (1) three caregivers named Anna, Jane, and Karl; (2) a pharmacist named Phillips and (3) a physician named Dr. Johnson. The patient 106 can control the information that can be viewed by each of these people separately by selecting the appropriate GUI element. For example, Anna has been enabled to view the personal information activity timeline by selection of element 716a; the activity trend chart by selecting element 716b; and the medication timeline by selecting element 716c. Phillipa (Pharmacist) is only able to view the activity trend chart and the medication timeline because only elements 716b and 716c were selected. Jane cannot share any data. Dr. Johnson (Physician) can only view the medication timeline because only element 716c was selected. Taking Karl as an example, section 704 shows that Karl has been enabled to share the activity timeline and the medication timeline based on selected corresponding elements 716a and 716c, but not the trend chart. Accordingly, Karl is able to monitor whether Kathryn is moving around and taking her medications. Since the trend chart element 716b is not selected, Kathryn has not granted Karl access to view her trend charts.

FIG. 8 illustrates one aspect of a third party caregiver (Karl) GUI 710 for a display screen of a mobile device 102b while sharing information with the patient 106 (Kathryn). The caregivers' mobile device 102b display shows a third party sharing GUI 710. The GUI 710 displays only the data that the patient 106 has granted permission for. As previously discussed, the patient 106 (Kathryn) invited the caregiver (Karl) to share some of her data. Accordingly, the GUI 710 shows the patient's name Kathryn in the upper left portion 712 of the GUI 710. Since the patient 106 Kathryn has granted Karl permission to view her activity timeline 714 and medication timeline 718, Karl is able to view these elements by selecting the activity timeline GUI element 708 on the GUI 710.

Figure 9:
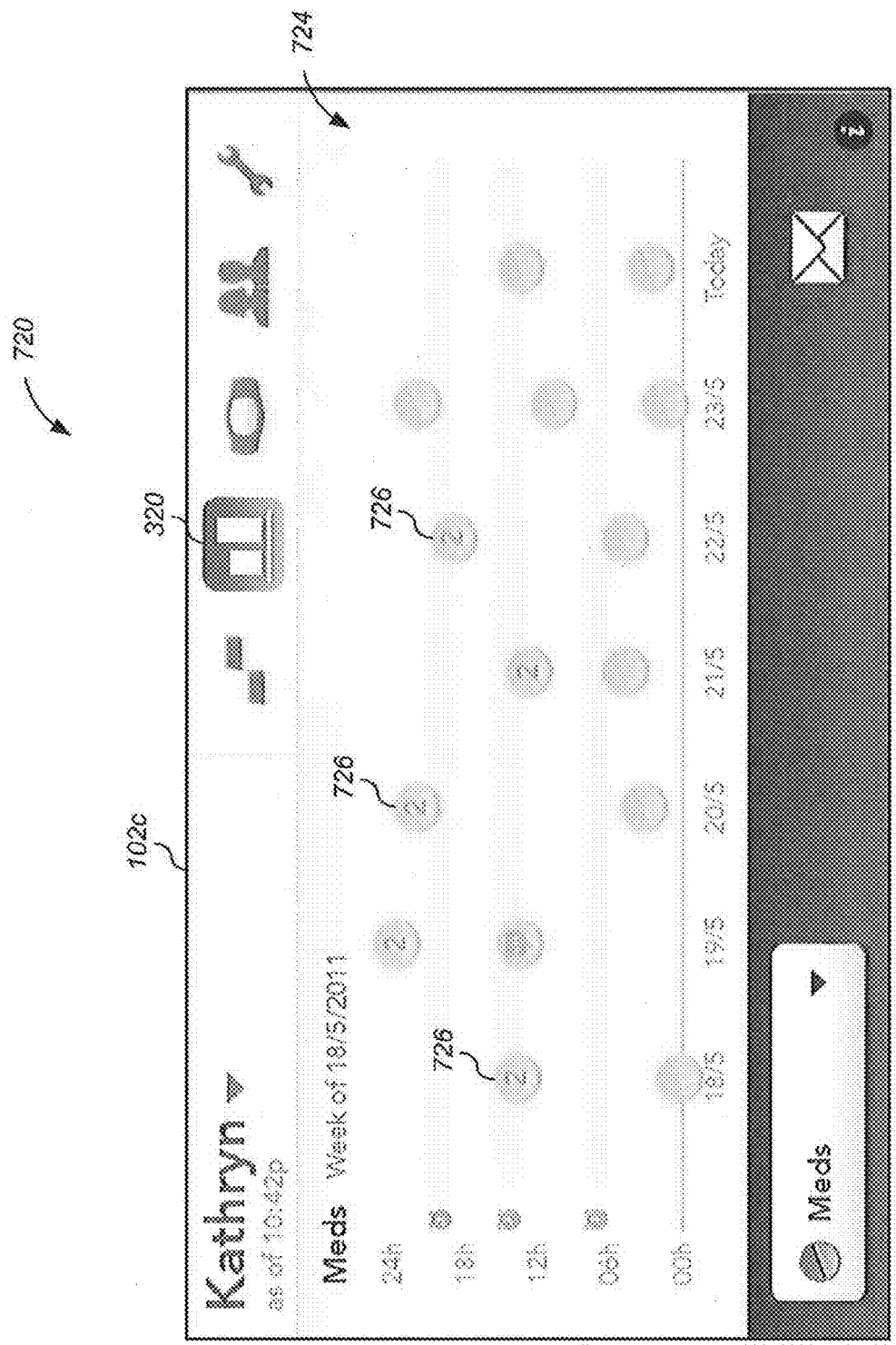
FIGS. 9-11 illustrate various aspects of support GUIs for a display screen of a mobile device.
Figure 10:
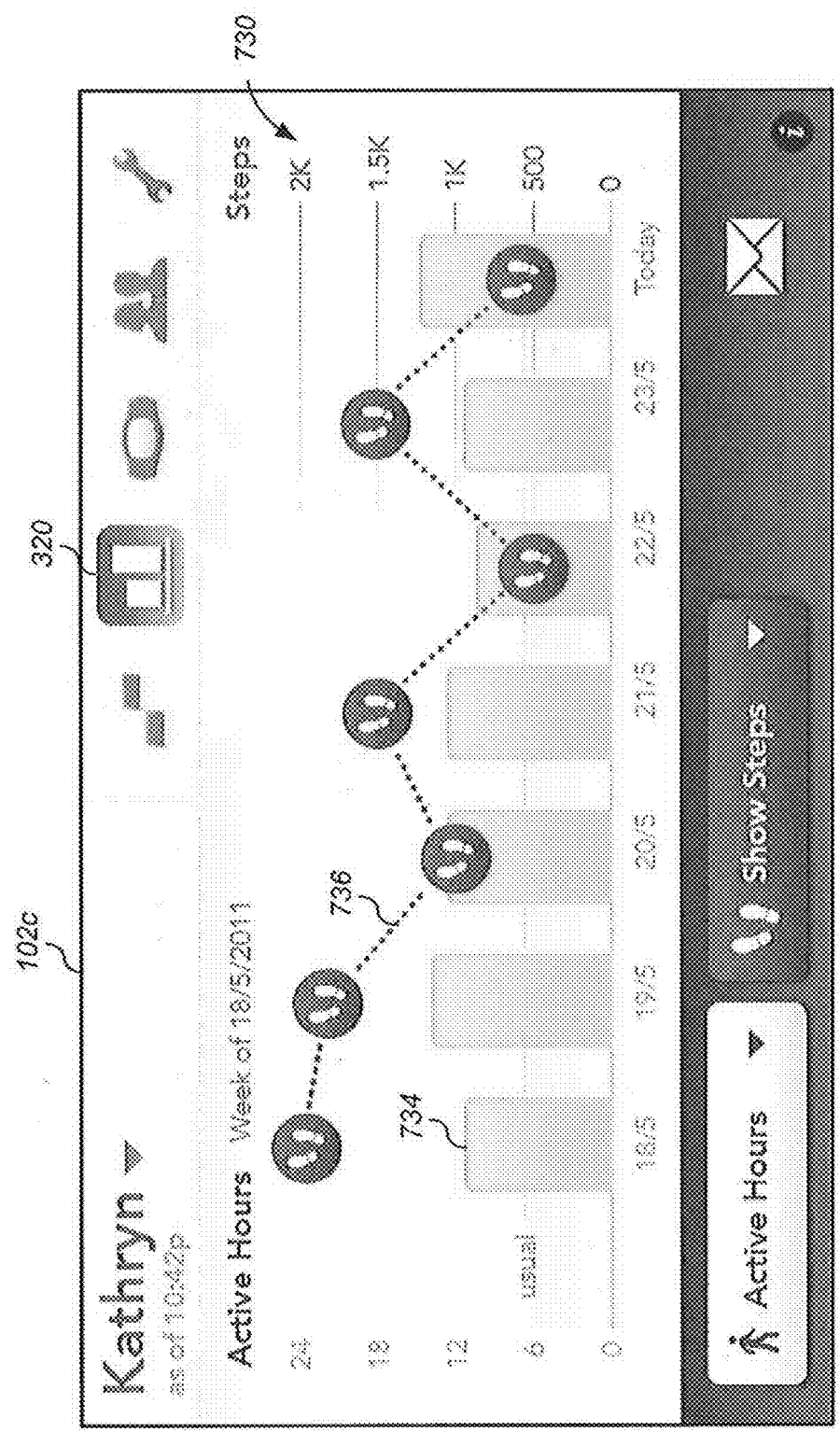
Figure 11:
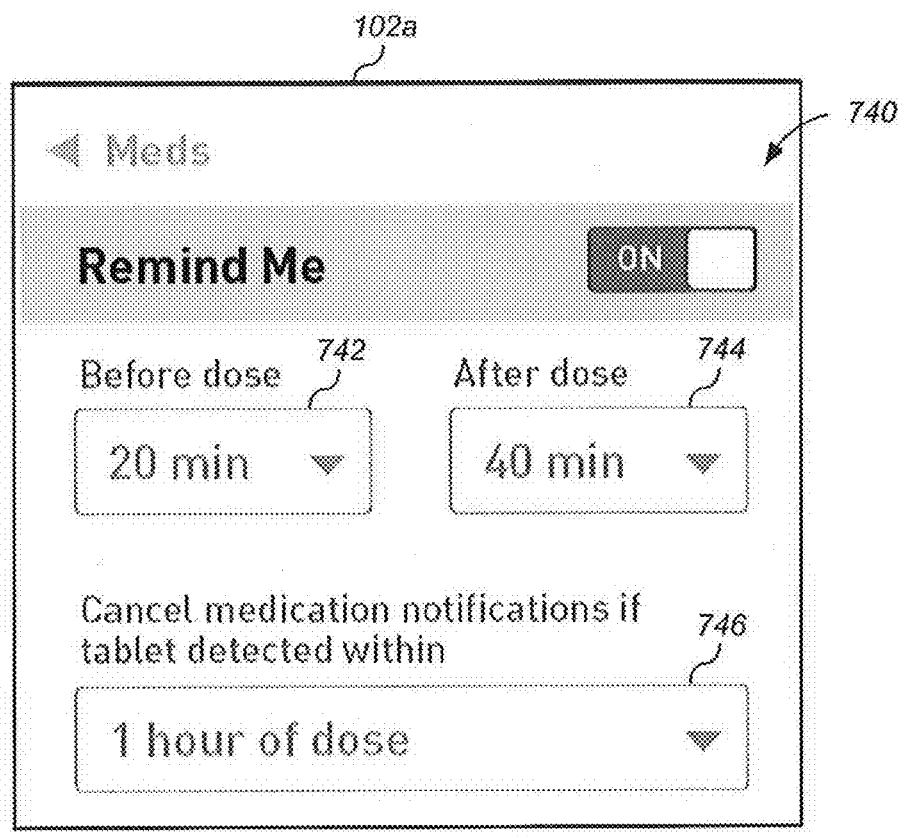

FIGS. 9-11 illustrate various aspects of support GUIs for a display screen of a mobile device 102. FIG. 9 illustrates one aspect of a "Medication trends" GUI 720 for a display screen of a third party mobile device 102c. In the illustrated example, the third party mobile device 102c belongs to the patient's physician. As shown, the "Medication trends" GUI 720 shows a daily medication trend chart 724 recorded events over a one week period. The physician is able to view the daily medication trend chart 724 if the patient 106 previously enabled this action using the "Manage sharing" GUI 700 as described in FIG. 7. Returning to FIG. 9, the physician can display the daily medication trend chart 724 by selecting the activity trend chart element 722. The medication trend chart 724 shows the number of doses taken by the patient 106 and at what time on a daily basis over a one week period. The days of the week are shown along a bottom horizontal portion of the "Medication trends" GUI 720 and dosing times are shown along the left vertical portion of the "Medication trends" GUI 720. As shown, the physician is able to see that the patient 106 often takes the mid-day dose along with the evening dose as shown by the tablet icon 726 with the number two located thereon.

FIG. 10 illustrates one aspect of an "Activity trends" GUI 730 for a display screen of a third party (e.g., physician) mobile device 102c. As illustrated in FIG. 10, if the physician was granted permission to view the patient's activity trend chart, the physician simply selects the activity trend charts element 722 to display the activity trend charts 734, 736. The first activity trend chart 734 corresponds to the number of daily active hours over a one week period. Days of the week are shown along a bottom horizontal portion of the "Activity trends" GUI 730 and the hours 0-24 are shown along the left vertical portion of the "Activity trends" GUI 730. The second activity trend chart 736 corresponds to the number of steps taken by the patient 106 on a daily basis over a one week period. The number of steps from 0-2 k is shown along the right vertical portion of the "Activity trends" GUI 730. Accordingly, the physician is able to see the patient's level of activity over the week period.

FIG. 11 illustrates one aspect of a custom notification GUI 740 for a display screen of a patient's mobile device 102a. The custom notification GUI 740 is used by the patient to set notifications before or after a medication dose is due to be taken or to cancel medication notifications if an IEM device 104 is detected within a predetermined period of taking the medication (e.g., ingesting the IEM device 104). In particular, a drop-down list element 742 may be used to set a reminder at a predetermined time before the dose is due (e.g., 20 minutes). A second drop-down list element 744 may be used to set a reminder at a predetermined time after the dose is due (e.g., 40 minutes). A third drop-down list element 746 may be used to cancel medication notifications if an IEM device is detected with in a predetermined time (e.g., 1 hours) of taking the dose.

In respect to sharing the patient's data with a caregiver or other party, in one aspect, applications associated with the subscription information system according to the present disclosure whether they are executed on the mobile device 102 or the remote processing system 122, provide a mechanism to ensure that the person with whom the patient intends to share the data is really the intended person. It is the industry standard, for example with web sites like Google Health or Microsoft Health Vault, that such applications requests that the user enter their email address in twice and then press send.

It is very common, however, that a person incorrectly enters their email address both times. Therefore, in conventional applications there is no real guarantee that entering an email address twice assures that the intended party receives the information being shared by the patient. In accordance with one aspect, for security and privacy reasons, the present application requests that the user enter their email address once and then select the "send" button. The patient receives a personal code and an email from the remote system 122 saying that the patient has invited a caregiver, or other third party, to share the patient's medical data. The patient then must communicate separately with the invitee either over the phone or separate email to disclose to the invitee the patient's personal code. The caregiver must enter the personal code to accept the patient's invitation to share data. The subscription information system according to the present disclosure does not replace any sort of interpersonal communication with the caregiver, but rather strengthens those relationships and opens up a different line of communication between patient and caregiver.

FIGS. 12-51 will now focus on a specific implementation of the mobile device 102 functionality from creating an account, pairing the wearable receiver with the mobile device, viewing timelines, managing and replacing the wearable receiver, setting up invitees to share data, and using tools to configure the system to the specifications of the patient. Accordingly, turning now to FIGS. 12-14, where a mobile device 102 display showing a series of GUIs for a display screen of a mobile device 102 that are displayed during the process of creating an account. Once the create account application is launched, the patient mobile device 102 display screen shows a "Sign In" GUI 1200 shown in FIG. 12. The "Sign In" GUI 1200 comprises a "username" text box 1202 as well as a "password" text box 1024 that enables the patient 106 to enter the appropriate information.

Figures 12, 13, 14:
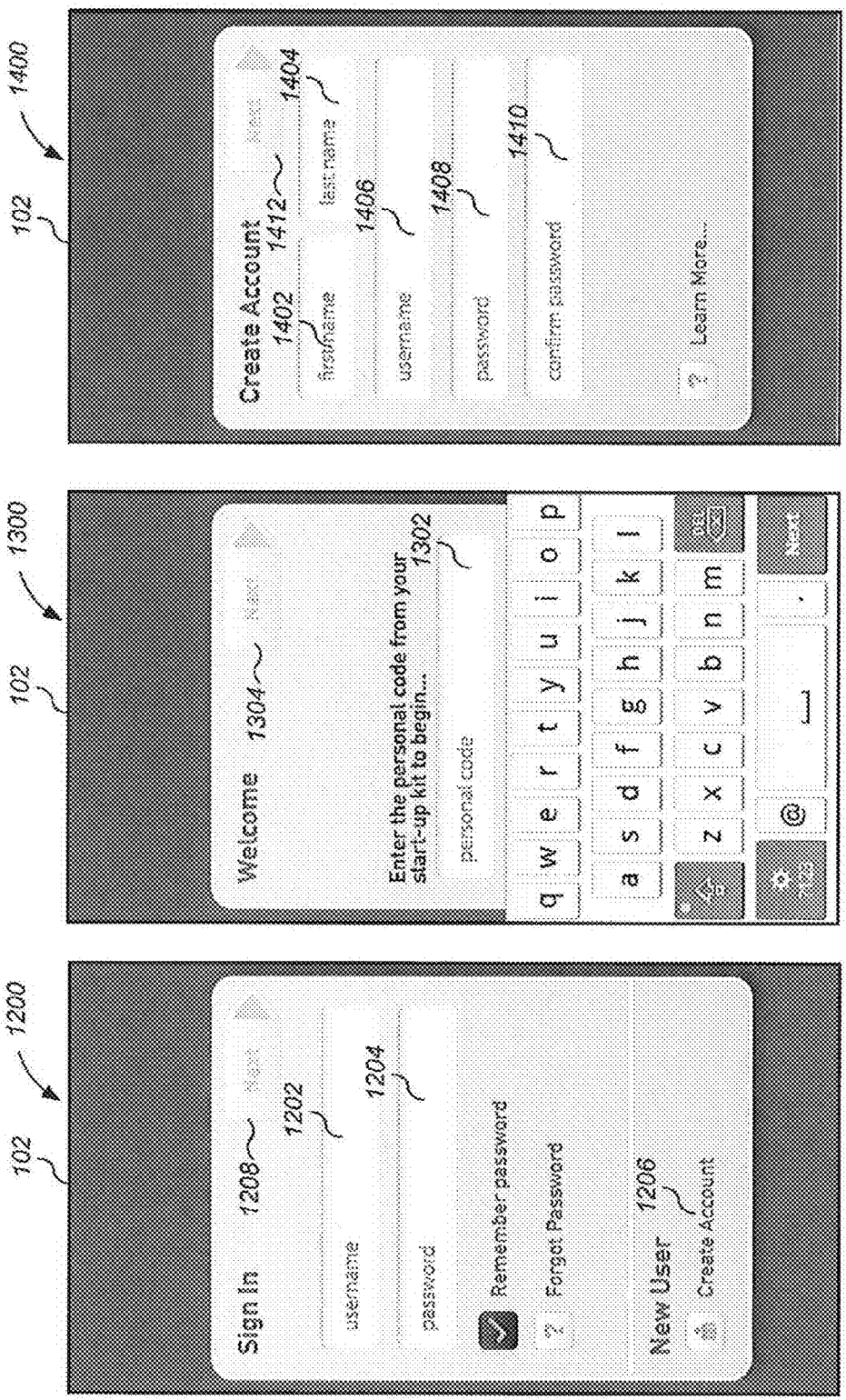
FIGS. 12-14 illustrate various aspects of GUIs for a display screen of a mobile device for creating an account.

Once the appropriate information is entered into the "username" text box 1202 and the "password" text box 1204 and the "Create Account" button 1206 is selected, the display screen of the mobile device 102 shows the "Welcome" GUI 1300 as shown in FIG. 13. The "Welcome" GUI 1300 comprises a "personal code" text box 1302 for the patient to enter the personal code located on the start-up kit in before moving to the next screen by selecting the "Next" button 1304. As briefly mentioned above, the personal code comes with the start-up kit and for security reasons is communicated to an invitee to share data on a separate communication by the patient.

Upon entering the personal code from the start-up kit into the "personal code" text box 1302 and selecting the "Next" button 1302, the display screen of the mobile device 102 shows a "Create Account" GUI 1400 as shown in FIG. 14. The "Create Account" GUI 1400 comprises a "first name" text box 1402, a "last name" text box 1404, a "username" text box 1406, a "password" text box 1408, and a "confirm password" text box 1410. Selecting the "Next" button 1412 sends the information entered by the user to the remote processing system 122 (e.g., the backend processing system) and creates an account in the name of the patient.

FIGS. 15-18 illustrate various aspects of GUIs for a display screen of a mobile device 102 for wearing and demonstrating the wearable receiver. As shown in FIG. 15, a first GUI 1550 provides instructions to set up the wearable receiver (e.g., electronic patch). The GUI 1500 shows a wearable receiver element 1502 having a flashing button element 1504 and provides instructions to push the corresponding button on the actual wearable receiver 108 (patch) until the light blinks. Accordingly, at this time the patient removes the wearable receiver from the start-up kit and pushes the button on the receiver 108. The patient then selects (taps) the "Next" button 1506 to proceed to the subsequent GUI.

FIG. 16 shows a subsequent GUI 1600 on the display screen of the mobile device 102. The GUI 1600 shows a wearable receiver element 1602, a mobile device element 1604, and a wireless element 1606 indicating that the mobile device 102 and the wearable receiver 108 are in the process of connecting. During the connecting process, the wearable receiver 108 is paired with the mobile device 102 so that the two devices can communicate with each other.

FIG. 17 shows a new GUI 1700 on the display screen of the mobile device 102 when the wearable receiver 108 and the mobile device 102 are connected. The GUI 1700 provides feedback that the mobile device 102 and the wearable receiver 108 are connected and provides instructions to place the wearable receiver 108 on the left side of the patient's torso. The screen also displays a patient element 1702 with a wearable receiver element 1704 placed on the left side of the torso of the patient element 1702. Upon accomplishing this task, selecting the "Next" button 1706 launches the next GUI 1800.

Figure 18:
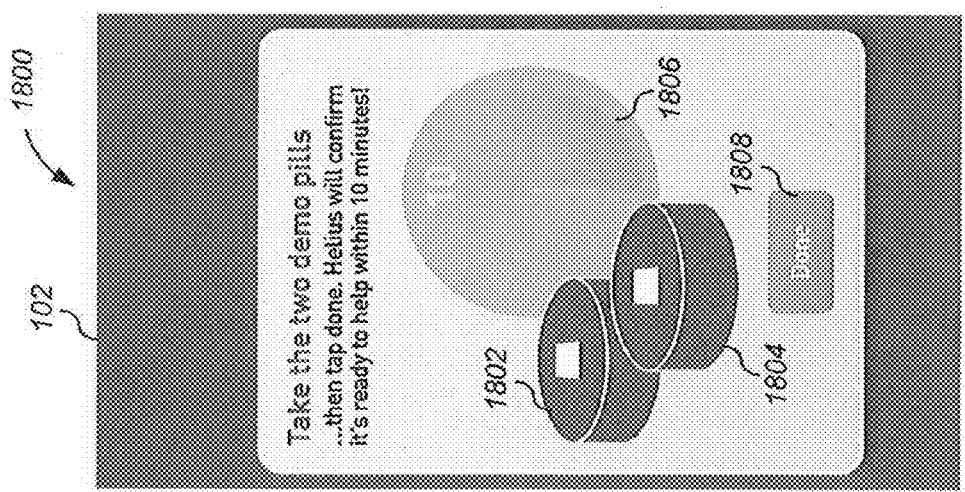

FIG. 18 shows a GUI 1800 on the display screen of the display device 102. The GUI 1800 provides instructions for the patient 106 to take the two demonstration pills that were provided with the start-up kit and then select the "Done" button 1808. The GUI 18000 also displays two demonstration pill elements 1802, 1804 and a clock element 1806 to indicate to the patient that the remote processing system 122 will confirm that the system 100 will be ready to help the patient in a predetermined amount of time. As illustrated by the screen 1800, the patient 106 is advised that the remote processing system 122 will be ready to assist within 10 minutes, for example. It will be appreciated that additional GUIs may be provided to indicate to the patient 106 that the mobile device 102 is waiting for a response back from the remote processing system 122. Another GUI may be provided to inform the patient 106 that the remote processing system 122 has detected the two demonstration pills and further display two buttons: (1) A first button "See may data" and (2) a second button "Share my data," for example. An additional GUI may be provided to indicate that the remote processing system 122 has not yet detected the demonstration pills and display an additional "Troubleshoot" button.

Figure 19:
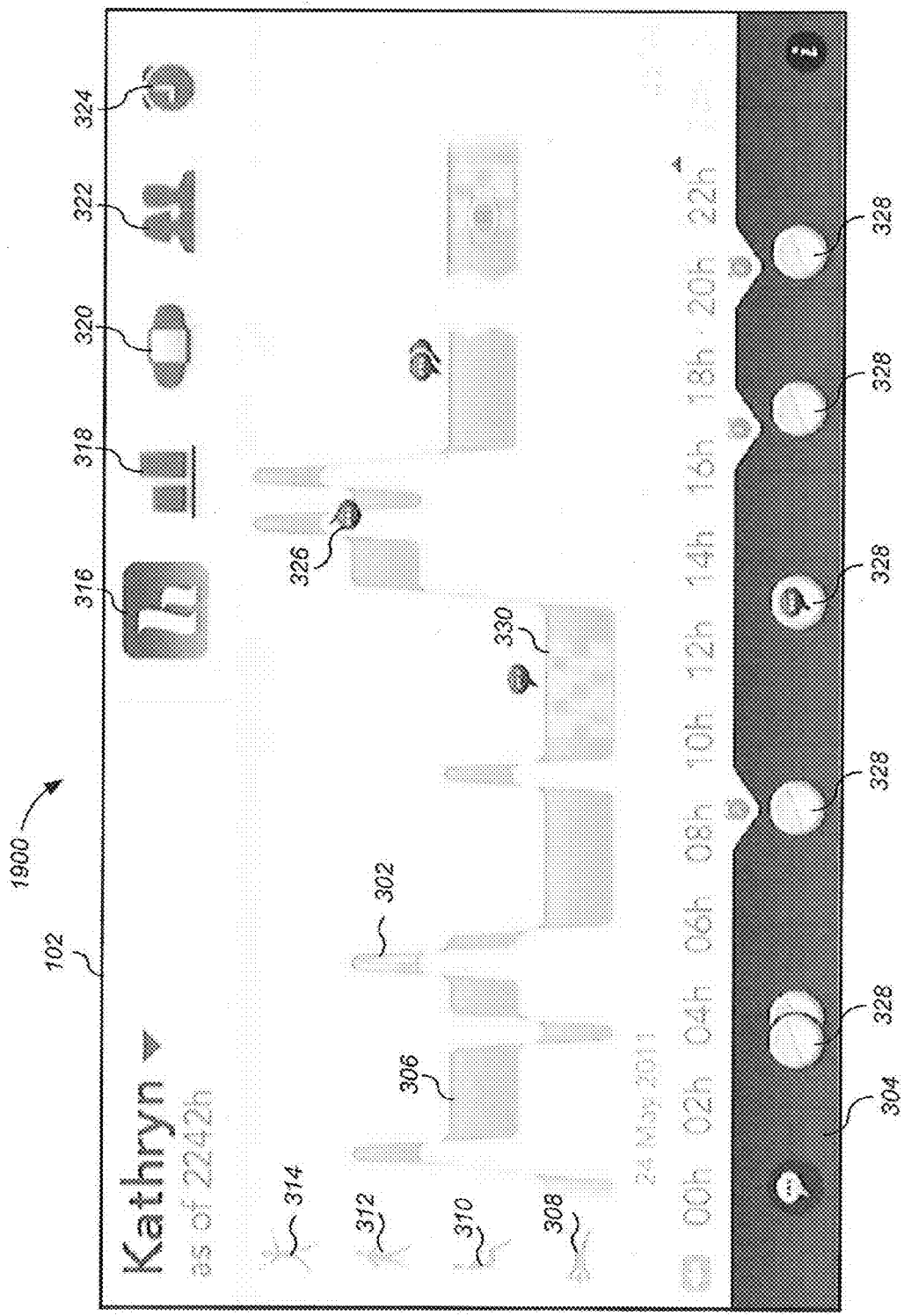
FIG. 19 illustrates one aspect of a home GUI for a display screen of a mobile device.

Once the patient 106 has completed the tasks associated with the wear and demonstrate phase as shown and described in connection with FIGS. 15-18 and the remote processing system 122 has successfully detected the ingestion of the demonstration pills, the display screen of the mobile device 102 shows a home GUI 1900 as shown in FIG. 19. The home GUI 1900 shows the timeline view that characterizes the patient's daily activities and medication ingestions. The GUI 1900 is similar to the GUI 300 shown and described in connection with FIG. 3 and for the sake of conciseness will not be repeated here.

Figure 20:
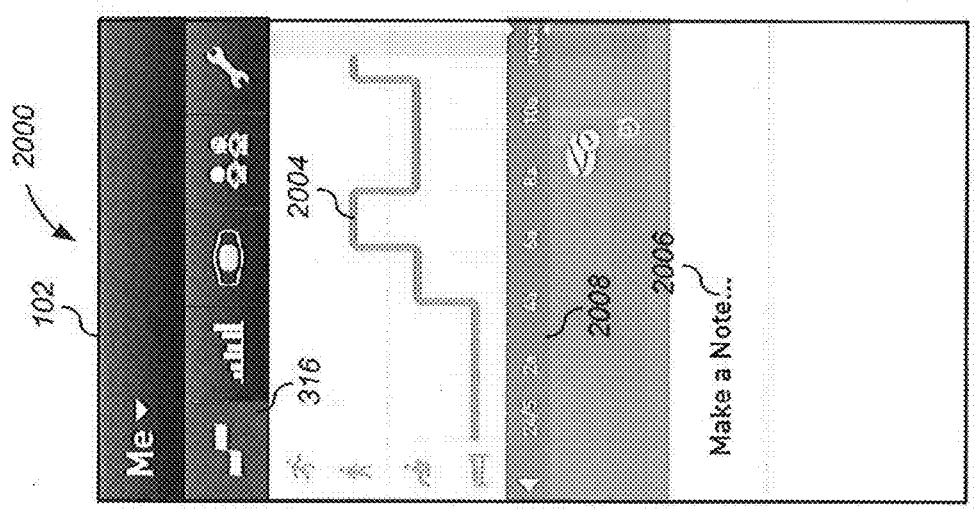

FIGS. 20-23 illustrate various aspects of timeline GUIs for a display screen of a mobile device 102 characterizing a patient's daily physical activity and medication ingestions. FIG. 20 illustrates a GUI 2000 for a display screen of a mobile device 102 showing an activity timeline 2004 and a medication timeline 2008 that characterizes the patient's daily physical activity and medication ingestions, respectively. The GUI 2000 is displayed when the timeline element first GUI element 316 corresponding to the display of activity and medication timelines is selected from a group of elements displayed along the top horizontal portion of the screen layout 2000. To enter a note that will be displayed either on the activity timeline 2004 or the medication timeline 2008, the lower portion of the screen 2006 where the text "Make a Note . . . " appears is selected.

Figure 21:
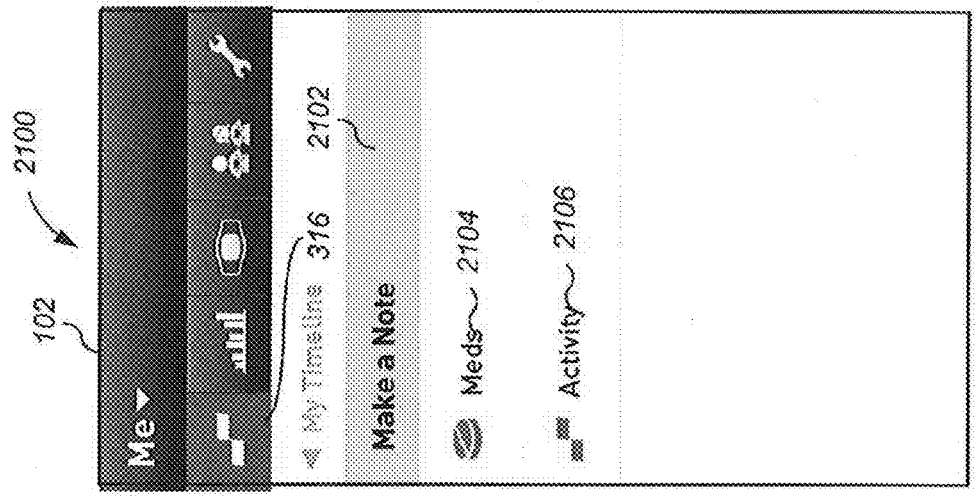
FIGS. 20-23 illustrate various aspects of timeline GUIs for a display screen of a mobile device characterizing a patient's daily physical activity and medication ingestions.

Upon selecting the lower portion of the screen 2006, the display screen of the mobile device 102 shows a "Make a Note" GUI 2100 to select whether the note will appear on the activity timeline 2004 or the medication timeline 2008, as shown in FIG. 20. As shown in FIG. 21, selecting the "Meds" element 2104 will place the note in the medication timeline 2008 and selecting the "Activity" element 2106 will place the note in the activity timeline 2004.

Figure 22:
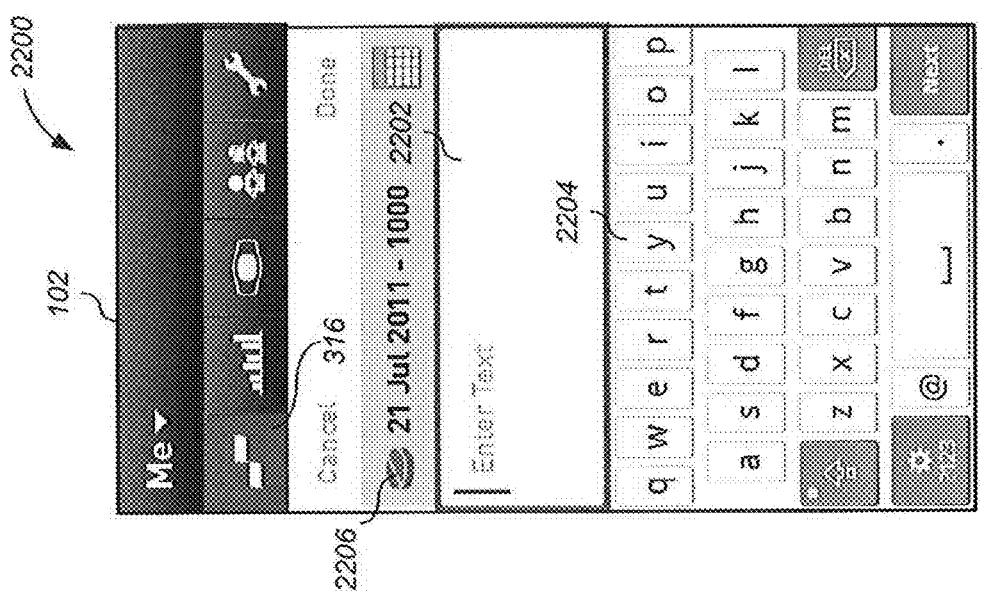

When the "Meds" element 2004 is selected in the "Make a Note" GUI 2100 of FIG. 21, the display screen of the mobile device 102 shows a GUI 2200 as shown in FIG. 22. A "text box" 2202 is provided to enter the note using the virtual keyboard 2204. A medication element 2206 is shown along with the current date to reinforce that the note will be placed in the medication timeline rather than the activity timeline.

Figure 23:
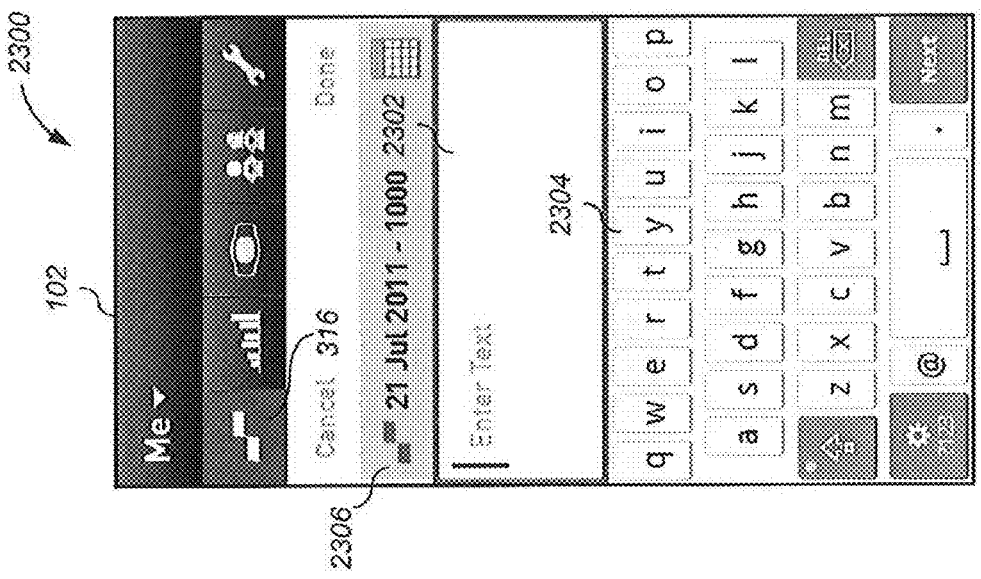

When the "Activity" element 2006 is selected in the "Make a Note" GUI 2100 of FIG. 21, the display screen of the mobile device 102 shows a GUI 2300 as shown in FIG. 23. A "text box" 2302 is provided to enter the note using the virtual keyboard 2304. An activity timeline element 2306 is shown along with the current date to reinforce that the note will be associated in the activity timeline rather than the medication timeline.

Figure 24:
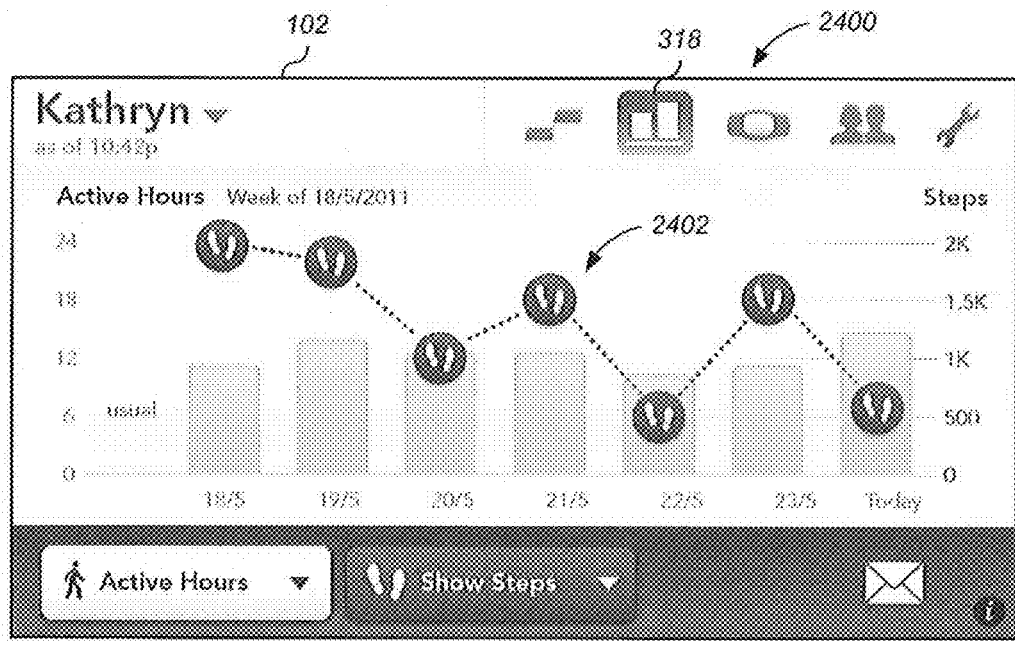
FIG. 24 illustrates one aspect of an activity trend chart GUI for a display screen of a mobile device showing a patient's activity trend over a one week period.
Figure 25:
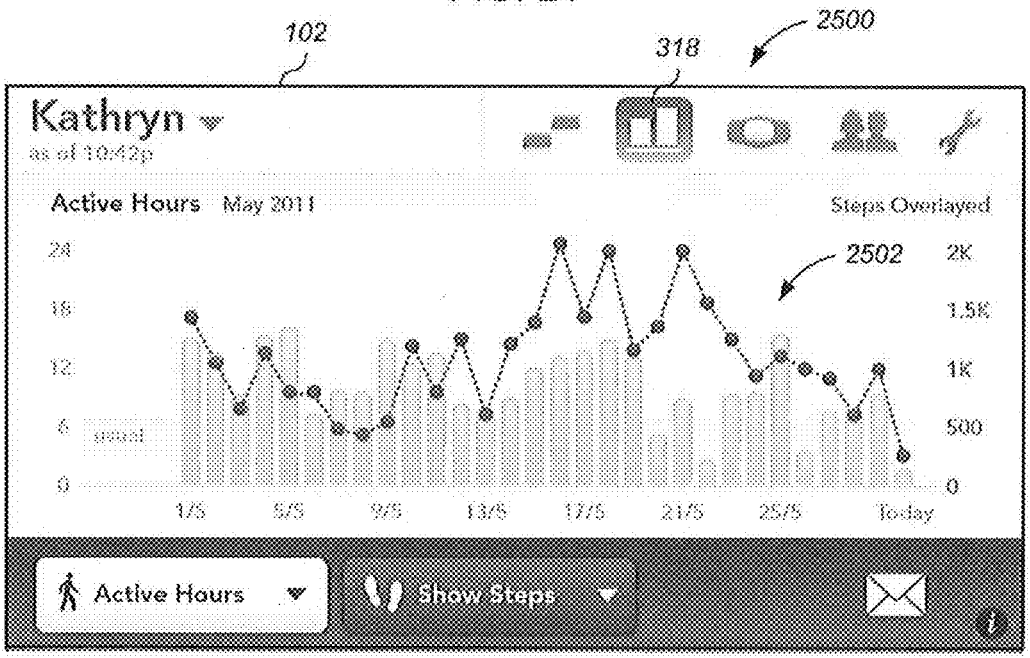
FIG. 25 illustrates one aspect of an activity trend chart GUI for a display screen of a mobile device showing a patient's activity trend over a one month period.

FIG. 24 illustrates one aspect of an activity trend chart GUI 2400 for a display screen of a mobile device 102 showing a patient's activity trend over a one week period. The activity trend chart 2402 can be customized to show the patient's the patient's metrics (e.g., activity trend) over any predetermined period. For example, as shown in FIG. 25, the activity trend chart 2502 shown in GUI 2500 shows the patient's activity trend over a one month period. The GUI 2400 may be opened by selecting the GUI element 318 corresponding to the display of activity and/or medication trends.

Figure 26:
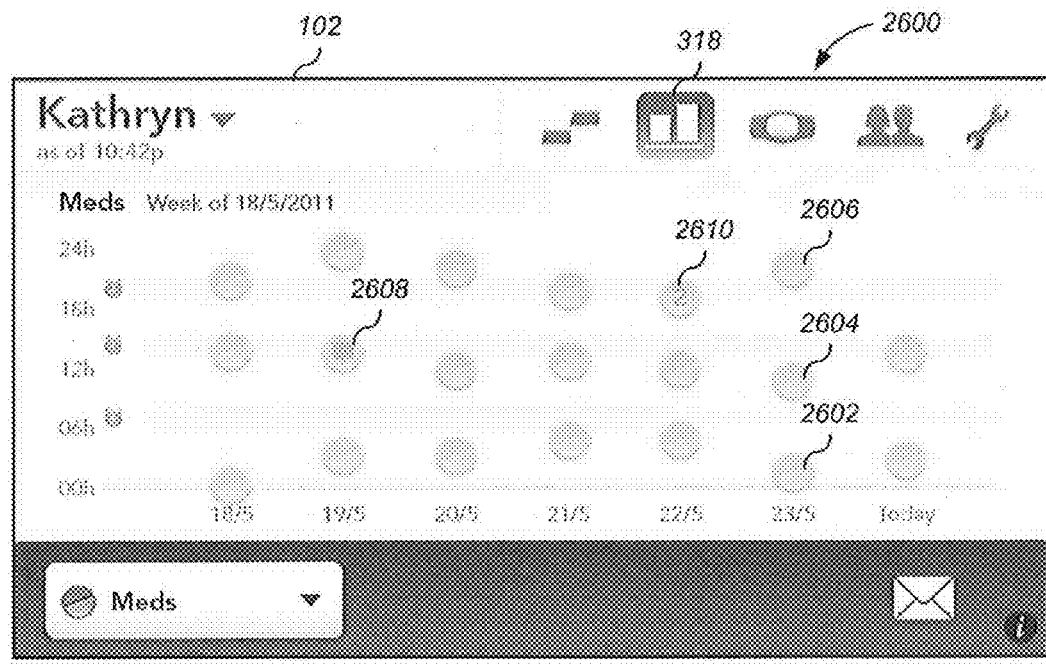
FIG. 26 illustrates one aspect of a medication trend GUI for a display screen of a mobile device showing a patient's medication trend over a one week period.

FIG. 26 illustrates one aspect of a medication trend GUI 2600 for a display screen of a mobile device 102 showing a patient's medication trend over a one week period. The GUI 2600 may be opened by selecting the GUI element 318 corresponding to the display of activity and/or medication trends. The medication trend chart 2602 shows the time of day when medication was ingested by the patient 106. The ingestion time and medication type are communicated by the IEM device 210 to the wearable receiver 108, which is communicated to the mobile device 102 and eventually to the remote processing system 122. The medication trend chart 2602 may be illustrated as follows, for example, on day 23/5 the patient 106 took medication in the morning as indicated by pill element 2602, medication at mid-day as indicated by pill element 2604, and medication in the evening as indicated by pill element 2606. On day 19/5 the patient 106 entered a note in the medication trend chart 2602 as indicated by pill element 2608. On day 22/5 the patient 106 took two doses of medication in the evening as indicated by pill element 2610. Under "Today," the medication trend chart 2602 shows that as of 10:42 pm, the patient 106 has not yet taken the evening medication. Overall, the medication trend chart 2602 shows that for the most part, the patient 106 has been taking their medication at the appropriate times and in the appropriate amounts.

Figure 27:
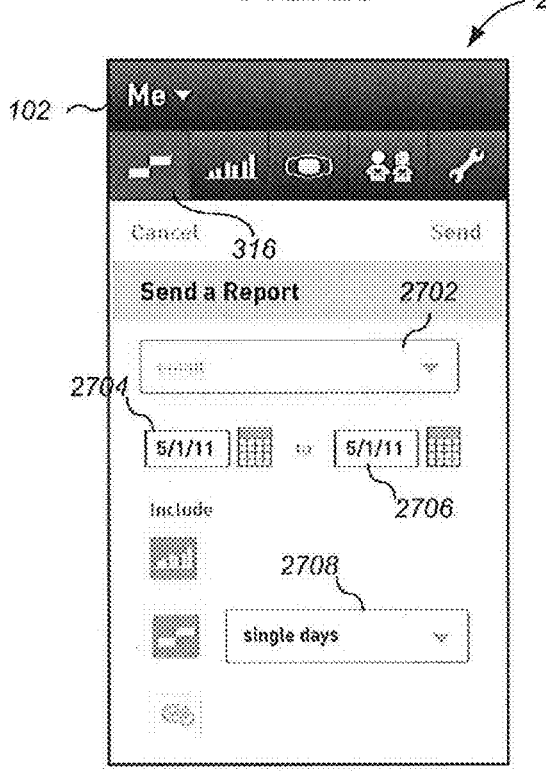
FIG. 27 illustrates one aspect of a "Send a Report" GUI for a display screen of a mobile device for sending a report.

FIG. 27 illustrates one aspect of a "Send a Report" GUI 2700 for a display screen of a mobile device 102 for sending a report. The GUI 2700 provides an email entry box 2702 for selecting or entering an email address where to send the report. The reporting period begin and end dates can be chosen by selecting the calendar elements 2704 and 2706, respectively. Alternatively, the reporting period begin and end dates can be entered into respective text boxes next to the calendar elements 2704, 2706. A resolution text box 2708 is provided to select the resolution of the report, e.g., single days, weeks, months, and so on. The email text box 2702 and the resolution text box 2708 are provided with a drop-down list option to make the selecting process more convenient.

Figure 28:
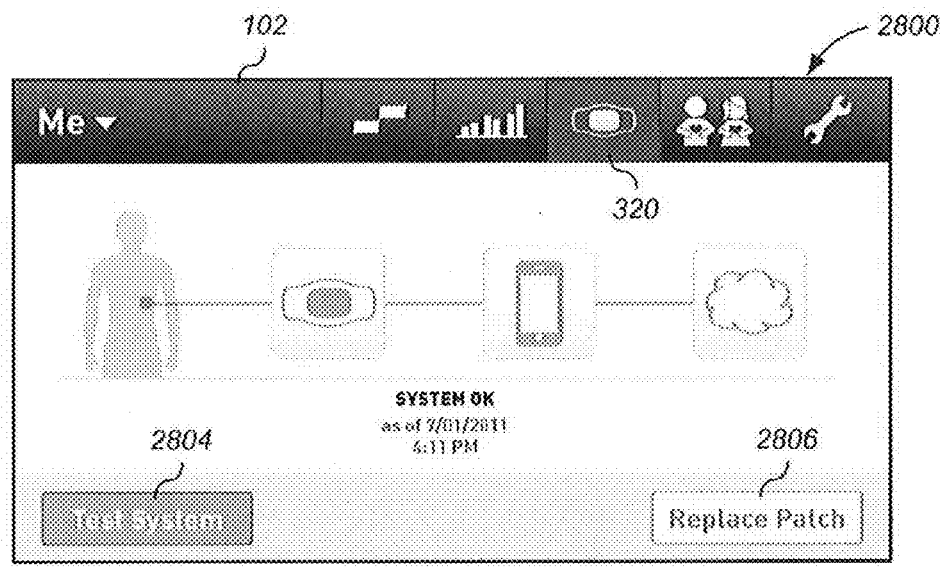
FIG. 28 illustrates one aspect of a "Test System" GUI for a display screen of a mobile device for managing a wearable receiver (e.g., patch).
Figure 29:
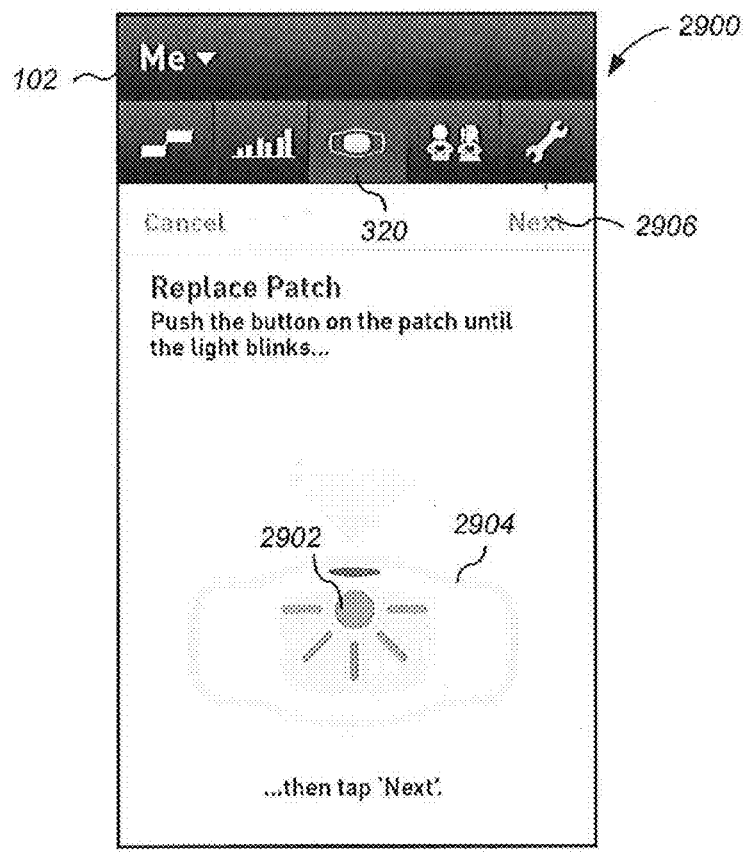
FIG. 29 illustrates one aspect of "Replace Patch" GUI for a display screen of a mobile device for replacing a wearable receiver (e.g., patch).

FIG. 28 illustrates one aspect of a "Test System" GUI 2800 for a display screen of a mobile device for managing a wearable receiver (e.g., patch). FIG. 29 illustrates one aspect of "Replace Patch" GUI 2900 for a display screen of a mobile device for replacing a wearable receiver (e.g., patch). With reference to FIGS. 28 and 29, the "Test System" GUI 2800 and "Replace Patch" GUI 2900, respectively, are associated with a wearable receiver (e.g., patch) system management and a wearable receiver (e.g., patch) replacement. Both GUIs 2800, 2900 can be opened by selecting the patch element 2802, 2902 displayed on the top horizontal portion of the screen. As shown in FIG. 28, the system can be tested by selecting the "Test System" button 2804. Selecting the "Replace Patch" button 2806 opens the "Replace Patch" GUI 2900 shown in FIG. 29 for replacing the wearable receiver (e.g., patch). The "Replace Patch" GUI 2900 displays a patch element 2902 corresponding to the wearable receiver 108 and a flashing button element 2904. The wearable receiver 108 can be replaced by pushing the button located on the wearable receiver 108 until the light blinks and then selecting (e.g., tap) the "Next" element 2906.

Figure 31:
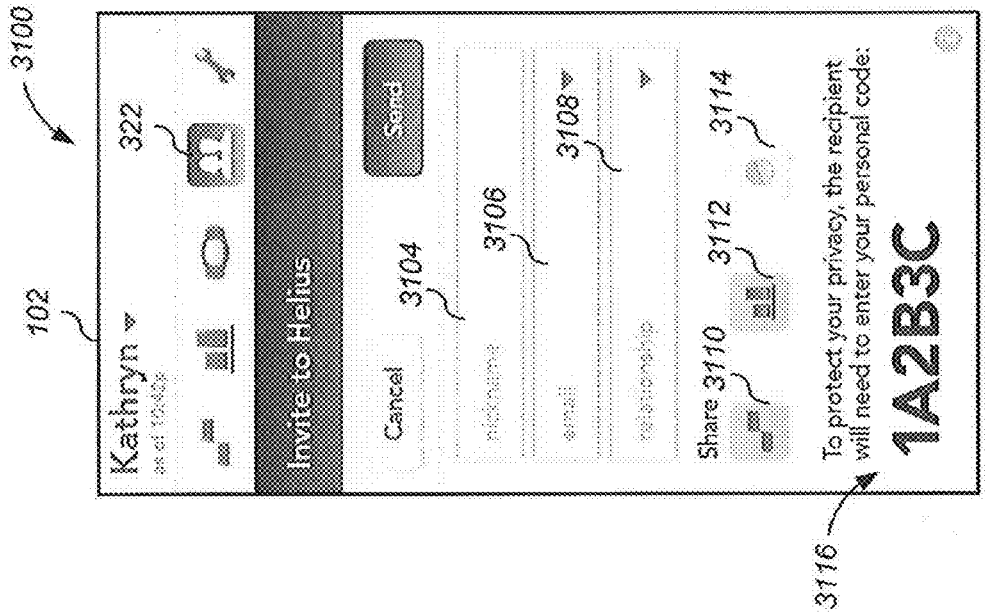
FIG. 31 illustrates one aspect of an "Invite" GUI for a display screen of a mobile device for inviting caregivers to share and controlling data sharing.
Figure 30:
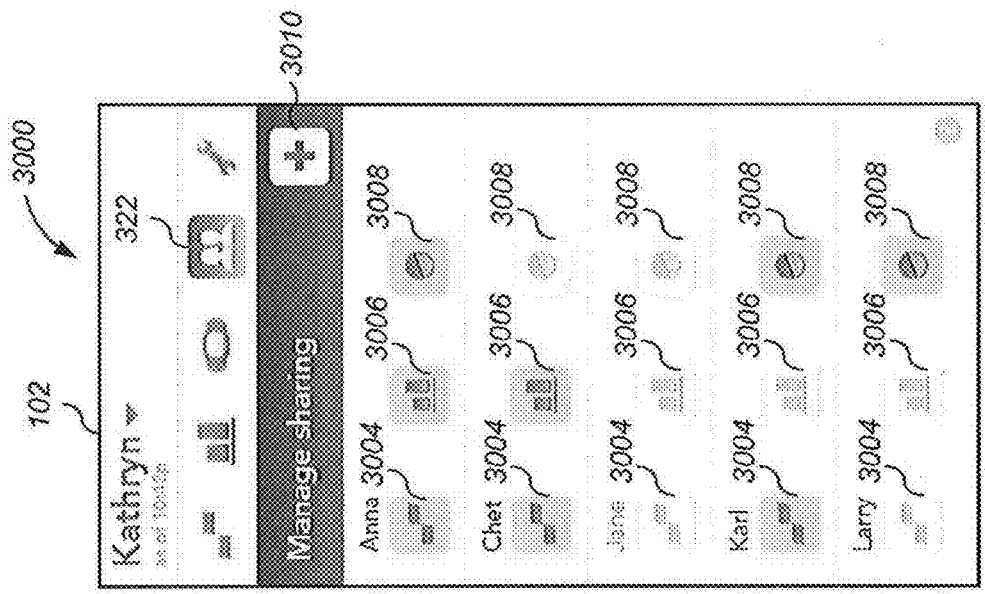
FIG. 30 illustrates one aspect of a "Manage sharing" GUI for a display screen of a mobile device for inviting caregivers to data sharing.

FIG. 30 illustrates one aspect of a "Manage sharing" GUI 3000 for a display screen of a mobile device for inviting caregivers to data sharing. FIG. 31 illustrates one aspect of an "Invite" GUI 3100 for a display screen of a mobile device for inviting caregivers to share and controlling data sharing. With reference to FIGS. 30 and 31, the "Manage sharing" GUI 3000 and "Invite" GUI 3100, respectively, are employed for inviting caregivers and controlling data sharing. The "Manage sharing" GUI 3000 and the "Invite" GUI 3100 can be opened by selecting the respective share GUI element 322 displayed at the top horizontal portion of the GUIs 3000, 3100. Turning now to FIG. 30, the "Manage sharing" GUI 3000 is used to manage the data sharing with third parties, such as caregivers, whom the patient 106 wishes to share their personal data. Both a person with whom to share the data as well as the type of data to be shared can be selected. The selected elements are highlighted. In the aspect illustrated in FIG. 30, Anna has been selected to share data associated with the activity timeline 3004, activity trend chart 3006, and medication timeline 3008. Chet, however, has been selected to share only data associated with the activity timeline 3002 and activity trend chart 3006, but not data associated with the medication timeline 3008. No data is being shared Jane. Karl has been selected to share only data associated with the activity timeline 3004 and the medication timeline 3008, but not data associated with the activity trend chart 3006. Larry has been selected to share only data associated with the medication timeline 3008. A new person with whom to share data can be added by selecting the add element 3010. As previously discussed, data can be shared with anyone who is trusted such as a caregiver, loved one, family member, physician, pharmacist, friend, among others.

In FIG. 31, the "Invite" GUI 3100 for creating an invitation to share data provides several text boxes for the purpose of identifying the person to send the invitation such as the nickname text box 3104, an email text box 3106 to enter the person's email address, and a relationship text box 3108 to enter the relationship between the patient and the person they are about to invite to share data. As illustrated in FIG. 31, both the email test box 3106 and the relationship text box 3108 include a drop-down list element to select email addresses and relationship identifiers from a predetermined list. The type of data to share with the new person may be selected using the activity timeline element 3110, the activity trending chart element 3112, and/or the medication timeline element 3116. All the data elements 3110, 3112, 3114, a subset, or none at all may be selected. Toward the bottom portion of the "invite" GUI 3100, the display provides a notification to protect the patient's privacy along with a personal code. As shown in FIG. 31, the privacy notification informs the patient that the recipient of the invitation will need to enter the personal code shown on the display, which in the present illustrative example is "1A2B3C."

Figures 32, 33, 34, 35:
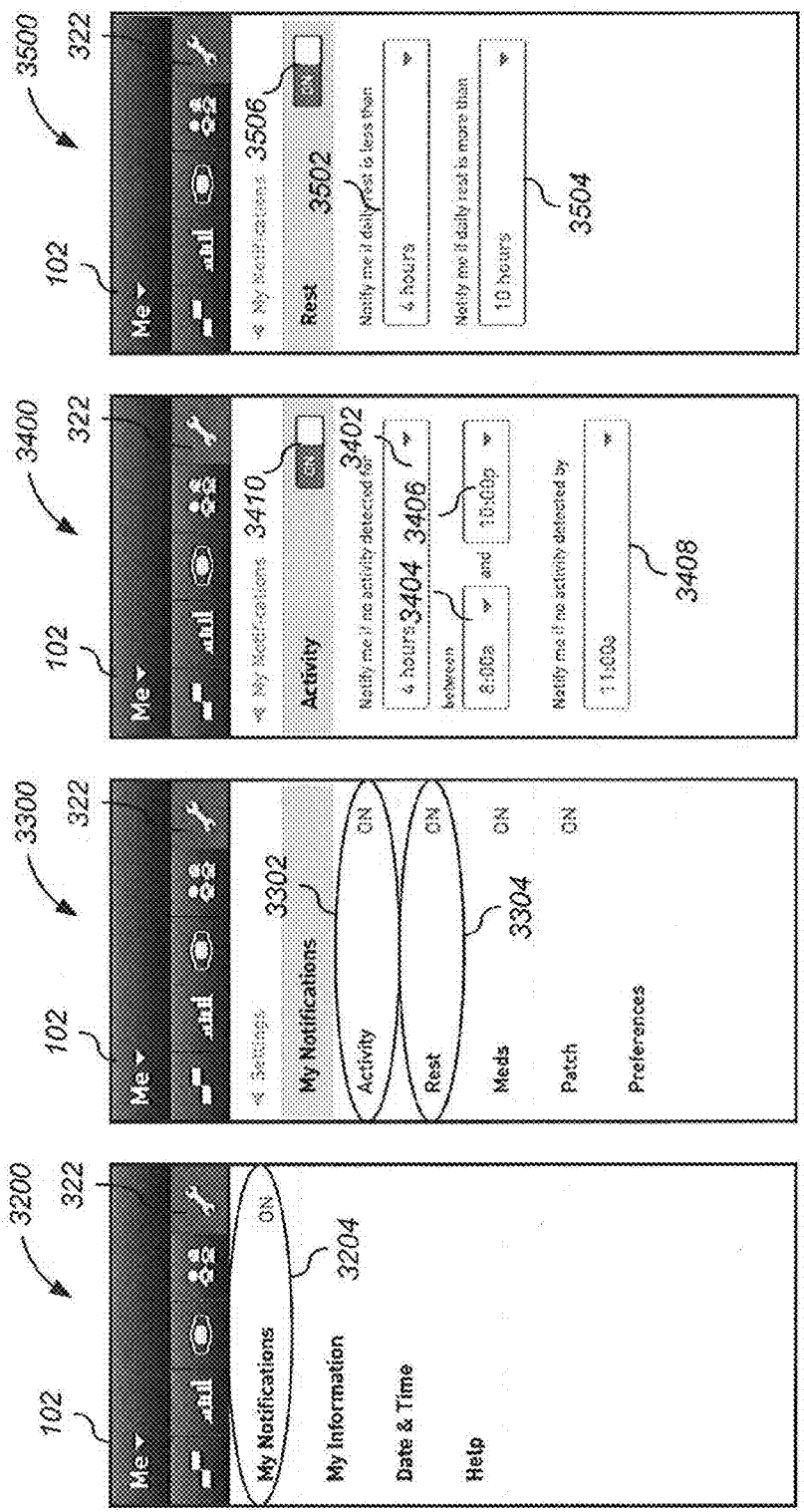
FIGS. 32-35 illustrate various aspects of utility tools GUIs for a display screen of a mobile device for tailoring the subscription information system based on personal needs and requirements of a patient.

FIGS. 32-35 illustrate various aspects of utility tools GUIs 3200, 3300, 3400, and 3500 for a display screen of a mobile device for tailoring the subscription information system based on personal needs and requirements of the patient 106. Turning now to FIG. 32, the utilities GUI 3200 may be opened by selecting the tool element 324 displayed at the top horizontal portion of the GUI 3200. The display then shows a menu of four selectable elements: "My Notification," "My Information," "Date & Time," and "Help." Selecting any of these menu items results in a different function to be executed and opens a new GUI. As shown in FIG. 32, the "My Notifications" element 3204 is encircled to illustrate that it has been selected. In actual operation, the selected is not encircled, but rather may be highlighted.

When the "My Notifications" element 3204 is selected, the display screen of the mobile device 102 shows the "My Notifications" GUI 3300 as shown in the FIG. 33. The "My Notifications" GUI 3300 shows several elements that may be selected for notification: "Activity" notification element, "Rest" notification element, "Meds" notification element, "Patch" notification element, and "Preferences" notification element. When the Activity notification element 3302 is selected, the display screen of the mobile device 102 shows the "Activity" GUI 3400 as shown in FIG. 34. Now specific regarding the "Activity" notification can be entered into the system. For example, a notification will be sent to the mobile device 102 if no activity has been detected for 4 hours, as indicated in the text box 3402. A drop-down list element may be employed to select from various predetermined values. Also, a window of time when the "No Activity" notification should be sent can be entered using text boxes 3404 and 3406. As shown, the selected notification window is between the hours of 8:00 am and 10:00 pm. These times may be selected using the respective drop-down lists. Finally, a notification may be requested if no activity is detected by a certain time as indicated in the text box 3408. Again, a drop-down list element may be employed to select from predetermined values. A virtual slide switch element 3410 may be used to toggle the Activity notification function ON and OFF.

When the Rest notification element 3304 is selected the display screen of the mobile device 102 shows the "Rest" GUI 3500. A "Rest" notification can be sent to the mobile device 102 if the daily rest is less than a selected amount of time (e.g., 4 hours) as shown in text box 3502. Also, a "Rest" notification may be sent to the mobile device 102 if daily rest is more than a selected amount of time (e.g., 10 hours) as shown in text box 3504. In the aspect illustrated in FIG. 35, each of the text boxes 3502, 3504 also include a drop-down list element to simplify the selection process.

FIGS. 36-39 illustrate various aspects of Utilities GUIs 3600, 3700, 3800, and 3900 for a display screen of a mobile device 102 for tailoring the subscription information system based on the personal needs and requirements of the patient 106. In FIG. 36, the display screen of the mobile device 102 shows the "My Notifications" screen 3600 with the Meds element 3602 selected.

When the Meds element 3602 is selected the display screen of the mobile device 102 shows the "Meds" notification screen 3700 as shown in FIG. 37. From within the "Meds" notification screen 3700, the number of daily medication doses can be selected via "My Doses" element 3702 and whether to be reminded of taking the medication doses can be selected via the "Remind Me" element 3704. As shown, the four medication doses have been selected and the "Remind Me" element is set to ON.

Selecting the "My Doses" element 3702 in FIG. 37 opens the "My Doses" notification screen 3800 shown in FIG. 38. For each of the daily medication doses selected in the "Meds" notification screen 3700 shown in FIG. 37, the "My Doses" notification screen 3800 display shows a corresponding text box in which a scheduled time for taking the medication is entered. Control buttons 3810 and 3812 can be used to change the times.

Selecting the "Remind Me" element 3704 in FIG. 37 opens the "Remind Me" notification screen 3900 shown in FIG. 39. The screen 3900 enables setting both a reminder before the scheduled medication time in text box 3902 (e.g., 20 min) and after the scheduled medication time in text box 3904 (e.g., 40 min). In addition, the medication notification can be cancelled if the ingestion of an IEM device 114 (FIG. 1) is detected within the time indicated in text box 3906. Each of the text boxes 3902, 3904, 3906 may include a drop-down list element for selecting times from a predetermined list. Also, a virtual slide switch element 3908 may be used to toggle the Remind Me notification function ON and OFF.

Figure 41:
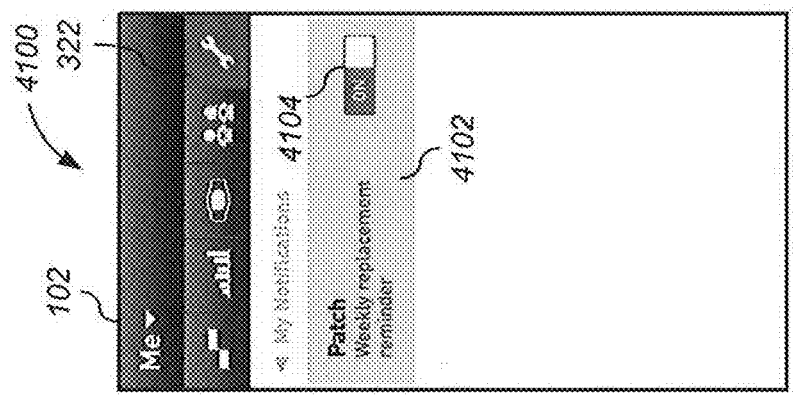
FIGS. 40-41 illustrate various aspects of GUIs for a display screen of a mobile device for tailoring the subscription information system based on personal needs of a patient.
Figure 40:
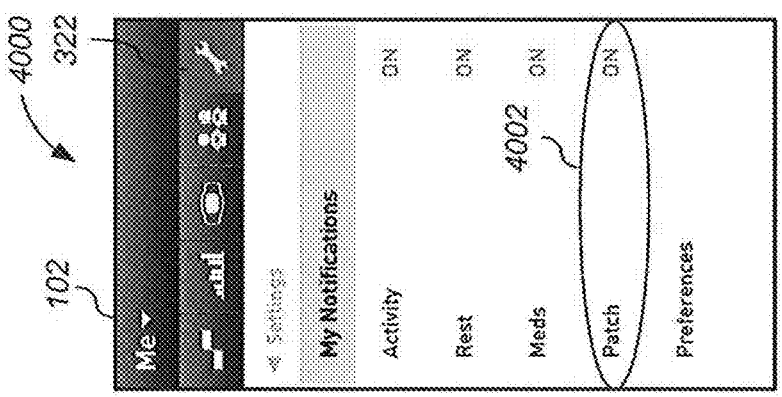

FIGS. 40-41 illustrate various aspects of GUIs 4000, 4100 for a display screen of a mobile device 102 for tailoring the subscription information system based on the personal needs of the patient 106. In FIG. 40, the display screen of the mobile device 102 shows the "My Notifications" screen 4000, similar to the "My Notifications" screen 3300 shown in FIG. 33, except that the "My Notifications" screen 4000 in FIG. 40 shows that the Patch notification element 4002 has been selected. Upon selecting the Patch notification element 4002, the display screen of the mobile device 102 shows a Patch notification screen 4100 in FIG. 41. A weekly replacement reminder for the patch may be set by selecting the Patch notification reminder element 4102. A virtual slide switch element 4104 may be used to toggle the weekly patch replacement notification function ON and OFF.

FIGS. 42-45 illustrate various aspects of GUIs 4200, 4300, 4400, 4500 for a display screen of a mobile device 102 for tailoring the subscription information system based on the personal needs of the patient. In FIG. 42, the display screen of the mobile device 102 shows the "My Notifications" screen 4200, similar to the "My Notifications" screen 3300 shown in FIG. 33, except that the "My Notifications" screen 4000 in FIG. 40 shows that the Preferences notification element 4202 has been selected. Upon selecting the Preferences notification element 4202, the display screen of the mobile device 102 shows a Preferences notification screen 4300 in FIG. 43, where additional notification delivery services can be set. Upon selecting the additional notification delivery 4302 element, an Additional Notification Delivery screen 4400 is opened as shown in FIG. 44, where either Short Message Service (SMS) 4402 or Email 4404 can be selected as an additional notification delivery service if email notification had been previously selected. Otherwise, if the SMS had been previously selected, the Email notification service may be selected as an additional notification delivery service. If SMS 4402 is selected, the display screen of the mobile device 102 shows the SMS screen 4500 shown in FIG. 45. A text box 4502 can be used to enter the telephone number where to send the SMS notification. The text box 4502 may include a dropdown list element for selecting telephone numbers associated with SMS notification from a predetermined list. Also, a virtual slide switch element 4504 may be used to toggle the SMS additional notification function ON and OFF.

Figure 47:
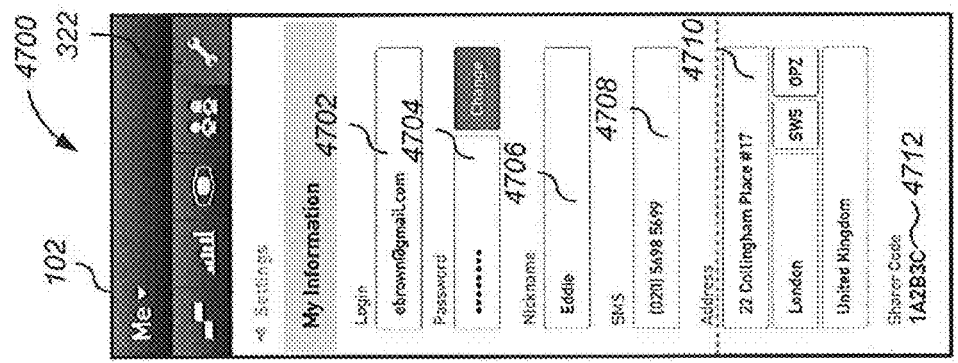
FIGS. 46-47 illustrate various aspects of GUIs for a display screen of a mobile device for tailoring the subscription information system based on personal needs of a patient.
Figure 46:
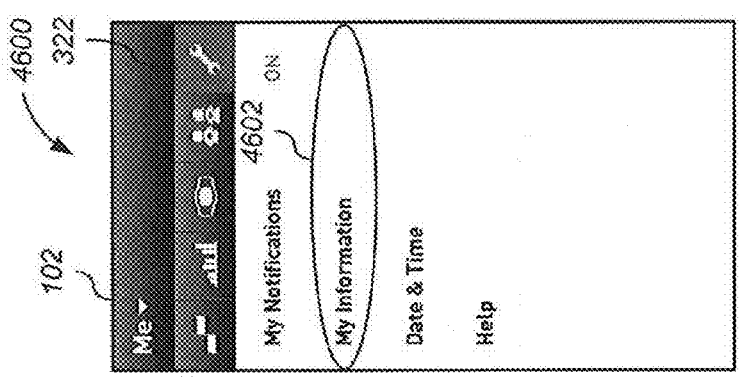

FIGS. 46-47 illustrate various aspects of GUIs 4600 and 4700 for a display screen of a mobile device 102 for tailoring the subscription information system based on the personal needs of the patient 106. In FIG. 46, the display screen of the mobile device 102 shows the tools screen 4600 similar to the tools screen shown in FIG. 32, which may be opened by selecting the tool element 3202 displayed at the top horizontal portion of the screen 4600. The display then shows four selectable menu items: "My Notification," "My Information," "Date & Time," and "Help." As shown in FIG. 46, the "My Information" tool 4602 is encircled to illustrate that it has been selected. Upon selecting the "My Information" tool 4602, the mobile device 102 application opens the My Information screen 4700 shown in FIG. 47. As shown in FIG. 47, the My Information screen 4700 provides several text boxes for entering personal information such as a Login text box 4702 to enter an email address, a Password text box 4704 to enter a user password, a Nickname text box 4706 to enter a nickname, an SMS text box 4708 to enter an SMS telephone number, and an Address text box 4710 to enter an address. A sharer code 4712 is provided at the bottom portion of the My information screen 4700 (e.g., 1A2B3C), which is the code that the patient communicates to a person invited to share the patient's information. As previously discussed, after receiving an invitation to share personal data from the patient, for security and privacy reasons the sharer must enter the sharer code 4712 before being able to share any information. The sharer code 4712 may be communicated to the sharer by the patient using any suitable means.

Figures 48, 49, 50, 51:
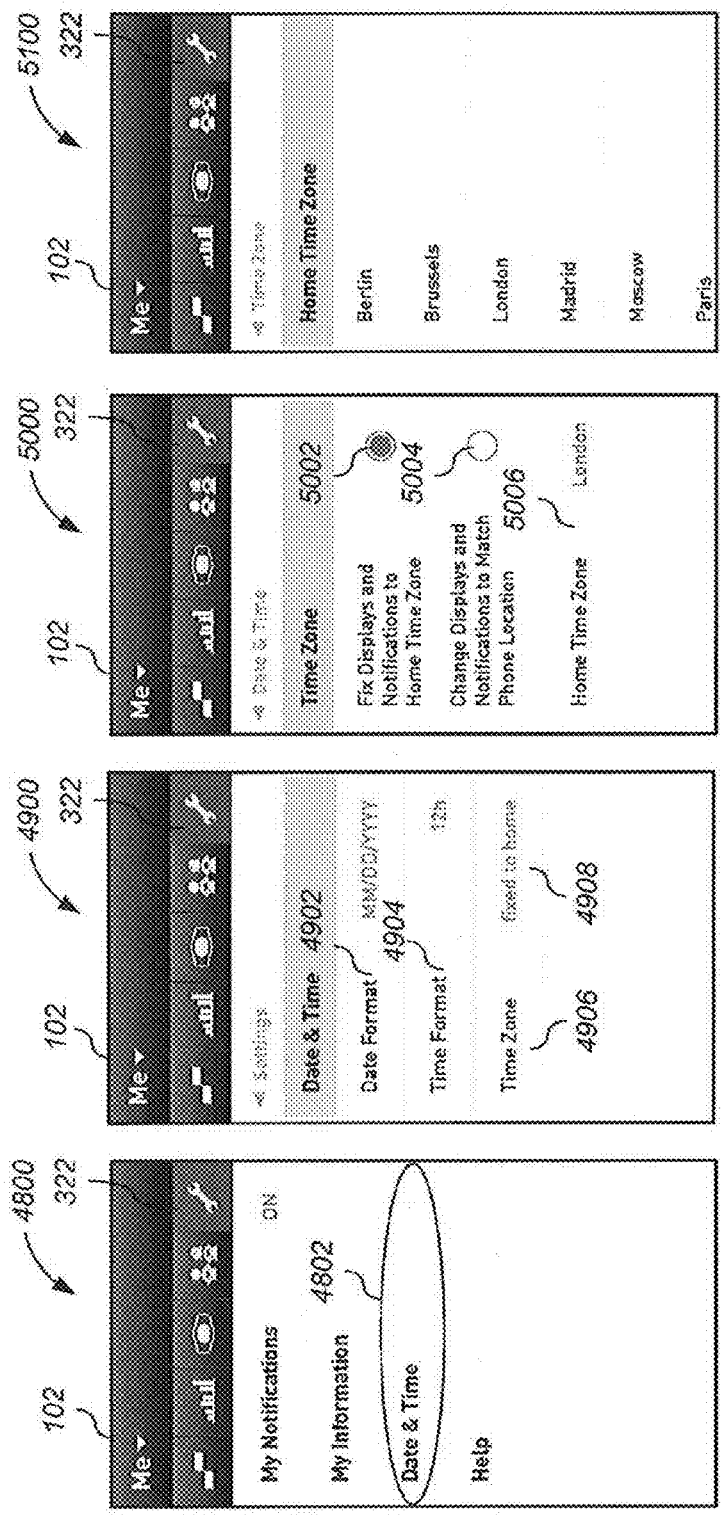
FIGS. 48-51 illustrate various aspects of GUIs for a display screen of a mobile device for tailoring the subscription information system based on personal needs of a patient.

FIGS. 48-51 illustrate various aspects of GUIs 4800, 4900, 5000, 5100 for a display screen of a mobile device 102 for tailoring the subscription information system based on the personal needs of the patient. In FIG. 48, the display screen of the mobile device 102 shows the tools screen 4800 similar to the tools screen shown in FIG. 32, which may be opened by selecting the tool element 3202 displayed at the top horizontal portion of the screen 4800. The display then shows four selectable menu items: "My Notification," "My Information," "Date & Time," and "Help." As shown in FIG. 48, the "Date & Time" tool 4802 is encircled to illustrate that it has been selected. Upon selecting the "Date & Time" tool 4802, the mobile device 102 application opens the Date & Time screen 4900 shown in FIG. 49. As shown in FIG. 49, the Date Format 4902, Tine Format 4904, and Time Zone 4906 may be selected within the Date & Time screen 4900. In addition, the time zone may be "fixed to home" 4908, which may be useful when the patient travels in different time zones and wants to keep the home time zone as a reference time frame for ingestions their medications. As shown in FIG. 50, selecting the Time Zone element 4906 opens the Time Zone screen 5000. Therein, selecting the top radio button 5002, fixes displays and notifications to the home time zone, whereas selecting the bottom radio button 5004 changes the display and notifications may be fixed to the home time zone. If the bottom radio button 5004 is selected, the displays and notifications are changed to match the location of the mobile device 102, e.g., using the GPS location based function available in most modern smartphones. As a matter of convenience, the Home Time Zone is displayed toward the bottom portion of the Time Zone screen 5000. As shown in FIG. 50, the Home Time Zone is London. This may be changed by selecting the Home Time Zone element 5006 and invoking the Home Time Zone selection screen 5100 as shown in FIG. 51 where a new Home Time Zone may be selected.

With reference now back to FIG. 1, in one aspect, the mobile device 102 and/or the wireless node 110 may provide voice and/or data communications functionality in accordance with different types of cellular radiotelephone systems. Examples of cellular communication systems may include Code Division Multiple Access (CDMA) cellular radiotelephone communication systems, Global System for Mobile Communications (GSM) cellular radiotelephone systems, North American Digital Cellular (NADC) cellular radiotelephone systems, Time Division Multiple Access (TDMA) cellular radiotelephone systems, Extended-TDMA (E-TDMA) cellular radiotelephone systems, Narrowband Advanced Mobile Phone Service (NAMPS) cellular radiotelephone systems, third generation (3G) systems such as Wide-band CDMA (WCDMA), CDMA-2000, Universal Mobile Telephone System (UMTS) cellular radiotelephone systems compliant with the Third-Generation Partnership Project (3GPP), fourth generation systems (4G), and so forth.

In addition to voice communication services, the mobile device 102 and the wireless node 110 may be arranged to communicate using a number of different wireless wide area network (WWAN) data communication services. Examples of cellular data communication systems offering WWAN data communication services may include GSM with General Packet Radio Service (GPRS) systems (GSM/GPRS), CDMA/1xRTT systems, Enhanced Data Rates for Global Evolution (EDGE) systems, Evolution Data Only or Evolution Data Optimized (EV-DO) systems, Evolution For Data and Voice (EV-DV) systems, High Speed Downlink Packet Access (HSDPA) systems, and so forth.

In one aspect, the wireless node 110 may be connected by wired communications medium to additional nodes and connections to other networks, including a voice/data network such as the Public Switched Telephone Network (PSTN), a packet network such as the Internet, a local area network (LAN), a metropolitan area network (MAN), a wide area network (WAN), an enterprise network, a private network, and so forth. In one aspect, for example, network 130 may be arranged to communicate information in accordance with one or more Internet protocols as defined by the Internet Engineering Task Force (IETF), such as the Transmission Control Protocol/Internet Protocol (TCP/IP), for example. The network also may include other cellular radio telephone system infrastructure and equipment, such as base stations, mobile subscriber centers, central offices, and so forth.

In various aspects, the mobile device 102 and the wireless node 110 also may be capable of voice and/or data communications. Communications between the mobile device 102 and the wireless node 110 may be performed over wireless shared media 134 in accordance with a number of wireless protocols. Examples of wireless protocols may include various wireless local area network (WLAN) protocols, including the Institute of Electrical and Electronics Engineers (IEEE) 802.xx series of protocols, such as IEEE 802.11a/b/g/n, IEEE 802.16, IEEE 802.20, and so forth. Other examples of wireless protocols may include various WWAN protocols, such as GSM cellular radiotelephone system protocols with GPRS, CDMA cellular radiotelephone communication systems with 1xRTT, EDGE systems, EV-DO systems, EV-DV systems, HSDPA systems, and so forth. Further examples of wireless protocols may include wireless personal area network (PAN) protocols, such as an Infrared protocol, a protocol from the Bluetooth Special Interest Group (SIG) series of protocols, including Bluetooth Specification versions v1.0, v1.1, v1.2, v2.0, v2.0 with Enhanced Data Rate (EDR), as well as one or more Bluetooth Profiles, and so forth. In one aspect, the Bluetooth wireless technology uses short wavelength radio transmissions in the industrial, scientific, and medical (ISM) radio band from 2400-2480 MHz) from fixed and mobile devices, creating personal area networks (PANs) with high levels of security. Yet another example of wireless protocols may include near-field communication techniques and protocols, such as electro-magnetic induction (EMI) techniques. An example of EMI techniques may include passive or active radio-frequency identification (RFID) protocols and devices. Other suitable protocols may include Ultra Wide Band (UWB), Digital Office (DO), Digital Home, Trusted Platform Module (TPM), Zig Bee, and other protocols.

In various aspects, the mobile device 102 may have one or more application client modules. In one aspect, an application client module receives information from the detection arrangement 108 and process the information to confirm that the patient 106 has ingested the IEM device 104. The application client module records a time and date that the IEM device 104 was detected, which corresponds approximately to the time and date when the IEM device 104 was ingested by the patient 106. In addition, client application module may store information encoded in the unique electrical current signature such as the identity of the IEM device 104, the type of medication associated with the IEM device 104, the manufacturer of the medication and/or IEM device 104, among other information. In some aspects, the client application module may implement a data logging function tracking the ingestible events associated with the patient 106. The client application module can initiate communication with other devices and/or networks.

Other client application modules may be arranged to retrieve and process information from a network (e.g., servers) and display the information on a display or audibly announce the information by way of speaker. The mobile device 102 may be implemented as an open platform adaptable to execute one or more application client programs and integrate with third party software application client programs. The application client modules may provide the necessary interface to existing data sources or backend services, such as web related and wireless services, support GPS navigation modules, process browser based content, and operate with one or more wireless mobile computing devices and web applications, for example. In one aspect, the application client modules may integrate with third party application client programs via APIs to retrieve location information, such as, for example, geographic coordinates, map interfaces, queries for search engines, interfaces to third party location based services (LBS), and any other services provided via servers, and the like. The application client modules may include a GUI layer to process search queries, search results, display maps (e.g., zoom/pan), provide turn-by-turn directions, provide voice activated turn-by-turn directions, and provide permission based interface for LBS type location information, among others. The application client modules also may include an interface layer to process local information, point of interface (POI) data, and a data abstraction layer to process map data, for example. The application client modules also may process data from various data sources or backend services distributed throughout a network (e.g., servers) such as, for example, GPS integrated circuits located either on or off the mobile device 500, carrier AGPS, various prolific search engines (e.g., GOOGLE, YAHOO, and the like), vector data, tile data, among others, for example. It will be appreciated by those skilled in the art that tile data may be defined as a spatial unit representing a sub-region of an image, usually of rectangular nature, by which geographic data is organized, subdivided, and stored in a map library.

In one aspect, for example, the mobile device 102 may employ a software architecture for retrieving and processing information from a communications network. The software architecture may enable the mobile device 102 to communicate and process information from the network and servers, for example. The software architecture includes component implementations and specifies standard programmatic interfaces such as APIs to assist in the common requirements of retrieving information wirelessly between an application client and multiple data source servers. As a result, the software architecture may provide a method to enable application clients to interact with disparate data providers.

In one aspect, for example, the software architecture may be implemented using object-oriented programming (OOP) techniques. OOP is a computer programming paradigm. OOP assumes that a computer program is composed of a collection of individual units, or objects, as opposed to a traditional assumption that a program is a list of instructions to the computer. Each object is capable of receiving messages, processing data, and sending messages to other objects. Almost any concept may be represented as an object. Examples of an object may include menu objects, image objects, frame objects, title objects, border objects, tab objects, list objects, color blue objects, button objects, scroll bar objects, input field objects, text and image objects, and so forth. Although the software architecture may be described in the context of OOP by way of example, it may be appreciated that other software paradigms may be used as desired for a given implementation. For example, the software architecture may be implemented using a model-view-controller (MVC) architecture as well. The aspects are not limited in this context.

In various aspects, a node may comprise an optional display. The display may be implemented using any type of visual interface such as a liquid crystal display (LCD), capacitive touch screen panel, and the like.

In various aspects, a node may comprise a memory. In various aspects, the memory may comprise any machine-readable or computer-readable media capable of storing data, including both volatile and non-volatile memory. For example, memory may include read-only memory (ROM), random-access memory (RAM), dynamic RAM (DRAM), Double-Data-Rate DRAM (DDR-RAM), synchronous DRAM (SDRAM), static RAM (SRAM), programmable ROM (PROM), erasable programmable ROM (EPROM), electrically erasable programmable ROM (EEPROM), flash memory (e.g., NOR or NAND flash memory), content addressable memory (CAM), polymer memory (e.g., ferroelectric polymer memory), phase-change memory (e.g., ovonic memory), ferroelectric memory, silicon-oxide-nitride-oxide-silicon (SONOS) memory, disk memory (e.g., floppy disk, hard drive, optical disk, magnetic disk), or card (e.g., magnetic card, optical card), or any other type of media suitable for storing information.

The various aspects, a node may comprise a processor such as a central processing unit (CPU). In various aspects, the processor may be implemented as a general purpose processor, a chip multiprocessor (CMP), a dedicated processor, an embedded processor, a digital signal processor (DSP), a network processor, a media processor, an input/output (I/O) processor, a media access control (MAC) processor, a radio baseband processor, a co-processor, a microprocessor such as a complex instruction set computer (CISC) microprocessor, a reduced instruction set computing (RISC) microprocessor, and/or a very long instruction word (VLIW) microprocessor, or other processing device. The processor also may be implemented by a controller, a microcontroller, an application specific integrated circuit (ASIC), a field programmable gate array (FPGA), a programmable logic device (PLD), and so forth.

In various aspects, the processor may be arranged to run an operating system (OS) and various mobile applications. Examples of an OS include, for example, operating systems generally known under the trade name of Microsoft Windows OS, and any other proprietary or open source OS. Examples of mobile applications include, for example, a telephone application, a camera (e.g., digital camera, video camera) application, a browser application, a multimedia player application, a gaming application, a messaging application (e.g., e-mail, short message, multimedia), a viewer application, and so forth.

In various aspects, the processor may be arranged to receive information through a communications interface. The communications interface may comprise any suitable hardware, software, or combination of hardware and software that is capable of coupling a node 110 to one or more networks and/or devices. In one aspect, the wireless node 110 is in wireless communication with the mobile device 102 via the wireless medium 134. The wireless node 110 also may communicate with the remote node 122 via a wired communication medium 134 or a wireless communication medium 120. The communications interface may be arranged to operate using any suitable technique for controlling information signals using a desired set of communications protocols, services or operating procedures. The communications interface may include the appropriate physical connectors to connect with a corresponding communications medium, whether wired or wireless.

Vehicles of communication include a network. In various aspects, the network may comprise LANs as well as WANs including without limitation Internet, wired channels, wireless channels, communication devices including telephones, computers, wire, radio, optical or other electromagnetic channels, and combinations thereof, including other devices and/or components capable of/associated with communicating data. For example, the communication environments include in-body communications, various devices, various modes of communications such as wireless communications, wired communications, and combinations of the same.

Wireless communication modes include any mode of communication between points that utilizes, at least in part, wireless technology including various protocols and combinations of protocols associated with wireless transmission, data, and devices. The points include, for example, wireless devices such as wireless headsets, audio and multimedia devices and equipment, such as audio players and multimedia players, telephones, including mobile telephones and cordless telephones, and computers and computer-related devices and components, such as tablet computers, printers.

Wired communication modes include any mode of communication between points that utilizes wired technology including various protocols and combinations of protocols associated with wired transmission, data, and devices. The points include, for example, devices such as audio and multimedia devices and equipment, such as audio players and multimedia players, telephones, including mobile telephones and cordless telephones, and computers and computer-related devices and components, such as tablet computers, printers.

Accordingly, in various aspects, the communications interface may comprise one or more interfaces such as, for example, a wireless communications interface, a wired communications interface, a network interface, a transmit interface, a receive interface, a media interface, a system interface, a component interface, a switching interface, a chip interface, a controller, and so forth. When implemented by a wireless device or within wireless system, for example, the wireless node 110 may include a wireless communication interface comprising one or more antennas, transmitters, receivers, transceivers, amplifiers, filters, control logic, and so forth.

In various aspects, the wireless node 110 may comprise the functionality to wirelessly receive and/or wirelessly transmit data received from the mobile device 102 and transmit that data to other nodes, such as the external node 122 or other nearby nodes, for example. Further, in various aspects, the wireless node 110 may incorporate and/or be associated with, e.g., communicate with, various devices. Such devices may generate, receive, and/or communicate data, e.g., physiologic data. The devices include, for example, "intelligent" devices such as gaming devices, e.g., electronic slot machines, handheld electronic games, electronic components associated with games and recreational activities.

In addition to the standard voice function of a telephone, various aspects of mobile telephones may support many additional services and accessories such as short message service (SMS) for text messaging, email, packet switching for access to the Internet, java gaming, wireless, e.g., short range data/voice communications, infrared, camera with video recorder, and multimedia messaging system (MMS) for sending and receiving photos and video. Some aspects of mobile telephones connect to a cellular network of base stations (cell sites), which is, in turn, interconnected to the public switched telephone network (PSTN) or satellite communications in the case of satellite phones. Various aspects of mobile telephones can connect to the Internet, at least a portion of which can be navigated using the mobile telephones.

Some aspects may be implemented, for example, using a machine-readable medium or article which may store an instruction or a set of instructions that, if executed by a machine, may cause the machine to perform a method and/or operations in accordance with the aspects. Such a machine may include, for example, any suitable processing platform, computing platform, computing device, processing device, computing system, processing system, computer, processor, or the like, and may be implemented using any suitable combination of hardware and/or software. The machine-readable medium or article may include, for example, any suitable type of memory unit, memory device, memory article, memory medium, storage device, storage article, storage medium and/or storage unit, for example, memory, removable or non-removable media, erasable or non-erasable media, writeable or re-writeable media, digital or analog media, hard disk, floppy disk, Compact Disk Read Only Memory (CD-ROM), Compact Disk Recordable (CD-R), Compact Disk Rewriteable (CD-RW), optical disk, magnetic media, magneto-optical media, removable memory cards or disks, various types of Digital Versatile Disk (DVD), a tape, a cassette, or the like. The instructions may include any suitable type of code, such as source code, compiled code, interpreted code, executable code, static code, dynamic code, and the like. The instructions may be implemented using any suitable high-level, low-level, object-oriented, visual, compiled and/or interpreted programming language, such as C, C++, Java, BASIC, Perl, Matlab, Pascal, Visual BASIC, arrangement language, machine code, and so forth.

In one aspect, the wireless node 110 may be configured as a communication hub and may include any hardware device, software, and/or communications component(s), as well as systems, subsystems, and combinations of the same which generally function to communicate information received from the mobile device 102 to the remote node 122. Communication of the information includes receiving, storing, manipulating, displaying, processing, and/or transmitting the data to the remote node 122 via wired or wireless media 118, 120.

In various aspects, the wireless node 110 also functions to communicate, e.g., receive and transmit, non-physiologic data. Example of non-physiologic data include gaming rules and data generated by a separate cardiac-related device such as an implanted pacemaker and communicated to the hub (wireless node 110) directly or indirectly, e.g., via the mobile device 102.

Broad categories of each of the mobile device 102 and/or the wireless node 110 include, for example, base stations, personal communication devices, handheld devices, mobile telephones, and mobile computing devices having wireless capabilities generally known as smartphones capable of executing computer applications, as well as voice communications and/or data communications. Examples of mobile computing devices include any type of wireless device, mobile station, or portable computing device with a self-contained power source, e.g., battery. Examples of smartphones include, for example, products generally known under the trade designations Palm, Blackberry, iPhone, Android, Windows Phone, among others. In various aspects, the mobile device 102 and/or the wireless node 110 may comprise, or be implemented as, a PDA, laptop computer, ultra-laptop computer, combination cellular telephone/PDA, mobile unit, subscriber station, user terminal, portable computer, handheld computer, palmtop computer, wearable computer, media player, messaging device, data communication device, a laptop computer, ultra-laptop computer, portable computer, handheld computer, palmtop computer, tablet computer, e-book reader, cellular telephone, pager, one-way pager, two-way pager, messaging device, data communication device, and so forth. Examples of a mobile device 102 and/or wireless node 110 also may include computers that are arranged to be worn by a person, such as a wrist computer, finger computer, ring computer, eyeglass computer, belt-clip computer, arm-band computer, shoe computers, clothing computers, and other wearable computers. A fixed computing device, for example, may be implemented as a desk top computer, workstation, client/server computer, and so forth.

The mobile device 102 and/or wireless node 110 may comprise personal communication devices including, for example, devices having communication and computer functionality and typically intended for individual use, e.g., mobile computers, sometimes referred to as "handheld devices." Base stations comprise any device or appliance capable of receiving data such as physiologic data. Examples include computers, such as desktop computers and laptop computers, and intelligent devices/appliances. Intelligent devices/appliances include consumer and home devices and appliances that are capable of receipt of data such as physiologic data. Intelligent devices/appliances may also perform other data-related functions, e.g., transmit, display, store, and/or process data. Examples of intelligent devices/appliances include refrigerators, weight scales, toilets, televisions, door frame activity monitors, bedside monitors, bed scales. Such devices and appliances may include additional functionality such as sensing or monitoring various physiologic data, e.g., weight, heart rate. Mobile telephones include telephonic communication devices associated with various mobile technologies, e.g., cellular networks.

Figure 52:
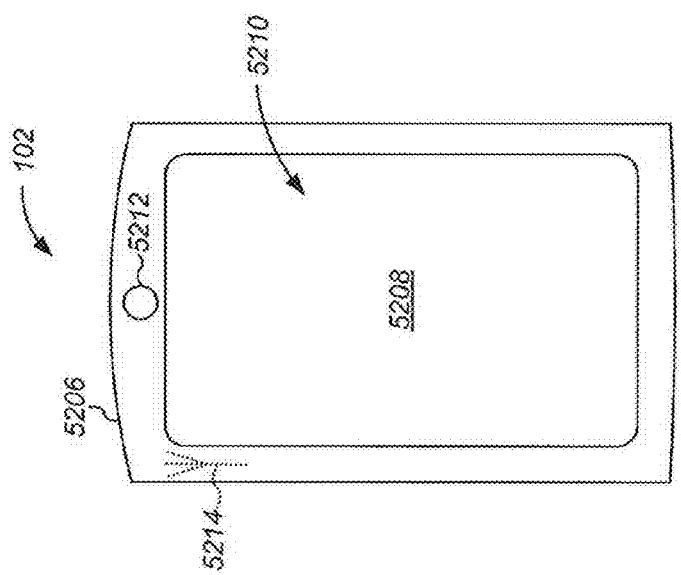
FIG. 52 illustrates one aspect of a mobile device.

FIG. 52 illustrates one aspect of a mobile device 102. The mobile device 102 comprises a housing 5206, a display 5208, an input/output (I/O) system 5210 (e.g., a touch sensitive screen), an aperture 5212 for capturing digital images, and an antenna 5214. The functional modules of the mobile device 102 are described below in connection with FIG. 52.

The display 5208 may comprise any suitable display unit for displaying information appropriate for a mobile device 102. The I/O system 5210 may comprise any suitable I/O device for entering information into the mobile device 102. Examples for the I/O system 5210 may include an alphanumeric keyboard, a numeric keypad, a touch pad, a capacitive touch screen panel, input keys, buttons, switches, rocker switches, voice recognition device and software, and so forth. The I/O system 5210 may comprise a microphone and speaker, for example. Information also may be entered into the mobile device 102 by way of the microphone. Such information may be digitized by a voice recognition device. As used throughout the present disclosure the term "button" may be used to refer to a mechanical type switch, an electromechanical switch, or a "virtual button" that may be selected using a simple touch over a touch sensitive screen or a point/click with a mouse pointer.

Figure 53:
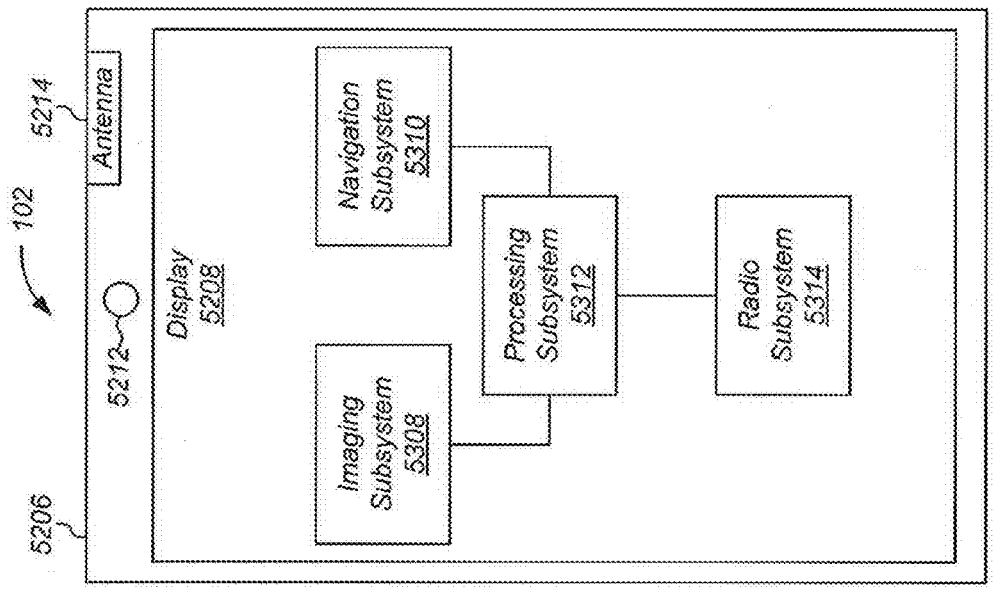
FIG. 53 is a functional system diagram of one aspect of a mobile device.

FIG. 53 illustrates a system diagram of one aspect of a mobile device 102 for detecting an electrical signal generated by an ingestible event marker, such as the IEM device 104 (FIG. 1), for example, configured to couple to an external detection arrangement. FIG. 53 illustrates a more detailed block diagram of the mobile computing device 102 described with reference to FIG. 1. As shown in FIG. 53, for example, the mobile device 102 may comprise multiple elements. Although FIG. 53 shows a limited number of elements in a certain topology by way of example, it can be appreciated that additional or fewer elements in any suitable topology may be used in the mobile device 102 as desired for a given implementation. Furthermore, any element as described herein may be implemented using hardware, software, or a combination of both, as previously described with reference to node implementations. Aspects of the mobile device 102, however, are not limited in this context.

In various aspects, the mobile device 102 comprises a housing 5206, an antenna 5214, a radio subsystem 5314, and a processing subsystem 5312 connected to the radio subsystem 5314 via a bus. The radio subsystem 5314 may perform voice and data communications operations using wireless shared media for the mobile device 102. The processing subsystem 5312 may execute software for the mobile device 102. A bus may comprise a universal serial bus (USB), micro-USB bus, dataport, and appropriate interfaces, as well as others. In one aspect the radio subsystem 5314 may be arranged to communicate voice information and control information over one or more assigned frequency bands of the wireless shared media.

In one aspect, the mobile device 102 may comprise an imaging subsystem 5308 for processing images captured through the aperture 5212. A camera may be coupled (e.g., wired or wirelessly) to the processing subsystem 5312 and is configured to output image data (photographic data of a person or thing, e.g., video data, digital still image data) to the processing subsystem 5312 and to the display 5208. In one aspect, the imaging subsystem 5208 may comprise a digital camera implemented as an electronic device used to capture and store images electronically in a digital format. Additionally, in some aspects the digital camera may be capable of recording sound and/or video in addition to still images.

In one aspect, the imaging subsystem 5208 may comprise a controller to provide control signals to components of a digital camera, including lens position component, microphone position component, and a flash control module, to provide functionality for the digital camera. In some aspects, the controller may be implemented as, for example, a host processor element of the processing subsystem 5312 of the mobile device 102. Alternatively, the imaging controller may be implemented as a separate processor from the host processor.

In various aspects, the imaging subsystem 5308 may comprise memory either as an element of the processing subsystem 5312 of the mobile device 102 or as a separate element. It is worthy to note that in various aspects some portion or the entire memory may be included on the same integrated circuit as the controller. Alternatively, some portion or the entire memory may be disposed on an integrated circuit or other medium (e.g., hard disk drive) external to the integrated circuit of the controller.

In various aspects, the imaging subsystem 5308 may comprise an aperture 5212 with a lens component and a lens position component. The lens component may consist of a photographic or optical lens or arrangement of lenses made of a transparent material such as glass, plastic, acrylic or Plexiglass, for example. In one aspect, the one or more lens elements of the lens component may reproduce an image of an object and allow for zooming in or out on the object by mechanically changing the focal length of the lens elements. In various aspects, a digital zoom may be employed in the imaging subsystem 5308 to zoom in or out on an image. In some aspects, the one or more lens elements may be used to focus on different portions of an image by varying the focal length of the lens elements. The desired focus can be obtained with an autofocus feature of the digital imaging subsystem 5308 or by manually focusing on the desired portion of the image, for example.

A navigation subsystem 5310 supports navigation using the mobile device 102. In various aspects the mobile device 102 may comprise location or position determination capabilities and may employ one or more location determination techniques including, for example, Global Positioning System (GPS) techniques, Cell Global Identity (CGI) techniques, CGI including timing advance (TA) techniques, Enhanced Forward Link Trilateration (EFLT) techniques, Time Difference of Arrival (TDOA) techniques, Angle of Arrival (AOA) techniques, Advanced Forward Link Trilateration (AFTL) techniques, Observed Time Difference of Arrival (OTDOA), Enhanced Observed Time Difference (EOTD) techniques, Assisted GPS (AGPS) techniques, hybrid techniques (e.g., GPS/CGI, AGPS/CGI, GPS/AFTL or AGPS/AFTL for CDMA networks, GPS/EOTD or AGPS/EOTD for GSM/GPRS networks, GPS/OTDOA or AGPS/OTDOA for UMTS networks), among others.

In one aspect, the mobile device 102 may be configured to operate in one or more location determination modes including, for example, a standalone mode, a mobile station (MS) assisted mode, and/or a MS-based mode. In a standalone mode, such as a standalone GPS mode, the mobile device 102 may be configured to determine its position without receiving wireless navigation data from the network, though it may receive certain types of position assist data, such as almanac, ephemeris, and coarse data. In a standalone mode, the mobile device 102 may comprise a local location determination circuit such as a GPS receiver which may be integrated within the housing 5206 configured to receive satellite data via the antenna 5214 and to calculate a position fix. Local location determination circuit may alternatively comprise a GPS receiver in a second housing separate from the housing 5206 but in the vicinity of the mobile device 102 and configured to communicate with the mobile device 102 wirelessly (e.g., via a PAN, such as Bluetooth). When operating in an MS-assisted mode or an MS-based mode, however, the mobile device 102 may be configured to communicate over a radio access network (e.g., UMTS radio access network) with a remote computer (e.g., a location determination entity (LDE), a location proxy server (LPS) and/or a mobile positioning center (MPC), among others).

In various aspects, the mobile device 102 also may comprise a power management subsystem (not shown) to manage power for the mobile device 102, including the radio subsystem 5314, the processing subsystem 5312, and other elements of the mobile device 102. For example, the power management subsystem may include one or more batteries to provide direct current (DC) power, and one or more alternating current (AC) interfaces to draw power from a standard AC main power supply.

In various aspects, the radio subsystem 5314 may include an antenna 5214. The antenna 5214 may broadcast and receive RF energy over the wireless shared media 120 (FIG. 1). Examples for the antenna 5214 may include an internal antenna, an omni-directional antenna, a monopole antenna, a dipole antenna, an end fed antenna, a circularly polarized antenna, a micro-strip antenna, a diversity antenna, a dual antenna, an antenna array, a helical antenna, and so forth. The aspects are not limited in this context.

In various aspects, the antenna 5214 may be connected to a multiplexer. The multiplexer multiplexes signals from a power amplifier for delivery to the antenna 5214. The multiplexer demultiplexes signals received from the antenna for delivery to an RF chipset.

In various aspects, the multiplexer may be connected to a power amplifier, where the power amplifier may be used to amplify any signals to be transmitted over the wireless shared media 120 (FIG. 1). The power amplifier may work in all assigned frequency bands, such as four (4) frequency bands in a quad-band system. The power amplifier also may operate in various modulation modes, such as Gaussian Minimum Shift Keying (GMSK) modulation suitable for GSM systems and 8-ary Phase Shift Keying (8-PSK) modulation suitable for EDGE systems.

In various aspects, the power amplifier may be connected to an RF chipset. The RF chipset also may be connected to the multiplexer. In one aspect, the RF chipset may comprise an RF driver and an RF transceiver. The RF chipset performs all of the modulation and direct conversion operations required for GMSK and 8-PSK signal types for quad-band E-GPRS radio. The RF chipset receives analog in-phase (I) and quadrature (Q) signals from a baseband processor, and converts the I/Q signals to an RF signal suitable for amplification by the power amplifier. Similarly, the RF chipset converts the signals received from the wireless shared media 120 (FIG. 1) via the antenna 5214 and the multiplexer to analog I/Q signals to be sent to the baseband processor. Although the RF chipset may use two chips by way of example, it may be appreciated that the RF chipset may be implemented using more or less chips and still fall within the intended scope of the aspects. In addition, other aspects of amplification are in commonly owned application bearing U.S. Publication No. 2008-0316020 A1, titled "RFID Antenna for In-Body Device," published Dec. 25, 2008 which is incorporated by reference in its entirety.

In various aspects, the RF chipset may be connected to the baseband processor, where the baseband processor may perform baseband operations for the radio subsystem 5314. The baseband processor may comprise both analog and digital baseband sections. The analog baseband section includes I/Q filters, analog-to-digital converters, digital-to-analog converters, audio circuits, and other circuits. The digital baseband section may include one or more encoders, decoders, equalizers/demodulators, GMSK modulators, GPRS ciphers, transceiver controls, automatic frequency control (AFC), automatic gain control (AGC), power amplifier (PA) ramp control, and other circuits.

In various aspects, the baseband processor also may be connected to one or more memory units via a memory bus. In one aspect, for example, the baseband processor may be connected to a flash memory unit and a secure digital (SD) memory unit. The memory units may be removable or non-removable memory. In one aspect, for example, the baseband processor may use approximately 1.6 megabytes of static read-only memory (SRAM) for E-GPRS and other protocol stack needs.

In various aspects, the baseband processor also may be connected to a subscriber identity module (SIM). The baseband processor may have a SIM interface for the SIM, where the SIM may comprise a smart card that encrypts voice and data transmissions and stores data about the specific user so that the user can be identified and authenticated to the network supplying voice or data communications. The SIM also may store data such as personal phone settings specific to the user and phone numbers. The SIM can be removable or non-removable.

In various aspects, the baseband processor may further include various interfaces for communicating with a host processor of the processing subsystem 5312. For example, the baseband processor may have one or more universal asynchronous receiver-transmitter (UART) interfaces, one or more control/status lines to the host processor, one or more control/data lines to the host processor, and one or more audio lines to communicate audio signals to an audio subsystem of processing subsystem 5314. The aspects are not limited in this context.

In various aspects, the processing subsystem 5314 may provide computing or processing operations for the mobile device 102. For example, the processing subsystem 5314 may be arranged to execute various software programs for the mobile device 102. Although the processing subsystem 5314 may be used to implement operations for the various aspects as software executed by a processor, it may be appreciated that the operations performed by the processing subsystem 5314 also may be implemented using hardware circuits or structures, or a combination of hardware and software, as desired for a particular implementation.

In various aspects, the processing subsystem 5312 may include a processor implemented using any processor or logic device, such as a complex instruction set computer (CISC) microprocessor, a reduced instruction set computing (RISC) microprocessor, a very long instruction word (VLIW) microprocessor, a processor implementing a combination of instruction sets, or other processor device. In one aspect, for example, a processor may be implemented as a general purpose processor, such as a processor made by Intel Corporation, Santa Clara, Calif. The processor also may be implemented as a dedicated processor, such as a controller, microcontroller, embedded processor, a digital signal processor (DSP), a network processor, a media processor, an input/output (I/O) processor, a media access control (MAC) processor, a radio baseband processor, a field programmable gate array (FPGA), a programmable logic device (PLD), and so forth.

In one aspect, the processing subsystem 5314 may include a memory to connect to the processor. The memory may be implemented using any machine-readable or computer-readable media capable of storing data, including both volatile and non-volatile memory. For example, the memory may include ROM, RAM, DRAM, DDRAM, SDRAM, SRAM, PROM, EPROM, EEPROM, flash memory, polymer memory such as ferroelectric polymer memory, ovonic memory, phase change or ferroelectric memory, silicon-oxide-nitride-oxide-silicon (SONOS) memory, magnetic or optical cards, or any other type of media suitable for storing information. It is worthy to note that some portion or all of the memory may be included on the same integrated circuit as the processor thereby obviating the need for a memory bus. Alternatively some portion or all of the memory may be disposed on an integrated circuit or other medium, for example a hard disk drive, that is external to the integrated circuit of the processor, and the processor may access the memory via a memory bus, for example.

In various aspects, the memory may store one or more software components (e.g., application client modules). A software component may refer to one or more programs, or a portion of a program, used to implement a discrete set of operations. A collection of software components for a given device may be collectively referred to as a software architecture or application framework. A software architecture for the mobile device 500 is described in more detail below.

A software architecture suitable for use with the mobile device 500 may include a GUI module, an interface module, a data source or backend services module (data source), and a third party API module. An optional LBS module may comprise a user based permission module, a parser module (e.g., National Maritime Electronic Association or NMEA), a location information source module, and a position information source module. In some aspects, some software components may be omitted and others added. Further, operations for some programs may be separated into additional software components, or consolidated into fewer software components, as desired for a given implementation. The mobile device 500 software architecture may comprise several elements, components or modules, collectively referred to herein as a "module." A module may be implemented as a circuit, an integrated circuit, an application specific integrated circuit (ASIC), an integrated circuit array, a chipset comprising an integrated circuit or an integrated circuit array, a logic circuit, a memory, an element of an integrated circuit array or a chipset, a stacked integrated circuit array, a processor, a digital signal processor, a programmable logic device, code, firmware, software, and any combination thereof.

Figure 54:
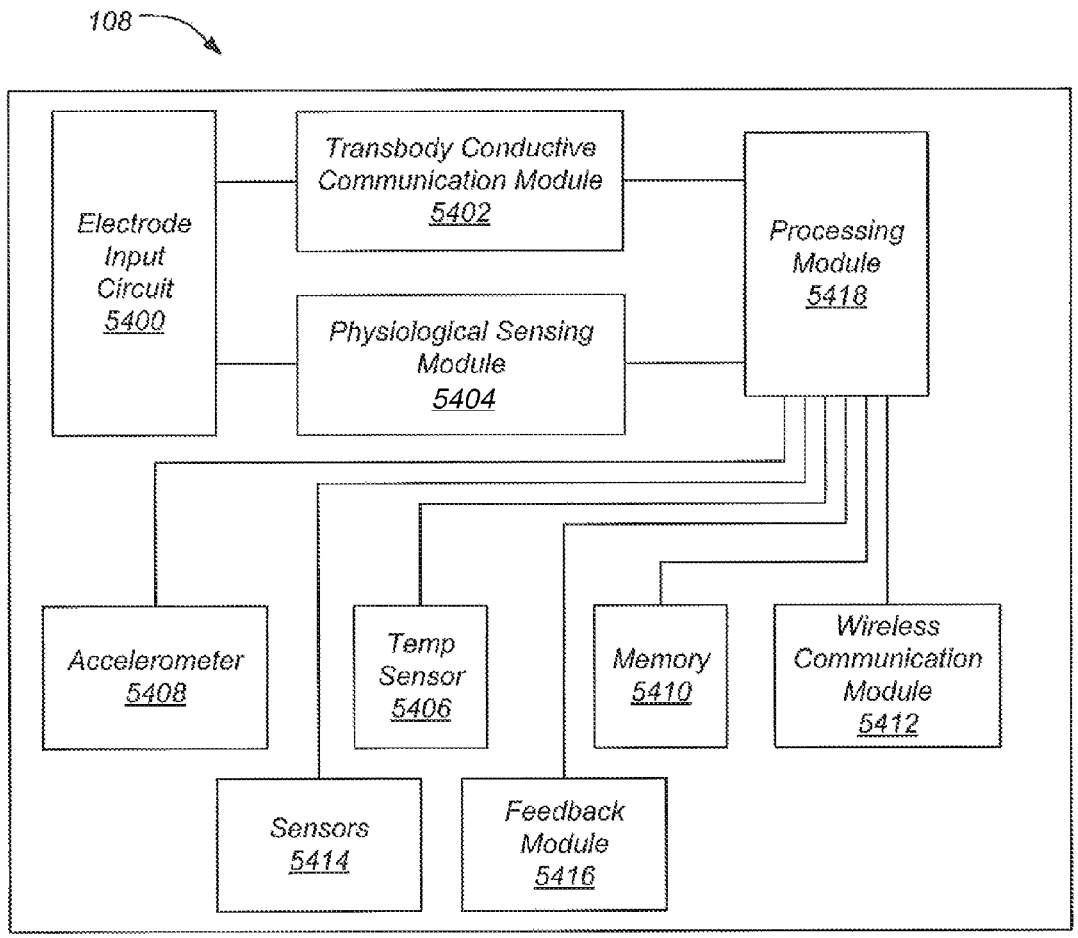
FIG. 54 is a block functional diagram of one aspect of an integrated circuit component of a wearable receiver.

FIG. 54 is a system diagram of one aspect of a wearable receiver 108. The wearable receiver is configured to detect an electrical signal generated by an ingestible event marker, such as the IEM device 104 (FIG. 1), for example. FIG. 54 is a block functional diagram of one aspect of an integrated circuit component. As shown in FIG. 54, the wearable receiver 108 comprises an electrode input circuit 5400, which receives the electrical current signature generated by the IEM device 104. In one aspect, electrically coupled to the electrode input circuit 5400 is a transbody conductive communication module 5402 and, in another aspect, a physiological sensing module 5404 optionally may be coupled to the electrode input circuit 5400. In one aspect, the transbody conductive communication module 5402 may be implemented as a first, e.g., high, frequency (HF) signal chain and the physiological sensing module 5404 may be implemented as a second, e.g., low, frequency (LF) signal chain. In one aspect, the wearable receiver 108 also may include a temperature sensing module 5406 for detecting ambient temperature and a 3-axis accelerometer 5408. In one aspect, the temperature sensing module 5406 may be implemented using complementary oxide semiconductor (CMOS) circuit elements. In various aspects, additional modules may be provided for sensing of the environment around the IEM device 104, for example, including, without limitation, Ph sensing, impedance sensing. The wearable receiver 108 also may comprise a memory 5410 for data storage (similar to any of the previously discussed memory elements), and a wireless communication module 5412 to receive data from and/or transmit data to another device, for example in a data download/upload action, respectively. In various aspects, the sensors 5414 and the feedback modules 5416 also may be included in the wearable receiver 108. In one aspect, as shown in FIG. 54, the various functional modules are coupled to the processing subsystem 5418 of the mobile device 102 (FIGS. A, B). In other aspects, a detection subsystem may comprise its own dedicated processing engine. For example, in one aspect, the wearable receiver 108 may comprise a dedicated processing engine, for example, a microcontroller or a digital signal processor that is separate from the processing subsystem 5418 of the mobile device 102.

With reference back to FIG. 54, in various aspects, the transbody conductive communication module 5402 and the wireless communication module 5412 each may comprise one or more transmitters/receivers ("transceiver") modules. As used herein, the term "transceiver" may be used in a very general sense to include a transmitter, a receiver, or a combination of both, without limitation. In one aspect, the transbody conductive communication module 5402 is configured to communicate with the IEM device 104 (FIG. 1). In one aspect, the wireless communication module 5412 may be configured to communicate with the wireless access point 110 (FIG. 1). In another aspect, the wireless communication module 5412 may be configured to communicate with other mobile devices.

In various aspects, the sensors 5414 typically contact the patient 106 (FIG. 1), e.g., can be removably attached to the torso. In various other aspects, the sensors 5414 may be removably or permanently attached to the wearable receiver 108. For example, the sensors 5414 may be removably connected to the wearable receiver 108 by snapping metal studs. The sensors 5414 may comprise, for example, various devices capable of sensing or receiving the physiologic data. The types of sensors 5414 include, for example, electrodes such as wet or dry biocompatible electrodes. The sensors 5414 may be configured, for example, as a pressure sensor, a motion sensor, an accelerometer 5408, an electromyography (EMG) sensor, an IEM device 104 (FIG. 1), a biopotential sensor, an electrocardiogram sensor, a temperature sensor, a tactile event marker sensor, an impedance sensor, among other sensors.

In various aspects, the feedback module 5416 may be implemented with software, hardware, circuitry, various devices, and combinations thereof. The function of the feedback module 5416 is to provide communication with the patient 106 (FIG. 1) in a discreet, tactful, circumspect manner as described above. In various aspects the feedback module 5416 may be implemented to communicate with the patient 106 using techniques that employ visual, audio, vibratory/tactile, olfactory, and taste.

Figure 55:
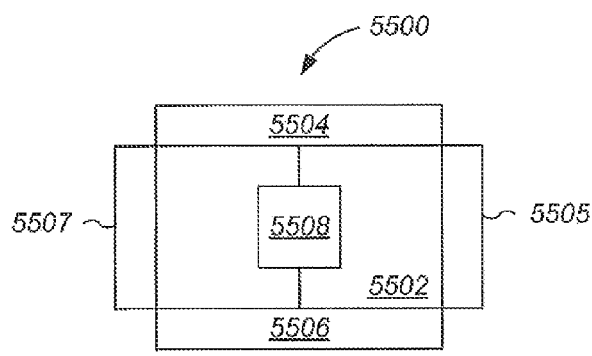
FIG. 55 illustrates a system corresponding to one aspect of an ingestible event marker device.

FIG. 55 illustrates a system 5500 corresponding to one aspect of an ingestible event marker device. In various aspects the IEM devices 104 shown in FIG. 1, for example, may be implemented in accordance with the system 5500 shown in FIG. 55. The system 5500 can be used in association with any medication product, as mentioned above, to determine the origin of the medication and to confirm that at least one of the right type and the right dosage of medication was delivered to the patient and in some aspects to determine when a patient takes the medication product. The scope of the present disclosure, however, is not limited by the environment and the medication product that may be used with the system 5500. For example, the system 5500 may be activated either in wireless mode, in galvanic mode by placing the system 5500 within a capsule and then placing the capsule within a conducting fluid, or a combination thereof, or exposing the system 5500 to air. Once placed in a conducting fluid, for example, the capsule would dissolve over a period of time and release the system 5500 into the conducting fluid. Thus, in one aspect, the capsule would contain the system 5500 and no product. Such a capsule may then be used in any environment where a conducting fluid is present and with any product. For example, the capsule may be dropped into a container filled with jet fuel, salt water, tomato sauce, motor oil, or any similar product. Additionally, the capsule containing the system 5500 may be ingested at the same time that any pharmaceutical product is ingested in order to record the occurrence of the event, such as when the product was taken. Such pharma products and methods of encapsulating such pharma products are described in the commonly owned applications U.S. Publication No. 2008-0284599 A1, titled "Pharma Informatics System," published Nov. 20, 2008, U.S. Publication No. 2011-0054265 A1, titled "Highly Reliable Ingestible Event Markers and Methods for using the Same," published Mar. 3, 2011 and U.S. Application No. 61/416,150, titled: "Ingestible Device with Pharmaceutical Product," filed Nov. 22, 2010 which applications are incorporated by reference in their entirety.

In the specific example of the system 5500 shown in FIG. 55, when the system 5500 is combined with a medication or pharmaceutical product, as the product or pill is ingested, or exposed to air, the system 5500 is activated in galvanic mode. The system 5500 controls conductance to produce a unique electrical current signature that is detected by the electrode assemblies (e.g., wet or dry electrodes), for example, thereby signifying that the pharmaceutical product has been taken. When activated in wireless mode, the system controls modulation of capacitive plates to produce a unique voltage signature associated with the system 5500 that is detected. Various aspects of the system 2100 are described in commonly assigned U.S. Pat. No. 7,978,064, issued Jul. 12, 2011 titled "Communication System with Partial Power Source, and U.S. patent application Ser. No. 13/153,312 titled "Communication System with Partial Power Source" filed Jun. 3, 2011, and U.S. patent application Ser. No. 13/180,516, titled "Communication System With Remote Activation," filed Jul. 11, 2011; and U.S. patent application Ser. No. 13/180,498, titled "Communication System with Multiple Sources of Power," filed Jul. 11, 2011; and U.S. patent application Ser. No. 13/180,539, titled "Communication System Using an Implantable Device," filed Jul. 11, 2011; and U.S. patent application Ser. No. 13/180,525, titled "Communication System With Enhanced Partial Power And Method Of Manufacturing Same," filed Jul. 11, 2011; and U.S. patent application Ser. No. 13/180,538, titled "Communication System using Polypharmacy Co-packaged Medication Dosing Unit," filed Jul. 11, 2011; and U.S. patent application Ser. No. 13/180, 507, titled "Communication System Incorporated in an Ingestible Product," filed Jul. 11, 2011, U.S. Publication No. 2010-0214033 A1 titled "In-vivo Low Voltage Oscillator for Medical Devices Stable Output With Varying Supply Voltage," published Aug. 26, 2010, U.S. Publication No. 2011-0065983 A1, titled "Ingestible Circuitry," published Mar. 17, 2011 and U.S. Publication No. 2010-0239616 A1, titled:

"Controlled Activation Ingestible Identifier," published Sep. 23, 2010 all of which are entirely herein incorporated by reference.

In one aspect, the system D includes a framework 5502. The framework 5502 is a chassis for the system 5500 and multiple components are attached to, deposited upon, or secured to the framework 5502. In this aspect of the system 5500, a digestible material 5504 is physically associated with the framework 5502. The material 5504 may be chemically deposited on, evaporated onto, secured to, or built-up on the framework all of which may be referred to herein as "deposit" with respect to the framework 5502. The material 5504 is deposited on one side of the framework 5502. The materials of interest that can be used as material 5504 include, but are not limited to: Cu, CuCl, or CuI. The material 5504 is deposited by physical vapor deposition, electrodeposition, or plasma deposition, among other protocols. The material 5504 may be from about 0.05 to about 500 µm thick, such as from about 5 to about 100 µm thick. The shape is controlled by shadow mask deposition, or photolithography and etching. Additionally, even though only one region is shown for depositing the material, each system 5500 may contain two or more electrically unique regions where the material 5504 may be deposited, as desired.

At a different side, which is the opposite side as shown in FIG. 55, another digestible material 5506 is deposited, such that the materials 5504, 5506 are dissimilar and insulated from each other. Although not shown, the different side selected may be the side next to the side selected for the material 5504. The scope of the present disclosure is not limited by the side selected and the term "different side" can mean any of the multiple sides that are different from the first selected side. In various aspects, the dissimilar material may be located at different positions on a same side. Furthermore, although the shape of the system is shown as a square, the shape may be any geometrically suitable shape. The materials 5504, 5506 are selected such that they produce a voltage potential difference when the system 5500 is in contact with conducting liquid, such as body fluids. The materials of interest for material 5506 include, but are not limited to: Mg, Zn, or other electronegative metals. As indicated above with respect to the material 5504, the material 5506 may be chemically deposited on, evaporated onto, secured to, or built-up on the framework. Also, an adhesion layer may be necessary to help the material 5506 (as well as material 5504 when needed) to adhere to the framework 2102. Typical adhesion layers for the material 2106 are Ti, TiW, Cr or similar material. Anode material and the adhesion layer may be deposited by physical vapor deposition, electrodeposition or plasma deposition. The material 5506 may be from about 0.05 to about 500 µm thick, such as from about 5 to about 100 µm thick. The scope of the present disclosure, however, is not limited by the thickness of any of the materials nor by the type of process used to deposit or secure the materials to the framework 5502.

According to the disclosure set forth, the materials 5504, 5506 can be any pair of materials with different electrochemical potentials. Additionally, in the aspects wherein the system 5500 is used in-vivo, the materials 5504, 5506 may be vitamins that can be absorbed. More specifically, the materials 5504, 5506 can be made of any two materials appropriate for the environment in which the system 5500 will be operating. For example, when used with an ingestible product, the materials 5504, 5506 are any pair of materials with different electrochemical potentials that are ingestible. An illustrative example includes the instance when the system 5500 is in contact with an ionic solution, such as stomach acids. Suitable materials are not restricted to metals, and in certain aspects the paired materials are chosen from metals and non-metals, e.g., a pair made up of a metal (such as Mg) and a salt (such as CuCl or CuI). With respect to the active electrode materials, any pairing of substances—metals, salts, or intercalation compounds—with suitably different electrochemical potentials (voltage) and low interfacial resistance are suitable.

Materials and pairings of interest include, but are not limited to, those reported in TABLE 1 below. In one aspect, one or both of the metals may be doped with a non-metal, e.g., to enhance the voltage potential created between the materials as they come into contact with a conducting liquid. Non-metals that may be used as doping agents in certain aspects include, but are not limited to: sulfur, iodine, and the like. In another aspect, the materials are copper iodine (CuI) as the anode and magnesium (Mg) as the cathode. Aspects of the present disclosure use electrode materials that are not harmful to the human body.

TABLE 1

|  | Anode | Cathode |
| --- | --- | --- |
| Metals | Magnesium, Zinc Sodium, Lithium Iron |  |
| Salts |  | Copper salts: iodide, chloride, bromide, sulfate, formate, (other anions possible) $Fe^{3+}$ salts: e.g. orthophosphate, pyrophosphate, (other anions possible) Oxygen or Hydrogen Ion (H+) on platinum, gold or other catalytic surfaces |
| Intercalation compounds | Graphite with Li, K, Ca, Na, Mg | Vanadium oxide Manganese oxide |

Thus, when the system 5500 is in contact with the conducting fluid, a current path is formed through the conducting fluid between the dissimilar materials 5504, 5506. A control device 5508 is secured to the framework 5502 and electrically coupled to the materials 5504, 5506. The control device 5508 includes electronic circuitry, for example control logic that is capable of controlling and altering the conductance between the materials 5504, 5506.

The voltage potential created between the dissimilar materials 5504, 5506 provides the power for operating the system as well as produces the current flow through the conducting fluid and the system 5500. In one aspect, the system 5500 operates in direct current mode. In an alternative aspect, the system 5500 controls the direction of the current so that the direction of current is reversed in a cyclic manner, similar to alternating current. As the system reaches the conducting fluid or the electrolyte, where the fluid or electrolyte component is provided by a physiological fluid, e.g., stomach acid, the path for current flow between the dissimilar materials 5504, 5506 is completed external to the system 5500; the current path through the system 5500 is controlled by the control device 5508. Completion of the current path allows for the current to flow and in turn a receiver, not shown, can detect the presence of the current and recognize that the system 2100 has been activate and the desired event is occurring or has occurred.

In one aspect, the two dissimilar materials 5504, 5506 are similar in function to the two electrodes needed for a direct current power source, such as a battery. The conducting liquid acts as the electrolyte needed to complete the power source. The completed power source described is defined by the physical chemical reaction between the dissimilar materials 5504, 5506 of the system 5500 and the surrounding fluids of the body. The completed power source may be viewed as a power source that exploits reverse electrolysis in an ionic or a conduction solution such as gastric fluid, blood, or other bodily fluids and some tissues. Additionally, the environment may be something other than a body and the liquid may be any conducting liquid. For example, the conducting fluid may be salt water or a metallic based paint.

In certain aspects, the two dissimilar materials 5504, 5506 are shielded from the surrounding environment by an additional layer of material. Accordingly, when the shield is dissolved and the two dissimilar materials 5504, 5506 are exposed to the target site, a voltage potential is generated.

In certain aspects, the complete power source or supply is one that is made up of active electrode materials, electrolytes, and inactive materials, such as current collectors, packaging. The active materials are any pair of materials with different electrochemical potentials. Suitable materials are not restricted to metals, and in certain aspects the paired materials are chosen from metals and non-metals, e.g., a pair made up of a metal (such as Mg) and a salt (such as CuI). With respect to the active electrode materials, any pairing of substances—metals, salts, or intercalation compounds—with suitably different electrochemical potentials (voltage) and low interfacial resistance are suitable.

A variety of different materials may be employed as the materials that form the electrodes. In certain aspects, electrode materials are chosen to provide for a voltage upon contact with the target physiological site, e.g., the stomach, sufficient to drive the system of the identifier. In certain aspects, the voltage provided by the electrode materials upon contact of the metals of the power source with the target physiological site is 0.001 V or higher, including 0.01 V or higher, such as 0.1 V or higher, e.g., 0.3 V or higher, including 0.5 volts or higher, and including 1.0 volts or higher, where in certain aspects, the voltage ranges from about 0.001 to about 10 volts, such as from about 0.01 to about 10 V.

Still referring to FIG. 55, the dissimilar materials 5504, 5506 provide the voltage potential to activate the control device 5508. Once the control device 5508 is activated or powered up, the control device 2108 can alter conductance between the first and second materials 5504, 5506 in a unique manner. By altering the conductance between the first and second materials 5504, 5506, the control device 5508 is capable of controlling the magnitude of the current through the conducting liquid that surrounds the system 5500. This produces a unique current signature that can be detected and measured by a receiver (not shown), which can be positioned internal or external to the body. The receiver is disclosed in greater detail in U.S. patent application Ser. No. 12/673,326 entitled "BODY-ASSOCIATED RECEIVER AND METHOD" filed on Dec. 15, 2009, and published as 2010/0312188 A1 dated Dec. 9, 2010 which is incorporated herein by reference in its entirety. In addition to controlling the magnitude of the current path between the materials, non-conducting materials, membrane, or "skirt" are used to increase the "length" of the current path and, hence, act to boost the conductance path, as disclosed in the U.S. Publication No. 2009-0082645 A1, titled "In-Body Device With Virtual Dipole Signal Amplification," published Mar. 26, 2009, and U.S. Publication No. 2009-0256702 A1, titled "Multi-Mode Communication Ingestible Event Markers, and Methods of Using the Same" published Oct. 15, 2009, the entire content of which is incorporated herein by reference. Alternatively, throughout the disclosure herein, the terms "non-conducting material," "membrane," and "skirt" are interchangeably used with the term "current path extender" without impacting the scope or the present aspects and the claims herein. The skirt, shown in portion at 5505, 5507, respectively, may be associated with, e.g., secured to, the framework 5502. Various shapes and configurations for the skirt are contemplated as within the scope of the various aspects of the present invention. For example, the system 5500 may be surrounded entirely or partially by the skirt and the skirt maybe positioned along a central axis of the system 5500 or off-center relative to a central axis. Thus, the scope of the present disclosure as claimed herein is not limited by the shape or size of the skirt. Furthermore, in other aspects, the dissimilar materials 5504, 5506 may be separated by one skirt that is positioned in any defined region between the dissimilar materials 5504, 5506.

The system 5500 may be grounded through a ground contact. The system 5500 also may include a sensor module. In operation, ion or current paths are established between the first material 5504 to the second material 5506 and through a conducting fluid in contact with the system 5500. The voltage potential created between the first and second materials 5504, 5506 is created through chemical reactions between the first and second materials 5504, 5506 and the conducting fluid. In one aspect, the surface of the first material 5504 is not planar, but rather an irregular surface. The irregular surface increases the surface area of the material and, hence, the area that comes in contact with the conducting fluid.

In one aspect, at the surface of the first material 5504, there is chemical reaction between the material 5504 and the surrounding conducting fluid such that mass is released into the conducting fluid. The term mass as used herein refers to protons and neutrons that form a substance. One example includes the instant where the material is CuCl and when in contact with the conducting fluid, CuCl becomes Cu (solid) and Cl— in solution. The flow of ions into the conduction fluid is via ion paths. In a similar manner, there is a chemical reaction between the second material 5506 and the surrounding conducting fluid and ions are captured by the second material 5506. The rate of ionic exchange and, hence the ionic emission rate or flow, is controlled by the control device 5508. The control device 5508 can increase or decrease the rate of ion flow by altering the conductance, which alters the impedance, between the first and second materials 5504, 5506. Through controlling the ion exchange, the system 5500 can encode information in the ionic exchange process. Thus, the system 5500 uses ionic emission to encode information in the ionic exchange.

The control device 5508 can vary the duration of a fixed ionic exchange rate or current flow magnitude while keeping the rate or magnitude near constant, similar to when the frequency is modulated and the amplitude is constant. Also, the control device 5508 can vary the level of the ionic exchange rate or the magnitude of the current flow while keeping the duration near constant. Thus, using various combinations of changes in duration and altering the rate or magnitude, the control device 5508 encodes information in the current flow or the ionic exchange. For example, the control device 5508 may use, but is not limited to any of the following techniques namely, Binary Phase-Shift Keying (PSK), Frequency Modulation (FM), Amplitude Modulation (AM), On-Off Keying, and PSK with On-Off Keying.

Various aspects of the system 5500 may comprise electronic components as part of the control device 5508. Components that may be present include but are not limited to: logic and/or memory elements, an integrated circuit, an inductor, a resistor, and sensors for measuring various parameters. Each component may be secured to the framework and/or to another component. The components on the surface of the support may be laid out in any convenient configuration. Where two or more components are present on the surface of the solid support, interconnects may be provided.

The system 5500 controls the conductance between the dissimilar materials and, hence, the rate of ionic exchange or the current flow. Through altering the conductance in a specific manner the system is capable of encoding information in the ionic exchange and the current signature. The ionic exchange or the current signature is used to uniquely identify the specific system. Additionally, the system 5500 is capable of producing various different unique exchanges or signatures and, thus, provides additional information. For example, a second current signature based on a second conductance alteration pattern may be used to provide additional information, which information may be related to the physical environment. To further illustrate, a first current signature may be a very low current state that maintains an oscillator on the chip and a second current signature may be a current state at least a factor of ten higher than the current state associated with the first current signature.

Figures 56, 57, 58:
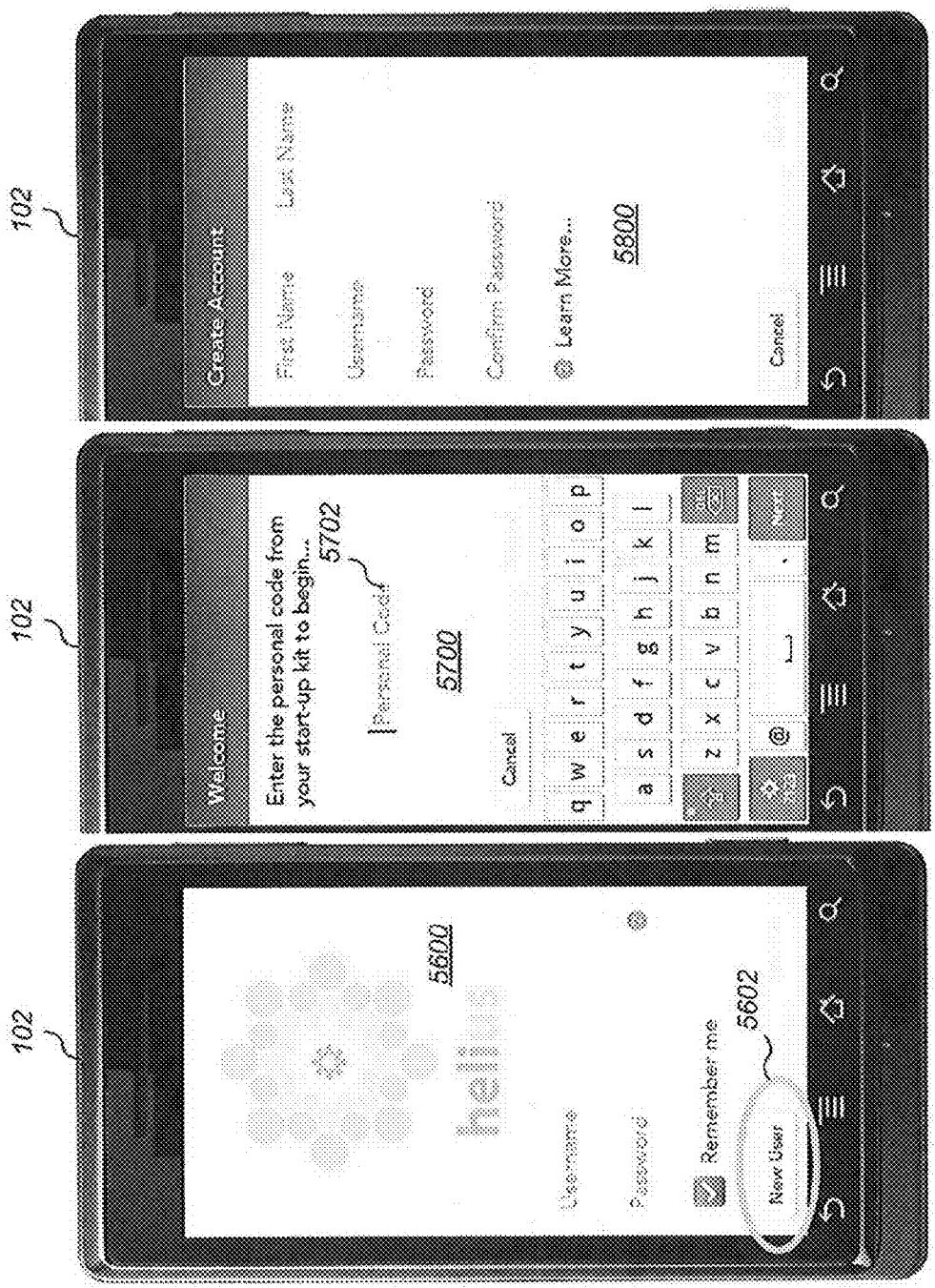

FIGS. 56-58 illustrate various aspects of ornamental designs for various GUIs for a display screen of a mobile device 102. FIGS. 56-58 illustrate the ornamental design for various "Onboarding" GUIs for a display screen of a mobile device for creating an account. FIG. 56 shows a GUI 5600 for creating an account. A "New User" button 5602 launches a "Welcome" GUI 5700, as shown in FIG. 57, when the "New User" button 5602 is selected. The "Welcome" GUI 5700 requests that the user enter the personal code from the start-up kit to begin. A text box 5702 is provided for entering the personal code. In FIG. 58, a "Create Account" GUI 5800 is displayed for entering the user's First Name, Last Name, Username, Password, and to Confirm Password.

FIGS. 59-61 illustrate ornamental designs for several additional "Onboarding" GUIs for a display screen of a mobile device 102 for setting up a wearable receiver 108, e.g., a patch. FIG. 59 shows a GUI 5900 for setting up the wearable receiver 108. A GUI element 5902 of the wearable receiver 108 is displayed with a blinking button 5904 along with text instructing the user to press and hold the button on the patch (wearable receiver 108) until the light blinks. FIG. 60 shows a GUI 6000 that is displayed while the wearable receiver 108 and the mobile device 102 are connecting. A GUI 6100 shown in FIG. 61 is displayed when the wearable receiver 108 and the mobile device 102 are connected. The GUI 6100 also instructs the user to place the wearable receiver 108 patch on the left side of the torso and also displays a silhouette of a person 6102 wearing a receiver 6104 on the left side of the torso as indicated.

FIGS. 62-65 illustrate ornamental designs for several additional "Onboarding" GUIs for a display screen of a mobile device 102 for demonstrating the healthcare subscription information system according to the present disclosure. FIG. 62 shows a GUI 6200 for instructing to the user to take the two demonstration tablets 6202, 6204 located in the starter kit and then tap the "Done" button 6206. The healthcare subscription information system will confirm that it is ready to help within 10 minutes, for example, to set up the wearable receiver 108. While waiting for a confirmation from the healthcare subscription information system, a GUI 6300 is displayed, as shown in FIG. 63. When the healthcare subscription information system successfully detects the ingestion of the demonstration tablets, a GUI 6400, as shown in FIG. 64, is displayed. A silhouette of a person 6402 is displayed in conjunction with a check mark element 6404. At this point, the user can select a "View Data" button 6406 or a "Share Data" button 6408 to view or share data, respectively. When the healthcare subscription information system fails to detect the ingestion of the demonstration tablets, a GUI 6500, as shown in FIG. 65, is displayed. The GUI 6500 displays a silhouette 6502 of a person with a question mark element 6506 to indicate that it has been over ten minutes and the healthcare subscription information system has not yet detected the ingestion of the demonstration tablets. A "Troubleshoot" button 6508 is provided to troubleshoot the situation.

FIGS. 66-71 illustrate ornamental designs for several additional "Ribbon" GUIs for a display screen of a mobile device 102 for viewing annotations. FIG. 66 shows a GUI 6600 for displaying an activity ribbon 6602 and a medication timeline 6604 with several annotations 6606. A pop-up text bubble 6700 is displayed to provide additional information about the activity ribbon 6602 is shown in FIG. 67, where the user entered "Ran to catch bus" at "1519 h." Another pop-up text bubble 6800 is displayed to provide additional information about the activity ribbon 6602 is shown in FIG. 68 where the user entered "Extra TV time" at "1811 h" and "Waited for repairmen" at "1816 h." FIG. 69 shows a pop-up text bubble 6900 that is displayed to provide additional information about the medication timeline 6604 to indicate that a "dose" was taken by the patient 108 at "0819 h." Another pop-up text bubble 7000 is displayed to provide additional information about the medication timeline 6604 is shown in FIG. 70 to indicate "Dose entered manually" at "1616 h." FIG. 71 shows another pop-up text bubble 7100 displayed to provide additional information about the medication timeline 6604 to indicate that at "0366 h" the patient took "3 Doses."

FIGS. 72-74 illustrate ornamental designs for several additional "Ribbon" GUIs for a display screen of a mobile device 102 for making annotations. FIG. 72 shows a GUI 7202 for entering an annotation on the activity ribbon 6602 or the medication timeline 6604. To display the annotation GUI 7202, the user taps the activity ribbon/medication timeline GUI element 7208. When the "Annotation" element 7206 is selected, the display screen of the mobile device 102 shows a GUI 7303 for entering annotation text in a text box 7304 associated with the activity ribbon 6602 as indicated by highlighted GUI element 7308. The annotation on the activity ribbon 6602 can be saved by tapping on the "Save" button 7306. FIG. 74 shows a GUI 7402 for entering an annotation 7404 associated with the medication timeline 6604 to manually record a dose as indicated by highlighted GUI element 7406. To save the manually recorded dose, the user taps the "Save" button 7408.

Figure 75:
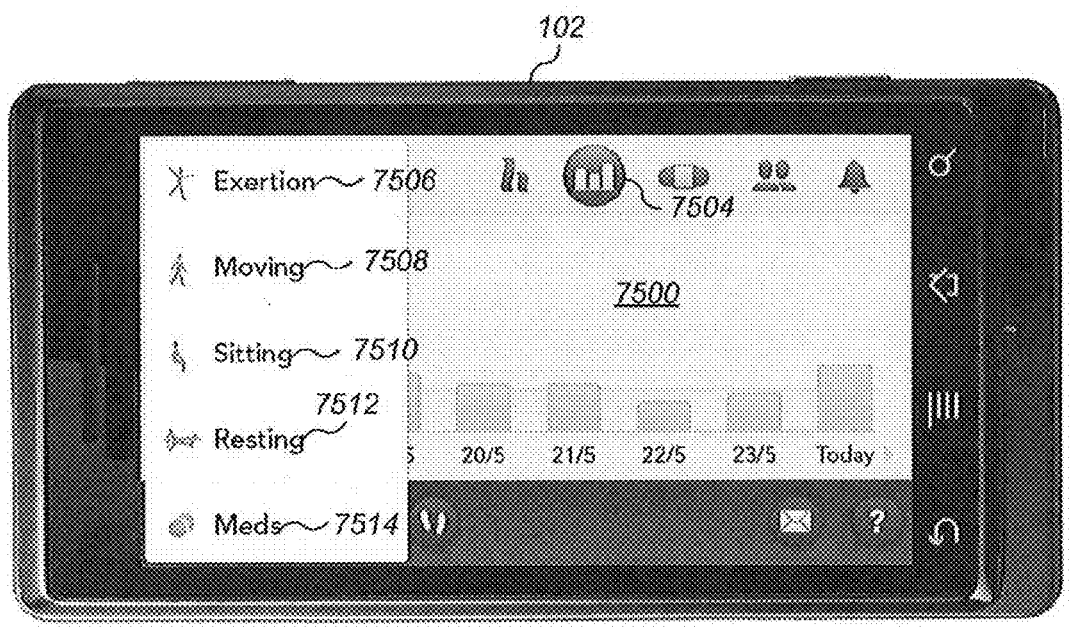
FIG. 75 illustrates an ornamental design for a charts selection GUI for a display screen of a mobile device.

FIG. 75 illustrates an ornamental design for a charts selection GUI 7500 for a display screen of a mobile device 102. The charts selection GUI 7500 is displayed by tapping or selecting the charts GUI element 7504. A charts selection box 7502 includes several GUI elements for opening corresponding display screens associated with charts: "Exertion" chart GUI element 7506, "Moving" chart GUI element 7508, "Sitting" chart GUI element 7510, "Resting" chart GUI element 7512, and "Meds" chart GUI element 7514. Each of these elements open corresponding "Charts" GUIs as described hereinbelow.

FIGS. 76-78 illustrate ornamental designs for several additional "Charts" GUIs for a display screen of a mobile device 102 for displaying charts associated with patient exertion periods. FIG. 76 shows an exertion chart GUI 7600 displaying a bar graph 7602 for tracking and quantifying patient exertion periods on a daily basis. The exertion chart GUI 7600 can be displayed by selecting or tapping the charts GUI element 7504 and the "Exertion" chart GUI element 7506 (FIG.

75). The bar graph 7602 quantifies the patient's daily active hours along the vertical axis. The patient's active hours over a one week period (seven days) including the present day 7606 are displayed along the horizontal axis. A usual level 7608 of active hours per day is shown for comparison purposes. The GUI 7700 shown in FIG. 77 is displayed after tapping or selecting the Steps GUI element 7702 to show the number of steps taken by the patient per day. The number of daily steps taken by the patient is shown for a week along the horizontal axis. FIG. 78 shows a GUI 7800 displaying a bar graph 7802 for tracking and quantifying patient exertion on a daily basis where the patient exertion in terms of active hours is quantified along the vertical axis over a period of one month along the horizontal axis. Tapping or selecting the "Exertion" button 7610 displays the charts selection box 7502 as shown in FIG. 75.

FIGS. 79-81 illustrate ornamental designs for several additional "Charts" GUIs for a display screen of a mobile device 102 for displaying charts associated with patient rest periods. FIG. 79 shows a rest chart GUI 7900 displaying a bar graph 7902 for tracking and quantifying patient rest periods on a daily basis. The rest chart GUI 7900 is can be displayed by selecting or tapping the charts GUI element 7504 and the "Resting" chart GUI element 7512 (FIG. 75). The bar graph 7902 quantifies the patient's daily resting hours along the vertical axis. The patient's resting hours over a one week period (seven days) including the present day 7906 is displayed along the horizontal axis. A usual level 7908 of active hours per day is shown for comparison purposes. The GUI 8000 shown in FIG. 80 is displayed after tapping or selecting the moon GUI element 8002, which shows the quality of rest by the patient per day. The quality of daily rest is indicated by a variety of face elements 8004 along the horizontal axis. A face element 8004 with a smile indicates good quality rest. A face element 8004 with a neutral face indicates average rest. A face element 8004 with a yawning face indicates poor quality rest. FIG. 81 shows a GUI 8100 displaying a pop-up text bubble 8102 to provide additional information about the day such as the number of resting hours for a given day. As shown in FIG. 81, on day "19/5" the patient rested for "8 h 04 m." Tapping or selecting the "Resting" button 7904 displays the charts selection box 7502 as shown in FIG. 75.

Figure 82:
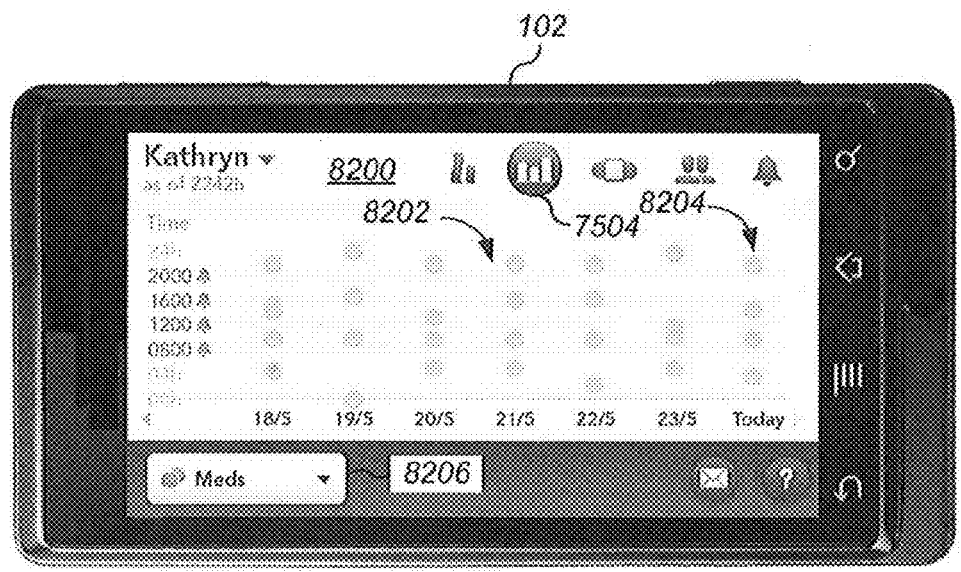
FIGS. 82-83 illustrate ornamental designs for several additional "Charts" GUIs for a display screen of a mobile device for displaying charts associated with patient rest periods.
Figure 83:
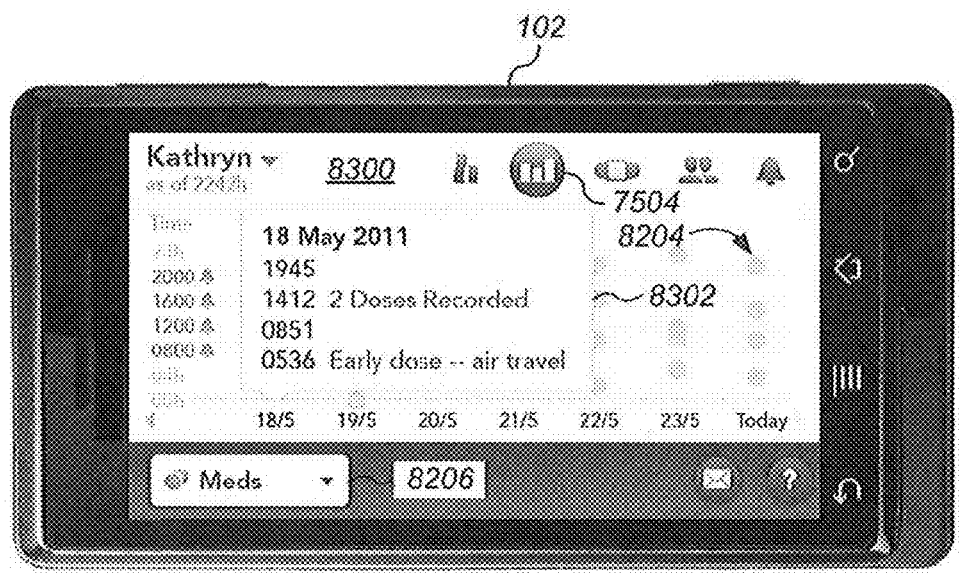

FIGS. 82-83 illustrate ornamental designs for several additional "Charts" GUIs for a display screen of a mobile device 102 for displaying charts associated with patient rest periods. FIG. 82 shows a meds GUI 8200 displaying a medications chart 8202 for tracking and quantifying patient medication periods on a daily basis. The med chart GUI 8200 can be displayed by selecting or tapping the charts GUI element 7504 and the "Meds" chart element 7512 (FIG. 75). The medications chart 8202 tabulates daily times and doses of medication taken by the patient along the vertical axis. The medications chart 8202 shown in FIG. 82 tracks medication doses over a one week period (seven days) including the present day 8204 is displayed along the horizontal axis. The GUI 8300 shown in FIG. 83 is displayed after tapping or selecting the zone near the day of the week along the horizontal axis. A pop-up text bubble 8302 is displayed to provide additional information about the selected day such as day of the week ("18 May 2011"), times of the day when the doses were taken, and special notes such as multiple doses detected, early dosing, and the like. Tapping or selecting the "Meds" button 8206 displays the charts selection box 7502 as shown in FIG. 75.

FIGS. 84-86 illustrate ornamental designs for several additional "Charts" GUIs for a display screen of a mobile device 102 for sending reports associated with patient via email.

FIG. 84 shows a "Send Report" GUI 8400 displaying a destination email address input field 8402. FIG. 85 shows the "Send Report" GUI 8400 with the destination email address field 8401 filled in. Tapping or selecting the "Next" button 8502 opens the "Send Report" GUI 8600 shown in FIG. 86. The "Send Report" GUI 8600 displays the date range 8602 for the reporting period and a "Send" button 8604 for sending the report via email.

FIGS. 87-89 illustrate ornamental designs for several additional "Charts" GUIs for a display screen of a mobile device 102 for sending reports associated with patient via the post. FIG. 87 shows a "Send Report" GUI 8700 displaying destination Name, Street, City, Postcode, and Country input fields. FIG. 88 shows the "Send Report" GUI 8700 with the destination address fields filled in. Tapping or selecting the "Next" button 8702 opens the "Send Report" GUI 8900 shown in FIG. 89. The "Send" button 8902 sends the paper report to the printer so that it can be sent to the destination via post.

Figure 90:
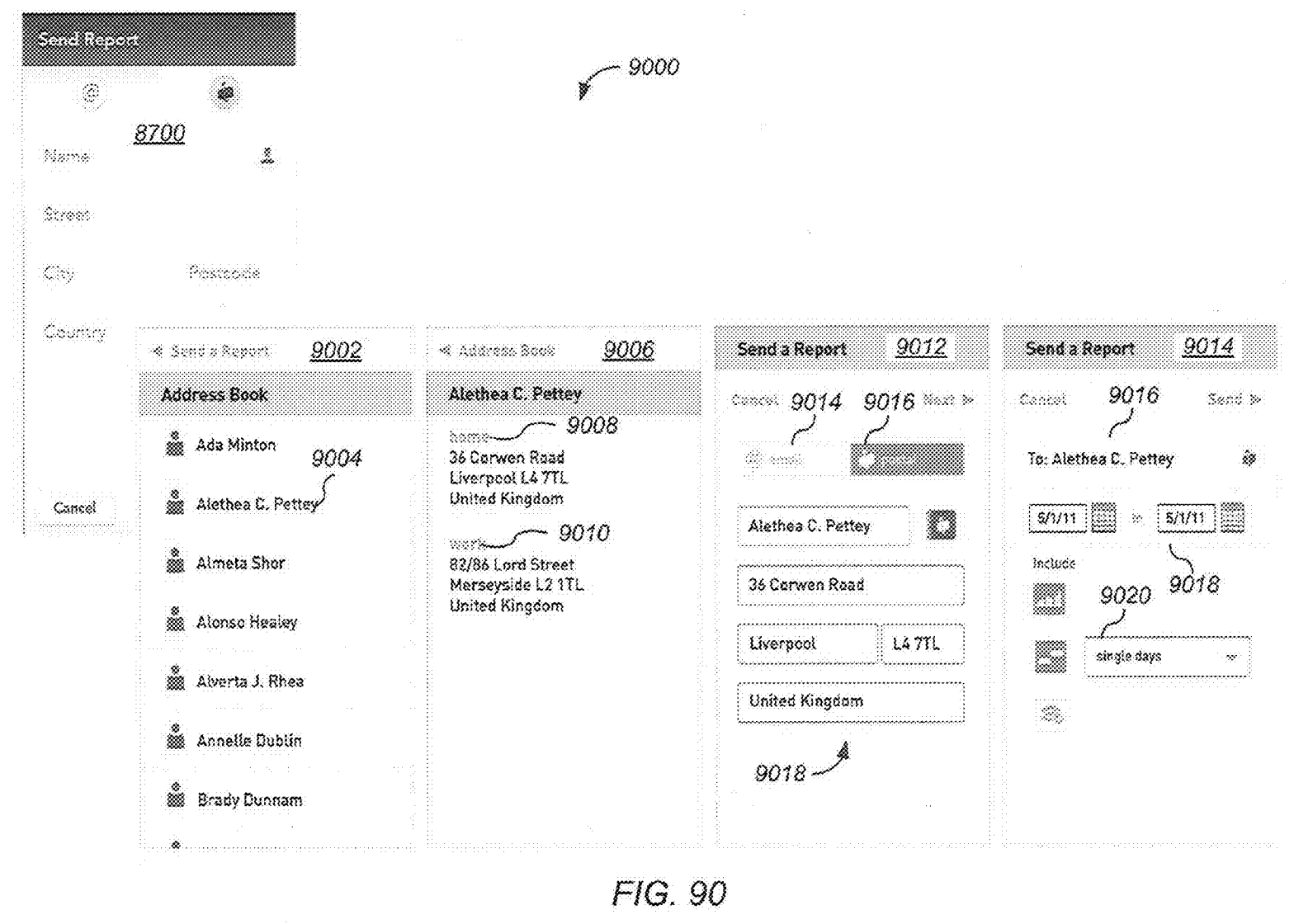

FIG. 90 illustrates the "Send Report" GUI 8700 shown previously in FIG. 87, with a series of address book GUI screens for a display screen of a mobile device 102 for populating the "Send Report" GUI 8700 using a local address book. A first address book GUI 9002 is displayed by selecting an address book element 9000 in "Send Report" GUI 8700. The GUI 9002 provides an alphabetical list of names of contacts stored in a locally or remotely stored address book database. Tapping or selecting the second name on the list 9004 "Alethea C. Pettey" displays the next address book GUI 9006, which displays both a "home" address element 9008 associated with the contact's home address and a "work" address element 9010 associated with the contact's work address. The corresponding home and work addresses also are displayed. Tapping or selecting the "home" address element 90, for example, displays the next address book GUI 9012, which shows the contact's home address populated in the address fields 9018. Also displayed within the address book GUI 9012 is an "email" GUI element 9014 and a "postal" GUI element 9016 to enable the user to select the mode of send the report. Tapping or selecting the "postal" GUI element 9016 displays the next address book GUI 9014, which enables the user to select the date range 9018 of the report and the increment, e.g., single days or others such weekly, monthly, etc., by tapping or selecting the resolution GUI element 9020.

Figure 91:
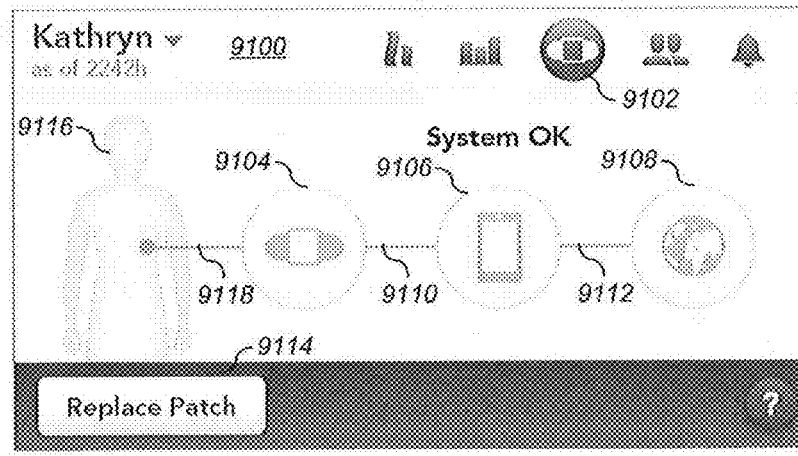
FIGS. 91-96 illustrate ornamental designs for several "Patch" GUIs for a display screen of a mobile device for managing the wearable receiver communication system.
Figure 92:
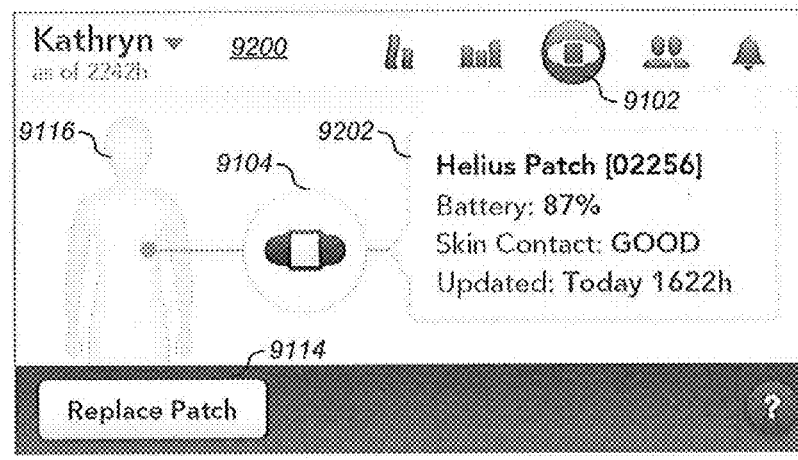
Figure 93:
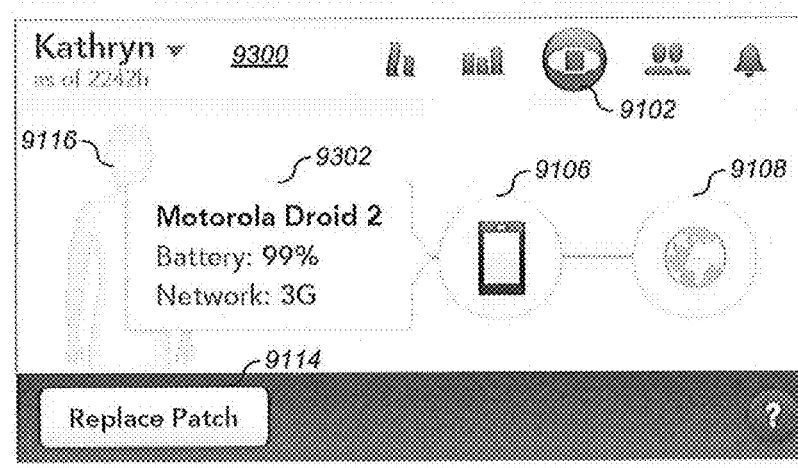
Figure 94:
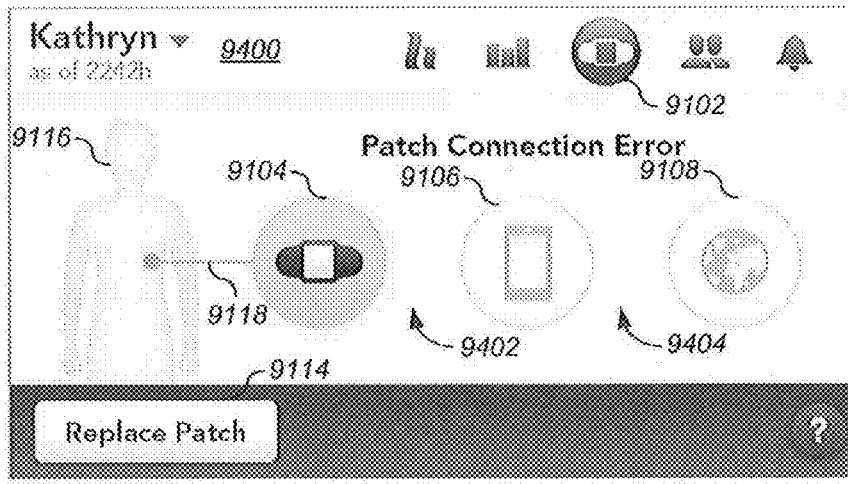
Figure 95:
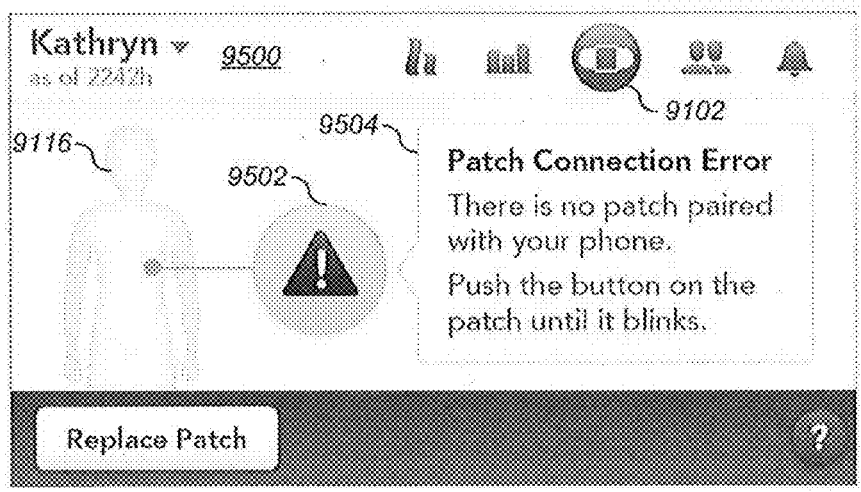
Figure 96:
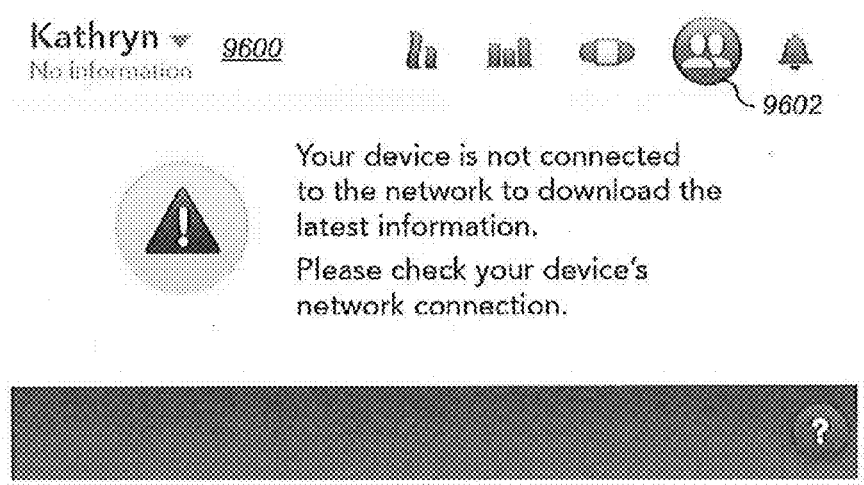

FIGS. 91-96 illustrate ornamental designs for several "Patch" GUIs for a display screen of a mobile device 102 for managing the wearable receiver 108 communication system. FIGS. 91-93 show "Patch" GUIs 9100, 9200, 9300 that are displayed when the receiver communication system is functioning properly. FIGS. 94-96 show "Patch" GUIs 9400, 9500, 9600 that are displayed when the receiver communication system is not functioning properly and an error occurs during a system test.

Turning now to FIG. 91, the "Patch" GUI 9100 can be displayed by selecting the wearable receiver (e.g., patch) GUI element 9102 when the communication system is functioning properly. The GUI 9100 displays an icon of the patient 9116 and a wearable receiver element 9104 shown connected to the patient 9116 via connection 9118. The wearable receiver element 9104 is shown connected to a mobile device element 9106 via connection 9110 indicating that the wearable receiver 108 is paired with the mobile device 102. The mobile device element 9106 is shown connected to a network element 9108 via connection 9112 indicating that the mobile device 102 is connected to an external network such as the Internet, for example. If the wearable receiver 108 is connected to the network "System OK" is displayed by the GUI

9100. Additional information in regards to the wearable receiver 108 or the mobile device 102 may be obtained by tapping or selecting the corresponding element 9104 or 9106. FIG. 92 shows a GUI 9200 that is displayed after tapping the wearable receiver element 9104. In response, the GUI 9200 displays a pop-up text bubble 9202 to provide additional information about the wearable receiver 108 such as the serial number of the wearable receiver 108 (Helius Patch [02256]), battery charge level (Battery: 87%), skin contact (Skin Contact: GOOD), last update (Updated: Today 1622 h). Additional information about the mobile device 102 can be obtained by tapping or selecting the mobile device element 9106 which displays the GUI 9300 shown in FIG. 93. As shown, a pop-up text bubble 9302 is displayed to provide additional information about the mobile device 102 such as the mobile device type and model number (Motorola Droid 2), mobile device battery level (Battery: 99%), communication network (Network: 3G). When it is time to replace the wearable receiver 108, the "Replace Patch" button 9114 is tapped or selected.

Turning now to FIG. 94, the "Patch" GUI 9400 can be displayed by selecting the wearable receiver (e.g., patch) GUI element 9102 when the communication system is not functioning properly. The GUI 9400 displays an icon of the patient 9116 and a wearable receiver element 9104 shown connected to the patient 9116 via connection 9118. The wearable receiver element 9104, however, is not connected to the mobile device element 9106 as shown by arrow 9402 indicating that the wearable receiver 108 is not paired with the mobile device 102. Also, the mobile device element 9106 is not connected to the network element 9108 as shown by arrow 9404 indicating that the mobile device 102 is not connected to an external network such as the Internet, for example. If the wearable receiver 108 is not connected to the mobile device 102 and/or the network, "Patch Connection Error" is displayed by the GUI 9400. Additional information in regards to the wearable receiver 108 or the mobile device 102 may be obtained by tapping or selecting the wearable receiver element 9104. FIG. 95 shows a GUI 9500 that is displayed after tapping the wearable receiver element 9104 when there is a connection error. In response, the GUI 9500 displays a pop-up text bubble 9504 to provide additional information about the wearable receiver 108 connection error. In one aspect, the pop-up text bubble 9504 provides additional information such as "Patch Connection Error—There is no patch paired with your phone. Push the button on the patch until it blinks." In other words, the pop-up text box 9504 provides instructions to pair the wearable receiver 108 with the mobile device 102. To check network connectivity, the share GUI element 9602 may be selected. Since, the GUI 9600 presents instructional text such as "Your device is not connected to the network to download the latest information. Please check your device's network connection."

FIGS. 97-99 illustrate ornamental designs for several additional "Patch" GUIs for a display screen of a mobile device 102 for replacing the wearable receiver 108. As shown in FIGS. 91-95, to replace the wearable receiver 108, the "Replace Patch" button 9114 is tapped or selected. Upon selecting the "Replace Patch" button 9114, the "Patch" GUI 9700 shown in FIG. 7 is shown. The replace patch GUI 9700 provides textual instructions 9702 to "Press an hold the button on your old patch until the light blinks . . . " on the old wearable receiver 108. A wearable receiver GUI element 9704 includes a blinking GUI element 9706 and text to indicate that the wearable receiver GUI element 9704 is associated with the old patch receiver. Once the light on the wearable receiver 108 blinks, the GUI 9700 instructs to " . . . then tap 'Next.'" Accordingly, upon tapping or selecting the "Next" button 9708 the replace patch GUI 9800 shown in FIG. 98 is shown to indicate that the mobile device 102 is uploading the information to the remote processing system 122. FIG. 99 shows a replace patch GUI 9900 that provides instructional text 9902 to "Press and hold the button on your new patch until the light blinks . . . " on the new wearable receiver 108. The GUI 9900 also displays a wearable receiver GUI element 9904 that includes a blinking GUI element 9906 and text to indicate that the wearable receiver GUI element 9904 is associated with the new patch receiver.

Figure 103:
Figure 104:

FIGS. 100-104 illustrate ornamental designs for several "Share" GUIs for a display screen of a mobile device 102 for managing permissions and adding/removing caregivers. FIG. 100 illustrates one aspect of a "Manage Sharing" GUI 10000 for a display screen of a mobile device 102 for viewing the current data sharing status of caregivers. The "Manage sharing" GUI 10000 is displayed when the sharing GUI element 9602 is tapped or selected. The GUI 10000 shows a list of caregivers Anna, Dr. Rinderknecht, Jane, Karl, Megan and their current data sharing permission status indicated by the activity timeline element 10002, the activity trend chart element 10004, and the medication timeline element 10006. Permission is indicated by the any of these elements 10002, 10004, 10006 is highlighted. As shown by the GUI 10000, for example, Anna has permission for sharing activity timeline data as indicated by the highlighted element 10002. Dr. Rinderknecht has permission for sharing activity timeline data, activity trend chart data, and medication timeline data as indicated by the highlighted elements 10002, 10004, 10006. Jane has permission only for sharing medication timeline data as indicated by highlighted element 10006. Karl has permission for sharing activity timeline data and activity trend chart data as indicated by highlighted elements 10002, 10004. Megan's permissions are not visible because they appear below the screen. To view Megan's permissions, the touch sensitive display screen of the mobile device 102 can be tapped and dragged upwardly using a commonly employed gesturing technique in modern smart phone and touch pad computer technology. Tapping or selecting the edit (pencil) GUI element 10008 displays the "Add/Remove" GUI 10100. The "Add/Remove" GUI 10100 can be used to add a new caregiver by tapping or selecting the plus ("+") element 10102 or to remove a caregiver by tapping or selecting the minus ("−") element 10104 associated with a current caregiver. For example, to remove Karl, the minus ("−") element 10104 to the right of Karl's name can be tapped or selected. The "Remove" GUI 10200 as shown in FIG. 102 is then displayed along with a confirmatory query "Remove Karl?" 10202. In response either the "No" button 10204 or the "Yes" button 10206 can be selected. To invite a new caregiver, or add a new giver, the plus ("+") element in GUI 10100 is selected and then "Invite to Helius" GUI 10300 is displayed as shown in FIG. 103. The GUI 10300 provides a "nickname" field 10302, an "email" field 10304, and a "relationship" field 10306 for entering corresponding information associated with the caregiver being invited to share data. In addition, the type of data 10308 to be shared is displayed such as activity timeline data, activity trend chart data, and medication timeline data as indicated by the highlighted elements 10002, 10004, 10006 by tapping or selecting the corresponding element 1002, 10004, 10006. The security code 10310 (e.g., "1A2B3C"), which is to be shared with the invitee is also displayed along with the text "For your protection, the recipient will be required to enter the above code." The transaction can be cancelled by tapping or selecting the "Cancel" button 10312 or the invitation can be sent by tapping or selecting the "Invite" button 10314. Once the invitation is send, the caregiver invitee sees a "Caregiver View" GUI 10400 as shown in FIG. 104. The new caregiver has been invited to share the activity timeline data as indicated by the highlighted element 10002.

Figures 105, 106, 107:
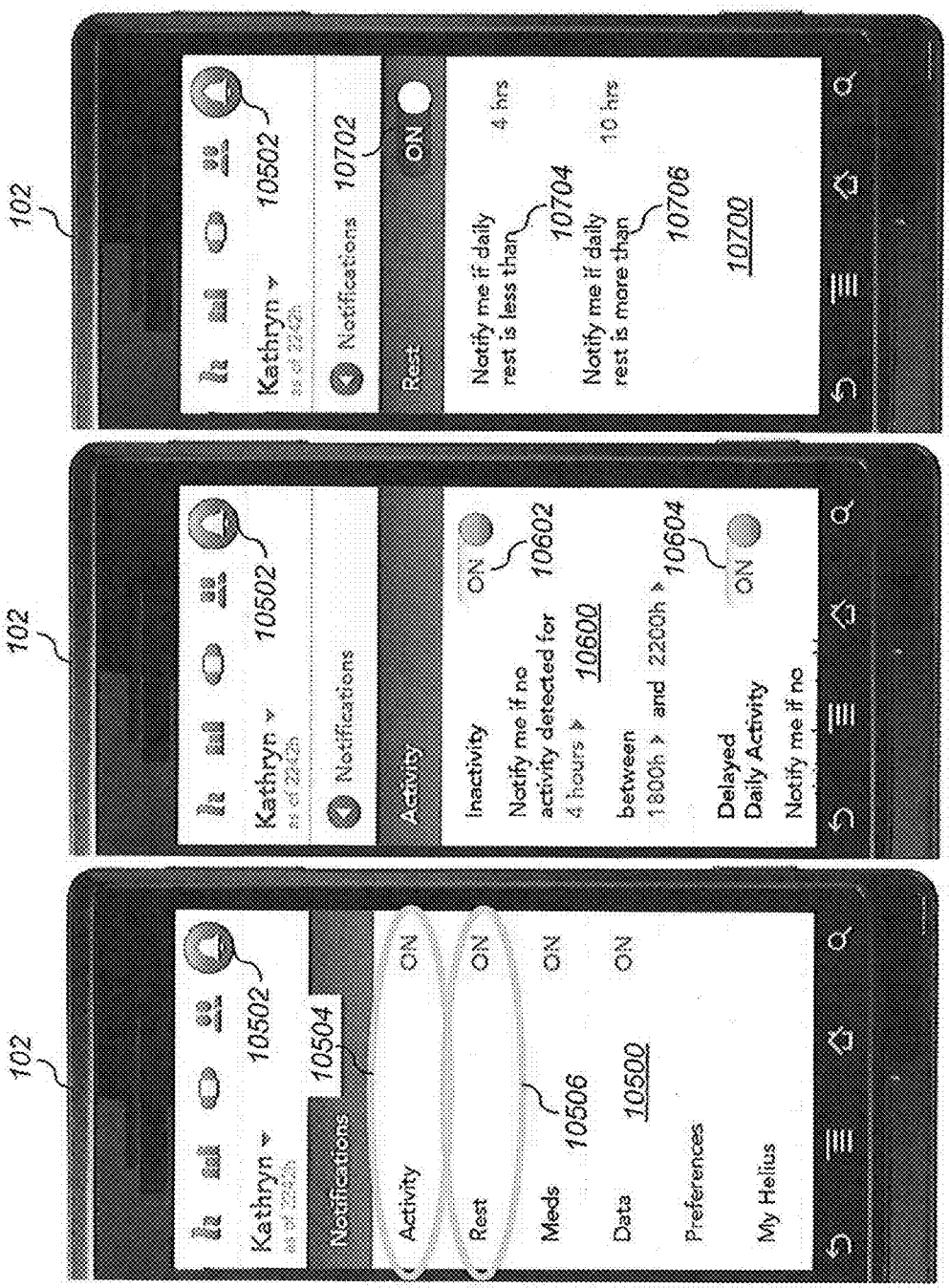
FIGS. 105-107 illustrate ornamental designs for several "Notifications" GUIs for a display screen of a mobile device for notifying patients of activity and rest information.

FIGS. 105-107 illustrate ornamental designs for several "Notifications" GUIs for a display screen of a mobile device 102 for notifying patients of activity and rest information. FIG. 105 illustrates one aspect of a "Notifications" GUI 10500 for a display screen of a mobile device 102 for displaying which notifications have been enabled for sharing. The GUI 10500 is displayed by tapping or selecting the notifications GUI element 10502. As shown, activity, rest, medications, and data have been turned ON for notifications. Selecting the "Activity" element 10504 displays the "Activity" GUI 10600 shown in FIG. 106, which provides an "inactivity" button 10602 and a "Delayed Daily Activity" button 10604 that can be turned "ON" or "OFF." As shown both buttons 10602, 10604 are both turned "ON" and will provide notifications if no activity is detected for 4 hours between the hours of 1800 h and 2200 h, for example. These values are user selectable. In one aspect, the no activity value can be selected from 4-24 hours with 4 hour increments, then 36 hours and 48 hours, and so on. The inactivity period can be selected from any time between 0000 h-2300 h with 1 hour increments to any time between 0000 h-2300 h in 1 hour increments. Notification in regards to delayed daily activity can be sent anytime between 0500 h-1800 h with 1 hour increments. Selecting the "Activity" element 10504 displays the "Activity" GUI 10600 shown in FIG. 106, which provides an "inactivity" button 10602 and a "Delayed Daily Activity" button 10604 that can be turned "ON" or "OFF." Selecting the "Rest" element 10506 in FIG. 105 displays the "Rest" GUI 10700 shown in FIG. 107, which provides a "rest" button 10702 that can be turned "ON" or "OFF." The GUI 10700 provides a first portion 10704 where notification is provided if daily rest is less than a predetermined time from 1 hour-1 hours with 1 hour increments, e.g., 4 hrs as shown, and a second portion 10706 where notification is provided if daily rest is more than a predetermined time from 8 hours-20 hours with 1 hour increments, e.g., 10 hrs as shown.

FIGS. 108-111 illustrate ornamental designs for several additional "Notifications" GUIs for a display screen of a mobile device 102 for notifying patients of medication dosing times and reminders. FIG. 108 illustrates one aspect of a "Notifications" GUI 10800 for a display screen of a mobile device 102. Selecting element 10802 displays the "Meds Notification" GUI 10900 shown in FIG. 109. The GUI 10900 provides two options, a first option 10902 to notify the patient when to take the daily medication doses and a second option 10904 to remind the patient when to take the daily medication doses. As shown in GUI 10900, the patient is currently taking 4 daily doses and the reminder option is set to "ON." Tapping or selecting the first option 10902 displays the "My Doses" GUI 11000, which indicates the times when the patient is scheduled to take their medications. Since 4 doses were selected in GUI 10900 in FIG. 109, the GUI 11000 displays the four times of the day when the patient is scheduled to take their medications. As shown, the first scheduled medication time 11002 is due at 0800 h, the second scheduled medication time 11004 is due at 1200 h, the third scheduled medication time 11006 is due at 1600 h, and the fourth schedule medication time 11008 is 2000 h. A new medication time may be added or removed by tapping or selecting the plus ("+") GUI element 11010 or the minus ("−") GUI element 11012, respectively. Tapping or selecting the second option 10904 in GUI 10900 displays the "Remind Me" GUI 11100, which indicates the times when the patient is scheduled to be reminded about taking their medications. Since the "Remind Me" option was turned "ON" in GUI 10900, the "Remind Me" GUI 11100 shows the "ON" button 11108. The GUI 11100 also shows a "Before Dose" reminder 11102. In one aspect, the "Before Dose" reminder 11102 can be selected from a drop down menu, for example, such as: never, 2 hours, 1 hour, 45 minutes, 30 minutes, 15 minutes, 10 minutes, 5 minutes, or zero minutes. In other aspects, other suitable times may be provided for selection. An "After Dose" reminder 11104 can be selected from a drop down menu, for example, such as: never, 0 minutes, 5 minutes, 10 minutes, 15 minutes, 30 minutes, 45 minutes, 1 hour, 2 hours. In other aspects, other suitable times may be provided for selection. A "Cancel medication notifications if tablet detected within" 11106 a predetermined time from a pull down menu, for example, such as: never, 0 minutes, 15 minutes, 30 minutes, 45 minutes, 1 hour, 2 hours. In other aspects, other suitable times may be provided for selection.

FIGS. 112-115 illustrate ornamental designs for several additional "Notifications" GUIs for a display screen of a mobile device 102 for adding daily medications dose times. FIG. 112 illustrates one aspect of a "Notifications" GUI 11200 for a display screen of a mobile device 102. Selecting element 11202 displays GUI 11300 as shown in FIG. 113. Selecting the plus ("+") GUI element 11010 displays the "Add Dose" GUI 11400 shown in FIG. 114. Setting the medication dosing time can be done by tapping or selecting the plus ("+") or minus ("−") GUI elements 11402, 11404, respectively, to increase or decrease, respectively, the hour portion of the time and tapping or selecting the plus ("+") or minus ("−") GUI elements 11406, 11408, respectively, to increase or decrease, respectively, the minutes portion of the time. Once the clock time is set, the clock time can be cancelled by tapping or selecting the "Cancel" button 11410 or can be saved by tapping or selecting the "Save" button 11410. FIG. 115 shows "Edit Dose" GUI 11500 for editing the dosing time. As shown, editing the medication dosing time can be done by tapping or selecting the plus ("+") or minus ("−") GUI elements 11502, 11504, respectively, to increase or decrease, respectively, the hour portion of the time and tapping or selecting the plus ("+") or minus ("−") GUI elements 11506, 11508, respectively, to increase or decrease, respectively, the minutes portion of the time. Once the revised clock time is set, the clock time can be cancelled by tapping or selecting the "Cancel" button 11510 or can be saved by tapping or selecting the "Save" button 11510.

Figures 116, 117, 118, 119:
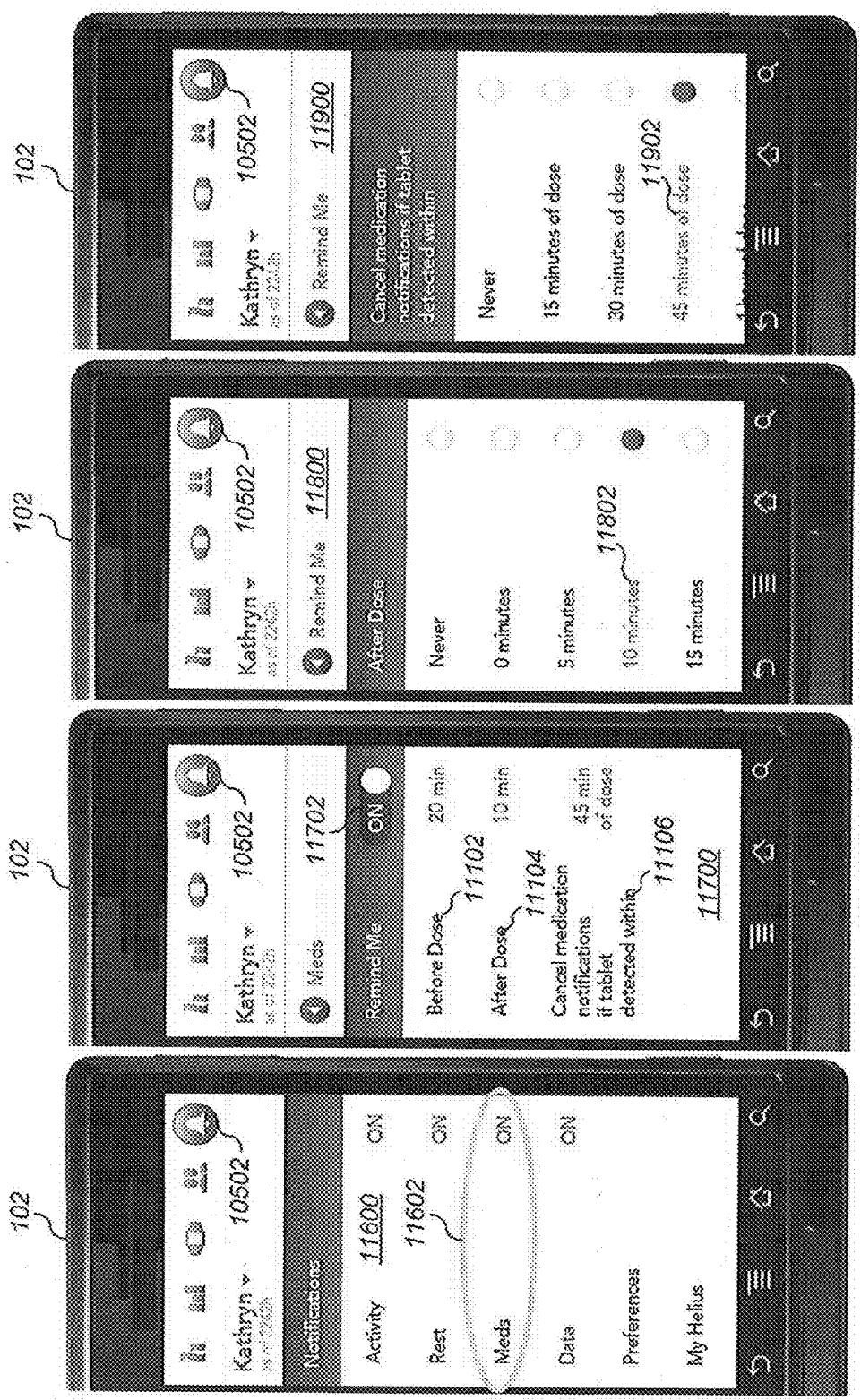
FIGS. 116-119 illustrate ornamental designs for several additional "Notifications" GUIs for a display screen of a mobile device for adding daily medication reminders for taking medications.

FIGS. 116-119 illustrate ornamental designs for several additional "Notifications" GUIs for a display screen of a mobile device 102 for adding daily medication reminders for taking medications. FIG. 116 illustrates one aspect of a "Notifications" GUI 11600 for a display screen of a mobile device 102. Selecting element 11602 displays the "Remind Me" GUI 11700 as shown in FIG. 117. As shown in FIG. 117, the GUI 11700 provides a "Remind Me" button element 11702, which indicates that reminders are enabled or turned "ON." As shown, the "Before Dose" reminder 11704 is set for 20 min, the "After Dose" reminder 11706 is set for 10 min, and the "Cancel medication notifications if tablet detected within" reminder 11708 is set for 45 min of dose. As discussed previously, the "Before Dose" 11704 reminder can be selected from a drop down menu, for example, such as: never, 2 hours, 1 hour, 45 minutes, 30 minutes, 15 minutes, 10 minutes, 5 minutes, or zero minutes. The "After Dose" reminder 11706 can be selected from a drop down menu, for example, such as: never, 0 minutes, 5 minutes, 10 minutes, 15 minutes, 30 minutes, 45 minutes, 1 hour, 2 hours. The "Cancel" reminder

11708 can be selected from a pull down menu, for example, such as: never, 0 minutes, 15 minutes, 30 minutes, 45 minutes, 1 hour, 2 hours. An "After Dose" GUI 11800 shown in FIG. 118 is for selecting the "After Dose" reminder time from a menu list. As shown, "10 minutes" 11802 was selected. A "Cancel" reminder GUI 11900 shown in FIG. 19 is for selecting when to cancel medication notifications if a tablet is detected within a predetermined period. As shown, the reminder is cancelled if the tablet is detected within "45 minutes of dose" 11902.

FIGS. 120-123 illustrate ornamental designs for several additional "Notifications" GUIs for a display screen of a mobile device 102 for providing data alerts. FIG. 120 illustrates one aspect of a "Notifications" GUI 12000 for a display screen of a mobile device 102. Selecting element 12002 displays the "Data" GUI 12100 as shown in FIG. 121. The GUI 12100 displays a "Patch Replacement" GUI element 12102 and a "Missing Information" GUI element 12104. Selecting the "Patch Replacement" GUI element 12102 displays the "Patch Replacement" GUI 12200 shown in FIG. 122. A "Patch Replacement" button 12202 is set to "ON" indicating the patch notification function is enabled. A "Reminder" 12204 to replace the patch is scheduled to be delivered on Wednesday (Wed) at 1500 h. Selecting the "Missing Information" GUI element 12104 in FIG. 121 displays the "Missing Information" GUI 12300 as shown in FIG. 123A. A "Missing Information" button 12302 is set to "ON" indicating that the missing information notification function is enabled. As shown in FIG. 123A, a notification of missing information 12304 is sent if no new information is received in a predetermined time, such as, for example, 4 hrs. The notification can be set to any predetermined time. In one aspect, the notification can be sent if no new information is received in 12 hours, 24 hours, 36 hours, 48 hours, 72 hours, for example. FIG. 123B shows the "Missing Information" button 12302 is set to "OFF" to indicate that the missing information notification function is disabled.

FIGS. 124-127 illustrate ornamental designs for several additional "Notifications" GUIs for a display screen of a mobile device 102 for setting notification preferences. FIG. 124 illustrates one aspect of a "Notifications" GUI 12400 for a display screen of a mobile device 102. Selecting element 12402 displays the "Preferences" GUI 12500 as shown in FIG. 125. The GUI 12500 displays an "Additional Notifications" GUI element 12502 and a "Date & Time" GUI element 12504. Selecting the "Additional Notifications" GUI element 12502 displays the "Additional Notifications" GUI 12600, which indicates how the additional notifications will be sent such as by "Text Message" 12602 or "Email" 12604, which can be turned "ON" or "OFF." Selecting the "Date & Time" GUI element 12504 in FIG. 125 displays the "Date & Time" GUI 12700 in FIG. 127A. The "Date & Time" GUI 12700 enables the selection of the "Date Format" 12702, the "Time Format" 12704, and the "Time Zone" 12706. The "Date Format" 12702 can be selected, for example, as "MM/DD/YYY" or "DD/MM/YYYY" among other formats. The "Time Format" 12704 can be selected, for example, as "12 h" or "24 h" among other formats. The "Time Zone" 12706 can be fixed to home, for example, as shown in FIG. 127A. The "Time Zone" GUI 12708 in FIG. 127B shows the location of the "Home Time Zone" 12710, for example, London. The "Time Zone" GUI 12708 also shows that the data is shown and notifications are sent based on the home time zone.

FIGS. 128-131 illustrate ornamental designs for several additional "Notifications" GUIs for a display screen of a mobile device 102 for displaying information about the account and about the system. FIG. 128 illustrates one aspect of a "Notifications" GUI 12800 for a display screen of a mobile device 102. Selecting element 12802 displays information about the system (e.g., Helius) in the "My Helius" GUI 12900 as shown in FIG. 129. The GUI 12900 displays an "Account Information" GUI element 12902 and an "About Helius" GUI element 12904. Selecting the "Account Information" GUI element 12902 displays the "Account Information" GUI 13000, which provides the "Login" 13002, "Password" 13004, "Nickname" 13006, "SMS" 13008, "Address" 13010. Selecting the "About Helius" GUI element 12904 in FIG. 129 displays the "About Helius" GUI 13100 in FIG. 131. The "About Helius" GUI 13100 provides the software version 13102 and the underlying powering and supporting system 13104.

Figures 132, 133, 134, 135:
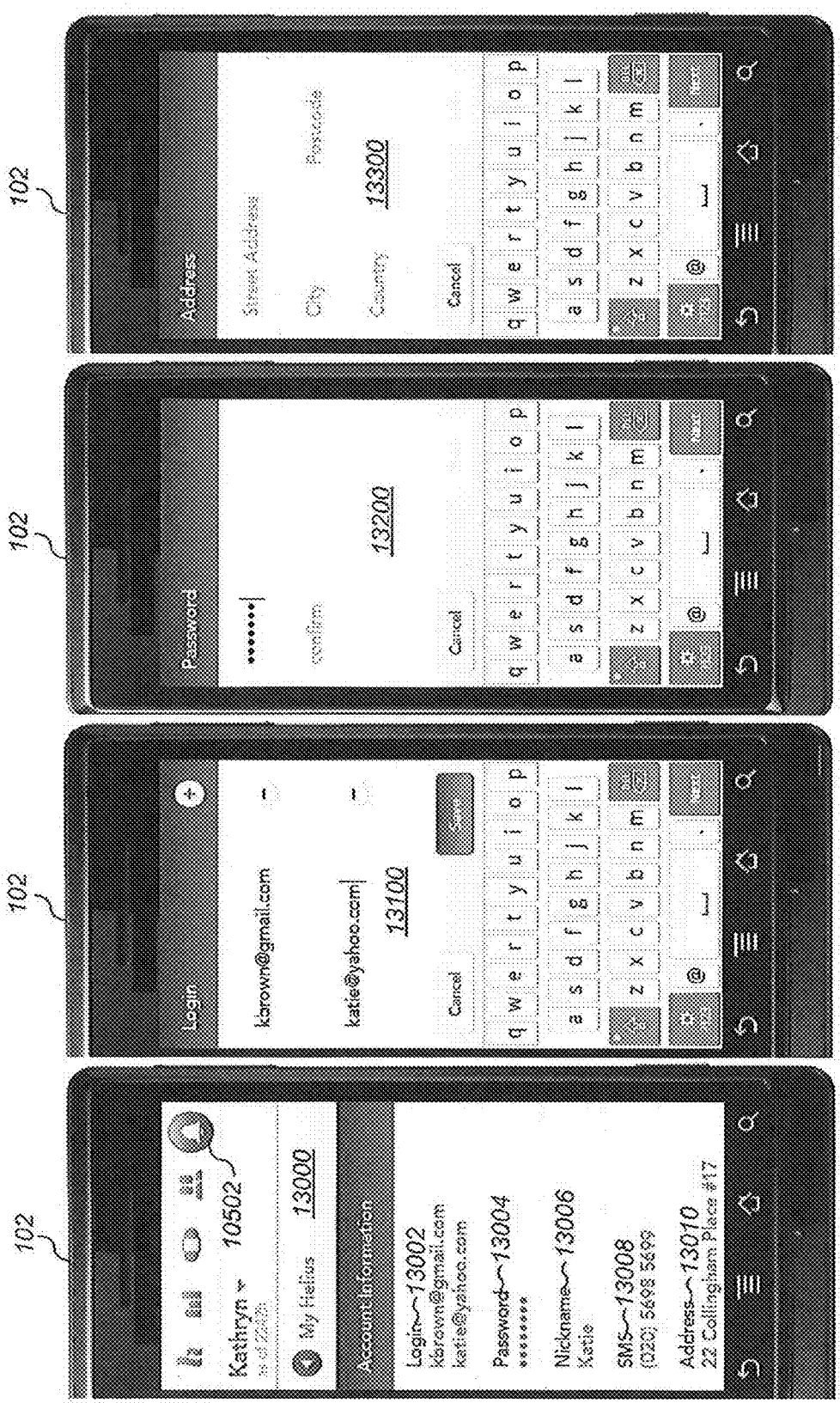

FIGS. 132-135 illustrate ornamental designs for several additional "Notifications" GUIs for a display screen of a mobile device 102 for editing account. FIG. 132 illustrates one aspect of the "Account Information" GUI 13000 for a display screen of a mobile device 102. Selecting the "Login" element 13002 displays the "Login" GUI 13300 as shown in FIG. 133 to enable editing the login email account. Selecting the "Password" element 13004 displays the "Password" GUI 13400 as shown in FIG. 134 to enable editing the password. Selecting the "Address" element 13010 displays the "Address" GUI 13500 as shown in FIG. 135 to enable editing the address.

It will be appreciated that the term "mobile device" may refer generally to any device which can be configured as a communication node for receiving a first communication from a first device and transmitting a second communication to a second device. In one aspect, the mobile device may comprise various physical or logical elements implemented as hardware, software, or any combination thereof, as desired for a given set of design parameters or performance constraints. In various aspects, the physical or logical elements may be connected by one or more communications media. For example, communication media may comprise wired communication media, wireless communication media, or a combination of both, as desired for a given implementation.

In various aspects, the mobile device or elements of the mobile device such as the physical or logical elements of the device may be incorporated in any suitable device including, without limitation, a personal digital assistant (PDA), laptop computer, ultra-laptop computer, combination cellular telephone/PDA, smartphone, mobile unit, subscriber station, user terminal, portable computer, handheld computer, palmtop computer, wearable computer, media player, messaging device, data communication device, a laptop computer, ultralaptop computer, portable computer, handheld computer, palmtop computer, tablet computer, e-book reader, cellular telephone, pager, one-way pager, two-way pager, messaging device, data communication device, computers that are arranged to be worn by a person, such as a wrist computer, finger computer, ring computer, eyeglass computer, belt-clip computer, arm-band computer, shoe computers, clothing computers, and other wearable computers, media or multimedia controllers (e.g., audio and/or visual remote control devices), intelligent devices/appliances such as consumer and home devices and appliances that are capable of receipt of data such as physiologic data and perform other data-related functions, e.g., transmit, display, store, and/or process data, refrigerators, weight scales, toilets, televisions, door frame activity monitors, bedside monitors, bed scales, mobile telephones, portable telephones, eyeglasses, hearing aids, headwear (e.g., hats, caps, visors, helmets, goggles, earmuffs, headbands), wristbands, jewelry, furniture, and/or any suitable object that may be configured to incorporate the appropriate physical and/or logical elements for implementing the mobile device and to receive a first communication from a first device and transmit a second communication to a second device.

It will be appreciated that the term "medication" or "medicinal dose" as used throughout this disclosure may include, without limitation, various forms of ingestible, inhalable, injectable, absorbable, or otherwise consumable medicaments and/or carriers therefor such as, for example, pills, capsules, gel caps, placebos, over capsulation carriers or vehicles, herbal, over-the-counter (OTC) substances, supplements, prescription-only medication, and the like, to be taken in conjunction with an IEM. Such carriers are described in commonly owned applications U.S. application Ser. No. 12/673,150 titled "Pharmaceutical Dosages Delivery System," filed Feb. 11, 2010 which is incorporated by reference in its entirety.

It also will be appreciated that as described in the present disclosure, that the mobile devices that incorporate an image capture device (e.g., a digital camera) may be used to capture an image of the IEM device, medication, container in which the medication, among others. Once the image is captured it can be used to verify the patient taking the medication, the medication itself, expiration dates on the package, among other information. The digitally captured image can be stored, compressed, transmitted over local and wide area networks (such as the Internet), and so on.

It is worthy to note that any reference to "one aspect" or "an aspect" means that a particular feature, structure, or characteristic described in connection with the aspect is included in at least one aspect. Thus, appearances of the phrases "in one aspect" or "in an aspect" in various places throughout the specification are not necessarily all referring to the same aspect. Furthermore, the particular features, structures or characteristics may be combined in any suitable manner in one or more aspects.

Some aspects may be described using the expression "coupled" and "connected" along with their derivatives. It should be understood that these terms are not intended as synonyms for each other. For example, some aspects may be described using the term "connected" to indicate that two or more elements are in direct physical or electrical contact with each other. In another example, some aspects may be described using the term "coupled" to indicate that two or more elements are in direct physical or electrical contact. The term "coupled," however, also may mean that two or more elements are not in direct contact with each other, but yet still co-operate or interact with each other.

While certain features of the aspects have been illustrated as described herein, many modifications, substitutions, changes and equivalents will now occur to those skilled in the art. It is therefore to be understood that the appended claims are intended to cover all such modifications and changes as fall within the true spirit of the aspects.

The invention claimed is:

1. A method of managing adherence to a regimen in a subscription based computer implemented healthcare information environment, the method comprising:
   automatically receiving a first wireless transmission, at a mobile device, the first wireless transmission including dosage ingestion information detected from a marker embedded within a corresponding dose of medicine ingested by a living subject, the mobile device comprising a processor, a memory coupled to the processor, and a display coupled to the processor, wherein the mobile device automatically receives the dosage ingestion information from one or more wireless, wearable receivers coupled to a body of the living subject, wherein the mobile device continuously receives the dosage ingestion information as the dose of medicine is ingested by the living subject;
   automatically addressing a second wireless transmission to a backend computer processing system, the second wireless transmission including the dosage ingestion information;
   receiving, from a computer at the backend computer processing system, a personal information stream characterizing behavior of the living subject based at least in part on the dosage ingestion information sent to the computer over a predetermined period;
   displaying a graphical user interface screen on the display;
   displaying, within the graphical user interface screen, a plurality of selectable graphical user interface elements, wherein selection of one of the plurality of selectable graphical user interface elements causes the graphical user interface screen to display information associated with the living subject,
   wherein the plurality of selectable graphical user interface elements comprises at least one graphical user interface element which corresponds to the display of an activity timeline based at least in part on the personal information stream;
   receiving by the mobile device an input selecting the at least one graphical user interface element;
   in response to the input selecting the at least one graphical user interface element, displaying, within the graphical user interface screen, the activity timeline, wherein the activity timeline comprises an activity ribbon showing the level of activity of the living subject over the predetermined period; and
   displaying the ingestion of the dose within the graphical user interface screen relative to the activity ribbon and the activity timeline,
   wherein the graphical user interface screen presents scheduled medication times as one set of icons and actual detected medication ingestion times based on the dosage ingestion information by another set of icons along the activity timeline such that scheduled versus actual medication times are visually correlated by the graphical user interface screen.

2. The method of claim 1, further comprising:
   continuously tracking the level of activity of the living subject over the predetermined period; and
   displaying the activity ribbon.

3. The method of claim 1, further comprising displaying a comment bubble on the activity ribbon.

4. The method of claim 1, further comprising displaying a sub-activity element within the activity ribbon to indicate a first level of activity when a second level of activity is expected.

5. The method of claim 1, wherein the plurality of selectable graphical user interface elements comprises at least one other graphical user interface element which corresponds to the display of a dose timeline based on the personal information stream, the method further comprising:
   receiving by the mobile device an input selecting the at least one other graphical user interface element; and
   in response to the input selecting the at least one other graphical user interface element, displaying, within the graphical user interface screen, the dose timeline,
   wherein the dose timeline indicates a time during when a dose was ingested by the living subject over a predetermined period.

6. The method of claim 5, comprising:
tracking the dose timeline over the predetermined period; and
displaying dose events.

7. The method of claim 5, further comprising displaying a comment bubble in the dose timeline.

8. The method of claim 1, wherein the plurality of selectable graphical user interface elements comprises at least a one other graphical user interface element which corresponds to the display of a physical activity trend of the living subject based on the personal information stream, the method further comprising:
receiving by the mobile device an input selecting the at least one other graphical user interface element; and
in response to the input selecting the at least one other graphical user interface element, displaying, within the graphical user interface screen, a physical activity trend timeline,
wherein the physical activity trend timeline comprises the level of physical activity over a first predetermined period and wherein the physical activity trend timeline extends over a second predetermined period.

9. The method of claim 8, wherein the first predetermined period is a 24-hour day and the second predetermined period is a week, the method further comprising:
displaying a bar graph element to show the level of activity over the 24-hour period; and
displaying additional bar graph elements over the week for each additional 24-hour period, wherein each of the additional bar graph elements show corresponding levels of activity for each of the additional 24-hour period over the week.

10. The method of claim 8, wherein the first predetermined period is a 24-hour day and the second predetermined period is a week, the method further comprising:
displaying an icon element to show the number of steps taken by the living subject over the 24-hour period; and
displaying icon elements over the week for each additional 24-hour period, wherein each of the additional icon elements graph elements show corresponding number of steps taken by the living subject for each of the additional 24-hour periods over the week.

11. The method of claim 1, wherein the plurality of selectable graphical user interface elements comprises at least one other graphical user interface element which corresponds to the display of a dose trend of the living subject based on the personal information stream, the method further comprising:
receiving by the mobile device an input selecting the at least one other graphical user interface element; and
in response to the input selecting the at least one other graphical user interface element, displaying, within the graphical user interface screen, a dose trend timeline,
wherein the dose trend timeline comprises a number of doses ingested by the living subject and a time stamp associated with the ingestion of the dose over a first predetermined period and wherein the dose trend timeline extends over a second predetermined period.

12. The method of claim 11, wherein the first predetermined period is a 24-hour day and the second predetermined period is a week, the method further comprising:
displaying an element to show when over the 24-hour period the dose was ingested by the living subject; and
displaying additional elements over the week for each additional 24-hour period, wherein each of the additional elements show corresponding times when the dose was ingested by the living subject for each of the additional 24-hour period over the week.

13. The method of claim 11, further comprising displaying the number of doses ingested at the same time on the element.

14. The method of claim 11, further comprising displaying a note on the element.

15. The method of claim 1, wherein the plurality of selectable graphical user interface elements comprises at least one other graphical user interface element which corresponds to the display of configurations, initial set-up, management, and replacement of the receiver, the method further comprising:
receiving by the mobile device an input selecting the at least one other graphical user interface element; and
in response to the input selecting the at least one other graphical user interface element, displaying, within the graphical user interface screen, a button element.

16. The method of claim 15, further comprising:
receiving by the mobile device a second input associated with the button element, wherein the button element is associated with testing the operation of the receiver, mobile device, and backend computer processing system; and
in response to the second input, testing the operation of the receiver, the mobile device, and the backend computer processing system.

17. The method of claim 15, further comprising: receiving by the mobile device a second input associated with the button element, wherein the button element is associated with replacing the receiver; and in response to the second input, replacing the receiver.

18. The method of claim 1, wherein the plurality of selectable graphical user interface elements comprises at least one other graphical user interface element which corresponds to managing and controlling data sharing functions such as invitations and control of which data is shared with at least one invitee, the method further comprising:
receiving by the mobile device an input selecting the at least one other graphical user interface element;
in response to the input selecting the at least one other graphical user interface element, displaying, within the graphical user interface screen, a manage sharing screen comprising elements associated with the at least one invitee and at least one selection element associated with the at least one invitee, wherein the at least one element corresponds to any of an activity timeline element, an activity trend chart element, and a dose timeline element;
receiving by the mobile device a second input associated with selecting one of the elements associated with the invitee;
in response to the second input, selecting one of the elements associated with the at least one invitee; and
sending an invitation to the at least one invitee for sharing data associated with the selected element.

19. The method of claim 18, further comprising:
receiving by the mobile device a communication from the at least one invitee, wherein the communication comprises a personal code associated with the living subject; and
enabling sharing data associated with the selected element only when the personal code is received and verified by the backend computer processing system.

20. The method of claim 1, further comprising receiving a communication from an ingestible device.

21. The method of claim 1, wherein the mobile device further comprises an application stored on the mobile device that is configured to automatically receive the first wireless transmission.

22. The method of claim 1, wherein the dosage ingestion information includes data about the dose of medicine ingested by the living subject and the data is selected from the group consisting of: a first identity of the dose of medicine, a second identity of a manufacturer of the dose of medicine, a unique identity of the marker, and a combination thereof.

23. The method of claim 1, further comprising determining a time when the dosage ingestion information is received, wherein the wireless transmission to the backend computer further includes the time.

24. The method of claim 1, wherein the personal information stream is further based on data stored at a memory of the computer in association with a unique identity of the marker.

25. The method of claim 1, further comprising addressing a third wireless transmission to a second mobile device, the third wireless transmission including the personal information stream.

26. The method of claim 1, further comprising addressing a third wireless transmission to the backend computer processing system, third wireless transmission including subscription information associated with the living subject.

27. A system for managing adherence to a regimen in a subscription based computer implemented healthcare information environment, the system comprising:
a mobile device comprising a processor, a memory coupled to the processor, and a display coupled to the processor, the mobile device configured to:
automatically receive a first wireless transmission including dosage ingestion information detected from a marker embedded within a corresponding dose of medicine ingested by a living subject, wherein the mobile device automatically receives the dosage ingestion information from one or more wireless, wearable receivers coupled to the living subject's body and wherein the mobile device continuously receives the dosage ingestion information as the dose of medicine is ingested by the living subject;
in response to automatically receiving the first wireless transmission, automatically and wirelessly communicate the dosage ingestion information over a wireless network to a computer at a backend computer processing system;
receive from the computer at the backend processing system a personal information stream characterizing behavior of the living subject based at least in part on the received dosage ingestion information over a predetermined period,
display a graphical user interface screen on the display;
display within a graphical user interface screen, a plurality of selectable graphical user interface elements, wherein selection of one of the plurality of graphical user interface elements causes the graphical user interface screen to display information associated with the living subject; wherein the plurality of selectable graphical user interface elements comprises at least one graphical user interface element which corresponds to the display of an activity timeline based at least in part on the personal information stream;
receive an input selecting the at least one graphical user interface element;
in response to the input selecting the at least one graphical user interface element, display, within the graphical user interface screen, the activity timeline, wherein the activity timeline comprises an activity ribbon showing the level of activity of the living subject over the predetermined period, and
display the ingestion of the dose within the graphical user interface screen relative to the activity ribbon and the activity timeline; wherein the graphical user interface presents scheduled medication times as one set of icons and actual detected medication ingestion times by another set of icons along the activity timeline such that scheduled versus actual medication times are visually correlated by the graphical user interface screen.

28. A method comprising the steps of:
automatically receiving a first wireless transmission, at a mobile device, the first wireless transmission including dosage ingestion information detected from a marker embedded within a corresponding dose of medicine ingested by a subject, the mobile device comprising a processor, a memory coupled to the processor, and a display coupled to the processor, wherein the mobile device automatically receives the dosage ingestion information from one or more wireless, wearable receivers coupled to the subject's body and wherein the mobile device continuously receives the dosage ingestion information as the dose of medicine is ingested by the subject;
in response to automatically receiving the first wireless transmission, automatically addressing a second wireless transmission to a computer, the second wireless transmission including the dosage ingestion information;
receiving, from the computer, a personal information stream characterizing behavior of the subject based at least in part on the dosage ingestion information sent to the computer over a predetermined period;
displaying, on the mobile device, the personal information stream characterizing the level of activity of the subject over a predetermined period of time based on the received information,
displaying a graphical user interface screen on the display;
displaying within the graphical user interface screen, a plurality of selectable graphical user interface elements, wherein selection of one of the plurality of graphical user interface elements causes the graphical user interface screen to display information associated with the subject,
wherein the plurality of selectable graphical user interface elements comprises at least one graphical user interface element which corresponds to the display of an activity timeline based on a personal information stream;
receiving an input selecting the at least one graphical user interface element; and
in response to the input selecting the at least one graphical user interface element, displaying, within the graphical user interface screen, the activity timeline,
wherein the activity timeline comprises an activity ribbon showing the level of activity of the subject over the predetermined period, and
displaying the ingestion of the dose within the graphical user interface screen relative to the activity ribbon and the activity timeline;
wherein the graphical user interface screen presents scheduled medication times as one set of icons and actual detected medication ingestion times by another set of icons along the activity timeline such that scheduled versus actual medication times are visually correlated by the graphical user interface screen.

* * * * *